United States Patent
Gersbach et al.

(10) Patent No.: US 10,676,735 B2
(45) Date of Patent: Jun. 9, 2020

(54) HIGH-THROUGHPUT SCREENING OF REGULATORY ELEMENT FUNCTION WITH EPIGENOME EDITING TECHNOLOGIES

(71) Applicant: Duke University, Durham, NC (US)

(72) Inventors: Charles A. Gersbach, Durham, NC (US); Gregory E. Crawford, Chapel Hill, NC (US); Timothy E. Reddy, Carrboro, NC (US); Tyler S. Klann, Durham, NC (US)

(73) Assignee: Duke University, Durham, NC (US)

( * ) Notice: Subject to any disclaimer, the term of this patent is extended or adjusted under 35 U.S.C. 154(b) by 66 days.

(21) Appl. No.: 15/746,653

(22) PCT Filed: Jul. 22, 2016

(86) PCT No.: PCT/US2016/043756
§ 371 (c)(1),
(2) Date: Jan. 22, 2018

(87) PCT Pub. No.: WO2017/015637
PCT Pub. Date: Jan. 26, 2017

(65) Prior Publication Data
US 2018/0291370 A1  Oct. 11, 2018

Related U.S. Application Data

(60) Provisional application No. 62/195,680, filed on Jul. 22, 2015, provisional application No. 62/293,313, filed on Feb. 9, 2016.

(51) Int. Cl.
*C12N 15/10* (2006.01)
*C12N 9/22* (2006.01)
*C07K 14/47* (2006.01)

(52) U.S. Cl.
CPC ...... *C12N 15/1079* (2013.01); *C07K 14/4703* (2013.01); *C07K 14/4705* (2013.01); *C12N 9/22* (2013.01); *C12Y 301/00* (2013.01); *C07K 2319/00* (2013.01); *C12N 2740/16043* (2013.01)

(58) Field of Classification Search
None
See application file for complete search history.

(56) References Cited

U.S. PATENT DOCUMENTS

| | | |
|---|---|---|
| 5,139,941 A | 8/1992 | Muzyczka et al. |
| 5,593,972 A | 1/1997 | Weiner et al. |
| 5,658,784 A | 8/1997 | Eckner et al. |
| 5,741,683 A | 4/1998 | Zhou et al. |
| 5,773,700 A | 6/1998 | Van Grinsven et al. |
| 5,962,428 A | 10/1999 | Carrano et al. |
| 6,057,152 A | 5/2000 | Samulski et al. |
| 6,204,059 B1 | 3/2001 | Samulski et al. |
| 6,268,213 B1 | 7/2001 | Samulski et al. |
| 6,491,907 B1 | 12/2002 | Rabinowitz et al. |
| 6,596,535 B1 | 7/2003 | Carter |
| 6,660,514 B1 | 12/2003 | Zolotukhin et al. |
| 6,951,753 B2 | 10/2005 | Shenk et al. |
| 7,094,604 B2 | 8/2006 | Snyder et al. |
| 7,125,717 B2 | 10/2006 | Carter |
| 7,172,893 B2 | 2/2007 | Rabinowitz et al. |
| 7,201,898 B2 | 4/2007 | Monahan et al. |
| 7,229,823 B2 | 6/2007 | Samulski et al. |
| 7,282,199 B2 | 10/2007 | Gao et al. |
| 7,439,065 B2 | 10/2008 | Ferrari et al. |
| 7,456,683 B2 | 11/2008 | Takano et al. |
| 7,588,772 B2 | 9/2009 | Kay et al. |
| 7,790,449 B2 | 9/2010 | Gao et al. |
| 7,906,111 B2 | 3/2011 | Wilson et al. |
| 10,011,850 B2 | 7/2018 | Joung et al. |
| 2004/0175727 A1 | 9/2004 | Draghia-Akli et al. |
| 2011/0236353 A1 | 9/2011 | Wilson et al. |
| 2011/0263682 A1 | 10/2011 | De Kimpe et al. |
| 2011/0286957 A1 | 11/2011 | Prieve et al. |
| 2012/0195917 A1 | 8/2012 | Sahin et al. |
| 2013/0323001 A1 | 12/2013 | Ueki et al. |
| 2014/0068797 A1 | 3/2014 | Doudna et al. |
| 2014/0179006 A1 | 6/2014 | Zhang |
| 2014/0356956 A1 | 12/2014 | Church et al. |
| 2014/0377868 A1 | 12/2014 | Joung et al. |
| 2015/0031089 A1 | 1/2015 | Lindstrom |
| 2015/0045413 A1 | 2/2015 | De Visser et al. |
| 2015/0056705 A1 | 2/2015 | Conway et al. |
| 2015/0166980 A1 | 6/2015 | Liu et al. |
| 2016/0177278 A1 | 6/2016 | Wolfe et al. |
| 2016/0201089 A1 | 7/2016 | Gersbach et al. |

FOREIGN PATENT DOCUMENTS

| | | |
|---|---|---|
| EP | 2620161 | 7/2013 |
| JP | 2015-534817 A | 12/2015 |
| JP | 2016-521452 A | 7/2016 |

(Continued)

OTHER PUBLICATIONS

International Search Report and Written Opinion for Application No. PCT/US2017/046282 dated Jan. 12, 2018 (20 pages).
Zhou et al., "High-throughput screening of a CRISPR/Cas9 library for functional genomics in human cells," Nature, 2014, 509(7501): 487-491.
European Patent Office Partial Supplementary Search Report for Application No. 16828669.8 dated Dec. 6, 2018 (21 pages).
Adler, A.F. et al., "Nonviral direct conversion of primary mouse embryonic fibroblasts to neuronal cells," Molecular therapy, 2012 Nucleic acids 1, e32.
Anders et al., "Differential expression analysis for sequence count data," Genome biology 11, 2010, R106.

(Continued)

*Primary Examiner* — Nancy A Treptow
(74) *Attorney, Agent, or Firm* — Michael Best & Friedrich LLP

(57) ABSTRACT

Disclosed herein are methods of using Clustered Regularly Interspaced Short Palindromic Repeats (CRISPR)/CRISPR-associated (Cas) 9-based epigenomic editing systems for high-throughput screening of regulatory element function.

17 Claims, 156 Drawing Sheets

Specification includes a Sequence Listing.

(56) References Cited

FOREIGN PATENT DOCUMENTS

| | | |
|---|---|---|
| JP | 2016-521975 A | 7/2016 |
| JP | 2016-523082 A | 8/2016 |
| WO | WO 1993/024640 | 12/1993 |
| WO | WO 1994/016737 | 8/1994 |
| WO | WO 2003/042397 | 5/2003 |
| WO | WO 2005/033321 | 4/2005 |
| WO | WO 2006/110689 | 10/2006 |
| WO | WO 2010/053572 | 5/2010 |
| WO | WO 2011/126808 | 10/2011 |
| WO | WO 2012/170930 | 12/2012 |
| WO | WO 2013/049493 | 4/2013 |
| WO | WO 2013/143555 | 10/2013 |
| WO | WO 2013/182683 | 12/2013 |
| WO | 2014/081855 A1 | 5/2014 |
| WO | 2014/093595 A1 | 6/2014 |
| WO | WO 2014/152432 | 9/2014 |
| WO | 2014/172470 A2 | 10/2014 |
| WO | 2014/191128 | 12/2014 |
| WO | 2014/204728 A1 | 12/2014 |
| WO | WO 2014/197748 | 12/2014 |
| WO | WO 2015/017519 | 2/2015 |
| WO | 2015/089419 A2 | 6/2015 |
| WO | 2015/089486 A2 | 6/2015 |
| WO | WO 2015/089465 | 6/2015 |
| WO | WO 2015/126927 | 8/2015 |
| WO | 2016/094880 A1 | 6/2016 |
| WO | 2016/130600 | 8/2016 |
| WO | WO 2016/130600 | 8/2016 |
| WO | WO 2017/180915 | 10/2017 |

OTHER PUBLICATIONS

Anders et al., "Structural basis of PAM-dependent target DNA recognition by the Cas9 endonuclease," Nature (2014) 513: 569-73.
Arnold, C.D., et al., Genome-wide quantitative enhancer activity maps identified by STARR-seq. Science, 2013. 339(6123): p. 1074-1077.
Asokan et al., "The AAV Vector Toolkit: Poised at the Clinical Crossroads," Mol Ther 20, 699-708 (2012).
Ayyanathan, K. et al. Regulated recruitment of HP1 to a euchromatic gene induces mitotically heritable, epigenetic gene silencing: a mammalian cell culture model of gene variegation. Genes Dev 17, 1855-1869 (2003).
Bartsevich, V.V. et al., "Engineered zinc finger proteins for controlling stem cell fate," Stem Cells 21, 2003, 632-637.
Beerli, R.R. et al., "Engineering polydactyl zinc-finger transcription factors," Nat Biotechnol 20, 2002, 135-141.
Beerli, R.R. et al., "Positive and negative regulation of endogenous genes by designed transcription factors," Proc Natl Acad Sci U S A 97, 2000, 1495-1500.
Beerli, R.R. et al., "Toward controlling gene expression at will: specific regulation of the erbB-2/HER-2 promoter by using polydactyl zinc finger proteins constructed from modular building blocks," Proc Natl Acad Sci U S A 95, 1998, 14628-14633.
Beltran, A. et al., "Re-activation of a dormant tumor suppressor gene maspin by designed transcription factors," Oncogene 26, 2007, 2791-2798.
Bender, M.A. et al. Independent formation of DnaseI hypersensitive sites in the murine beta-globin locus control region. Blood 95, 3600-3604 (2000).
Bernstein, B.E., Stamatoyannopoulos, J.A., Costello, J.F., Ren, B., Milosavljevic, A., Meissner, A. et al. The NIH Roadmap Epigenomics Mapping Consortium. Nat Biolechnol 28, 1045-1048 (2010).
Blancafort, P. et al., "3rd Scanning the human genome with combinatorial transcription factor libraries," Nat Biotechnol 21, 2003, 269-274.
Boshart et al., "A very strong enhancer is located upstream of an immediate early gene of human cytomegalovirus," Cell, 1985, 41:521-530.
Boyle, A.P., et al., High-resolution mapping and characterization of open chromatin across the genome. Cell, 2008. 132(2): p. 311-322.
Bultmann, S. et al., "Targeted transcriptional activation of silent oct4 pluripotency gene by combining designer TALEs and inhibition of epigenetic modifiers," Nucleic Acids Res 40, 2012, 5368-5377.
Carrillo et al., "The Multiple Sequence Alignment Problem in Biology" SIAM J. Applied Math., 1988, 48, 1073.
Carter, D., Chakalova, L., Osborne, C.S., Dai, Y.F. & Fraser, P. Long-range chromatin regulatory interactions in vivo. Nat Genet 32, 623-626 (2002).
Chakraborty, S. et al. A CRISPR/Cas9-Based System for Reprogramming Cell Lineage Specification. Stem cell reports 3, 940-947 (2014).
Chavez et al., "Comparison of Cas9 activators in multiple species," Nat Methods, 2016, 13: 563-67.
Chavez, A. et al. Highly efficient Cas9-mediated transcriptional programming. Nat Methods 12, 326-328 (2015).
Chen, J. & Li, Q. Life and death of transcriptional co-activator p300. Epigenetics 6,.957-961 (2011).
Chen, J.C., Love, C.M. & Goldhamer, D.J. Two upstream enhancers collaborate to regulate the spatial patterning and timing of MyoD transcription during mouse development. Dev Dyn 221, 274-288 (2001).
Cheng. A.W., Wang, H., Yang, H., Shi, L., Katz, Y Theunissen, T.W. et al. Multiplexed activation of endogenous genes by CRISPR-on, an RNA-guided transcriptional activator system Cell Res 23, 1163-1171 (2013).
Chew et al., "A multifunctional AAV-CRISPR-Cas9 and its host response," Nat Methods, 2016;13:868-74.
Cho, S.W. et al., "Targeted genome engineering in human cells with the Cas9 RNA-guided endonuclease," Nat Biotechnol 31, 2013, 230-232.
Choy, B. & Green, M.R. Eukaryotic activators function during multiple steps of preinitiation complex assembly. Nature 366, 531-536 (1993).
Chu et al., "SV40 DNA transfection of cells in suspension: analysis of efficiency of transcription and translation of T-antigen," Gene, 1981, 13:197.
Cong, L. et al., "Multiplex Genome Engineering Using CRISPR/Cas Systems," Science 339, 2013, 819-823.
Cong, L., Zhou, R., Kuo, Y.C., Cunniff, M. & Zhang, F. Comprehensive interrogation of natural TALE DNA-binding modules and transcriptional repressor domains. Nat Commun 3, 968 (2012).
Consortium, An integrated encyclopedia of DNA elements in the human genome. Nature 489, 57-74 (2012).
Cornu et al., "Quantification of zinc finger nuclease-associated toxicity," Meth Mol Biol, 2010, 649:237-245.
Crawford GE, Holt IE, Whittle J, Webb BO, Tai D, Davis S, Margulies EH, Chen Y, Bernat JA, Ginsburg D, Zhou D, Luo S, Vasicek T J, Daly MJ, Wolfsberg TG, Collins FS. Genome-wide mapping of DNase hypersensitive sites using massively parallel signature sequencing (MPSS). Genome Res. 2006, 16, 123-131.
Crocker, J. & Stern, D.L. TALE-mediated modulation of transcriptional enhancers in vivo. Nature methods 10, 762-767 (2013).
de Groote, M.L., Verschure, p. J. & Rots, M.G. Epigenetic Editing targeted rewriting of epigenetic marks to modulate expression of selected target genes. Nucleic Acids Res, 2012, vol. 40, No. 21, pp. 10596-10613.
Dean, A., Ley, T.J., Humphries, R.K., Fordis, M. & Schechter, A.N. Inducible transcription of five globin genes in K562 human leukemia cells. Proceedings of the National Academy of Sciences of the United States of America 80, 5515-5519 (1983).
Deltcheva et al., "CRISPR RNA maturation by trans-encoded small RNA and host factor RNase III," Nature, 2011, 471(7340):602-7.
Delvecchio, M., Gaucher, J., Aguilar-Gurrieri, C., Ortega, E. & Panne, D. Structure of the p300 catalytic core and implications for chromatin targeting and HAT regulation Nat Struct Mol Biol 20, 1040-1046 (2013).
Deng, W. et al. Reactivation of developmentally silenced globin genes by forced chromatin looping. Cell 158, 849-860 (2014).
Dijkema et al., "Cloning and expression of the chromosomal immune interferon gene of the rat," EMBO J., 1985, 4:761.

(56) References Cited

OTHER PUBLICATIONS

Ding et al., "Permanent Alteration of PCSK9 With In Vivo CRISPR-Cas9 Genome Editing," Circulation Research, 2014, vol. 115, No. 5, pp. 488-492.
Doench et al., "Optimized sgRNA design to maximize activity and minimize off-target effects of CRISPR-Cas9," Nat Biotechnol. (2016) 34:184-91.
Doench et al., "Rational design of highly active sgRNAs for CRISPR-Cas9-mediated gene inactivation," Nat Biotechnol. (2014) 32:1262-7.
Dostie, J. et al. Chromosome Conformation Capture Carbon Copy (5C): a massively parallel solution for mapping interactions between genomic elements. Genome research 16, 1299-1309 (2006).
Doudna, J.A. & Charpentier, E. Genome editing. The new frontier of genome engineering with CRISPR-Cas9. Science 346, 1258096 (2014).
Egger, G., Liang, G., Aparicio, A. &•Jones, P.A. Epigenetics in human disease and prospects for epigenetic therapy. Nature 429, 457-463 (2004).
Esvelt, K.M., Mali, P., Braff, J.L., Moosburner, M., Yaung, S.J. & Church, G.M. Orthogonal Cas9 proteins for RNA-guided gene regulation and editing. Nat Methods 10, 1116-1121 (2013).
Farzadfard, F., Perli, S.D. & Lu, T.K.. Tunable and multifunctional eukaryotic transcription factors based on CRISPR/Cas. ACS SynthBiol 2, 604-613 (2013).
Ferretti et al., "Complete genome sequence of an M1 strain of *Streptococcus pyogenes*," Proc Natl Acad Sci U S A. (2001); 98(8): 4658-63.
Fine et al., "Trans-spliced Cas9 allows cleavage of HBB and CCR5 genes in human cells using compact expression cassettes," Sci Rep. 2015;5:10777.
Fontenot JD, Rasmussen JP, Williams LM, Dooley JL, Farr AG, Rudensky AY. Regulatory T cell lineage specification by the forkhead transcription factor foxp3. Immumty, 2005, 22, 329-341.
Gaj, T., Gersbach, C.A. & Barbas, C.F., 3rd ZFN, TALEN, and CRISPR/Cas-based methods for genome engineering. Trends Biotechnol 31, 391-405 (2013).
Gao, X. et al. Comparison of TALE designer transcription factors and the CRISPR/dCas9 in regulation of gene expression by targeting enhancers. Nucleic Acids Res 42, e155 (2014).
Gao, X., et al., Reprogramming to Pluripotency Using Designer TALE Transcription Factors Targeting Enhancers. Stem Cell Reports, 2013. 1(2): p. 183-197.
Garg, A. et al., "Engineering synthetic TAL effectors with orthogonal target sites," Nucleic Acids Res 40, 2012, 7584-7595.
Garriga-Canut, M. et al. Synthetic zinc finger repressors reduce mutant huntingtin expression in the brain of R6/2 mice. Proceedings of the National Academy of Sciences of the United States of America 109, E3136-3145 (2012).
Gersbach, C.A. and P. Perez-Pinera, Activating human genes with zinc finger proteins, transcription activator-like effectors and CRISPR/Cas9 for gene therapy and regenerative medicine. Expert Opin Ther Targets, 2014. 18(8): p. 835-839.
Gersbach, C.A. Genome engineering: the next genomic revolution. Nat Methods 11, 1009-1011 (2014).
Gerstein, M.B. et al. Architecture of the human regulatory network derived fromENCODE data. Nature 489, 91-100 (2012).
Gertz, J. et al., "Transposase mediated construction of RNA-seq libraries," Genome Res 22, 2012, 134-141.
Gilbert et al., "Genome-Scale CRISPR-Mediated Control of Gene Repression and Activation," Cell 159, 647-661 (2014).
Gilbert, L.A. et al. CRISPR-mediated modular RNA-guided regulation of transcription in eukaryotes. Cell 154, 442-451 (2013).
Gorman et al., "The Rous sarcoma virus long terminal repeat is a strong promoter when introduced into a variety of eukaryotic cells by DNA-mediated transfection," Proc. Natl. Acad. Sci. USA, 1982, 79:6777.
Gou, D. et al., "A novel approach for the construction of multiple shRNA expression vectors," J Gene Med, 2007, 9(9): p. 751-763.
Graham et al., "A new technique for the assay of infectivity of human adenovirus 5 DNA," Virol., 1973, 52:456-467.
Graslund, T. et al., "Exploring strategies for the design of artificial transcription factors: targeting sites proximal to known regulatory regions for the induction of gamma-globin expression and the treatment of sickle cell disease," J Biol Chem 280, 2005, 3707-3714.
Grimmer, M.R. et al. Analysis of an artificial zinc finger epigenetic modulator: widespread binding but limited regulation. Nucleic acids research 42, 10856-10868 (2014).
Groner, A.C. et al. KRAB-zinc finger proteins and KAP1 can mediate long-range transcriptional repression through heterochromatin spreading. PLoS Genet 6, e1000869 (2010).
Guschin, D. Y. et al., "A rapid and general assay for monitoring endogenous gene modification," Methods Mol Biol 649, 2010, 247-256.
Hamar et al., "Small interfering RNA targeting Fas protects mice against renal ischemia-reperfusion injury," PNAS (2004) 101: 14883-8.
Hardison, R. et al. Locus control regions of mammalianbeta-globin gene clusters: combining phylogenetic analyses and experimental results to gain functional insights. Gene 205, 73-94 (1997).
Hathaway, N.A. et al. Dynamics and memory of heterochromatin in living cells. Cell 149, 1447-1460 (2012).
Heintzman, N.D., Stuart, R.K., Hon, G., Fu, Y., Ching, C.W., Hawkins, R.D. et al. Distinct and predictive chromatin signatures of transcriptional promoters and enhancers in the human genome. Nat Genet 39, 311-318 (2007).
Hilton, A.M.D.I., Christopher M. Vockley, Gregory E. Crawford, Timothy E. Reddy, Charles A. Gersbach Epigenome editing by a CRISPR-Cas9-based acetyltransferase activates genes from promoters and enhancers. Nature biotechnology, 2015, vol. 33, No. 5, pp. 510-519.
Hotta, A., Cheung A.Y., Farra, N., Vijayaragavan, K., Seguin, C.A., Draper, J.S. et al. Isolation of human iPS cells using EOS lentiviral vectors to select for pluripotency. Nat Methods 6, 370-376 (2009).
Hsu et al., "DNA targeting specificity of RNA-guided Cas9 nucleases," Nature Biotechnology 31, 2013, 827-832.
Hsu, P .D., Lander, E.S. & Zhang. F. Development and applications of CRISPR-Cas9 for genome engineering. Cell, 2014, 157, 1262-1278.
Hu, J., Lei, Y., Wong, W.K., Liu, S., Lee, K.C., He, X. et al. Direct activation of human and mouse Oct4 genes using engineered TALE and Cas9 transcription factors. Nucleic Acids Res 42, 4375-4390 (2014).
Ikonomi, P. et al. Levels of GATA-1/GATA-2 transcription factors modulate expression of embryonic and fetal hemoglobins. Gene 261, 277-287 (2000).
Ji, Q., Fischer, A.L., Brown, C.R., Eastlund, E.R., Dvash, T., Zhong, B. et al. Engineered zinc-finger transcription factors activate OCT4 (POU5FI), SOX2, KLF4, c-MYC (MYC) and miR302/367. Nucleic Acids Res 42, 6158-6167 (2014).
Jinek et al., "Structures of Cas9 endonucleases reveal RNA-mediated conformational activation," Science, 2014, 343: 1247997.
Jinek, M. et al., "A programmable dual-RNA-guided DNA endonuclease in adaptive bacterial immunity," Science 337, 2012, 816-821.
Jinek, M. et al., "RNA-programmed genome editing in human cells. eLife 2," e00471, 2013.
Kabadi, A.M., et al., Multiplex CRISPR/Cas9-based genome engineering from a single lentiviral vector. Nucleic Acids Res, 2014. 42(19): p. e147.
Kearns, N.A. et al. Functional annotation of native enhancers with a Cas9-histone demethylase fusion. Nat Methods (2015).
Keung, AJ., Bashor, CJ., Kiriakov, S., Collins, J.J. & Khalil, A.S. Using targeted chromatin regulators to engineer combinatorial and spatial transcriptional regulation Cell 158, 110-120 (2014).
Khoury et al., "Efficient new cationic liposome formulation for systemic delivery of small interfering RNA silencing tumor necrosis factor α in experimental arthritis," Arthritis Rheumatol. (2006) 54: 1867-77.
Kim et al., "Use of the human elongation factor 1α promoter as a versatile and efficient expression system," Gene, 1990, 91:217.

(56) References Cited

OTHER PUBLICATIONS

Kim, Y. W. & Kim, A. Histone acetylation contributes to chromatin looping between the locus control region and globin gene by influencing hypersensitive site formation. Biochim Biophys Acta 1829, 963-969 (2013).
Konermann et al., "Genome-scale transcriptional activation by an engineered CRISPRCas9 complex," Nature 517, 583-588 (2015).
Konermann, S. et al. Optical control of mammalian endogenous transcription and epigenetic states. Nature 500, 472-476 (2013).
Kotin, "Prospects for the use of adeno-associated virus as a vector for human gene therapy," Hum. Gene Ther., 1994, 5:793-801.
Kuscu, C., et al., Genome-wide analysis reveals characteristics of off-target sites bound by the Cas9 endonuclease. Nat Biotechnol, 2014. 32(7): p. 677-683.
Kyte et al., "A Simple Method for Displaying the Hydropathic Character of a Protein," J. Mol. Biol., 1982, 157:105-132.
Landen et al., "Intraperitoneal delivery of liposomal siRNA for therapy of advanced ovarian cancer," Cancer Biol. Ther. (2006) 5(12):1708-13.
Langmead, B. & Salzberg, S.L. Fast gapped-read alignment with Bowtie 2. Nature methods 9, 357-359 (2012).
Langmead, B. et al., "Ultrafast and memory-efficient alignment of short DNA sequences to the human genome," Genome biology 10, 2009, R25.
Lee et al., "Role of satellite cells versus myofibers in muscle hypertrophy induced by inhibition of the myostatin/activin signaling pathway," Proc Natl Acad Sci U S A, 2012, 109(35):E2353-60.
Lee, "Regulation of muscle mass by myostatin," Annu Rev Cell Dev Biol 20, 61-86 (2004).
Li, B., Carey, M. & Workman, J.L. The role of chromatin during transcription Cell 128, 707-719 (2007).
Li, G. et al. Extensive promoter-centered chromatin interactions provide a topological basis for transcription regulation. Cell 148, 84-98 (2012).
Li, H. et al. The Sequence Alignment/Map format and SAMtools. Bioinformatics 25, 2078-2079 (2009).
Li, Q., Peterson, K.R., Fang, X. & Stamatoyannopoulos, G. Locus control regions. Blood 100, 3077-3086 (2002).
Li, Y. et al., "Transcription activator-like effector hybrids for conditional control and rewiring of chromosomal transgene expression," Scientific reports 2, 2012, 897.
Liang, J.C. et al., "Engineering biological systems with synthetic RNA molecules," Mol Cell 43, 2011, 915-926.
Lohmueller, J.J. et al., "A tunable zinc finger-based framework for Boolean logic computation in mammalian cells," Nucleic Acids Res 40, 2012, 5180-5187.
Love, M.I., Huber, W. & Anders, S. Moderated estimation of fold change and dispersion for RNA-seq data with DESeq2. Genome biology 15, 550 (2014).
Maeder, M.L. et al. CRISPR RNA-guided activation of endogenous human genes. Nat Methods 10, 977-979 (2013).
Maeder, M.L. et al. Targeted DNA demethylation and activation of endogenous genes using programmable TALE-TET1 fusion proteins. Nat Biotechnol 31, 1137-1142 (2013).
Maeder, M.L. et al., "Robust, synergistic regulation of human gene expression using TALE activators," Nat Methods 10, 2013, 243-245.
Magnenat, L., Blancafort, P. & Barbas, C.F., 3rd In vivo selection of combinatorial libraries and designed affinity maturation of polydactyl zinc finger transcription factors for ICAM-1 provides new insights into gene regulation J Mol Biol 341, 635-649 (2004).
Mali, P. et al. CAS9 transcriptional activators for target specificity screening and paired nickases for cooperative genome engineering. Nat Biotechnol 31, 833-838 (2013).
Mali, P. et al. RNA-guided human genome engineering via Cas9. Science 339, 823-826 (2013).
Mamchaoui, K. et al., "Immortalized pathological human myoblasts: towards a universal tool for the study of neuromuscular disorders," Skelet Muscle 1, 2011, 1-11.
Maniatis et al., "Regulation of inducible and tissue-specific gene expression," Science, 1987, 236:1237.
Matsushita et al., "Adeno-associated virus vectors can be efficiently produced without helper virus," Gene Therapy, 1998, 5:938.
McCarty et al, "Self-complementary recombinant adeno-associated virus (scAAV) vectors promote efficient transduction independently of DNA synthesis," Gene Ther. 2001, 8:1248-54.
McDowell, J.C. & Dean, A. Structural and functional cross-talk between a distant enhancer and the epsilon-globin gene promoter shows interdependence ofthe two elements in chromatin Molecular and cellular biology 19, 7600- 7609 (1999).
Memedula, S. & Belmont, A.S. Sequential recruitment of HAT and SWI/SNF components to condensed chromatin by VP16. Curr Biol 13, 241-246 (2003).
Mendenhall, E.M. et al. Locus-specific editing of histone modifications at endogenous enhancers. Nat Biotechnol 31, 1133-1136 (2013).
Miller, J.C. et al., "A TALE nuclease architecture for efficient genome editing" Nat Biotechnol 29, 2011, 143-148.
Mittler, G., Stubler, T., Santolin L., Uhlmann, T., Kremmer, E., Lottspeich F. et al. A novel docking site on Mediator is critical for activationby VP 16 in mammalian cells. EMBO J 22, 6494-6504 (2003).
Mizushima et al., "pEF-BOS, a powerful mammalian expressionvector," Nucl. Acids. Res., 1990, 18:5322.
Morrissey et al., "Activity of stabilized short interfering RNA in a mouse model of hepatitis B virus replication," Hepatol. (2005) 41: 1349-56.
Murphy et al., "The in vitro transcription of the 7SK RNA gene by RNA polymerase III is dependable only on the presence of an upstream promoter," Cell, 1987, 51:81-87.
Muzycka, "Use of adeno-associated virus as a general transduction vector for mammalian cells," Curr. Top. Microbiol. Immunol 1992, 158:97-129.
Myslinski et al., "An unusually compact external promoter for RNA polymerase III transcription of the human H1RNA gene," Nucleic Acids Res, 2001, 29:2502-2509.
Nelson et al., "In vivo genome editing improves muscle function in a mouse model of Duchenne muscular dystrophy," Science, 2016, 351, 403-7.
Nishimasu et al., "Crystal structure of Cas9 in complex with guide RNA and target DNA," Cell, 2014, 156:935-49.
Nissim, L., Perli, S.D., Fridkin, A., Perez-Pinera, P. & Lu, T.K. Multiplexed and Programmable Regulation of Gene Networks with an Integrated RNA and CRISPR/Cas Toolkit in Human Cells. Mol Cell 54, 698-710 (2014).
Nordhoff, V., Hubner, K., Bauer, A., Orlova, I., Malapetsa, A. & Scholer, H.R. Comparative analysis of human, bovine, and murine Oct-4 upstreampromoter sequences. Mamm Genome 12, 309-317 (2001).
Ogryzko, V.V., Schiltz, R.L., Russanova, V., Howard, B.H. & Nakatani, Y. The transcriptional coactivators p300 and CBP are histone acetyltransferases. Cell 87, 953-959 (1996).
Ohshima et al., "Nucleotide sequence of mouse genomic loci including a gene or pseudogene for U6 (4.85) nuclear RNA," Nucleic Acids Res, 1981, 9:5145-5158.
Ong, C.T. & Corces, V.G. Enhancer function: new insights into the regulation of tissuespecific gene expression. Nature reviews. Genetics 12, 283-293 (2011).
Osakabe et al., "FLAG-NLS-SpCas9-2A-GFBSD2 [Binary vector pEgP526-2A-GFBSD2]," National Center for Biotechnology Information, Genbank Entry, Retrieved fromthe Internet on Sep. 18, 2017 <https://www.ncbi.nlm.nih.gov/protein/BAV01234>.
Ousterout et al., "Reading frame correction by targeted genome editing restores dystrophin expression in cells from Duchenne muscular dystrophy patients," Mol Ther, 2013, 21:1718-1726.
Park, K.S. et al., "Phenotypic alteration of eukaryotic cells using randomized libraries of artificial transcription factors," Nat Biotechnol 21, 2003, 1208-1214.
Perez-Pinera et al., "Gene targeting to the ROSA26 locus directed by engineered zinc finger nucleases," Nucleic Acids Research, 2012, 40:3741-3752.

(56) References Cited

OTHER PUBLICATIONS

Perez-Pinera et al., "RNA-guided gene activation by CRISPR-Cas9-based transcription factors," Nat Methods, 2013, 10:973-976.
Perez-Pinera, P. et al., "Synergistic and tunable human gene activation by combinations of synthetic transcription factors," Nat Methods 10, 2013, 239-242.
Piacentino et al., "X-Linked Inhibitor of Apoptosis Protein-Mediated Attenuation of Apoptosis, Using a Novel Cardiac-Enhanced Adeno-Associated Viral Vector," Human Gene Therapy, 2012, 23:635-646.
Polstein, L., et al., Genome-wide specificity of DNA-binding, gene regulation, and chromatin remodeling by TALE- and CRISPR/Cas9-based transcriptional activators. Genome Res, 2015.
Qi, L.S. et al., "Repurposing CRISPR as an RNA-guided platform for sequence-specific control of gene expression," Cell 152, 2013, 1173-1183.
Quinlan, A.R. & Hall, I.M. BEDTools: a flexible suite of utilities for comparing genomic features. Bioinformatics 26, 841-842 (2010).
Rada-Iglesias, A., Bajpai, R., Swigut, T., Brugmann, S.A., Flynn, R.A. & Wysocka. J. A unique chromatin signature uncovers early developmental enhancers in humans. Nature 470, 279-283 (2011).
Randar et al., "Synthetic CRISPR RNA-Cas9-Guided Genome Editing in Human Cells," Proceedings to the National Academy of Sciences of USA, 2015, vol. 112, No. 51, pp. E7110-7117.
Ran et al., "In vivo genome editing using *Staphylococcus aureus* Cas9," Nature 520, 2015, 186-91.
Rebar, E.J. et al., "Induction of angiogenesis in a mouse model using engineered transcription factors," Nat Med 8, 2002, 1427-1432.
Reynolds, N. et al. NuRD-mediated deacetylation of H3K27 facilitates recruitment of Polycomb Repressive Complex 2 to direct gene repression. The EMBO journal 31, 593- 605 (2012).
Rivenbark, A.G. et al. Epigenetic reprogramming of cancer cells via targeted DNA methylation. Epigenetics 7, 350-360 (2012).
Salmon, P. & Trono, D. Production and titration of lentiviral vectors. Current protocols in neuroscience / editorial board, Jacqueline N. Crawley . . . [et al.] Chapter 4, Unit 4 21 (2006).
Sambrook et al., Molecular Cloning and Laboratory manual, Second Ed., Cold Spring Harbor, 1989, pp. 16.7-16.8.
Schultz, D.C., Ayyanathan, K., Negorev, D., Maul, G.G. & Rauscher, F.J., 3rd SETDB1: a novel KAP-1-associated histone H3, lysine 9-specific methyltransferase that contributes to HP1-mediated silencing of euchromatic genes by KRAB zinc-finger proteins. Genes & development 16, 919-932 (2002).
Seto et al., "Gene Replacement Therapies for Duchenne Muscular Dystrophy Using Adeno-Associated Viral Vectors," Current Gene Therapy, 2012, 12:139-151.
Smith et al., "Myostatin inhibitors as therapies for muscle wasting associated with cancer and other disorders," Curr Opin Support Palliat Care, 2013, 7, 352-60.
Snowden, A.W., Gregory, P.D., Case, C.C. & Pabo, C.O. Gene-specific targeting of H3K9 methylation is sufficient for initiating repression in vivo. Curr Biol 12, 2159-2166 (2002).
Song, L. & Crawford, G.E. DNase-seq: a high-resolution technique for mapping active gene regulatory elements across the genome from mammalian cells. Cold Spring Harbor protocols 2010, pdb prot5384 (2010).
Song, L. et al., "Open chromatin defined by DNaseI and FAIRE identifies regulatory elements that shape cell-type identify," Genome Res 21, 2011, 1757-1767.
Soutschek et al., "Therapeutic silencing of an endogenous gene by systemic administration of modified siRNAs," Nature (2004) 432: 173-8.
Spitz F, Furlong EE. Transcription factors: from enhancer binding to developmental control. Nat. Rev. Genet 2012, 13, 613-626.
Sripathy, S.P., Stevens, J. & Schultz, D.C. The KAP1 corepressor functions to coordinate the assembly of de novo HP1-demarcated microenvironments of heterochromatin required for KRAB zinc finger protein-mediated transcriptional repression Molecular and cellular biology 26, 8623-8638 (2006).

Sternberg et al., "Conformational Control of DNA Target Cleavage by CRISPR-Cas9," Nature, 2015, vol. 527, No. 7576, pp. 110-113.
Sternberg et al., "DNA interrogation by the CRISPR RNA-guided endonuclease Cas9," Nature, 2014, 507, 62-67.
Su et al., "In vitro and in vivo mRNA delivery using lipid-enveloped pH-responsive polymer nanoparticles," Mol. Pharmaceutics, 2011, 8, 774-787.
Su, M.Y., Steiner, L.A., Bogardus, H., Mishra, T., Schulz, V.P., Handison, R.C. et al. Identification of biologically relevant enhancers in human erythroid cells. J Biol Chem 288, 8433-8444 (2013).
Tabebordbar et al., "In vivo gene editing in dystrophic mouse muscle and muscle stem cells," Science, 2016, 351, 407-11.
Takahashi, K., Tanabe, K., Ohnuki, M., Narita, M., Ichisaka, T., Tomoda, K. et al. Induction of pluripotent stem cells from adult human fibroblasts by defined factors. Cell 1131, 861-872 (2007).
Tanenbaum, M.E., Gilbert, L.A., Qi, L.S., Weissman, J.S. & Vale, R.D. A Protein-Tagging System for Signal Amplification in Gene Expression and Fluorescence Imaging. Cell, 2014, pp. 635-646.
Thakore et al., "Editing the epigenome: technologies for programmable transcription and epigenetic modulation," Nat Methods. 2016;13:127-37.
Thakore et al., "Highly specific epigenome editing by CRISPR-Cas9 repressors for silencing of distal regulatory elements," Nat Methods, 2015, 12, 1143-9.
Thomson et al., "Human herpesvirus 6 (HHV-6) is a helper virus for adeno-associated virus type 2 (AAV-2) and the AAV-2 rep gene homologue in HHV-6 can mediate AAV-2 DNA replication and regulate gene expression," Virol., 1994, 204:304-311.
Thurman, R.E. et al. The accessible chromatin landscape of the human genome. Nature 489, 75-82 (2012).
Tone Y, Furuuchi K, Kojima Y, Tykocinski ML, Greene MI, Tone M Smad3 and NFAT cooperate to induce Foxp3 expression through its enhancer. Nat. Immunol., 2008, 9, 194-202.
Truong et al., "Development of an intein-mediated split-Cas9 system for gene therapy," Nucleic Acids Res. 2015; 43: 6450-6458.
Tuan, D., Kong, S. & Hu, K. Transcription of the hypersensitive site HS2 enhancer in erythroid cells. Proceedings of the National Academy of Sciences of the United States of America 89, 11219-11223 (1992).
Uchida et al, "In Vivo Messenger RNA Introduction into the Central Nervous System Using Polyplex Nanomicelle," PLoS One, 2013, 8: e56220.
Uetsuki et al., "Isolation and characterization of the human chromosomal gene for polypeptide chain elongation factor-1 alpha," J. Biol. Chem., 1989, 264:5791.
Vakoc, C.R. et al. Proximity among distant regulatory elements at the beta-globin locus requires GATA-1 and FOG-1. Molecular cell 17, 453-462 (2005).
Vierbuchen, T. et al., "Direct conversion of fibroblasts to functional neurons by defined factors," Nature 463, 2010, 1035-1041.
Visel, A., Blow, M.J., Li, Z., Zhang, T., Akiyama, J.A., Holt, A. et al. ChIP-seq accurately predicts tissue-specific activity of enhancers. Nature 457, 854-858 (2009).
Voss et al., "The role of enhancers in the regulation of cell-type-specific transcriptional control," Trends Biochem. Sci., 1986, 11:287.
Wagner et al., "A phase I/IItrial of MYO-029 in adult subjects with muscular dystrophy," Ann Neurol 63, 561-71.
Wang L., Grossman, S.R. & Kieff, E. Epstein-Barr virus nuclear protein 2 interacts with p300, CBP, and PCAF histone acetyltransferases in activation of the LMP1 promoter. Proc Nail Acad Sci U S A 97, 430-435 (2000).
Wang Z., Zang. C., Cui, K., Schones, D.E., Barski, A., Peng. W. et al. Genome-wide mapping of HATs and HDACs reveals distinct functions inactive and inactive genes. Cell 138, 1019-1031 (2009).
Wu, X. et al. Genome-wide binding of the CRISPR endonuclease Cas9 in mammalian cells. Nat Biotechnol 32, 670-676 (2014).
Zhang et al., "Adenovirus—Adeno-Associated Virus Hybrid for Large-Scale Recombinant Adeno-Associated Virus Production," Hum Gene Ther. 2009;20:922-9.
Zhang, F. et al. "Efficient construction of sequence-specific TAL effectors for modulating mammalian transcription," Nat Biotechnol 29, 2011, 149-153.

(56) References Cited

OTHER PUBLICATIONS

Zhang, Y. et al. Model-based analysis of ChIP-Seq (MACS). Genome biology 9, R137 (2008).
Zheng Y, Josefowicz S, Chaudhry A, Peng XP, Forbush K, Rudensky AY. Role of conserved non-coding DNA elements in the Foxp3 gene in regulatory T-cell fate. Nature, 2010, 463, 808-812.
Zheng Y, Rudensky AY. Foxp3 in control of the regulatory T cell lineage. Nat. Immunol. 2007, 8, 457-462.
Zincarelli et al., "Analysis of AAV serotypes 1-9 mediated gene expression and tropism in mice after systemic injection," Mol Ther 16, 1073-80 (2008).
International Search Report and Written Opinion for Application No. PCT/US14/41190 dated Dec. 17, 2014 (14 pages).
International Search Report and Written Opinion for Application No. PCT/US14/17221 dated Oct. 26, 2016 (11 pages).
International Search Report and Written Opinion for Application No. PCT/US2017/027490 dated Sep. 28, 2017 (34 pages).
U.S. Appl. No. 61/831,481, filed Jun. 5, 2013.
U.S. Appl. No. 61/839,127, filed Jun. 25, 2013.
U.S. Appl. No. 61/967,466, filed Mar. 19, 2014.
U.S. Appl. No. 61/904,911, filed Nov. 15, 2013.
U.S. Appl. No. 61/981,757, filed Apr. 18, 2014.
U.S. Appl. No. 14/895,316, filed Dec. 2, 2015, U.S. Pat. No. 2016/0201089, dated Jul. 14, 2016.
U.S. Appl. No. 15/991,333, filed May 29, 2018.
U.S. Appl. No. 62/113,569, filed Feb. 9, 2015.
U.S. Appl. No. 15/549,842, filed Aug. 9, 2017, U.S. Pat. No. 2018/0023064, dated Jan. 25, 2018.
U.S. Appl. No. 62/373,343, filed Aug. 10, 2016.
U.S. Appl. No. 62/321,947, filed Apr. 13, 2016.
U.S. Appl. No. 62/369,248, filed Aug. 1, 2016.
U.S. Appl. No. 62/574,059, filed Oct. 18, 2017.
U.S. Appl. No. 62/593,985, filed Dec. 3, 2017.
Whisstock et al., "Prediction of protein function from protein sequence," Q. Rev. Biophysics., 2003, 36(3): 307-340.
United States Patent Office Action for U.S. Appl. No. 15/549,842 dated May 17, 2019 (29 pages).
European Patent Office Extended Search Report for Patent Application No. 16828669.8 dated Mar. 25, 2019 (16 pages).
Beverley, "Primer: making sense of T-cell memory," Nat. Clin. Pract. Rheumatol. 2008, 4, 43-49.
Okkenhaug et al., "PI3K in lymphocyte development, differentiation and activation," Nat. Rev. Immunol., 2003, 3(4): 317-330.
Riley, "PD-1 signaling in primary T cells," Immunological Reviews, 2009, 229: 114-125.
Youngblood et al., "Chronic virus infection enforces demethylation of the locus that encodes PD-1 in antigen-specific CD8+ T cells," Immunity, 2011, 35: 400-412.
Chen et al., "Expanding the CRISPR imaging toolset with *Staphylococcus aureus* Cas9 for simultaneous imaging of multiple genomic loci," Nucleic Acids Research, 2016, 44(8):e75, 13 pages.
La Russa et al., "The New State of the Art: Cas9 for Gene Activation and Repression," Molecular and Cellular Biology, 2015, 35(22):3800-3809.
Thakore et al., "RNA-guided transcriptional silencing in vivo with S. aureus CRISPR-Cas9 repressors," Nature Communications, 2018, 9(1):1674, 9 pages.
United States Patent Office Action for U.S. Appl. No. 15/549,842 dated Oct. 10, 2019 (14 pages).
EBI Accession No. GSP: BCJ39961 (2016).
Jörg, T., "Engineering of the epigenome: synthetic biology to define functional causality and develop innovative therapies," Epigenomics, 2016, 8(2):153-156.
United States Patent Office Notice of Allowance for U.S. Appl. No. 15/549,842 dated Jan. 30, 2020 (7 pages).

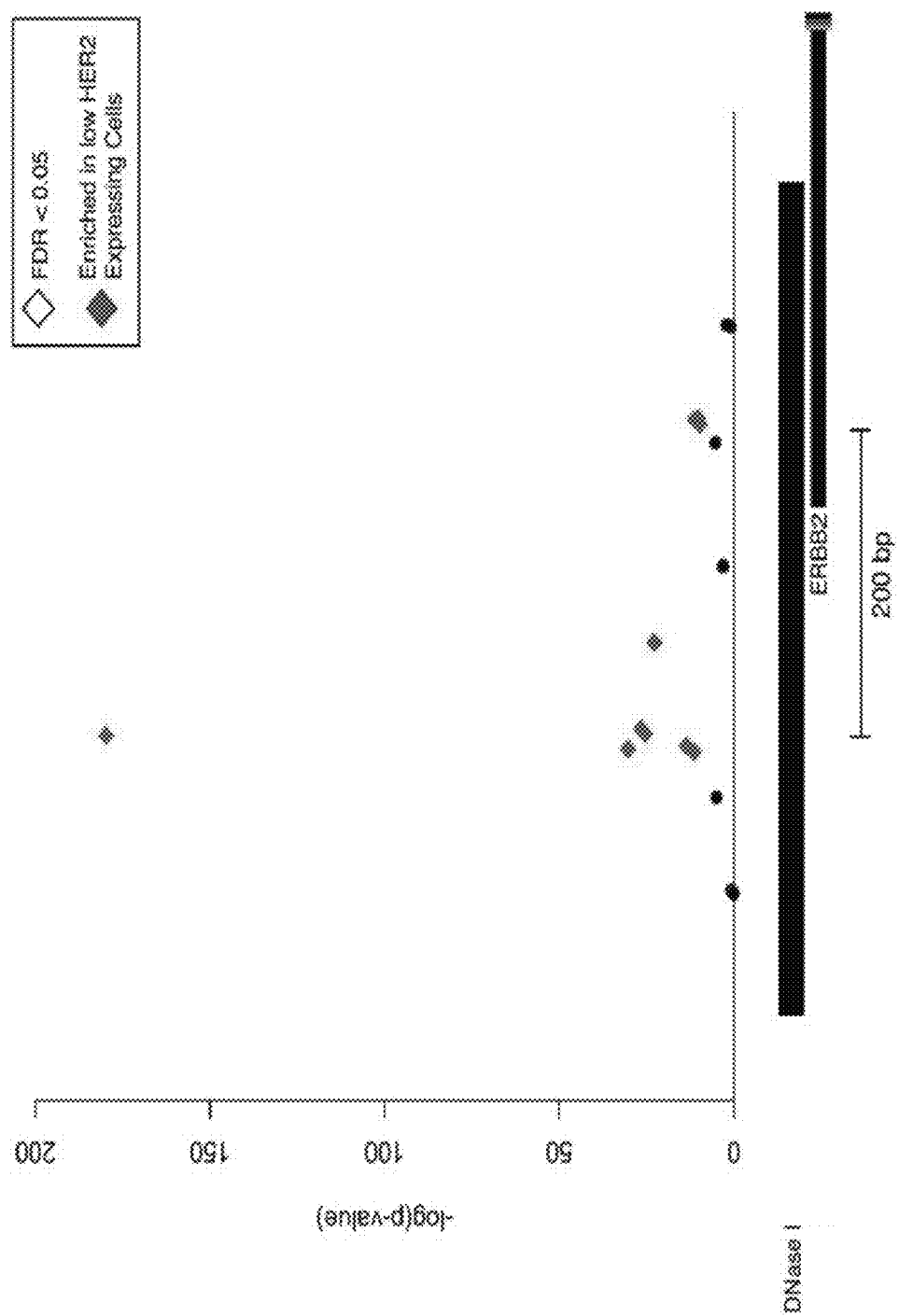

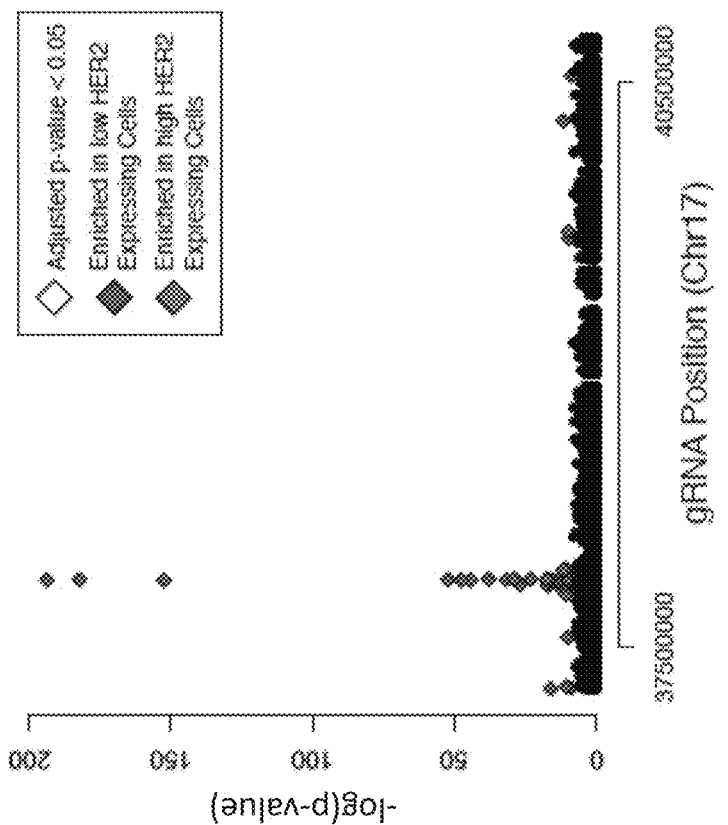
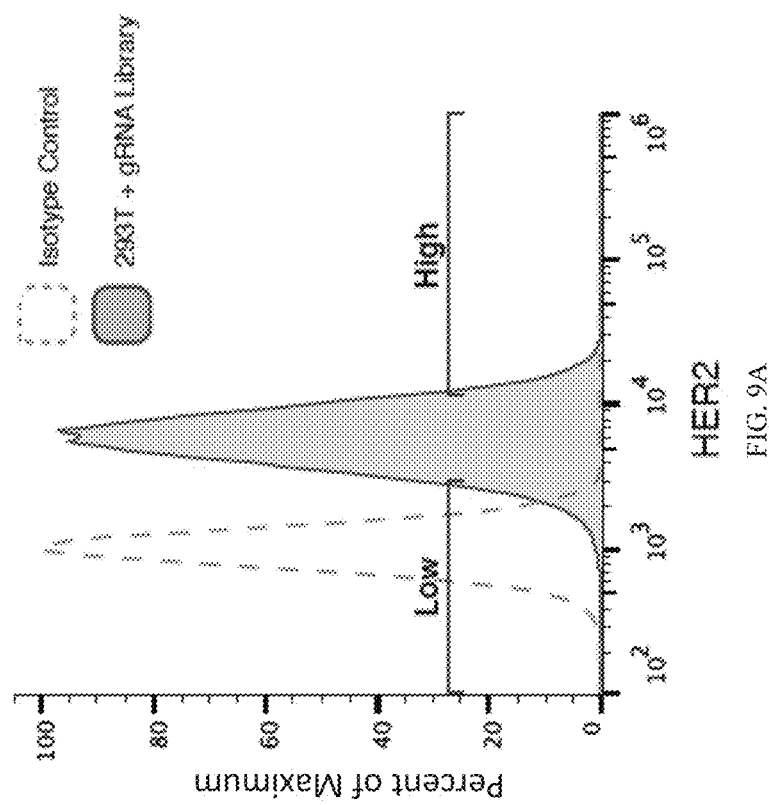

HIGH-THROUGHPUT SCREENING OF REGULATORY ELEMENT FUNCTION WITH EPIGENOME EDITING TECHNOLOGIES

CROSS-REFERENCE TO RELATED APPLICATIONS

This application is a national stage filing under 35 U.S.C. 371 of International Patent Application No. PCT/US2016/043756, which claims priority to U.S. Provisional Application No. 62/293,313, filed Feb. 9, 2016, and U.S. Provisional Application No. 62/195,680, filed Jul. 22, 2015, which are incorporated herein by reference in their entirety

STATEMENT OF GOVERNMENT INTEREST

This invention was made with Government support under Federal Grant Nos. R01DA036865 and 1DP2OD008586 awarded by the National Institutes of Health. The Government has certain rights to this invention.

SEQUENCE LISTING

The instant application includes a Sequence Listing which has been submitted electronically in ASCII format and is hereby incorporated by reference in its entirety. Said ASCII copy, created on Jan. 22, 2018, is named 028193-9198-US03_As_Filed_Sequence_Listing.txt and is 74,767 bytes in size.

TECHNICAL FIELD

The present disclosure is directed to methods of using CRISPR/Cas9-based epigenomic editing systems in high-throughput screening of regulatory element function.

BACKGROUND

The Human Genome Project was funded and pursued based on the premise that the sequencing of the human genome would reveal the genetic basis for complex diseases that have a strong inheritable component, including cardiovascular disease, neurodegenerative conditions, and metabolic diseases such as diabetes. It was believed that this information would lead to new drug targets for these widespread diseases. However, thousands of genome-wide association studies (GWAS) have shown that the genetic variation associated with these complex diseases does not occur within genes, but rather in intergenic regulatory regions that control the levels of particular genes. Similarly, approximately 20% of Mendelian disorders do not have a detectable coding mutation, suggesting that the causal mutation is in a gene regulatory element. It is very difficult to assign functional roles to these regulatory elements as they often are located in distant locations from their target genes.

The human genome encodes approximately 50,000 genes. Understanding how those genes are regulated and how this correlates to complex cell phenotypes is a focus. Many genes and regulatory elements fall into each positive hit of each GWAS study, and the actual target gene(s) that causes disease may fall outside of the regions identified by GWAS studies. Follow-up projects to the Human Genome Project, such as the NIH-funded Encyclopedia of DNA Elements (ENCODE) and the Roadmap Epigenomics Project, have identified millions of putative regulatory elements across the human genome for many human cell types and tissues. These regulatory elements determine the gene expression patterns responsible for complex cell phenotypes including cell differentiation, tissue specificity, oncogenesis, immunomodulation, and disease. However, the function of these regulatory elements and their relationships to these phenotypes are largely unknown. Additionally, conventional screening tools for perturbing cellular processes, such as small molecules and RNA interference, cannot directly target genomic regulatory elements.

Conventional screening technologies include small molecule screens that inhibit protein function and RNA interference screens that block protein translation. Although successful in many cases, these screening technologies have also been plagued by confounding off-target effects. Furthermore, as described above, it has been discovered that gene regulatory elements play a critical role in determining cell phenotype, susceptibility to various diseases and disorders, and response to drug treatment. Conventional screening technologies are unable to directly probe the function of gene regulatory elements. There remains a need for the ability to target direct manipulation of epigenetic properties.

SUMMARY

The present invention is directed a method of high-throughput screening for one or more putative gene regulatory elements in a genome that modulate a phenotype. The method includes a) contacting a plurality of modified target cells with a library of single guide RNAs (sgRNAs) that target a plurality of gene regulatory elements within the genome, thereby generating a plurality of test cells, b) selecting a population of test cells or an organism having a modulated phenotype; c) quantitating the frequency of the sgRNAs within the population of selected cells or the organism, wherein the sgRNAs that target gene regulatory elements that modulate the phenotype are overrepresented or underrepresented in the selected cells; and d) identifying and characterizing the sgRNAs within the population of selected test cells or the organism thereby identifying the gene regulatory elements that modulate the phenotype. The modified target cell or organism includes a fusion protein, the fusion protein comprising a first polypeptide domain comprising a nuclease-deficient Cas9 and a second polypeptide domain having an activity selected from the group consisting of transcription activation activity, transcription repression activity, nuclease activity, transcription release factor activity, histone modification activity, nucleic acid association activity, DNA methylase activity, and direct or indirect DNA demethylase activity.

BRIEF DESCRIPTION OF THE DRAWINGS

FIG. 2A shows the location of the control gRNAs for validating the reporter cell line. FIG. 2B shows the 2A-mCherry donor construct. FIG. 2C show the results of the reporter cell line validation.

FIG. 3A shows that following lentiviral transduction of a library of 10,739 gRNAs targeting all DNase I hypersensitive sites in a 5 megabase window around HBE1 (segment shown as SEQ ID NO: 50, a portion thereof translated to SEQ ID NO: 51), the fraction of RFP-negative cells increased from 6% to 20%. These RFP-negative cells were isolated by fluorescence-activated cell sorting, and the gRNAs within in these cells were recovered by PCR from the lentiviral vector. FIGS. 3B and 3C show that high-throughput sequencing of the sgRNA library showed enrichment of sequences targeting known regulatory elements at the HBE1 promoter (FIG. 2B) and the HS1 and HS2 enhancers (FIG. 2C), demonstrating successful identification of specific known regulator elements from this complex library.

FIG. 5A shows the enrichment and location of the pooled gRNA library targeting DHSs (indicated by DNase I susceptibility) in K562 cells, both the HBE1 full library and 3-globin locus. FIG. 5B shows representative flow cytometry data of dCas9$^{KRAB}$ repressing a mCherry reporter knocked into the endogenous HBE1 locus in K562 cells. FIG. 5C shows a Manhattan plot showing the results of a high-throughput screen for regulatory elements in the 4.5 Mb surrounding the globin locus (HBE1 gene) of 10,739 gRNAs targeting 281 DHSs (limit 50 gRNAs per DHS) using the dCas9$^{KRAB}$ repressor. FIG. 5D shows that enriched DHSs following selection for decreased HBE expression were found only in the well-known HBE promoter and enhancers (HS1-4).

FIG. 6A shows a Manhattan plot showing enrichment of individual gRNAs across the entire library in the 4.5 Mb region surrounding HBE1. FIG. 6B shows a closer view of the globin locus control region (HS1-5). FIG. 6C shows enriched gRNAs within the HS2 enhancer.

FIG. 7A shows flow cytometry data of dCas9$^{KRAB}$ repressing HER2 in A431 cells measured via cell surface staining with a monoclonal antibody. FIG. 7B shows a Manhattan plot showing the results of a screen for regulatory elements in the 4 Mb surrounding the HER2 gene using the dCas9$^{KRAB}$ repressor. FIG. 7C shows a zoomed view of the HER2 region. FIG. 7D shows a Manhattan plot showing the results of a high-throughput screen for regulatory elements in the 4 Mb surrounding the globin locus (HBE1 gene) of 12,189 gRNAs targeting 433 DHSs (limit 30 gRNAs per DHS) using the dCas9$^{KRAB}$ repressor.

FIGS. 8A-8C show HER2 screen gRNA enrichment. FIG. 8A shows a Manhattan plot showing enrichment of individual gRNAs across the entire library surrounding the 4 Mb region surrounding HER2. FIG. 8B shows enrichment of gRNAs near HER2. FIG. 8C shows enriched gRNAs by the HER2 promoter.

FIGS. 9A-9D show screening HER2 enhancers with HER2 dCas9$^{p300}$. FIG. 9A shows flow cytometry data of dCas9$^{p300}$ activating HER2 in 293Tcells measured via cell surface staining with a monoclonal antibody. FIG. 9B shows a Manhattan plot showing results of a screen for regulatory elements in the 4 Mb surrounding the HER2 gene using the dCas9$^{p300}$ activator. FIG. 9C shows a zoomed view of the HER2 region. When comparing high and low expressing HER2 cell populations, gRNAs are enriched in the promoter and three intronic DHSs of HER2 as well as several nearby DHSs. FIG. 9D shows a closer view of the beginning of the HER2 gene. Interestingly, the intronic DHS enriched in the dCas9$^{KRAB}$ screen did not appear enriched in the p300 screen.

FIG. 10A shows HER2 mRNA fold change versus log 2 fold change in the screen for dCas9$^{KRAB}$ hits. FIG. 10B shows HER2 mean fluorescent intensity measured via antibody staining versus log 2 fold change in the screen for dCas9$^{KRAB}$ hits.

FIG. 12A shows the frequency and location of the pooled gRNA library targeting DHSs in A431 cells, where the vertical highlighted band indicates the location of gRNA 1549. FIG. 12B shows flow cytometry data of dCas9$^{KRAB}$ repressing HER2 in A431 cells measured via cell surface staining with a monoclonal antibody. FIG. 12C shows normalized counts for all gRNAs per DHS (left panel) and individual gRNA used (right panel) where "0" is input (no Cas9 Effector), "1" is unsorted bulk population, "2" is lowest 10% sorted, and "3" is highest 10% sorted.

FIGS. 13A and 13D show the frequency and location of the pooled gRNA library targeting DHSs in A431 cells, where the vertical highlighted band indicates the location of gRNA 1553.1 (FIG. 13A) and 1553.2 (FIG. 13D). FIGS. 13B and 13E show flow cytometry data of dCas9$^{KRAB}$ repressing HER2 in A431 cells measured via cell surface staining with a monoclonal antibody. FIGS. 13C and 13F show normalized counts for all gRNAs per DHS (left panel) and individual gRNA used (right panel) where "0" is input (no Cas9 Effector), "1" is unsorted bulk population, "2" is lowest 10% sorted, and "3" is highest 10% sorted.

FIG. 14A shows the frequency and location of the pooled gRNA library targeting DHSs in A431 cells, where the vertical highlighted band indicates the location of gRNA 1543. FIG. 14B shows flow cytometry data of dCas9$^{KRAB}$ repressing HER2 in A431 cells measured via cell surface staining with a monoclonal antibody. FIG. 14C shows normalized counts for all gRNAs per DHS (left panel) and individual gRNA used (right panel) where "0" is input (no Cas9 Effector), "1" is unsorted bulk population, "2" is lowest 10% sorted, and "3" is highest 10% sorted.

FIG. 15A shows the frequency and location of the pooled gRNA library targeting DHSs in A431 cells, where the vertical highlighted band indicates the location of gRNA 1544. FIG. 15B shows flow cytometry data of dCas9$^{KRAB}$ repressing HER2 in A431 cells measured via cell surface staining with a monoclonal antibody. FIG. 15C shows normalized counts for all gRNAs per DHS (left panel) and individual gRNA used (right panel) where "0" is input (no Cas9 Effector), "1" is unsorted bulk population, "2" is lowest 10% sorted, and "3" is highest 10% sorted.

FIG. 16A shows the frequency and location of the pooled gRNA library targeting DHSs in A431 cells, where the vertical highlighted band indicates the location of gRNA 1561. FIG. 16B shows flow cytometry data of dCas9$^{KRAB}$ repressing HER2 in A431 cells measured via cell surface staining with a monoclonal antibody. FIG. 16C shows normalized counts for all gRNAs per DHS (left panel) and individual gRNA used (right panel) where "0" is input (no Cas9 Effector), "1" is unsorted bulk population, "2" is lowest 10% sorted, and "3" is highest 10% sorted.

FIG. 17A shows the frequency and location of the pooled gRNA library targeting DHSs in A431 cells, where the vertical highlighted band indicates the location of gRNA 1769. FIG. 17B shows flow cytometry data of dCas9$^{KRAB}$ repressing HER2 in A431 cells measured via cell surface staining with a monoclonal antibody. FIG. 17C shows normalized counts for all gRNAs per DHS (left panel) and individual gRNA used (right panel) where "0" is input (no Cas9 Effector), "1" is unsorted bulk population, "2" is lowest 10% sorted, and "3" is highest 10% sorted.

FIG. 18A shows the frequency and location of the pooled gRNA library targeting DHSs in A431 cells, where the vertical highlighted band indicates the location of gRNA 1592. FIG. 18B shows flow cytometry data of dCas9$^{KRAB}$ repressing HER2 in A431 cells measured via cell surface staining with a monoclonal antibody. FIG. 18C shows normalized counts for all gRNAs per DHS (left panel) and individual gRNA used (right panel) where "0" is input (no Cas9 Effector), "1" is unsorted bulk population, "2" is lowest 10% sorted, and "3" is highest 10% sorted.

FIG. 19A shows the frequency and location of the pooled gRNA library targeting DHSs in A431 cells, where the vertical highlighted band indicates the location of gRNA 1856. FIG. 19B shows flow cytometry data of dCas9$^{KRAB}$ repressing HER2 in A431 cells measured via cell surface staining with a monoclonal antibody. FIG. 19C shows normalized counts for all gRNAs per DHS (left panel) and individual gRNA used (right panel) where "0" is input (no Cas9 Effector), "1" is unsorted bulk population, "2" is lowest 10% sorted, and "3" is highest 10% sorted.

FIG. 20A shows the frequency and location of the pooled gRNA library targeting DHSs in A431 cells, where the vertical highlighted band indicates the location of gRNA 1562. FIG. 20B shows flow cytometry data of dCas9$^{KRAB}$ repressing HER2 in A431 cells measured via cell surface staining with a monoclonal antibody. FIG. 20C shows normalized counts for all gRNAs per DHS (left panel) and individual gRNA used (right panel) where "0" is input (no Cas9 Effector), "1" is unsorted bulk population, "2" is lowest 10% sorted, and "3" is highest 10% sorted.

FIG. 21A shows the frequency and location of the pooled gRNA library targeting DHSs in A431 cells, where the vertical highlighted band indicates the location of gRNA 1826. FIG. 21B shows flow cytometry data of dCas9$^{KRAB}$ repressing HER2 in A431 cells measured via cell surface staining with a monoclonal antibody. FIG. 21C shows normalized counts for all gRNAs per DHS (left panel) and individual gRNA used (right panel) where "0" is input (no Cas9 Effector), "1" is unsorted bulk population, "2" is lowest 10% sorted, and "3" is highest 10% sorted.

FIG. 22A shows the frequency and location of the pooled gRNA library targeting DHSs in A431 cells, where the vertical highlighted band indicates the location of gRNA 1559. FIG. 22B shows flow cytometry data of dCas9$^{KRAB}$ repressing HER2 in A431 cells measured via cell surface staining with a monoclonal antibody. FIG. 22C shows normalized counts for all gRNAs per DHS (left panel) and individual gRNA used (right panel) where "0" is input (no Cas9 Effector), "1" is unsorted bulk population, "2" is lowest 10% sorted, and "3" is highest 10% sorted.

FIG. 23A shows the frequency and location of the pooled gRNA library targeting DHSs in A431 cells, where the vertical highlighted band indicates the location of gRNA 1560. FIG. 23B shows flow cytometry data of dCas9$^{KRAB}$ repressing HER2 in A431 cells measured via cell surface staining with a monoclonal antibody. FIG. 23C shows normalized counts for all gRNAs per DHS (left panel) and individual gRNA used (right panel) where "0" is input (no Cas9 Effector), "1" is unsorted bulk population, "2" is lowest 10% sorted, and "3" is highest 10% sorted.

FIG. 24A shows the frequency and location of the pooled gRNA library targeting DHSs in A431 cells, where the vertical highlighted band indicates the location of gRNA 1782. FIG. 24B shows flow cytometry data of dCas9$^{KRAB}$ repressing HER2 in A431 cells measured via cell surface staining with a monoclonal antibody. FIG. 24C shows normalized counts for all gRNAs per DHS (left panel) and individual gRNA used (right panel) where "0" is input (no Cas9 Effector), "1" is unsorted bulk population, "2" is lowest 10% sorted, and "3" is highest 10% sorted.

FIG. 25A shows the frequency and location of the pooled gRNA library targeting DHSs in A431 cells, where the vertical highlighted band indicates the location of gRNA 1671. FIG. 25B shows flow cytometry data of dCas9$^{KRAB}$ repressing HER2 in A431 cells measured via cell surface staining with a monoclonal antibody. FIG. 25C shows normalized counts for all gRNAs per DHS (left panel) and individual gRNA used (right panel) where "0" is input (no Cas9 Effector), "1" is unsorted bulk population, "2" is lowest 10% sorted, and "3" is highest 10% sorted.

FIG. 26A shows the frequency and location of the pooled gRNA library targeting DHSs in A431 cells, where the vertical highlighted band indicates the location of gRNA 1556. FIG. 26B shows flow cytometry data of dCas9$^{KRAB}$ repressing HER2 in A431 cells measured via cell surface staining with a monoclonal antibody. FIG. 26C shows normalized counts for all gRNAs per DHS (left panel) and individual gRNA used (right panel) where "0" is input (no Cas9 Effector), "1" is unsorted bulk population, "2" is lowest 10% sorted, and "3" is highest 10% sorted.

FIG. 27A shows the frequency and location of the pooled gRNA library targeting DHSs in A431 cells, where the vertical highlighted band indicates the location of gRNA 1612. FIG. 27B shows flow cytometry data of dCas9$^{KRAB}$ repressing HER2 in A431 cells measured via cell surface staining with a monoclonal antibody. FIG. 27C shows normalized counts for all gRNAs per DHS (left panel) and individual gRNA used (right panel) where "0" is input (no Cas9 Effector), "1" is unsorted bulk population, "2" is lowest 10% sorted, and "3" is highest 10% sorted.

FIG. 8A shows the frequency and location of the pooled gRNA library targeting DHSs in A431 cells, where the vertical highlighted band indicates the location of gRNA 1535. FIG. 28B shows flow cytometry data of dCas9$^{KRAB}$ repressing HER2 in A431 cells measured via cell surface staining with a monoclonal antibody. FIG. 28C shows normalized counts for all gRNAs per DHS (left panel) and individual gRNA used (right panel) where "0" is input (no Cas9 Effector), "1" is unsorted bulk population, "2" is lowest 10% sorted, and "3" is highest 10% sorted.

FIG. 30A shows the frequency and location of the pooled gRNA library targeting DHSs in HEK293T cells, where the vertical highlighted band indicates the location of gRNA 1549. FIG. 30B shows the flow cytometry data of dCas9$^{p300}$ activating HER2 in HEK293T cells measured via cell surface staining with a monoclonal antibody. FIG. 30C shows normalized counts for all gRNAs per DHS (left panel) and individual gRNA used (right panel) where "0" is input (no Cas9 Effector), "1" is unsorted bulk population, "2" is lowest 10% sorted, and "3" is highest 10% sorted.

FIG. 31A shows the frequency and location of the pooled gRNA library targeting DHSs in HEK293T cells, where the vertical highlighted band indicates the location of gRNA 1550. FIG. 31B shows the flow cytometry data of dCas9$^{p300}$ activating HER2 in HEK293T cells measured via cell surface staining with a monoclonal antibody. FIG. 31C shows normalized counts for all gRNAs per DHS (left panel) and individual gRNA used (right panel) where "0" is input (no Cas9 Effector), "1" is unsorted bulk population, "2" is lowest 10% sorted, and "3" is highest 10% sorted.

FIG. 32A shows the frequency and location of the pooled gRNA library targeting DHSs in HEK293T cells, where the vertical highlighted band indicates the location of gRNA 1551. FIG. 32B shows the flow cytometry data of dCas9$^{p300}$ activating HER2 in HEK293T cells measured via cell surface staining with a monoclonal antibody. FIG. 32C shows normalized counts for all gRNAs per DHS (left panel) and individual gRNA used (right panel) where "0" is input (no Cas9 Effector), "1" is unsorted bulk population, "2" is lowest 10% sorted, and "3" is highest 10% sorted.

FIG. 33A shows the frequency and location of the pooled gRNA library targeting DHSs in HEK293T cells, where the vertical highlighted band indicates the location of gRNA 1552. FIG. 33B shows the flow cytometry data of dCas9$^{p300}$ activating HER2 in HEK293T cells measured via cell surface staining with a monoclonal antibody. FIG. 33C shows normalized counts for all gRNAs per DHS (left panel) and individual gRNA used (right panel) where "0" is input (no Cas9 Effector), "1" is unsorted bulk population, "2" is lowest 10% sorted, and "3" is highest 10% sorted.

FIG. 34A shows the frequency and location of the pooled gRNA library targeting DHSs in HEK293T cells, where the vertical highlighted band indicates the location of gRNA 1548. FIG. 34B shows the flow cytometry data of dCas9$^{p300}$ activating HER2 in HEK293T cells measured via cell surface staining with a monoclonal antibody. FIG. 34C shows normalized counts for all gRNAs per DHS (left panel) and individual gRNA used (right panel) where "0" is input (no Cas9 Effector), "1" is unsorted bulk population, "2" is lowest 10% sorted, and "3" is highest 10% sorted.

FIG. 35A shows the frequency and location of the pooled gRNA library targeting DHSs in HEK293T cells, where the vertical highlighted band indicates the location of gRNA 154. FIG. 35B shows the flow cytometry data of dCas9$^{p300}$ activating HER2 in HEK293T cells measured via cell surface staining with a monoclonal antibody. FIG. 35C shows normalized counts for all gRNAs per DHS (left panel) and individual gRNA used (right panel) where "0" is input (no Cas9 Effector), "1" is unsorted bulk population, "2" is lowest 10% sorted, and "3" is highest 10% sorted.

FIG. 36A shows the frequency and location of the pooled gRNA library targeting DHSs in HEK293T cells, where the vertical highlighted band indicates the location of gRNA 1542. FIG. 36B shows the flow cytometry data of dCas9$^{p300}$ activating HER2 in HEK293T cells measured via cell surface staining with a monoclonal antibody. FIG. 36C shows normalized counts for all gRNAs per DHS (left panel) and individual gRNA used (right panel) where "0" is input (no Cas9 Effector), "1" is unsorted bulk population, "2" is lowest 10% sorted, and "3" is highest 10% sorted.

FIG. 37A shows the frequency and location of the pooled gRNA library targeting DHSs in HEK293T cells, where the vertical highlighted band indicates the location of gRNA 1530. FIG. 37B shows the flow cytometry data of dCas9$^{p300}$ activating HER2 in HEK293T cells measured via cell surface staining with a monoclonal antibody. FIG. 37C shows normalized counts for all gRNAs per DHS (left panel) and individual gRNA used (right panel) where "0" is input (no Cas9 Effector), "1" is unsorted bulk population, "2" is lowest 10% sorted, and "3" is highest 10% sorted.

FIG. 38A shows the frequency and location of the pooled gRNA library targeting DHSs in HEK293T cells, where the vertical highlighted band indicates the location of gRNA 1531. FIG. 38B shows the flow cytometry data of dCas9$^{p300}$ activating HER2 in HEK293T cells measured via cell surface staining with a monoclonal antibody. FIG. 38C shows normalized counts for all gRNAs per DHS (left panel) and individual gRNA used (right panel) where "0" is input (no Cas9 Effector), "1" is unsorted bulk population, "2" is lowest 10% sorted, and "3" is highest 10% sorted.

FIG. 39A shows the frequency and location of the pooled gRNA library targeting DHSs in HEK293T cells, where the vertical highlighted band indicates the location of gRNA 1516. FIG. 39B shows the flow cytometry data of dCas9$^{p300}$ activating HER2 in HEK293T cells measured via cell surface staining with a monoclonal antibody. FIG. 39C shows normalized counts for all gRNAs per DHS (left panel) and individual gRNA used (right panel) where "0" is input (no Cas9 Effector), "1" is unsorted bulk population, "2" is lowest 10% sorted, and "3" is highest 10% sorted.

FIG. 40A shows the frequency and location of the pooled gRNA library targeting DHSs in HEK293T cells, where the vertical highlighted band indicates the location of gRNA 1563. FIG. 40B shows the flow cytometry data of dCas9$^{p300}$ activating HER2 in HEK293T cells measured via cell surface staining with a monoclonal antibody. FIG. 40C shows normalized counts for all gRNAs per DHS (left panel) and individual gRNA used (right panel) where "0" is input (no Cas9 Effector), "1" is unsorted bulk population, "2" is lowest 10% sorted, and "3" is highest 10% sorted.

FIG. 43A shows the frequency and location of the pooled gRNA library targeting DHSs in K562 cells, where the vertical highlighted band indicates the location of gRNA 783_784. FIG. 43B shows flow cytometry data of dCas9$^{KRAB}$ repressing HBE1 in K562 cells.

FIG. 43C shows normalized counts for all conditions: HBG1 promoter, HBG1 gRNA, HBG2 promoter, and HBG2 gRNA, where "1" is unsorted bulk population, "2" is lowest 10% sorted, and "3" is highest 10% sorted.

FIG. 44A shows the frequency and location of the pooled gRNA library targeting DHSs in K562 cells, where the vertical highlighted band indicates the location of gRNA 787. FIG. 44B shows flow cytometry data of dCas9$^{KRAB}$ repressing HBE1 in K562 cells. FIG. 44C shows normalized counts for all conditions: HBE1 promoter and HBE1 gRNA, where "1" is unsorted bulk population, "2" is lowest 10% sorted, and "3" is highest 10% sorted.

FIG. 45A shows the frequency and location of the pooled gRNA library targeting DHSs in K562 cells, where the vertical highlighted band indicates the location of gRNA 788. FIG. 45B shows flow cytometry data of dCas9$^{KRAB}$ repressing HBE1 in K562 cells. FIG. 45C shows normalized counts for all conditions: HS1 and HS1 gRNA, where "1" is unsorted bulk population, "2" is lowest 10% sorted, and "3" is highest 10% sorted.

FIG. 46A shows the frequency and location of the pooled gRNA library targeting DHSs in K562 cells, where the vertical highlighted band indicates the location of gRNA 790. FIG. 46B shows flow cytometry data of dCas9$^{KRAB}$ repressing HBE1 in K562 cells. FIG. 46C shows normalized counts for all conditions: HS2 and HS2 gRNA, where "1" is unsorted bulk population, "2" is lowest 10% sorted, and "3" is highest 10% sorted.

FIG. 47A shows the frequency and location of the pooled gRNA library targeting DHSs in K562 cells, where the vertical highlighted band indicates the location of gRNA 791. FIG. 47B shows flow cytometry data of dCas9$^{KRAB}$ repressing HBE1 in K562 cells. FIG. 47C shows normalized counts for all conditions: HS3 and HS3 gRNA, where "1" is unsorted bulk population, "2" is lowest 10% sorted, and "3" is highest 10% sorted.

FIG. 48A shows the frequency and location of the pooled gRNA library targeting DHSs in K562 cells, where the vertical highlighted band indicates the location of gRNA 792. FIG. 48B shows flow cytometry data of dCas9$^{KRAB}$ repressing HBE1 in K562 cells. FIG. 48C shows normalized counts for all conditions: HS4 and HS4 gRNA, where "1" is unsorted bulk population, "2" is lowest 10% sorted, and "3" is highest 10% sorted.

FIG. 49A shows the frequency and location of the pooled gRNA library targeting DHSs in A431 cells, where the vertical highlighted band indicates the location of the gRNAs. FIG. 49B shows flow cytometry data of dCas9$^{KRAB}$ repressing HBE1 in A431 cells for 1543.1 and 1544.1 gRNAs alone and in combination.

FIG. 50A shows the frequency and location of the pooled gRNA library targeting DHSs in A431 cells, where the vertical highlighted band indicates the location of the gRNAs. FIG. 50B shows flow cytometry data of dCas9$^{KRAB}$ repressing HBE1 in A431 cells for 1549.1 and 1553.1 gRNAs alone and in combination.

FIG. 51A shows the frequency and location of the pooled gRNA library targeting DHSs in A431 cells, where the vertical highlighted band indicates the location of the gRNAs. FIG. 51B shows flow cytometry data of dCas9$^{KRAB}$ repressing HBE1 in A431 cells for 1549.1 and 1553.2 gRNAs alone and in combination.

FIG. 52A shows the frequency and location of the pooled gRNA library targeting DHSs in A431 cells, where the vertical highlighted band indicates the location of the gRNAs. FIG. 52B shows flow cytometry data of dCas9$^{KRAB}$ repressing HBE1 in A431 cells for 1553.1 and 1561.1 gRNAs alone and in combination.

FIG. 53A and FIG. 53B show the frequency and location of the pooled gRNA library targeting DHSs in A431 cells, where the vertical highlighted band indicates the location of the gRNAs. FIG. 53C shows flow cytometry data of dCas9$^{KRAB}$ repressing HBE1 in A431 cells for 1553.2 and 1562.1 gRNAs alone and in combination.

FIG. 54A shows flow cytometry data of dCas9$^{KRAB}$ repressing HBE1 in A431 cells for 1553.2, 1543.1, and 1544.1 gRNAs alone. FIG. 54B shows flow cytometry data of dCas9$^{KRAB}$ repressing HBE1 in A431 cells for 1561.1 and 1562.1 gRNAs alone and the combination of 1553.2, 1543.1, 1544.1, 1561.1, and 1562.1.

FIG. 55A shows the frequency and location of the pooled gRNA library targeting DHSs in A431 cells, where the vertical highlighted band indicates the location of the gRNAs. FIG. 55B shows flow cytometry data of dCas9$^{KRAB}$ repressing HBE1 in A431 cells for 1556.1 and 1559.2 gRNAs alone and in combination.

FIG. 56A shows the frequency and location of the pooled gRNA library targeting DHSs in A431 cells, where the vertical highlighted band indicates the location of the gRNAs. FIG. 56B shows flow cytometry data of dCas9$^{KRAB}$ repressing HBE1 in A431 cells for 1559.2 and 1560.1 gRNAs alone and in combination.

FIG. 57A shows the frequency and location of the pooled gRNA library targeting DHSs in A431 cells, where the vertical highlighted band indicates the location of the gRNAs. FIG. 57B shows flow cytometry data of dCas9$^{KRAB}$ repressing HBE1 in A431 cells for 1561.1 and 1562.1 gRNAs alone and in combination.

FIG. 58A shows the frequency and location of the pooled gRNA library targeting DHSs in A431 cells, where the vertical highlighted band indicates the location of the gRNAs. FIG. 58B shows the frequency and location of the pooled gRNA library targeting DHSs in A431 cells, where the vertical highlighted band indicates the location of the gRNAs. FIG. 58C shows flow cytometry data of dCas9$^{KRAB}$ repressing HBE1 in A431 cells for 1782.1 and 1671.1 gRNAs alone and in combination.

DETAILED DESCRIPTION

Figure 1:
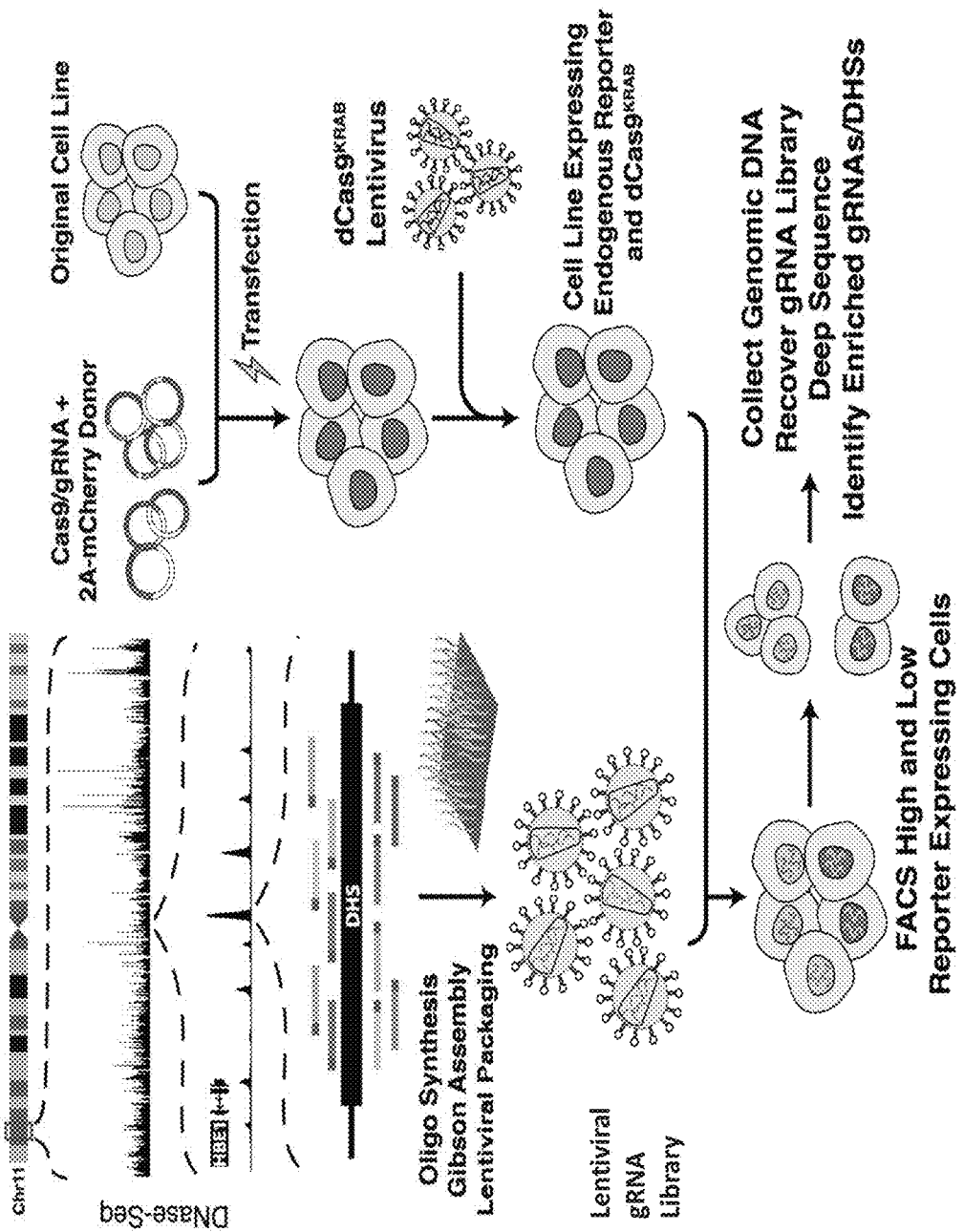
FIG. 1 shows a schematic of CRISPR/Cas9-based Epigenetic Regulatory Element Screening (CERES).

Disclosed herein are methods of high throughput screening for regulatory element function using CRISPR/Cas9-based epigenomic editing systems. The CRISPR/Cas9-based epigenomic editing systems directly activate or repress genomic regulatory elements in their natural chromosomal location. In particular, the CRISPR/Cas9-based epigenomic editing system includes a Cas9 fusion protein of a Cas9 protein that does not have nuclease activity and a protein having histone acetyltransferase activity, such as the catalytic histone acetyltransferase (HAT) core domain of the human E1A-associated protein p300, or repression activity, such as KRAB. Recruitment of the acetyltransferase function or repression function by dCas9 and a gRNA to the genomic target site allow direct modulation of epigenetic structure, and thus provide an effective means of epigenomic editing. The methods described herein use these tools for high-throughput identification of gene regulatory element activity. These methods allow the mapping and characterization of regulatory elements across the genome.

The disclosed methods can be used for high-throughput identification of the regulatory elements responsible for the expression level of any gene in any organism, such as any animal. For example, the disclosed methods can be used to identify how genetic variation in the human population is responsible for inherited risk for any genetically linked disease, including most cardiovascular, neurodegenerative, and metabolic disorders, or other traits such as intelligence, size, and regenerative potential. As a result, the technology can be used to identify drug targets for a vast array of disorders and conditions. Such screening of gene regulatory elements in their natural chromosomal location is not currently possible with any other technology.

1. DEFINITIONS

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "and" and "the" include plural references unless the context clearly dictates otherwise. The present disclosure also contemplates other embodiments "comprising," "consisting of" and "consisting essentially of," the embodiments or elements presented herein, whether explicitly set forth or not.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

"Cell phenotype" as used herein refers to the observable characteristics or traits of a cell, such as its morphology, development, biochemical or physiological properties, phenology, or behavior. A phenotype results from the expression of the cell's genes as well as the influence of environmental factors and the interactions between the two.

"Chromatin" as used herein refers to an organized complex of chromosomal DNA associated with histones.

"Cis-regulatory elements" or "CREs" as used interchangeably herein refers to regions of non-coding DNA which regulate the transcription of nearby genes. CREs are found in the vicinity of the gene, or genes, they regulate. CREs typically regulate gene transcription by functioning as binding sites for transcription factors. Examples of CREs include promoters, enhancers, super-enhancers, silencers, insulators, and locus control regions.

"Clustered Regularly Interspaced Short Palindromic Repeats" and "CRISPRs", as used interchangeably herein refers to loci containing multiple short direct repeats that are found in the genomes of approximately 40% of sequenced bacteria and 90% of sequenced archaea.

"Coding sequence" or "encoding nucleic acid" as used herein means the nucleic acids (RNA or DNA molecule) that comprise a nucleotide sequence which encodes a protein. The coding sequence can further include initiation and termination signals operably linked to regulatory elements including a promoter and polyadenylation signal capable of directing expression in the cells of an individual or mammal to which the nucleic acid is administered. The coding sequence may be codon optimize.

"Complement" or "complementary" as used herein means a nucleic acid can mean Watson-Crick (e.g., A-T/U and C-G) or Hoogsteen base pairing between nucleotides or nucleotide analogs of nucleic acid molecules. "Complementarity" refers to a property shared between two nucleic acid sequences, such that when they are aligned antiparallel to each other, the nucleotide bases at each position will be complementary.

"Demethylases" as used herein refers to an enzyme that removes methy (CH3-) groups from nucleic acids, proteins (in particular histones), and other molecules. Demethylase enzymes are important in epigenetic modification mechanisms. The demethylase proteins alter transcriptional regulation of the genome by controlling the methylation levels that occur on DNA and histones and, in turn, regulate the chromatin state at specific gene loci within organisms. "Histone demethylase" refers to a methylase that removes methy groups from histones. There are several families of histone demethylases, which act on different substrates and play different roles in cellular function. The Fe(II)-dependent lysine demethylases may be a JMJC demethylase. A JMJC demethylase is a histone demethylase containing a JumonjiC (JmjC) domain. The JMJC demethylase may be a member of the KDM3, KDM4, KDM5, or KDM6 family of histone demethylases.

"DNase I hypersensitive sites" or "DHS" as used interchangeably herein refers to docking sites for the transcription factors and chromatin modifiers, including p300 that coordinate distal target gene expression.

"Endogenous gene" as used herein refers to a gene that originates from within an organism, tissue, or cell. An endogenous gene is native to a cell, which is in its normal genomic and chromatin context, and which is not heterologous to the cell. Such cellular genes include, e.g., animal genes, plant genes, bacterial genes, protozoal genes, fungal genes, mitochondrial genes, and chloroplastic genes. An "endogenous target gene" as used herein refers to an endogenous gene that is targeted by gRNA and CRISPR/Cas9-based epigenomic editing system.

"Enhancer" as used herein refers to non-coding DNA sequences containing multiple activator and repressor binding sites. Enhancers range from 50 bp to 1500 bp in length and may be either proximal, 5' upstream to the promoter, within any intron of the regulated gene, or distal, in introns of neighboring genes, or intergenic regions far away from the locus, or on regions on different chromosomes. More than one enhancer may interact with a promoter. Similarly, enhancers may regulate more than one gene without linkage restriction and may "skip" neighboring genes to regulate more distant ones. Transcriptional regulation may involve elements located in a chromosome different to one where the promoter resides. Proximal enhancers or promoters of neighboring genes may serve as platforms to recruit more distal elements.

"Fusion protein" as used herein refers to a chimeric protein created through the joining of two or more genes that originally coded for separate proteins. The translation of the fusion gene results in a single polypeptide with functional properties derived from each of the original proteins.

"Genetic construct" as used herein refers to the DNA or RNA molecules that comprise a nucleotide sequence that encodes a protein. The coding sequence includes initiation and termination signals operably linked to regulatory elements including a promoter and polyadenylation signal capable of directing expression in the cells of the individual to whom the nucleic acid molecule is administered. As used herein, the term "expressible form" refers to gene constructs that contain the necessary regulatory elements operable linked to a coding sequence that encodes a protein such that when present in the cell of the individual, the coding sequence will be expressed.

"Genome" as used herein refers to the complete set of genes or genetic material present in a cell or organism. The genome includes DNA or RNA in RNA viruses. The genome includes both the genes, (the coding regions), the noncoding DNA and the genomes of the mitochondria and chloroplasts.

"Histone acetyltransferases" or "HATs" are used interchangeably herein refers to enzymes that acetylate conserved lysine amino acids on histone proteins by transferring an acetyl group from acetyl CoA to form ε-N-acetyllysine. DNA is wrapped around histones, and, by transferring an acetyl group to the histones, genes can be turned on and off. In general, histone acetylation increases gene expression as it is linked to transcriptional activation and associated with euchromatin. Histone acetyltransferases can also acetylate non-histone proteins, such as nuclear receptors and other transcription factors to facilitate gene expression.

"Histone deacetylases" or "HDACs" as used interchangeably herein refers to a class of enzymes that remove acetyl groups ($O=C-CH_3$) from an ε-N-acetyl lysine amino acid on a histone, allowing the histones to wrap the DNA more tightly. HDACs are also called lysine deacetylases (KDAC), to describe their function rather than their target, which also includes non-histone proteins.

"Histone methyltransferase" or "HMTs" as used interchangeably herein refers to histone-modifying enzymes (e.g., histone-lysine N-methyltransferases and histone-arginine N-methyltransferases), that catalyze the transfer of one, two, or three methyl groups tolysine and arginine residues of histone proteins. The attachment of methyl groups occurs predominantly at specific lysine or arginine residues on histones H3 and H4.

"Identical" or "identity" as used herein in the context of two or more nucleic acids or polypeptide sequences means that the sequences have a specified percentage of residues that are the same over a specified region. The percentage may be calculated by optimally aligning the two sequences, comparing the two sequences over the specified region, determining the number of positions at which the identical residue occurs in both sequences to yield the number of matched positions, dividing the number of matched positions by the total number of positions in the specified region, and multiplying the result by 100 to yield the percentage of sequence identity. In cases where the two sequences are of different lengths or the alignment produces one or more staggered ends and the specified region of comparison includes only a single sequence, the residues of single sequence are included in the denominator but not the numerator of the calculation. When comparing DNA and RNA, thymine (T) and uracil (U) may be considered equivalent. Identity may be performed manually or by using a computer sequence algorithm such as BLAST or BLAST 2.0.

"Insulators" as used herein refers to a genetic boundary element that blocks the interaction between enhancers and promoters. By residing between the enhancer and promoter, the insulator may inhibit their subsequent interactions. Insulators can determine the set of genes an enhancer can influence. Insulators are needed where two adjacent genes on a chromosome have very different transcription patterns and the inducing or repressing mechanisms of one does not interfere with the neighboring gene. Insulators have also been found to cluster at the boundaries of topological association domains (TADs) and may have a role in partitioning the genome into "chromosome neighborhoods"— genomic regions within which regulation occurs. Insulator activity is thought to occur primarily through the 3D structure of DNA mediated by proteins including CTCF. Insulators are likely to function through multiple mechanisms. Many enhancers form DNA loops that put them in close physical proximity to promoter regions during transcriptional activation. Insulators may promote the formation of DNA loops that prevent the promoter-enhancer loops from forming. Barrier insulators may prevent the spread of heterochromatin from a silenced gene to an actively transcribed gene.

"Locus control regions" as used herein refers to a long-range cis-regulatory element that enhances expression of linked genes at distal chromatin sites. It functions in a copy number-dependent manner and is tissue-specific, as seen in the selective expression of 3-globin genes in erythroid cells. Expression levels of genes can be modified by the LCR and gene-proximal elements, such as promoters, enhancers, and silencers. The LCR functions by recruiting chromatin-modifying, coactivator, and transcription complexes. Its sequence is conserved in many vertebrates, and conservation of specific sites may suggest importance in function.

"Modulate" as used herein may mean any altering of activity, such as regulate, down regulate, upregulate, reduce, inhibit, increase, decrease, deactivate, or activate.

"Multiplicity of infection" or "MOI" as used interchangeably herein refers to a ratio of agents (e.g., phage or more generally virus, bacteria) to infection targets (e.g., cell), such as when referring to a group of cells inoculated with virus particles, the multiplicity of infection or MOI is the ratio of the number of virus particles, which can include the sgRNA, to the number of target cells present in a defined space.

"Nucleic acid" or "oligonucleotide" or "polynucleotide" as used herein means at least two nucleotides covalently linked together. The depiction of a single strand also defines the sequence of the complementary strand. Thus, a nucleic acid also encompasses the complementary strand of a depicted single strand. Many variants of a nucleic acid may be used for the same purpose as a given nucleic acid. Thus, a nucleic acid also encompasses substantially identical nucleic acids and complements thereof. A single strand provides a probe that may hybridize to a target sequence under stringent hybridization conditions. Thus, a nucleic acid also encompasses a probe that hybridizes under stringent hybridization conditions.

Nucleic acids may be single stranded or double stranded, or may contain portions of both double stranded and single stranded sequence. The nucleic acid may be DNA, both genomic and cDNA, RNA, or a hybrid, where the nucleic acid may contain combinations of deoxyribo- and ribo-nucleotides, and combinations of bases including uracil, adenine, thymine, cytosine, guanine, inosine, xanthine hypoxanthine, isocytosine and isoguanine. Nucleic acids may be obtained by chemical synthesis methods or by recombinant methods.

"Operably linked" as used herein means that expression of a gene is under the control of a promoter with which it is spatially connected. A promoter may be positioned 5' (upstream) or 3' (downstream) of a gene under its control. The distance between the promoter and a gene may be approximately the same as the distance between that promoter and the gene it controls in the gene from which the promoter is derived. As is known in the art, variation in this distance may be accommodated without loss of promoter function.

"Organismal phenotype" as used herein refers to refers to the observable characteristics or traits of an organism, such as its morphology, development, biochemical or physiological properties, phenology, or behavior. A phenotype results from the expression of the organism's genes as well as the influence of environmental factors and the interactions between the two.

"p300 protein," "EP300," or "E1A binding protein p300" as used interchangeably herein refers to the adenovirus E1A-associated cellular p300 transcriptional co-activator protein encoded by the EP300 gene. p300 is a highly conserved acetyltransferase involved in a wide range of cellular processes. p300 functions as a histone acetyltransferase that regulates transcription via chromatin remodeling and is involved with the processes of cell proliferation and cell differentiation.

"Primary cell" as used herein refers to cells taken directly from living tissue (e.g. biopsy material). Primary cells can be established for growth in vitro. These cells have undergone very few population doublings and are therefore more representative of the main functional component of the tissue from which they are derived in comparison to continuous (tumor or artificially immortalized) cell lines thus representing a more representative model to the in vivo state. Primary cells may be taken from different species, such as mouse or humans.

"Promoter" as used herein means a synthetic or naturally-derived molecule which is capable of conferring, activating or enhancing expression of a nucleic acid in a cell. A promoter may comprise one or more specific transcriptional regulatory sequences to further enhance expression and/or to alter the spatial expression and/or temporal expression of same. A promoter may also comprise distal enhancer or repressor elements, which may be located as much as several thousand base pairs, or anywhere in the genome, from the start site of transcription. A promoter may be derived from sources including viral, bacterial, fungal, plants, insects, and animals. A promoter may regulate the expression of a gene component constitutively, or differentially with respect to cell, the tissue or organ in which expression occurs or, with respect to the developmental stage at which expression occurs, or in response to external stimuli such as physiological stresses, hormones, toxins, drugs, pathogens, metal ions, or inducing agents. Representative examples of promoters include the bacteriophage T7 promoter, bacteriophage T3 promoter, SP6 promoter, lac operator-promoter, tac promoter, SV40 late promoter, SV40 early promoter, RSV-LTR promoter, CMV IE promoter, SV40 early promoter or SV40 late promoter and the CMV IE promoter.

"Protospacer adjacent motif" or "PAM" as used herein refers to a DNA sequence immediately following the DNA sequence targeted by the Cas9 nuclease in the CRISPR bacterial adaptive immune system. PAM is a component of the invading virus or plasmid, but is not a component of the bacterial CRISPR locus. Cas9 will not successfully bind to or cleave the target DNA sequence if it is not followed by the PAM sequence. PAM is an essential targeting component (not found in bacterial genome) which distinguishes bacterial self from non-self DNA, thereby preventing the CRISPR locus from being targeted and destroyed by nuclease.

"Silencers" or "repressors" as used interchangeably herein refer to a DNA sequence capable of binding transcription regulation factors and preventing genes from being expressed as proteins. A silencer is a sequence-specific element that induces a negative effect on the transcription of its particular gene. There are many positions in which a silencer element can be located in DNA. The most common position is found upstream of the target gene where it can help repress the transcription of the gene. This distance can vary greatly between approximately −20 bp to −2000 bp upstream of a gene. Certain silencers can be found downstream of a promoter located within the intron or exon of the gene itself. Silencers have also been found within the 3 prime untranslated region (3' UTR) of mRNA. There are two main types of silencers in DNA, which are the classical silencer element and the non-classical negative regulatory element (NRE). In classical silencers, the gene is actively repressed by the silencer element, mostly by interfering with general transcription factor (GTF) assembly. NREs passively repress the gene, usually by inhibiting other elements that are upstream of the gene.

"Super enhancer" as used herein refers to a region of the mammalian genome comprising multiple enhancers that is collectively bound by an array of transcription factor proteins to drive transcription of genes involved in cell identity. Super-enhancers are frequently identified near genes important for controlling and defining cell identity and can be used to quickly identify key nodes regulating cell identity. Enhancers have several quantifiable traits that have a range of values, and these traits are generally elevated at super-enhancers. Super-enhancers are bound by higher levels of transcription-regulating proteins and are associated with genes that are more highly expressed. Expression of genes associated with super-enhancers is particularly sensitive to perturbations, which may facilitate cell state transitions or explain sensitivity of super-enhancer-associated genes to small molecules that target transcription.

"Target enhancer" as used herein refers to enhancer that is targeted by a gRNA and CRISPR/Cas9-based epigenomic editing system. The target enhancer may be within the target region.

"Target gene" as used herein refers to any nucleotide sequence encoding a known or putative gene product. The target gene includes the regulatory regions, such as the promoter and enhancer regions, the transcribed regions, which include the coding regions, and other functional sequence regions.

"Target region" as used herein refers to a cis-regulatory region or a trans-regulatory region of a target gene to which the guide RNA is designed to recruit the CRISPR/Cas9-based epigenomic editing system to modulate the epigenetic structure and allow the activation or repression of gene expression of the target gene.

"Target regulatory element" as used herein refers to a regulatory element that is targeted by a gRNA and CRISPR/Cas9-based epigenomic editing system. The target regulatory element may be within the target region.

"Transcribed region" as used herein refers to the region of DNA that is transcribed into single-stranded RNA molecule, known as messenger RNA, resulting in the transfer of genetic information from the DNA molecule to the messenger RNA. During transcription, RNA polymerase reads the template strand in the 3' to 5' direction and synthesizes the RNA from 5' to 3'. The mRNA sequence is complementary to the DNA strand.

"Transcriptional Start Site" or "TSS" as used interchangeably herein refers to the first nucleotide of a transcribed DNA sequence where RNA polymerase begins synthesizing the RNA transcript.

"Transgene" as used herein refers to a gene or genetic material containing a gene sequence that has been isolated from one organism and is introduced into a different organism. This non-native segment of DNA may retain the ability to produce RNA or protein in the transgenic organism, or it may alter the normal function of the transgenic organism's genetic code. The introduction of a transgene has the potential to change the phenotype of an organism.

"Trans-regulatory elements" as used herein refers to regions of non-coding DNA which regulate the transcription of genes distant from the gene from which they were transcribed. Trans-regulatory elements may be on the same or different chromosome from the target gene. Examples of trans-regulatory elements include enhancers, super-enhancers, silencers, insulators, and locus control regions.

"Variant" used herein with respect to a nucleic acid means (i) a portion or fragment of a referenced nucleotide sequence (including nucleotide sequences that have insertions or deletions as compared to the referenced nucleotide sequences); (ii) the complement of a referenced nucleotide sequence or portion thereof; (iii) a nucleic acid that is substantially identical to a referenced nucleic acid or the complement thereof; or (iv) a nucleic acid that hybridizes under stringent conditions to the referenced nucleic acid, complement thereof, or a sequences substantially identical thereto.

"Variant" with respect to a peptide or polypeptide that differs in amino acid sequence by the insertion, deletion, or conservative substitution of amino acids, but retain at least one biological activity. Variant may also mean a protein with an amino acid sequence that is substantially identical to a referenced protein with an amino acid sequence that retains at least one biological activity. A conservative substitution of an amino acid, i.e., replacing an amino acid with a different amino acid of similar properties (e.g., hydrophilicity, degree and distribution of charged regions) is recognized in the art as typically involving a minor change. These minor changes may be identified, in part, by considering the hydropathic index of amino acids, as understood in the art. Kyte et al., *J. Mol. Biol.* 157:105-132 (1982). The hydropathic index of an amino acid is based on a consideration of its hydrophobicity and charge. It is known in the art that amino acids of similar hydropathic indexes may be substituted and still retain protein function. In one aspect, amino acids having hydropathic indexes of ±2 are substituted. The hydrophilicity of amino acids may also be used to reveal substitutions that would result in proteins retaining biological function. A consideration of the hydrophilicity of amino acids in the context of a peptide permits calculation of the greatest local average hydrophilicity of that peptide. Substitutions may be performed with amino acids having hydrophilicity values within ±2 of each other. Both the hydrophobicity index and the hydrophilicity value of amino acids are influenced by the particular side chain of that amino acid. Consistent with that observation, amino acid substitutions that are compatible with biological function are understood to depend on the relative similarity of the amino acids, and particularly the side chains of those amino acids, as revealed by the hydrophobicity, hydrophilicity, charge, size, and other properties.

"Vector" as used herein means a nucleic acid sequence containing an origin of replication. A vector may be a viral vector, bacteriophage, bacterial artificial chromosome or yeast artificial chromosome. A vector may be a DNA or RNA vector. A vector may be a self-replicating extrachromosomal vector, and preferably, is a DNA plasmid. For example, the vector may encode a CRISPR/Cas9-based epigenomic editing system having an amino acid sequence of SEQ ID NO: 2 or 3.

2. METHODS OF HIGH THROUGHPUT SCREENING OF REGULATORY ELEMENT FUNCTION

The present disclosure is directed towards methods for high-throughput screening of regulatory element activity that involves the design and synthesis of libraries of gRNAs, using custom array synthesis, targeted to all active gene regulatory elements in a particular genomic region (targeted screen), or the entire genome (genome-wide screen), and screening for gain or loss of function following co-delivery with an epigenomic editing system that is a targeted modifier of gene expression or epigenetic state, such as a CRISPR/ dCas9-based epigenomic editing system. The screening is based on cell phenotype, organismal phenotype, or expression of a specific target gene. Sequencing the gRNAs in cells enriched with a gain or loss of gene expression can then be used to reveal active regulatory elements. The library may be screened in vitro, e.g., in cells, or in vivo, such as mouse heart. By selecting the cells with modulated phenotype or gene expression, the regulatory elements are identified that are responsible for these characteristics directly in the cell type of interest.

The present disclosure is directed to a method of high-throughput screening for one or more putative gene regulatory elements in a genome that modulate a phenotype. The method comprises: a) contacting a plurality of modified target cells with a library of single guide RNAs (sgRNAs, also referred to herein as gRNA) that target a plurality of gene regulatory elements within the genome, thereby generating a plurality of test cells; b) selecting a single cell or population of test cells having a modulated phenotype; c) quantitating the frequency of the sgRNAs within the population of selected cells, wherein the sgRNAs that target gene regulatory elements that modulate the phenotype are overrepresented or underrepresented in the selected cells; and d) identifying and characterizing the sgRNAs within the population of selected test cells thereby identifying the gene regulatory elements that modulate the phenotype. The modified target cell comprises a fusion protein. The fusion protein comprises a first polypeptide domain comprising a nuclease-deficient Cas9 and a second polypeptide domain. The second polypeptide domain has an activity such as transcription activation activity, transcription repression activity, nuclease activity, transcription release factor activity, histone modification activity, nucleic acid association activity, methylase activity, and direct or indirect demethylase activity. Examples of fusion proteins are described in U.S. Patent Publication No. 20160201089 and International Patent Publication NO. 2014/197748, which are incorporated by reference herein in their entirely.

The disclosed methods can include screening for differential endogenous gene expression using targeted qRT-PCR or genome-wide gene expression by RNA-seq. Hits from these screens can be further validated and characterized by RNA-seq, deletion of the regulatory element, and/or introduction of variants or other modifications using CRISPR/Cas9, as described below. In contrast to the development of CRISPR-based screens for genetic knockout or targeting of gene promoter regions, the disclosed method is specifically focused on targeting regulatory elements and is uniquely enabled by the development of tools that alter the activity of these elements.

The disclosed method involves the design and synthesis of libraries of gRNAs targeted to all candidate gene regulatory elements in a genomic region or whole or entire genome, such as those defined by DNase-seq, ATAC-seq, FAIRE-seq, or ChIP-seq. Lentiviral vectors encoding the gRNA library can be used to deliver the gRNA library to cell lines expressing a CRISPR/Cas9-based epigenomic editing system, such as dCas9$^{p300}$ for activation or dCas9$^{KRAB}$ for repression. The modified target cells can be screened for gain or loss of gene expression. Sequencing the gRNAs in the selected cell subpopulations then reveals active regulatory elements

3. CRISPR/CAS9-BASED EPIGENOMIC EDITING SYSTEM

Provided herein are CRISPR/Cas9-based epigenomic editing systems for use in activating or repressing gene expression of a target gene. The CRISPR/Cas9-based epigenomic editing system includes a fusion protein of a Cas9 protein that does not have nuclease activity, such as dCas9, and a second domain. The second domain may include a transcription activation domain, such as a VP64 domain or p300 domain, transcription repression domain, such as KRAB domain, nuclease domain, transcription release factor domain, histone modification domain, nucleic acid association domain, acetylase domain, deacetylase domain, methylase domain, such as a DNA methylase domain, demethylase domain, phosphorylation domain, ubiquitylation domain, or sulmoylation domain. The second domain may be a modifier of DNA methylation or chromatin looping.

In some embodiments, the fusion protein can include a dCas9 domain and a transcriptional activator. For example, the fusion protein can include the amino acid sequence of SEQ ID NO: 2. In other embodiments, the fusion protein can include a dCas9 domain and a transcriptional repressor. For example, the fusion protein comprises the amino acid sequence of SEQ ID NO:3. In further aspects, the fusion protein can include a dCas9 domain and a site-specific nuclease.

a) CRISPR System

The CRISPR system is a microbial nuclease system involved in defense against invading phages and plasmids that provides a form of acquired immunity. The CRISPR loci in microbial hosts contain a combination of CRISPR-associated (Cas) genes as well as non-coding RNA elements capable of programming the specificity of the CRISPR-mediated nucleic acid cleavage. Short segments of foreign DNA, called spacers, are incorporated into the genome between CRISPR repeats, and serve as a 'memory' of past exposures. Cas9 forms a complex with the 3' end of the single guide RNA ("sgRNA"), and the protein-RNA pair recognizes its genomic target by complementary base pairing between the 5' end of the sgRNA sequence and a predefined 20 bp DNA sequence, known as the protospacer. This complex is directed to homologous loci of pathogen DNA via regions encoded within the CRISPR RNA ("crRNA"), i.e., the protospacers, and protospacer-adjacent motifs (PAMs) within the pathogen genome. The non-coding CRISPR array is transcribed and cleaved within direct repeats into short crRNAs containing individual spacer sequences, which direct Cas nucleases to the target site (protospacer). By simply exchanging the 20 bp recognition sequence of the expressed chimeric sgRNA, the Cas9 nuclease can be directed to new genomic targets. CRISPR spacers are used to recognize and silence exogenous genetic elements in a manner analogous to RNAi in eukaryotic organisms.

Three classes of CRISPR systems (Types I, II and III effector systems) are known. The Type II effector system carries out targeted DNA double-strand break in four sequential steps, using a single effector enzyme, Cas9, to cleave dsDNA. Compared to the Type I and Type III effector systems, which require multiple distinct effectors acting as a complex, the Type II effector system may function in alternative contexts such as eukaryotic cells. The Type II effector system consists of a long pre-crRNA, which is transcribed from the spacer-containing CRISPR locus, the Cas9 protein, and a tracrRNA, which is involved in pre-crRNA processing. The tracrRNAs hybridize to the repeat regions separating the spacers of the pre-crRNA, thus initiating dsRNA cleavage by endogenous RNase III. This cleavage is followed by a second cleavage event within each spacer by Cas9, producing mature crRNAs that remain associated with the tracrRNA and Cas9, forming a Cas9:crRNA-tracrRNA complex.

An engineered form of the Type II effector system of *Streptococcus pyogenes* was shown to function in human cells for genome engineering. In this system, the Cas9 protein was directed to genomic target sites by a synthetically reconstituted "guide RNA" ("gRNA", also used interchangeably herein as a chimeric sgRNA, which is a crRNA-tracrRNA fusion that obviates the need for RNase III and crRNA processing in general.

The Cas9:crRNA-tracrRNA complex unwinds the DNA duplex and searches for sequences matching the crRNA to cleave. Target recognition occurs upon detection of complementarity between a "protospacer" sequence in the target DNA and the remaining spacer sequence in the crRNA. Cas9 mediates cleavage of target DNA if a correct protospacer-adjacent motif (PAM) is also present at the 3' end of the protospacer. For protospacer targeting, the sequence must be immediately followed by the protospacer-adjacent motif (PAM), a short sequence recognized by the Cas9 nuclease that is required for DNA cleavage. Different Type II systems have differing PAM requirements. The *S. pyogenes* CRISPR system may have the PAM sequence for this Cas9 (SpCas9) as 5'-NRG-3', where R is either A or G, and characterized the specificity of this system in human cells. A unique capability of the CRISPR/Cas9 system is the straightforward ability to simultaneously target multiple distinct genomic loci by co-expressing a single Cas9 protein with two or more sgRNAs. For example, the *Streptococcus pyogenes* Type II system naturally prefers to use an "NGG" sequence, where "N" can be any nucleotide, but also accepts other PAM sequences, such as "NAG" in engineered systems (Hsu et al., *Nature Biotechnology* (2013) doi:10.1038/nbt.2647). Similarly, the Cas9 derived from *Neisseria meningitidis* (NmCas9) normally has a native PAM of NNNNGATT, but has activity across a variety of PAMs, including a highly degenerate NNNNGNNN PAM (Esvelt et al. *Nature Methods* (2013) doi:10.1038/nmeth.2681).

b) Cas9

The CRISPR/Cas9-based epigenomic editing system may include a Cas9 protein or a Cas9 fusion protein. Cas9 protein is an endonuclease that cleaves nucleic acid and is encoded by the CRISPR loci and is involved in the Type II CRISPR system. The Cas9 protein may be from any bacterial or archaea species, such as *Streptococcus pyogenes, Streptococcus thermophiles,* or *Neisseria meningitides*. The Cas9 protein may be mutated so that the nuclease activity is inactivated. In some embodiments, an inactivated Cas9 protein from *Streptococcus pyogenes* (iCas9, also referred to as "dCas9"; SEQ ID NO: 1) may be used. As used herein, "iCas9" and "dCas9" both refer to a Cas9 protein that has the amino acid substitutions D10A and H840A and has its nuclease activity inactivated. In some embodiments, an inactivated Cas9 protein from *Neisseria meningitides*, such as NmCas9, may be used.

c) CRISPR/Cas9-Based Gene Activation System

The CRISPR/Cas9-based epigenomic editing system can be a CRISPR/Cas9-based gene activation system that can activate regulatory element function with exceptional specificity of epigenome editing. The CRISPR/Cas9-based gene activation system can be used to screen for enhancers, insulators, silencers, and locus control regions that can be targeted to increase or decrease target gene expression. This technology can be used to assign function to putative regulatory elements identified through genomic studies such as the ENCODE and the Roadmap Epigenomics projects.

The CRISPR/Cas9-based gene activation system may activate gene expression by modifying DNA methylation, chromatin looping or catalyzing acetylation of histone H3 lysine 27 at its target sites, leading to robust transcriptional activation of target genes from promoters and proximal and distal enhancers. The CRISPR/Cas9-based gene activation system is highly specific and may be guided to the target gene using as few as one guide RNA. The CRISPR/Cas9-based gene activation system may activate the expression of one gene or a family of genes by targeting enhancers at distant locations in the genome.

i) Histone Acetyltransferase (HAT) Protein

The CRISPR/Cas9-based gene activation system may include a histone acetyltransferase protein, such as a p300 protein, CREB binding protein (CBP; an analog of p300), GCN5, or PCAF, or fragment thereof. Acetylating histones in regulatory elements using a programmable CRISPR/Cas9-based fusion protein is an effective strategy to increase the expression of target genes. A CRISPR/Cas9-based histone acetyltransferase that can be targeted to any site in the genome is uniquely capable of activating distal regulatory elements. The histone acetyltransferase protein may include a human p300 protein or a fragment thereof. The histone acetyltransferase protein may include a wild-type human p300 protein or a mutant human p300 protein, or fragments thereof. The histone acetyltransferase protein may include the core lysine-acetyltransferase domain of the human p300 protein, i.e., the p300 HAT Core (also known as "p300 Core").

ii) CRISPR/dCas9$^{p300\ Core}$ Activation System

The p300 protein regulates the activity of many genes in tissues throughout the body. The p300 protein plays a role in regulating cell growth and division, prompting cells to mature and assume specialized functions (differentiate) and preventing the growth of cancerous tumors. The p300 protein may activate transcription by connecting transcription factors with a complex of proteins that carry out transcription in the cell's nucleus. The p300 protein also functions as a histone acetyltransferase that regulates transcription via chromatin remodeling.

The dCas9$^{p300\ Core}$ fusion protein is a potent and easily programmable tool to synthetically manipulate acetylation at targeted endogenous loci, leading to regulation of proximal and distal enhancer-regulated genes. The p300 Core acetylates lysine 27 on histone H3 (H3K27ac) and may provide H3K27ac enrichment. The fusion of the catalytic core domain of p300 to dCas9 may result in substantially higher transactivation of downstream genes than the direct fusion of full-length p300 protein despite robust protein expression. The dCas9$^{p300\ Core}$ fusion protein may also exhibit an increased transactivation capacity relative to dCas9$^{VP64}$ including in the context of the Nm-dCas9 scaffold, especially at distal enhancer regions, at which dCas9$^{VP64}$ displayed little, if any, measurable downstream transcriptional activity. Additionally, the dCas9$^{p300\ Core}$ displays precise and robust genome-wide transcriptional specificity. dCas9$^{p300\ Core}$ may be capable of potent transcriptional activation and co-enrichment of acetylation at promoters targeted by the epigenetically modified enhancer.

The dCas9$^{p300\ Core}$ may activate gene expression through a single gRNA that target and bind a promoter and/or a characterized enhancer. This technology also affords the ability to synthetically transactivate distal genes from putative and known regulatory regions and simplifies transactivation via the application of a single programmable effector and single target site. These capabilities allow multiplexing to target several promoters and/or enhancers simultaneously.

The mammalian origin of p300 may provide advantages over virally-derived effector domains for in vivo applications by minimizing potential immunogenicity.

Gene activation by dCas9$^{p300\ Core}$ is highly specific for the target gene. In some embodiments, the p300 Core includes amino acids 1048-1664 of SEQ ID NO: 2 (i.e., SEQ ID NO: 4). In some embodiments, the CRISPR/Cas9-based gene activation system includes a dCas9$^{p300\ Core}$ fusion protein of SEQ ID NO: 2 or an Nm-dCas9$^{p300\ Core}$ fusion protein of SEQ ID NO: 5.

d) CRISPR/Cas9-Based Gene Repression System

The CRISPR/Cas9-based epigenomic editing system can be a CRISPR/Cas9-based gene repression system which can inhibit regulatory element function with exceptional specificity of epigenome editing. In some embodiments, the CRISPR/Cas9-based gene repression system, such as one that include dCas9$^{KRAB}$, can interfere with distal enhancer activity by highly specific remodeling of the epigenetic state of targeted genetic loci.

i) CRISPR/dCas9$^{KRAB}$ Gene Repression System

The dCas9$^{KRAB}$ repressor is a highly specific epigenome editing tool that can be used in loss-of-function screens to study gene function and discover targets for drug development. The dCas9$^{KRAB}$ has exceptional specificity to target a particular enhancer, silence only the target genes of that enhancer, and create a repressive heterochromatin environment at that site. dCas9-KRAB can be used to screen for novel regulatory elements within the endogenous genomic context by silencing proximal or distal regulatory elements and corresponding gene targets. The specificity of dCas9-KRAB repressors allows it to be used for transcriptome-wide specificity for silencing endogenous genes. Epigenetic mechanisms for disruption at targeted locus such as histone methylation.

The KRAB domain, a common heterochromatin-forming motif in naturally occurring zinc finger transcription factors, has been genetically linked to dCas9 to create an RNA-guided synthetic repressor, dCas9$^{KRAB}$. The Kruppel-associated box ("KRAB") recruits heterochromatin-forming factors: Kap1, HP1, SETDB1, NuRD. It induces H3K0 tri-methylation, histone deacetylation. KRAB-based synthetic repressors can effectively silence the expression of single genes and have been employed to repress oncogenes, inhibit viral replication, and treat dominant negative diseases.

4. sgRNA LIBRARY

As disclosed herein, libraries of gRNAs are targeted to the set of regulatory elements defined for each screen are used in the disclosed methods. In some embodiments, the libraries of gRNAs may be used for a genome wide screen for regulatory elements associated with a particular modulated phenotype. In some embodiments, the libraries of gRNAs may be used to for a genome wide screen of regulatory elements of at least one target gene known or unknown to be associated with a particular modulated phenotype. The libraries of gRNAs may be designed using a custom algorithm that identifies gRNA target sites in user-defined lists of regulatory elements that have a high degree of targeting specificity in the human genome (Genomic Target Scan (GT-Scan); see O'Brien et al., Bioinformatics (2014) 30:2673-2675). In some embodiments, 100,000 gRNAs can be generated on a single array, providing more than enough gRNAs to comprehensively screen regulatory elements in a 5-10 Mb window around a particular gene of interest. This approach can also be scaled to genome-wide screens by the synthesis of multiple gRNA libraries in parallel. The exact number of gRNAs in the library can depend on whether the screen 1) targets genes or regulatory elements, 2) targets the complete genome, or 3) the number of regulatory elements determined by open chromatin studies such as DNase-seq, ChIP-seq, FAIRE-seq, ATAC-seq, MNase-seq, or related approaches. In some embodiments, between 1 and 100 gRNAs per regulatory element can be generated, depending on the scope of the screen, to compensate for variation in individual gRNA activity. For example, between about 1 and about 100, between about 5 and about 100, between about 10 and about 100, between about 50 and about 100, between about 1 and about 50, between about 5 and about 50, between about 10 and about 50 gRNAs are generated per regulatory element.

In other embodiments, gRNAs can be generated to target every PAM sequence overlapping a regulatory element. In other embodiments, the gRNAs may be designed to target individual alleles of a regulatory element whose DNA sequence varies between individuals. In other embodiments, gRNAs may be designed to target every or a subset of the PAM sequence within 10 million base pairs of one gene's transcription start site, regardless of the existence of naturally occurring regulatory elements in that region. In other embodiments, gRNAs may be designed to target every or a subset of the PAM sequence within 10 million base pairs of several genes' transcription start sites, regardless of the existence of naturally occurring regulatory elements in those regions. In some embodiments, the gRNA libraries can be synthesized by electrochemical means on arrays (e.g., CustomArray, Twist, Gen9), DNA printing method (e.g., Agilent), or generating individual oligos (e.g., by IDT). In some embodiments, gRNAs that do not target putative regulatory elements can be included as negative controls. The gRNAs can be amplified by PCR and cloned into a lentiviral expression vector that also expresses the CRISPR/Cas9-based epigenomic editing system, such as dCas9$^{p300\ Core}$ or dCas9$^{KRAB}$.

As disclosed herein, the library of sgRNAs can target a plurality of target sites. The target sites can include promoters, DNAse I hypersensitivity sites, Transposase-Accessible Chromatin sites, DNA methylation sites, transcription factor binding sites, epigenetic marks, expression quantitative trait loci, and/or regions associated with human traits or phenotypes in genetic association studies. The target sites can be determined by DNase-sequencing (DNase-seq), Assay for Transposase-Accessible Chromatin with high throughput sequencing (ATAC-seq), ChIP-sequencing, self-transcribing active regulatory region sequencing (STARR-Seq), single molecule real time sequencing (SMRT), Formaldehyde-Assisted Isolation of Regulatory Elements sequencing (FAIRE-seq), micrococcal nuclease sequencing (MNase-seq), reduced representation bisulfite sequencing (RRBS-seq), whole genome bisulfite sequencing, methyl-binding DNA immunoprecipitation (MEDIP-seq), or genetic association studies.

In some embodiments, the library of sgRNAs targets one or more gene regulatory elements in a genomic region of a target gene. In some embodiments, the library of sgRNAs targets one or more gene regulatory elements in the entire genome. The target gene can include an endogenous target gene. In some embodiments, between 5 and 50 gRNAs are generated per gene regulatory element. In some embodiments, the genomic region is between about 0 bp to about 10 Mb upstream and/or downstream of the transcription start site of at least one target gene. In some embodiments, the genomic region is greater than 10 Mb or on a different chromosome of at least one target gene.

In some embodiments, the library of sgRNAs includes between at least about 1,000 to about 150,000 or between at least about 1,000 to about 100,000,000 structurally distinct sgRNAs. For example, the library may include at least about 1,000 to about 200,000,000, at least about 1,000 to about 150,000,000, at least about 1,000 to about 100,000,000, at least about 1,000 to about 50,000,000, at least about 1,000 to about 25,000,000, at least about 1,000 to about 10,000,000, at least about 1,000 to about 1,000,000, at least about 1,000 to about 500,000, at least about 1,000 to about 250,000, at least about 1,000 to about 200,000, at least about 1,000 to about 150,000, at least about 1,000 to about 100,000, at least about 1,000 to about 75,000, at least about 1,000 to about 50,000, at least about 1,000 to about 25,000, at least about 1,000 to about 10,000, at least about 1,000 to about 5,000, at least about 5,000 to about 200,000,000, at least about 5,000 to about 150,000,000, at least about 5,000 to about 100,000,000, at least about 5,000 to about 50,000,000, at least about 5,000 to about 25,000,000, at least about 5,000 to about 10,000,000, at least about 5,000 to about 1,000,000, at least about 5,000 to about 500,000, at least about 5,000 to about 250,000, at least about 5,000 to about 200,000, at least about 5,000 to about 150,000, at least about 5,000 to about 100,000, at least about 5,000 to about 75,000, at least about 5,000 to about 50,000, at least about 5,000 to about 25,000, at least about 5,000 to about 10,000, at least about 10,000 to about 200,000,000, at least about 10,000 to about 150,000,000, at least about 10,000 to about 100,000,000, at least about 10,000 to about 50,000,000, at least about 10,000 to about 25,000,000, at least about 10,000 to about 10,000,000, at least about 10,000 to about 1,000,000, at least about 10,000 to about 500,000, at least about 10,000 to about 250,000, at least about 10,000 to about 200,000, at least about 10,000 to about 150,000, at least about 10,000 to about 100,000, at least about 10,000 to about 75,000, at least about 10,000 to about 50,000, at least about 10,000 to about 25,000, at least about 25,000 to about 200,000,000, at least about 25,000 to about 150,000,000, at least about 25,000 to about 100,000,000, at least about 25,000 to about 50,000,000, at least about 25,000 to about 25,000,000, at least about 25,000 to about 10,000,000, at least about 25,000 to about 1,000,000, at least about 25,000 to about 500,000, at least about 25,000 to about 250,000, at least about 25,000 to about 200,000, at least about 25,000 to about 150,000, at least about 25,000 to about 100,000, at least about 25,000 to about 75,000, at least about 25,000 to about 50,000, at least about 50,000 to about 200,000,000, at least about 50,000 to about 150,000,000, at least about 50,000 to about 100,000,000, at least about 50,000 to about 50,000,000, at least about 50,000 to about 25,000,000, at least about 50,000 to about 10,000,000, at least about 50,000 to about 1,000,000, at least about 50,000 to about 500,000, at least about 50,000 to about 250,000, at least about 50,000 to about 200,000, at least about 50,000 to about 150,000, at least about 50,000 to about 100,000, at least about 50,000 to about 75,000, at least about 100,000 to about 200,000,000, at least about 100,000 to about 150,000,000, at least about 100,000 to about 100,000,000, at least about 100,000 to about 50,000,000, at least about 100,000 to about 25,000,000, at least about 100,000 to about 10,000,000, at least about 100,000 to about 1,000,000, at least about 100,000 to about 500,000, at least about 100,000 to about 250,000, at least about 100,000 to about 200,000, or at least about 100,000 to about 150,000 sgRNAs. In some embodiments, the library of sgRNAs can tile across the entire genome, and not be limited to known cis-regulatory elements.

The CRISPR/Cas9-based epigenomic editing system may include at least one gRNA that targets a nucleic acid sequence. The gRNA provides the targeting of the CRISPR/Cas9-based epigenomic editing system. The gRNA is a fusion of two noncoding RNAs: a crRNA and a tracrRNA. The sgRNA may target any desired DNA sequence by exchanging the sequence encoding a 20 bp protospacer which confers targeting specificity through complementary base pairing with the desired DNA target. gRNA mimics the naturally occurring crRNA:tracrRNA duplex involved in the Type II Effector system. This duplex, which may include, for example, a 42-nucleotide crRNA and a 75-nucleotide tracr-RNA, acts as a guide for the Cas9.

The gRNA may target and bind a target region of a target gene. The target region may be a cis-regulatory region or trans-regulatory region of a target gene. In some embodiments, the target region is a distal or proximal cis-regulatory region of the target gene. The gRNA may target and bind a cis-regulatory region or trans-regulatory region of a target gene. In some embodiments, the gRNA may target and bind an enhancer region, a promoter region, an insulator region, a silencer region, a locus control region, or a transcribed region of a target gene. For example, the gRNA may target and bind the target region is at least one of HS2 enhancer of the human β-globin locus, distal regulatory region (DRR) of the MYOD gene, core enhancer (CE) of the MYOD gene, proximal (PE) enhancer region of the OCT4 gene, or distal (DE) enhancer region of the OCT4 gene. In some embodiments, the target region may be a viral promoter, such as an HIV promoter.

There are ~100,000 candidate regulatory elements in a typical cell type, and >2 million regulatory elements have been identified across all human cell types. While individually synthesizing gRNAs to target each enhancer is trivial, screening ~100,000 enhancers in that manner is infeasible. Hundreds of thousands of targeting gRNAs can be generated quickly and inexpensively by high-throughput DNA synthesis on arrays.

The target region may include a target enhancer or a target regulatory element. In some embodiments, the target enhancer or target regulatory element controls the gene expression of several target genes. In some embodiments, the target enhancer or target regulatory element controls a cell phenotype that involves the gene expression of one or more target genes. In some embodiments, the identity of one or more of the target genes is known. In some embodiments, the identity of one or more of the target genes is unknown. The CRISPR/Cas9-based epigenomic editing system allows the determination of the identity of these unknown genes that are involved in a cell phenotype. Examples of cell phenotypes include, but not limited to, T-cell phenotype, cell differentiation, such as T-cell, dendritic cell, or hematopoietic stem cell differentiation, oncogenesis, immunomodulation, cell response to stimuli, cell death, cell growth, cell motility, cell metabolism, cell immunogenicity, drug resistance, or drug sensitivity.

In some embodiments, at least one gRNA may target and bind a target enhancer or target regulatory element, whereby the expression of one or more genes is activated or repressed. For example, between 1 gene and 20 genes, between 1 gene and 15 genes, between 1 gene and 10 genes, between 1 gene and 5 genes, between 2 genes and 20 genes, between 2 genes and 15 genes, between 2 genes and 10 genes, between 2 genes and 5 genes, between 5 genes and 20 genes, between 5 genes and 15 genes, or between 5 genes and 10 genes are activated or repressed by at least one gRNA. In some embodiments, at least 1 gene, at least 2 genes, at least 3 genes, at least 4 genes, at least 5 gene, at least 6 genes, at least 7 genes, at least 8 genes, at least 9 gene, at least 10 genes, at least 11 genes, at least 12 genes, at least 13 gene, at least 14 genes, at least 15 genes, or at least 20 genes are activated or repressed by at least one gRNA.

The CRISPR/Cas9-based epigenomic editing system may activate genes at both proximal and distal locations relative the transcriptional start site (TSS). The CRISPR/Cas9-based epigenomic editing system may target a region anywhere in the genome to determine and identify regulatory elements. The CRISPR/Cas9-based epigenomic editing system may target a region that is at least about 1 base pair to about 10,000,000 base pairs, at least about 100 base pairs to about 10,000,000 base pairs, at least about 250 base pairs to about 10,000,000 base pairs, at least about 500 base pairs to about 10,000,000 base pairs, at least about 1,000 base pairs to about 10,000,000 base pairs, at least about 2,000 base pairs to about 10,000,000 base pairs, at least about 5,000 base pairs to about 10,000,000 base pairs, at least about 10,000 base pairs to about 10,000,000 base pairs, at least about 20,000 base pairs to about 10,000,000 base pairs, at least about 50,000 base pairs to about 10,000,000 base pairs, at least about 75,000 base pairs to about 10,000,000 base pairs, at least about 1 base pair to about 1,000,000 base pairs, at least about 100 base pairs to about 1,000,000 base pairs, at least about 250 base pairs to about 1,000,000 base pairs, at least about 500 base pairs to about 1,000,000 base pairs, at least about 1,000 base pairs to about 1,000,000 base pairs, at least about 2,000 base pairs to about 1,000,000 base pairs, at least about 5,000 base pairs to about 1,000,000 base pairs, at least about 10,000 base pairs to about 1,000,000 base pairs, at least about 20,000 base pairs to about 1,000,000 base pairs, at least about 50,000 base pairs to about 1,000,000 base pairs, at least about 75,000 base pairs to about 1,000,000 base pairs, at least about 1 base pair to about 500,000 base pairs, at least about 100 base pairs to about 500,000 base pairs, at least about 250 base pairs to about 500,000 base pairs, at least about 500 base pairs to about 500,000 base pairs, at least about 1,000 base pairs to about 500,000 base pairs, at least about 2,000 base pairs to about 500,000 base pairs, at least about 5,000 base pairs to about 500,000 base pairs, at least about 10,000 base pairs to about 500,000 base pairs, at least about 20,000 base pairs to about 500,000 base pairs, at least about 50,000 base pairs to about 500,000 base pairs, at least about 75,000 base pairs to about 500,000 base pairs, at least about 1 base pair to about 200,000 base pairs, at least about 100 base pairs to about 200,000 base pairs, at least about 250 base pairs to about 200,000 base pairs, at least about 500 base pairs to about 200,000 base pairs, at least about 1,000 base pairs to about 200,000 base pairs, at least about 2,000 base pairs to about 200,000 base pairs, at least about 5,000 base pairs to about 200,000 base pairs, at least about 10,000 base pairs to about 200,000 base pairs, at least about 20,000 base pairs to about 200,000 base pairs, at least about 50,000 base pairs to about 200,000 base pairs, at least about 75,000 base pairs to about 200,000 base pairs, at least about 1 base pair to about 150,000 base pairs, at least about 100 base pairs to about 150,000 base pairs, at least about 250 base pairs to about 150,000 base pairs, at least about 500 base pairs to about 150,000 base pairs, at least about 1,000 base pairs to about 150,000 base pairs, at least about 2,000 base pairs to about 150,000 base pairs, at least about 5,000 base pairs to about 150,000 base pairs, at least about 10,000 base pairs to about 150,000 base pairs, at least about 20,000 base pairs to about 150,000 base pairs, at least about 50,000 base pairs to about 150,000 base pairs, at least about 75,000 base pairs to about 150,000 base pairs, at least about 1 base pair to about 75,000 base pairs, at least about 100 base pairs to about 75,000 base pairs, at least about 250 base pairs to about 75,000 base pairs, at least about 500 base pairs to about 75,000 base pairs, at least about 1,000 base pairs to about 75,000 base pairs, at least about 2,000 base pairs to about 75,000 base pairs, at least about 5,000 base pairs to about 75,000 base pairs, at least about 10,000 base pairs to about 75,000 base pairs, at least about 20,000 base pairs to about 75,000 base pairs, at least about 50,000 base pairs to about 75,000 base pairs, at least about 1 base pair to about 50,000 base pairs, at least about 100 base pairs to about 50,000 base pairs, at least about 250 base pairs to about 50,000 base pairs, at least about 500 base pairs to about 50,000 base pairs, at least about 1,000 base pairs to about 50,000 base pairs, at least about 2,000 base pairs to about 50,000 base pairs, at least about 5,000 base pairs to about 50,000 base pairs, at least about 10,000 base pairs to about 50,000 base pairs, at least about 20,000 base pairs to about 50,000 base pairs, at least about 1 base pair to about 25,000 base pairs, at least about 100 base pairs to about 25,000 base pairs, at least about 250 base pairs to about 25,000 base pairs, at least about 500 base pairs to about 25,000 base pairs, at least about 1,000 base pairs to about 25,000 base pairs, at least about 2,000 base pairs to about 25,000 base pairs, at least about 5,000 base pairs to about 25,000 base pairs, at least about 10,000 base pairs to about 25,000 base pairs, at least about 20,000 base pairs to about 25,000 base pairs, at least about 1 base pair to about 10,000 base pairs, at least about 100 base pairs to about 10,000 base pairs, at least about 250 base pairs to about 10,000 base pairs, at least about 500 base pairs to about 10,000 base pairs, at least about 1,000 base pairs to about 10,000 base pairs, at least about 2,000 base pairs to about 10,000 base pairs, at least about 5,000 base pairs to about 10,000 base pairs, at least about 1 base pair to about 5,000 base pairs, at least about 100 base pairs to about 5,000 base pairs, at least about 250 base pairs to about 5,000 base pairs, at least about 500 base pairs to about 5,000 base pairs, at least about 1,000 base pairs to about 5,000 base pairs, or at least about 2,000 base pairs to about 5,000 base pairs upstream from the TSS of a target gene. The CRISPR/Cas9-based epigenomic editing system may target a region that is at least about 1 base pair, at least about 100 base pairs, at least about 500 base pairs, at least about 1,000 base pairs, at least about 1,250 base pairs, at least about 2,000 base pairs, at least about 2,250 base pairs, at least about 2,500 base pairs, at least about 5,000 base pairs, at least about 10,000 base pairs, at least about 11,000 base pairs, at least about 20,000 base pairs, at least about 30,000 base pairs, at least about 46,000 base pairs, at least about 50,000 base pairs, at least about 54,000 base pairs, at least about 75,000 base pairs, at least about 150,000 base pairs, at least about 200,000 base pairs, at least about 250,000 base pairs, at least about 300,000 base pairs, at least about 500,000 base pairs, at least about 750,000 base pairs, at least about 1,000,000 base pairs, at least about 2,000,000 base pairs, at least about 4,000,000 base pairs, at least about 5,000,000 base pairs, at least about 6,000,000 base pairs, at least about 7,000,000 base pairs, at least about 8,000,000 base pairs, at least about 9,000,000 base pairs, or at least 10,000,000 base pairs upstream or downstream from the TSS.

The CRISPR/Cas9-based epigenomic editing system may target a region that is at least about 1 base pair to at least about 1500 base pairs, at least about 1 base pair to at least about 1000 base pairs, at least about 1 base pair to at least about 500 base pairs, at least about 1 base pair to at least about 250 base pairs, at least about 1 base pair to at least about 200 base pairs, at least about 1 base pair to at least about 100 base pairs, is at least about 50 base pair to at least about 1500 base pairs, at least about 50 base pair to at least about 1000 base pairs, at least about 50 base pairs to at least about 500 base pairs, at least about 50 base pairs to at least about 250 base pairs at least about 50 base pairs to at least about 200 base pairs, at least about 50 base pairs to at least about 100 base pairs, is at least about 100 base pair to at least about 1500 base pairs, at least about 100 base pair to at least about 1000 base pairs, at least about 100 base pairs to at least about 500 base pairs, at least about 100 base pairs to at least about 250 base pairs, or at least about 100 base pairs to at least about 200 base pairs upstream downstream from the TSS. The CRISPR/Cas9-based epigenomic editing system may target a region that is at least about 1 base pair, at least about 2 base pairs, at least about 3 base pairs, at least about 4 base pairs, at least about 5 base pairs, at least about 10 base pairs, at least about 15 base pairs, at least about 20 base pairs, at least about 25 base pairs, at least about 30 base pairs, at least about 40 base pairs, at least about 50 base pairs, at least about 60 base pairs, at least about 70 base pairs, at least about 80 base pairs, at least about 90 base pairs, at least about 100 base pairs, at least about 110 base pairs, at least about 120, at least about 130, at least about 140 base pairs, at least about 150 base pairs, at least about 160 base pairs, at least about 170 base pairs, at least about 180 base pairs, at least about 190 base pairs, at least about 200 base pairs, at least about 210 base pairs, at least about 220, at least about 230, at least about 240 base pairs, at least about 250 base pairs, at least about 500 base pairs, at least about 750 base pairs, at least about 1000 base pairs, or at least about 1500 base pairs upstream or downstream from the TSS.

In some embodiments, the CRISPR/Cas9-based epigenomic editing system may target and bind a target region that is on the same chromosome as the target gene but more than 150,000 base pairs upstream or downstream from the TSS. In some embodiments, the CRISPR/Cas9-based epigenomic editing system may target and bind a target region that is on a different chromosome from the target gene.

The CRISPR/Cas9-based epigenomic editing system may use gRNA of varying sequences and lengths. The gRNA may comprise a complementary polynucleotide sequence of the target DNA sequence followed by NGG. The gRNA may comprise a "G" at the 5' end of the complementary polynucleotide sequence. The gRNA may comprise at least a 10 base pair, at least a 11 base pair, at least a 12 base pair, at least a 13 base pair, at least a 14 base pair, at least a 15 base pair, at least a 16 base pair, at least a 17 base pair, at least a 18 base pair, at least a 19 base pair, at least a 20 base pair, at least a 21 base pair, at least a 22 base pair, at least a 23 base pair, at least a 24 base pair, at least a 25 base pair, at least a 30 base pair, or at least a 35 base pair complementary polynucleotide sequence of the target DNA sequence followed by NGG. The gRNA may target at least one of a promoter region, an enhancer region, a repressor region, an insulator region, a silencer region, a region involved in DNA looping with the promoter region, a gene splicing region, or the transcribed region of the target gene.

The CRISPR/Cas9-based epigenomic editing system may include at least 10,000 gRNA, at least 20,000 different gRNAs, at least 30,000 different gRNAs at least 40,000 different gRNAs, at least 50,000 different gRNAs, at least 60,000 different gRNAs, at least 70,000 different gRNAs, at least 80,000 different gRNAs, at least 90,000 different gRNAs, at least 100,000 different gRNAs, at least 150,000 different gRNAs, at least 200,000 different gRNAs, at least 300,000 different gRNAs at least 400,000 different gRNAs, at least 500,000 different gRNAs, at least 600,000 different gRNAs, at least 700,000 different gRNAs, at least 800,000 different gRNAs, at least 900,000 different gRNAs, at least 1,000,000 different gRNAs, at least 5,000,000 different gRNAs, at least 10,000,000 different gRNAs, at least 50,000,000 different gRNAs, or at least 100,000,000 different gRNAs. The CRISPR/Cas9-based epigenomic editing system may include between at least 10,000 gRNA to at least 1,000,000 different gRNAs, at least 10,000 gRNA to at least 800,000 different gRNAs, at least 10,000 gRNA to at least 400,000 different gRNAs, at least 20,000 gRNA to at least 150,000 different gRNAs, at least 20,000 gRNA to at least 800,000 different gRNAs, at least 20,000 different gRNAs to at least 400,000 different gRNAs, at least 40,000 gRNA to at least 100,000 different gRNAs, at least 40,000 different gRNAs to at least 150,000 different gRNAs.

a) Target Gene

As disclosed herein, the CRISPR/Cas9-based epigenomic editing system may be designed to target and activate the expression of any target gene. The target gene may be an endogenous gene, a transgene, or a viral gene in a cell line. In some embodiments, the target gene may be a known gene that is known to be associated with a particular phenotype. In some embodiments, the target gene is an unknown gene that is associated with a particular phenotype, such as a known gene that is not known to be associated with a particular phenotype or a unknown gene that has not been characterized. In some embodiments, the target region is located on a different chromosome as the target gene. In some embodiments, the CRISPR/Cas9-based epigenomic editing system may activate or repress between about one target gene to about ten target genes, about one target genes to about five target genes, about one target genes to about four target genes, about one target genes to about three target genes, about one target genes to about two target genes, about two target gene to about ten target genes, about two target genes to about five target genes, about two target genes to about four target genes, about two target genes to about three target genes, about three target genes to about ten target genes, about three target genes to about five target genes, or about three target genes to about four target genes. In some embodiments, the CRISPR/Cas9-based epigenomic editing system may activate or repress at least one target gene, at least two target genes, at least three target genes, at least four target genes, at least five target genes, or at least ten target genes. For example, the may target the hypersensitive site 2 (HS2) enhancer region of the human β-globin locus and activate downstream genes (HBE, HBG, HBD and HBB).

In some embodiments, the CRISPR/Cas9-based epigenomic editing system induces or represses the gene expression of a target gene by at least about 1 fold, at least about 2 fold, at least about 3 fold, at least about 4 fold, at least about 5 fold, at least about 6 fold, at least about 7 fold, at least about 8 fold, at least about 9 fold, at least about 10 fold, at least 15 fold, at least 20 fold, at least 30 fold, at least 40 fold, at least 50 fold, at least 60 fold, at least 70 fold, at least 80 fold, at least 90 fold, at least 100 fold, at least about 110 fold, at least 120 fold, at least 130 fold, at least 140 fold, at least 150 fold, at least 160 fold, at least 170 fold, at least 180 fold, at least 190 fold, at least 200 fold, at least about 300 fold, at least 400 fold, at least 500 fold, at least 600 fold, at least 700 fold, at least 800 fold, at least 900 fold, at least 1000 fold, at least 1500 fold, at least 2000 fold, at least 2500 fold, at least 3000 fold, at least 3500 fold, at least 4000 fold, at least 4500 fold, at least 5000 fold, at least 600 fold, at least 7000 fold, at least 8000 fold, at least 9000 fold, at least 10000 fold, at least 100000 fold compared to a control level of gene expression. A control level of gene expression of the target gene may be the level of gene expression of the target gene in a cell that is not treated with any CRISPR/Cas9-based epigenomic editing system In some aspects, the target gene is a disease-relevant gene. In some embodiments, the unmodified target cell is a mammalian cell. In some embodiments, the genome includes a human genome. In some embodiments, the target gene may be a mammalian gene. For example, the CRISPR/Cas9-based epigenomic editing system may target a mammalian gene, such as IL1RN, MYOD1, OCT4, HBE, HBG, HBD, HBB, MYOCD (Myocardin), PAtX7 (Paired box protein Pax-7), FGF1 (fibroblast growth factor-1) genes, such as FGF1A, FGF1B, and FGF1C. Other target genes include, but not limited to, Atf3, Axud1, Btg2, c-Fos, c-Jun, Cxcl1, Cxcl2, Edn1, Ereg, Fos, Gadd45b, Ier2, Ier3, Ifrd1, Il1b, Il6, Irf1, Junb, Lif, Nfkbia, Nfkbiz, Ptgs2, Slc25a25, Sqstm1, Tieg, Tnf, Tnfaip3, Zfp36, Birc2, Ccl2, Ccl20, Ccl7, Cebpd, Ch25h, CSF1, Cx3cl1, Cxcl10, Cxcl5, Gch, Icam1, Ifi47, Ifngr2, Mmp10, Nfkbie, Npal1, p21, Relb, Ripk2, Rnd1, S1pr3, Stx11, Tgtp, Tlr2, Tmem140, Tnfaip2, Tnfrsf6, Vcam1, 1110004C05Rik (GenBank accession number BC010291), Abca1, AI561871 (GenBank accession number BI143915), AI882074 (GenBank accession number BB730912), Arts1, AW049765 (GenBank accession number BC026642.1), C3, Casp4, Ccl5, Ccl9, Cdsn, Enpp2, Gbp2, H2-D1, H2-K, H2-L, Ifit1, Ii, Il13ra1, Il1rl1, Lcn2, Lhfpl2, LOC677168 (GenBank accession number AK019325), Mmp13, Mmp3, Mt2, Naf1, Ppicap, Prnd, Psmb10, Saa3, Serpina3g, Serpinf1, Sod3, Stat1, Tapbp, U90926 (GenBank accession number NM_020562), Ubd, A2AR (Adenosine A2A receptor), B7-H3 (also called CD276), B7-H4 (also called VTCN1), BTLA (B and T Lymphocyte Attenuator; also called CD272), CTLA-4 (Cytotoxic T-Lymphocyte-Associated protein 4; also called CD152), IDO (Indoleamine 2,3-dioxygenase) KIR (Killer-cell Immunoglobulin-like Receptor), LAG3 (Lymphocyte Activation Gene-3), PD-1 (Programmed Death 1 (PD-1) receptor), TIM-3 (T-cell Immunoglobulin domain and Mucin domain 3), and VISTA (V-domain Ig suppressor of T cell activation).

In some embodiments, the genomic region can be the β-globin locus. In some embodiments, the modified target cell comprises an endogenous gene encoding hemoglobin subunit epsilon (HBE1) chain tagged with a reporter gene. In some embodiments, the reporter gene is red fluorescent protein. In some embodiments, the at least one target gene is HER2, KRAS, or Proprotein convertase subtilisin/kexin type 9 (PCSK9) gene.

i) HBE1

The HS2 enhancer is a potent activator of the developmentally regulated globin genes, which are involved in sickle cell anemia and beta thalassemia. dCas9$^{KRAB}$ targeted to HS2 by a single guide RNA (gRNA) can disrupt the expression of multiple downstream globin genes. These findings expand the capability capabilities of synthetic repressors by showing that dCas9$^{KRAB}$ targeted to a distal regulatory element by a gRNA can silence expression of multiple genes located 10 to 50 kb away ii) HER2

20% of breast cancers are driven by HER2. Herceptin (anti-HERS) extends life by 20-25 months. Less than 35% of patients respond while 70% of patients gain resistance. Resistance is often from protein regulation.

5. MODIFIED TARGET CELLS

As disclosed herein, the modified target cell can include an intracellular or cell-surface marker. In some embodiments, the intracellular or cell-surface marker is labelled by immunofluorescence staining. The modified target cell includes a target gene includes a reporter gene inserted within the coding region of the target gene. In some embodiments, the reporter gene encodes a fluorescent protein. In some embodiments, the cell-surface marker is labelled by a fluorescently-labelled specific binding protein for the cell-surface marker. For example, the fluorescent marker can be a green fluorescent protein (GFP), enhanced green fluorescent protein (EGFP), a yellow fluorescent protein (YFP), such as mBanana, a red fluorescent protein (RFP), such as mCherry, DsRed, dTomato, tdTomato, mHoneydew, or mStrawberry, TagRFP, far-red fluorescent pamidronate (FRFP), such as mGrape1 or mGrape2, a cyan fluorescent protein (CFP), a blue fluorescent protein (BFP), enhanced cyan fluorescent protein (ECFP), ultramarine fluorescent protein (UMFP), orange fluorescent protein (OFP), such as mOrange or mTangerine, red (orange) fluorescent protein (mROFP), TagCFP, or a tetracystein fluorescent motif.

In some embodiments, the modified target cell is a reporter cell line that has GFP gene inserted into the endogenous coding region of a target gene, such as a disease-relevant gene. In some embodiments, the modified target cell is a reporter cell line that produces a cell surface protein that is recognized by a cell surface antibody for staining. In some embodiments, the reporter cell line can be engineered to express a modifier of gene regulatory elements, such as the dCas9$^{p300\ Core}$ acetyltransferase or the dCas9$^{KRAB}$ repressor, and is then transduced with the gRNA libraries.

The CRISPR/Cas9-based epigenomic editing system may be used with any type of cell. In some embodiments, the cell is a bacterial cell, a fungal cell, an archaea cell, a plant cell or an animal cell. In some embodiments, this may be an organ or an animal organism. In some embodiments, the cell may be any cell type or cell line, including but not limited to, 293-T cells, 3T3 cells, 721 cells, 9L cells, A2780 cells, A2780ADR cells, A2780cis cells, A172 cells, A20 cells, A253 cells, A431 cells, A-549 cells, ALC cells, B16 cells, B35 cells, BCP-1 cells, BEAS-2B cells, bEnd.3 cells, BHK-21 cells, BR 293 cells, BxPC3 cells, C2C12 cells, C3H-10T1/2 cells, C6/36 cells, Cal-27 cells, CHO cells, COR-L23 cells, COR-L23/CPR cells, COR-L23/5010 cells, COR-L23/R23 cells, COS-7 cells, COV-434 cells, CML T1 cells, CMT cells, CT26 cells, D17 cells, DH82 cells, DU145 cells, DuCaP cells, EL4 cells, EM2 cells, EM3 cells, EMT6/AR1 cells, EMT6/AR10.0 cells, FM3 cells, H1299 cells, H69 cells, HB54 cells, HB55 cells, HCA2 cells, HEK-293 cells, HeLa cells, Hepalclc7 cells, HL-60 cells, HMEC cells, HT-29 cells, Jurkat cells, J558L cells, JY cells, K562 cells, Ku812 cells, KCL22 cells, KG1 cells, KYO1 cells, LNCap cells, Ma-Mel 1, 2, 3 . . . 48 cells, MC-38 cells, MCF-7 cells, MCF-10A cells, MDA-MB-231 cells, MDA-MB-468 cells, MDA-MB-435 cells, MDCK II cells, MDCK II cells, MG63 cells, MOR/0.2R cells, MONO-MAC 6 cells, MRC5 cells, MTD-1A cells, MyEnd cells, NCI-H69/CPR cells, NCI-H69/LX10 cells, NCI-H69/LX20 cells, NCI-H69/LX4 cells, NIH-3T3 cells, NALM-1 cells, NW-145 cells, OPCN/OPCT cells, Peer cells, PNT-1A/PNT 2 cells, Raji cells, RBL cells, RenCa cells, RIN-5F cells, RMA/RMAS cells, Saos-2 cells, Sf-9 cells, SiHa cells, SkBr3 cells, T2 cells, T-47D cells, T84 cells, THP1 cells, U373 cells, U87 cells, U937 cells, VCaP cells, Vero cells, WM39 cells, WT-49 cells, X63 cells, YAC-1 cells, YAR cells, GM12878, K562, H1 human embryonic stem cells, HeLa-S3, HepG2, HUVEC, SK-N-SH, IMR90, A549, MCF7, HMEC or LHCM, CD14+, CD20+, primary heart or liver cells, differentiated H1 cells, 8988T, Adult_CD4_naive, Adult_CD4 Th0, Adult_CD4 Th1, AG04449, AG04450, AG09309, AG09319, AG10803, AoAF, AoSMC, BC_Adipose_UHN00001, BC_Adrenal_Gland_H12803N, BC_Bladder_01-11002, BC_Brain_H11058N, BC_Breast_02-03015, BC_Colon_01-11002, BC_Colon_H12817N, BC_Esophagus_01-11002, BC_Esophagus_H12817N, BC_Jejunum_H12817N, BC_Kidney_01-11002, BC_Kidney_H12817N, BC_Left_Ventricle_N41, BC_Leukocyte_UHN00204, BC_Liver_01-11002, BC_Lung_01-11002, BC_Lung_H12817N, BC_Pancreas_H12817N, BC_Penis_H12817N, BC_Pericardium_H12529N, BC_Placenta_UHN00189, BC_Prostate_Gland_H12817N, BC_Rectum_N29, BC_Skeletal_Muscle_01-11002, BC_Skeletal_Muscle_H12817N, BC_Skin_01-11002, BC_Small_Intestine_01-11002, BC_Spleen_H12817N, BC_Stomach_01-11002, BC_Stomach_H12817N, BC_Testis_N30, BC_Uterus_BN0765, BE2_C, BG02ES, BG02ES-EBD, BJ, bone_marrow_HS27a, bone_marrow_HS5, bone_marrow_MSC, Breast_OC, Caco-2, CD20+_RO01778, CD20+_RO01794, CD34+_Mobilized, CD4+_Naive_Wb11970640, CD4+_Naive_Wb78495824, Cerebellum_OC, Cerebrum_frontal_OC, Chorion, CLL, CMK, Colo829, Colon_BC, Colon_OC, Cord_CD4_naive, Cord_CD4_Th0, Cord_CD4_Th1, Decidua, Dnd41, ECC-1, Endometrium_OC, Esophagus_BC, Fibrobl, Fibrobl_GM03348, FibroP, FibroP_AG08395, FibroP_AG08396, FibroP_AG20443, Frontal_cortex_OC, GC_B_cell, Globla, GM04503, GM04504, GM06990, GM08714, GM10248, GM10266, GM10847, GM12801, GM12812, GM12813, GM12864, GM12865, GM12866, GM12867, GM12868, GM12869, GM12870, GM12871, GM12872, GM12873, GM12874, GM12875, GM12878-XiMat, GM12891, GM12892, GM13976, GM13977, GM15510, GM18505, GM18507, GM18526, GM18951, GM19099, GM19193, GM19238, GM19239, GM19240, GM20000, H0287, H1-neurons, H7-hESC, H9ES, H9ES-AFP-, H9ES-AFP+, H9ES-CM, H9ES-E, H9ES-EB, H9ES-EBD, HAc, HAEpiC, HA-h, HAL, HAoAF, HAoAF_6090101.11, HAoAF_6111301.9, HAoEC, HAoEC_7071706.1, HAoEC_8061102.1, HA-sp, HBMEC, HBVP, HBVSMC, HCF, HCFaa, HCH, HCH 0011308.2P, HCH_8100808.2, HCM, HConF, HCPEpiC, HCT-116, Heart_OC, Heart_STL003, HEEpiC, HEK293, HEK293T, HEK293-T-REx, Hepatocytes, HFDPC, HFDPC_0100503.2, HFDPC_0102703.3, HFF, HFF-Myc, HFL11W, HFL24W, HGF, HHSEC, HIPEpiC, HL-60, HMEpC, HMEpC_6022801.3, HMF, hMNC-CB, hMNC-CB 8072802.6, hMNC-CB 9111701.6, hMNC-PB, hMNC-PB 0022330.9, hMNC-PB_0082430.9, hMSC-AT, hMSC-AT_0102604.12, hMSC-AT_9061601.12, hMSC-BM, hMSC-BM_0050602.11, hMSC-BM_0051105.11, hMSC-UC, hMSC-UC_0052501.7, hMSC-UC_0081101.7, HMVEC-dAd, HMVEC-dBl-Ad, HMVEC-dBl-Neo, HMVEC-dLy-Ad, HMVEC-dLy-Neo, HMVEC-dNeo, HMVEC-LB1, HMVEC-LLy, HNPCEpiC, HOB, HOB_0090202.1, HOB_0091301, HPAEC, HPAEpiC, HPAF, HPC-PL, HPC-PL_0032601.13, HPC-PL_0101504.13, HPDE6-E6E7, HPdLF, HPF, HPIEpC, HPIEpC_9012801.2, HPIEpC_9041503.2, HRCEpiC, HRE, HRGEC, HRPEpiC, HSaVEC, HSaVEC_0022202.16, HSaVEC_9100101.15, HSMM, HSMM_emb, HSMM_F-SHD, HSMMtube, HSMMtube_emb, HSMMtube_FSHD, HT-1080, HTR8svn, Huh-7, Huh-7.5, HVMF, HVMF_6091203.3, HVMF_6100401.3, HWP, HWP_0092205, HWP_8120201.5, iPS, iPS_CWRU1, iPS_hFib2_iPS4, iPS_hFib2_iPS5, iPS_NIHi1, iPS_NIHi7, Ishikawa, Jurkat, Kidney_BC, Kidney_OC, LHCN-M2, LHSR, Liver_OC, Liver_STL004, Liver_STL011, LNCaP, Loucy, Lung_BC, Lung_OC, Lymphoblastoid_cell_line, M059J, MCF10A-Er-Src, MCF-7, MDA-MB-231, Medullo, Medullo_D341, Mel_2183, Melano, Monocytes-CD14+, Monocytes-CD 14+_R001746, Monocytes-CD14+_R001826, MRT_A204, MRT_G401, MRT_TTC549, Myometr, Naive_B_cell, NB4, NH-A, NHBE, NHBE_RA, NHDF, NHDF_0060801.3, NHDF_7071701.2, NHDF-Ad, NHDF-neo, NHEK, NHEM.f_M2, NHEM.f_M2_5071302.2, NHEM.f_M2_6022001, NHEM_M2, NHEM_M2_7011001.2, NHEM_M2_7012303, NHLF, NT2-D1, Olf_neurosphere, Osteobl, ovcar-3, PANC-1, Pancreas_OC, PanIsletD, PanIslets, PBDE, PBDEFetal, PBMC, PFSK-1, pHTE, Pons_OC, PrEC, ProgFib, Prostate, Prostate_OC, Psoas_muscle_OC, Raji, RCC_7860, RPMI-7951, RPTEC, RWPE1, SAEC, SH-SY5Y, Skeletal_Muscle_BC, SkMC, SKMC, SkMC_8121902.17, SkMC_9011302, SK-N-MC, SK-N-SH_RA, Small_intestine_OC, Spleen_OC, Stellate, Stomach_BC, T_cells_CD4+, T-47D, T98G, TBEC, Th1, Th1_Wb33676984, Th1_Wb54553204, Th17, Th2, Th2_Wb33676984, Th2_Wb54553204, Treg_Wb78495824, Treg_Wb83319432, U2OS, U87, UCH-1, Urothelia, WERI-Rb-1, and WI-38. In some embodiments, the unmodified target cell can be any cell, such as a primary cell, a HEK293 cell, 293 Ts cell, SKBR3 cell, A431 cell, K562 cell, HCT116 cell, HepG2 cell, or K-Ras-dependent and K-Ras-independent cell groups.

6. MODULATED PHENOTYPES

Figure 59:
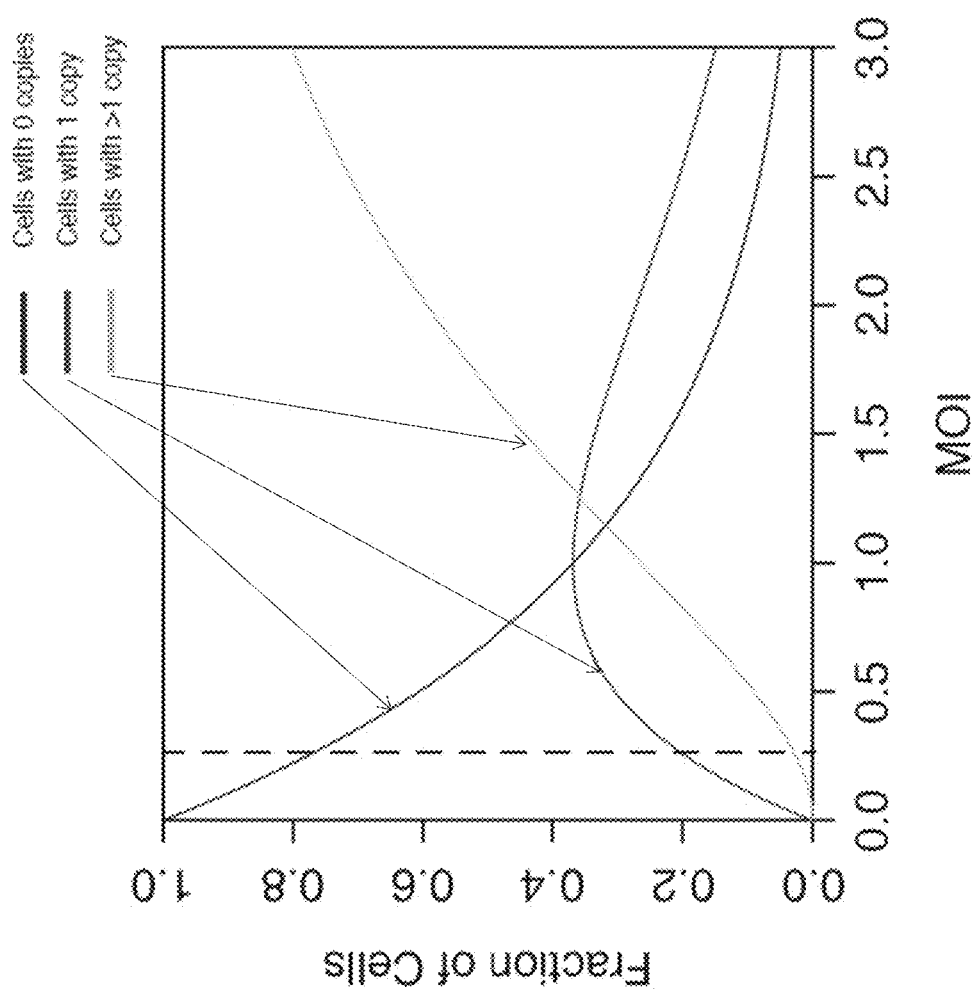
FIG. 59 shows percent of cells having 0, 1, or more than 1 copy of sgRNA.

As described herein, the modified target cells can be transduced with a sgRNA library, such as a gRNA library lentiviral pool, at low multiplicity of infection (MOI) such that >90% of cells express a single gRNA (see FIG. 59). In some embodiments, the optimal balance between percent of cells transduced and percent of cells with one gRNA can be obtained. For example, the optimal balance may be obtained with at least about 10% transduction efficiency or about MOI 0.1, at least about 20% transduction efficiency or about MOI 0.2, at least about 30% transduction efficiency or about MOI 0.3, at least about 40% transduction efficiency or about MOI 0.4, at least about 50% transduction efficiency or about MOI 0.5, at least about 60% transduction efficiency or about MOI 0.6, at least about 70% transduction efficiency or about MOI 0.7, at least about 80% transduction efficiency or about MOI 0.8, at least about 90% transduction efficiency or about MOI 0.9, at least about 99% transduction efficiency or about MOI 0.99, or at least about 100% transduction efficiency or about MOI 1.0. In some embodiments, the cells can be transduced with at least about 100-fold to about 2000-fold coverage of the library at a particular MOI, such as 0.2. For example, the cells can be transduced with at least about 100-fold to about 2000-fold, at least about 100-fold to about 1500-fold, at least about 100-fold to about 1000-fold, at least about 100-fold to about 500-fold, at least about 200-fold to about 2000-fold, at least about 200-fold to about 1500-fold, at least about 200-fold to about 1000-fold, at least about 200-fold to about 500-fold, at least about 500-fold to about 2000-fold, at least about 500-fold to about 1500-fold, or at least about 500-fold to about 1000-fold, or with at least about 100-fold, at least about 200-fold, at least about 500-fold, at least about 1000-fold, at least about 1500-fold, or at least about 2000-fold coverage of the library. In some embodiments, the modified target cells are transduced with a high multiplicity of infection so that target cells express multiple gRNAs. The number of cells that are transfected After an appropriate period of time, cells with modulated gene expression or cell phenotype will be isolated using techniques described below, for example by fluorescence-activated cell sorting (FACS) or by magnetic-activated cell sorting. The modulated phenotype may be recognized by intracellular or cell-surface markers. In some embodiments, the intracellular or cell-surface markers can be labelled by immunofluorescence staining. In some embodiments, an endogenous target gene can be tagged with fluorescent reporters, such as by genome editing. Other possible modulated phenotypic screens include isolating unique cell populations based on a change in response to stimuli, cell death, cell growth, cell proliferation, cell survival, drug resistance, or drug sensitivity. In some embodiments, this phenotypic change in response can be detected in an intact animal organism.

As disclosed herein, the modulated phenotype can be a change in gene expression of at least one target gene or a change in cell or organismal phenotype. The gene regulatory element can modulate the gene expression or the cell phenotype. In some embodiments, the cell phenotype can be a cell response to stimuli, cell death, cell growth, drug resistance, drug sensitivity, or combinations thereof. The stimuli can be a physical signal, an environmental signal, a hormone, a growth factor, an inflammatory cytokine, an anti-inflammatory cytokine, a transcription factor, or combinations thereof. In some embodiments, the cell phenotype is T-cell phenotype or hematopoietic cell differentiation. In some embodiments, the modulated phenotype can be a modulation in T-cell phenotype or hematopoietic cell differentiation.

7. IDENTIFICATION OF REGULATORY ELEMENTS THAT MODULATE TARGET GENE EXPRESSION OR CELL PHENOTYPE

As disclosed herein, the disclosed methods may further include enriching cells expressing differential levels of the reporter gene. In some embodiments, enriching cells may include flow cytometry, for example by fluorescence-activated cell sorting (FACS) or immunopurification with a cell surface marker. In some embodiments, enriching cells may include magnetic-activated cell sorting. In some embodiments, the regulatory elements responsible for the altered target gene expression or cell phenotype is identified based on an alignment of the significantly enriched gRNAs to the genome.

As disclosed herein, the sgRNAs are selected to inhibit transcription of the target gene, activate transcription of the target gene, or knockout at least one target gene. In some embodiments, the identifying and characterizing the sgRNAs within the population of selected test cells can include high-throughput sequencing of the sgRNA-expressing DNA, RT-PCR, qRT-PCR, RNA-seq, emulsion PCR, affinity hybridization of the sgRNAs or of DNA expressing the sgRNA to microarrays, affinity hybridization of the sgRNA or of the DNA expressing the sgRNA to colored probes followed by image-based quantitation potentially with a Nanostring nCounter instrument, or direct RNA sequencing. In some embodiments, identifying and characterizing the sgRNAs within the population of selected test cells includes deep sequencing of the genomic DNA of the test cell. Statistical methods may be used to confirm the identity of the sgRNAs, including such methods known to one of skill, such a linear regression, generalized linear regression, hierarchical regression, penalized regression, mixed effects regression models, Bayesian graphical models, support vector machines, random forests, principle component analysis, or neural networks.

As disclosed herein, the methods include further comparing the gene expression of at least one target gene in the test cells with the gene expression of the target gene in a plurality of control cells. In some embodiments, the change in gene expression of the target gene is an increase or decrease in gene expression compared to a control plurality of cells. The change in gene expression can be determined by a change in protein expression, RNA expression, or protein activity. In some embodiments, the control cells are cells that do not express the CRISPR/Cas9-based epigenomic editing system. In some embodiments, the control cells are cells that have not been exposed to the stimuli or drug.

In some aspects, selecting the test cells for a change in gene expression of the target gene further includes culturing the cells and selecting the cells on the basis of cellular proliferation or survival. In some embodiments, the culturing the cells is performed in the presence of a selection agent. The selection agent can be a chemotherapeutic, a DNA damaging agent, a cytotoxic agent, a growth factor, a transcription factor, a kinase, a drug, an exogenous gene under the control of a heterologous promoter, or a hormone. In some embodiments, the plurality of control cells is cultured in the same conditions as the plurality of test cell but without the presence of the selection agent. In some embodiments, selection can occur at the level of entire animal organism.

For example, the gRNAs in the sorted cell pool can be recovered by PCR of the integrated lentiviral vector and sequenced on Illumina MiSeq. In some embodiments, the screening of sgRNA library can be repeated in one or more independent cell populations to adequately power the identification of gRNAs that modulate gene expression. In some embodiments, between about 1 and about 100, between about 1 and about 50, between about 1 and about 10, between about 1 and about 9, between about 1 and about 8, between about 1 and about 7, between about 1 and about 6, between about 1 and about 5, between about 2 and about 20, between about 2 and about 9, between about 2 and about 8, between about 2 and about 7, between about 2 and about 6, between about 2 and about 5, between about 3 and about 30, between about 3 and about 9, between about 3 and about 8, between about 3 and about 7, between about 3 and about 6, between about 3 and about 5, or at least one, at least two, at least 3, at least 4, at least 5, at least 6, at least 7, at least 8, at least 9, at least 10, at least 20, at least 30, at least 40, at least 50, at least 60, at least 70, at least 80, at least 90, or at least 100 independent cell population can be used.

In some embodiments, at least 1 or more replicates are used to detect the regulatory elements. For example, between about 1 and about 100, between about 1 and about 50, between about 1 and about 10, between about 1 and about 9, between about 1 and about 8, between about 1 and about 7, between about 1 and about 6, between about 1 and about 5, between about 2 and about 20, between about 2 and about 9, between about 2 and about 8, between about 2 and about 7, between about 2 and about 6, between about 2 and about 5, between about 3 and about 30, between about 3 and about 9, between about 3 and about 8, between about 3 and about 7, between about 3 and about 6, between about 3 and about 5, or at least one, at least two, at least 3, at least 4, at least 5, at least 6, at least 7, at least 8, at least 9, at least 10, at least 20, at least 30, at least 40, at least 50, at least 60, at least 70, at least 80, at least 90, at least 100 replicates are used to detect the regulatory elements.

8. VALIDATION OF REGULATORY ELEMENT ACTIVITY

As disclosed herein, the hits from the CRISPR/Cas9-based epigenomic editing system, such as dCas9$^{p300\text{-}Core}$ and dCas9$^{KRAB}$, library screen can be validated by delivering each strongly enriched gRNA individually to independent cell cultures and measuring changes in gene expression by qRT-PCR and immunofluorescence cell surface staining. In some embodiments, ChIP PCR, ChIP-qPCR, or ChIP-seq can be used to validate the gRNA target site. In some embodiments, the specificity of gene regulation can be determined by RNA-seq. The activity of any particular enhancer can be further validated by excising the element from the genome via genome editing, by editing the sequences of putative transcription factor binding sites that fall within these elements, or by confirming the effect of regulatory element function on various aspects of cell phenotype or differentiation state.

9. CONSTRUCTS AND PLASMIDS

The compositions, as described above, may comprise genetic constructs that encodes the CRISPR/Cas9-based epigenomic editing system, as disclosed herein. The genetic construct, such as a plasmid or expression vector, may comprise a nucleic acid that encodes the CRISPR/Cas9-based epigenomic editing system, such as the CRISPR/Cas9-based gene activation or gene repression systems, and/or at least one of the gRNAs. The compositions, as described above, may comprise genetic constructs that encodes the modified lentiviral vector and a nucleic acid sequence that encodes the CRISPR/Cas9-based epigenomic editing system, as disclosed herein. The genetic construct, such as a plasmid, may comprise a nucleic acid that encodes the CRISPR/Cas9-based epigenomic editing system. The compositions, as described above, may comprise genetic constructs that encodes a modified lentiviral vector. The genetic construct, such as a plasmid, may comprise a nucleic acid that encodes the CRISPR/Cas9-based epigenomic editing system, such as the CRISPR/Cas9-based gene activation or gene repression systems, and at least one sgRNA. The genetic construct may be present in the cell as a functioning extrachromosomal molecule. The genetic construct may be a linear minichromosome including centromere, telomeres or plasmids or cosmids.

The genetic construct may also be part of a genome of a recombinant viral vector, including recombinant lentivirus, recombinant adenovirus, and recombinant adenovirus associated virus. The genetic construct may be part of the genetic material in attenuated live microorganisms or recombinant microbial vectors which live in cells. The genetic constructs may comprise regulatory elements for gene expression of the coding sequences of the nucleic acid. The regulatory elements may be a promoter, an enhancer, an initiation codon, a stop codon, or a polyadenylation signal.

The nucleic acid sequences may make up a genetic construct that may be a vector. The vector may be capable of expressing the fusion protein, such as the CRISPR/Cas9-based epigenomic editing system, in the cell of a mammal. The vector may be recombinant. The vector may comprise heterologous nucleic acid encoding the fusion protein, such as the CRISPR/Cas9-based epigenomic editing system. The vector may be a plasmid. The vector may be useful for transfecting cells with nucleic acid encoding the CRISPR/Cas9-based epigenomic editing system, which the transformed host cell is cultured and maintained under conditions wherein expression of the CRISPR/Cas9-based epigenomic editing system takes place.

Coding sequences may be optimized for stability and high levels of expression. In some instances, codons are selected to reduce secondary structure formation of the RNA such as that formed due to intramolecular bonding.

The vector may comprise heterologous nucleic acid encoding the CRISPR/Cas9-based epigenomic editing system and may further comprise an initiation codon, which may be upstream of the CRISPR/Cas9-based epigenomic editing system coding sequence, and a stop codon, which may be downstream of the CRISPR/Cas9-based epigenomic editing system coding sequence. The initiation and termination codon may be in frame with the CRISPR/Cas9-based epigenomic editing system coding sequence. The vector may also comprise a promoter that is operably linked to the CRISPR/Cas9-based epigenomic editing system coding sequence. The CRISPR/Cas9-based epigenomic editing system may be under the light-inducible or chemically inducible control to enable the dynamic control of epigenomic editing in space and time. The promoter operably linked to the CRISPR/Cas9-based epigenomic editing system coding sequence may be a promoter from simian virus 40 (SV40), a mouse mammary tumor virus (MMTV) promoter, a human immunodeficiency virus (HIV) promoter such as the bovine immunodeficiency virus (BIV) long terminal repeat (LTR) promoter, a Moloney virus promoter, an avian leukosis virus (ALV) promoter, a cytomegalovirus (CMV) promoter such as the CMV immediate early promoter, Epstein Barr virus (EBV) promoter, or a Rous sarcoma virus (RSV) promoter. The promoter may also be a promoter from a human gene such as human ubiquitin C (hUbC), human actin, human myosin, human hemoglobin, human muscle creatine, or human metalothinein. The promoter may also be a tissue specific promoter, such as a muscle or skin specific promoter, natural or synthetic. Examples of such promoters are described in US Patent Application Publication No. US20040175727, the contents of which are incorporated herein in its entirety.

The vector may also comprise a polyadenylation signal, which may be downstream of the CRISPR/Cas9-based epigenomic editing system. The polyadenylation signal may be a SV40 polyadenylation signal, LTR polyadenylation signal, bovine growth hormone (bGH) polyadenylation signal, human growth hormone (hGH) polyadenylation signal, or human β-globin polyadenylation signal. The SV40 polyadenylation signal may be a polyadenylation signal from a pCEP4 vector (Invitrogen, San Diego, Calif.).

The vector may also comprise an enhancer upstream of the CRISPR/Cas9-based epigenomic editing system, i.e., the CRISPR/Cas9-based gene activation or gene repression systems coding sequence, and/or sgRNAs. The enhancer may be necessary for DNA expression. The enhancer may be human actin, human myosin, human hemoglobin, human muscle creatine or a viral enhancer such as one from CMV, HA, RSV or EBV. Polynucleotide function enhancers are described in U.S. Pat. Nos. 5,593,972, 5,962,428, and WO94/016737, the contents of each are fully incorporated by reference. The vector may also comprise a mammalian origin of replication in order to maintain the vector extrachromosomally and produce multiple copies of the vector in a cell. The vector may also comprise a regulatory sequence, which may be well suited for gene expression in a mammalian or human cell into which the vector is administered. The vector may also comprise a reporter gene, such as green fluorescent protein ("GFP") and/or a selectable marker, such as hygromycin ("Hygro").

The vector may be expression vectors or systems to produce protein by routine techniques and readily available starting materials including Sambrook et al., Molecular Cloning and Laboratory Manual, Second Ed., Cold Spring Harbor (1989), which is incorporated fully by reference. In some embodiments the vector may comprise the nucleic acid sequence encoding the CRISPR/Cas9-based epigenomic editing system, including the nucleic acid sequence encoding the CRISPR/Cas9-based gene activation or gene repression systems, and the nucleic acid sequence encoding the at least one gRNA.

In some embodiments, the sgRNA is encoded by a polynucleotide sequence and packaged into a lentiviral vector, thereby generating a gRNA library lentiviral pool. In some embodiments, the lentiviral vector includes an expression cassette. The expression cassette can includes a promoter operably linked to the polynucleotide sequence encoding the sgRNA. In some embodiments, the promoter operably linked to the polynucleotide encoding the sgRNA is inducible. In some embodiments, the target cells are transduced with the gRNA library lentiviral pool at a low multiplicity of infection such that >90% of the target cells express a single gRNA. In some embodiments, the target cells are transduced with the gRNA library lentiviral pool at a high multiplicity of infection so that target cells express multiple gRNAs.

10. METHODS OF DELIVERY

Provided herein is a method for delivering the CRISPR/Cas9-based epigenomic editing system for providing genetic constructs and/or proteins of the CRISPR/Cas9-based epigenomic editing system. The delivery of the CRISPR/Cas9-based epigenomic editing system may be the transfection or electroporation of the CRISPR/Cas9-based epigenomic editing system as one or more nucleic acid molecules that is expressed in the cell and delivered to the surface of the cell. The CRISPR/Cas9-based epigenomic editing system protein may be delivered to the cell. The nucleic acid molecules may be electroporated using BioRad Gene Pulser Xcell or Amaxa Nucleofector IIb devices or other electroporation device. Several different buffers may be used, including BioRad electroporation solution, Sigma phosphate-buffered saline product # D8537 (PBS), Invitrogen OptiMEM I (OM), or Amaxa Nucleofector solution V (N.V.). Transfections may include a transfection reagent, such as Lipofectamine 2000.

The vector encoding a CRISPR/Cas9-based epigenomic editing system protein may be delivered to the modified target cell in a tissue or subject by DNA injection (also referred to as DNA vaccination) with and without in vivo electroporation, liposome mediated, nanoparticle facilitated, and/or recombinant vectors. The recombinant vector may be delivered by any viral mode. The viral mode may be recombinant lentivirus, recombinant adenovirus, and/or recombinant adeno-associated virus.

The nucleotide encoding a CRISPR/Cas9-based epigenomic editing system protein may be introduced into a cell to induce gene expression of the target gene. For example, one or more nucleotide sequences encoding the CRISPR/Cas9-based epigenomic editing system directed towards a target gene may be introduced into a mammalian cell. Upon delivery of the CRISPR/Cas9-based epigenomic editing system to the cell, and thereupon the vector into the cells of the mammal, the transfected cells will express the CRISPR/Cas9-based epigenomic editing system. The CRISPR/Cas9-based epigenomic editing system may be administered to a mammal to induce or modulate gene expression of the target gene in a mammal. The mammal may be human, non-human primate, cow, pig, sheep, goat, antelope, bison, water buffalo, bovids, deer, hedgehogs, elephants, llama, alpaca, mice, rats, or chicken, and preferably human, cow, pig, or chicken.

Methods of introducing a nucleic acid into a host cell are known in the art, and any known method can be used to introduce a nucleic acid (e.g., an expression construct) into a cell. Suitable methods include, include e.g., viral or bacteriophage infection, transfection, conjugation, protoplast fusion, lipofection, electroporation, calcium phosphate precipitation, polyethyleneimine (PEI)-mediated transfection, DEAE-dextran mediated transfection, liposome-mediated transfection, particle gun technology, calcium phosphate precipitation, direct micro injection, nanoparticle-mediated nucleic acid delivery, and the like. In some embodiments, the composition may be delivered by mRNA delivery and ribonucleoprotein (RNP) complex delivery.

11. KITS

Provided herein is a kit, which may be used in high throughput screening of regulatory elements of a target gene. The kit comprises a composition for epigenomic editing, as described above, and instructions for using said composition. Instructions included in kits may be affixed to packaging material or may be included as a package insert. While the instructions are typically written or printed materials they are not limited to such. Any medium capable of storing such instructions and communicating them to an end user is contemplated by this disclosure. Such media include, but are not limited to, electronic storage media (e.g., magnetic discs, tapes, cartridges, chips), optical media (e.g., CD ROM), and the like. As used herein, the term "instructions" may include the address of an internet site that provides the instructions.

The composition for epigenomic editing may include a modified lentiviral vector and a nucleotide sequence encoding a CRISPR/Cas9-based epigenomic editing system, as described above. The CRISPR/Cas9-based epigenomic editing system may include CRISPR/Cas9-based activation or repression system, as described above, that specifically binds and targets a cis-regulatory region or trans-regulatory region of a target gene and modulates gene expression of a target gene or target a target enhancer or target regulatory element. The CRISPR/Cas9-based epigenomic editing system, as described above, may be included in the kit to specifically bind and target a particular regulatory region of the target gene.

12. EXAMPLES

The foregoing may be better understood by reference to the following examples, which are presented for purposes of illustration and are not intended to limit the scope of the invention.

Example 1 gRNA Library Generation gRNA Library. Two libraries of gRNAs targeting DNase I hypersensitivity sites (DHSs), which are strong predictors of gene regulatory element activity, were developed within ~5 megabase regions surrounding target genes of interest. The gRNA libraries were generated using DNase-seq data generated by us as part of the ENCODE Consortium, which were derived from the cell lines in which we will do the screening. The DHSs were used as input to search for gRNA sequences using a modified version of GT-Scan software. Identified gRNAs were then aligned to the genome using Bowtie to identify possible off-target binding locations. For each DHS, the top 50 gRNAs ranked based on predicted off-targets were selected, which resulted in 10,739 gRNAs in a 4.5 megabase region surrounding the 3-globin locus (HBE1 locus) and 10,137 gRNAs in a 5 megabase region surrounding the HER2 gene. Another ~2,000 gRNAs targeting non-DHS regions were included as controls. These sequences were synthesized in parallel on arrays, cloned as a pool into a lentiviral transfer plasmid, and packaged into lentivirus for pooled delivery to the cell type of interest.

Example 2 gRNA Library Cell Lines and Screening

To screen these libraries, two cell lines were used. For the globin-targeting library, the K562 chronic myelogenous leukemia cell line was used because it expresses all the genes in the globin locus. Also, the globin locus has well-characterized regulatory elements that serve as a positive control for this technology. This line was modified by tagging hemoglobin subunit epsilon (HBE1) with red fluorescent protein. This allows monitoring of gene expression through fluorescence intensity using flow cytometry.

For the HER2 targeting library, the A431 cells (which are used in studies of the cell cycle and cancer-associated cell signaling pathways since they express abnormally high levels of the Epidermal growth factor receptor (EGFR)) were used. The SKBR3 adenocarcinoma HER2 over-expressing line was also used. This line has multiple copies of HER2 duplicated in tandem in its genome, providing an ideal target for identifying regions of the genome in this area that modulate its expression. Modulation of HER2 levels by gRNA library members was evaluated by cell surface immunostaining.

Both cell types were also transduced with a lentivirus to stably express a suppressor dCas9-KRAB fusion protein. For both libraries, cells with differential target gene expression were isolated by fluorescence-activated cell sorting and the responsible gRNAs recovered from the lentiviral vector in the genomic DNA by PCR. These recovered libraries were then subjected to high-throughput next generation DNA sequencing to identify the genomic regulatory elements associated with altering the expression of each gene.

Example 3

Individual gRNA Validation Methods

The same modified cell lines used in the screen are used for the individual gRNA validations. For the HBE1 dCas9$^{KRAB}$ screen, K562s with an HBE1-2A-mCherry reporter and constitutively expressing dCas9$^{KRAB}$ were used. For the HER2 dCas9$^{KRAB}$ screen, A431 s with constitutively expressing dCas9$^{KRAB}$ were used. For the HER2 dCas9$^{p300}$ screen, HEK293 Ts with constitutively expressing dCas9$^{p300}$ were used. The cells were transduced with individual gRNAs and after 2 days were selected with Blasticidin S (ThermoFisher, A1113903). Cells were selected for 12 days for the HBE1 dCas9$^{KRAB}$ screen hits, 9 days for HER2 dCas9$^{KRAB}$ screen hits, and 7 days for the HER2 dCas9$^{p300}$ screen hits.

For all screen validations, mRNA expression was done in triplicate. Total mRNA was harvested from cells using the Qiagen RNeasy Plus Mini kit (Qiagen, 74136). cDNA was generated using the SuperScript VILO cDNA Synthesis Kit (ThermoFisher, 11754250). qRT-PCR was performed using the Perfecta SYBR Green FastMix (Quanta Biosciences, 95072-012) with the FX96 Real-Time PCR Detection System (Bio-Rad) with the primers listed in Table 1. The results are expressed as fold-increase mRNA expression of the gene of interest normalized to GAPDH expression by the ΔΔCt method.

TABLE 1

| Primer Name | Sequence | SEQ ID NO: | Annealing Temp (° C.) |
|---|---|---|---|
| hGAPDH fwd | CAATGACCCCTTCATTGACC | 6 | 53 |
| hGAPDH rev | TTGATTTTGGAGGGATCTCG | 7 | 53 |
| hERBB2 fwd | AGACCATGTCCGGGAAAACC | 8 | 57.5 |
| hERBB2 Rev | GCCAGCCCGAAGTCTGTAAT | 9 | 57.5 |
| hHBG1 fwd | GCTGAGTGAACTGCACTGTGA | 10 | 62 |
| hHBG1 rev | GAATTCTTTGCCGAAATGGA | 11 | 62 |
| hHBE1 fwd | TCACTAGCAAGCTCTCAGGC | 12 | 58 |
| hHBE1 rev | AACAACGAGGAGTCTGCCC | 13 | 58 |

For flow cytometry analysis of the HBE1 dCas9$^{KRAB}$ screen validations, cells were harvested, washed once in PBS, and resuspended in PBS. For the HER2 dCas9$^{KRAB}$ and dCas9$^{p300}$ screen validations, cells were harvested, washed once with PBS, then resuspended in 5% goat serum in PBS and blocked for 30 minutes at 4° C. HER2 primary antibody (Monoclonal Mouse IgG2B Clone 191924, R&D Systems) was then added and allowed to incubated for 30 minutes at 4° C. Cells were then washed once in 5% goat serum in PBS. Secondary antibody (Goat anti-Mouse IgG2b Secondary Antibody, Alexa Fluor® 488 conjugate, ThermoFisher A-21141) was then added and cells were allowed to incubate at 4° C. for 30 minutes. Cells were then washed once in PBS. All cells were analyzed using the MACSQuant VYB flow cytometer (Miltenyi Biotec).

Example 4

HBE1 Regulatory Element Screening with CRISPR/dCas9-$^{KRAB}$ Repressor

Figure 2A:
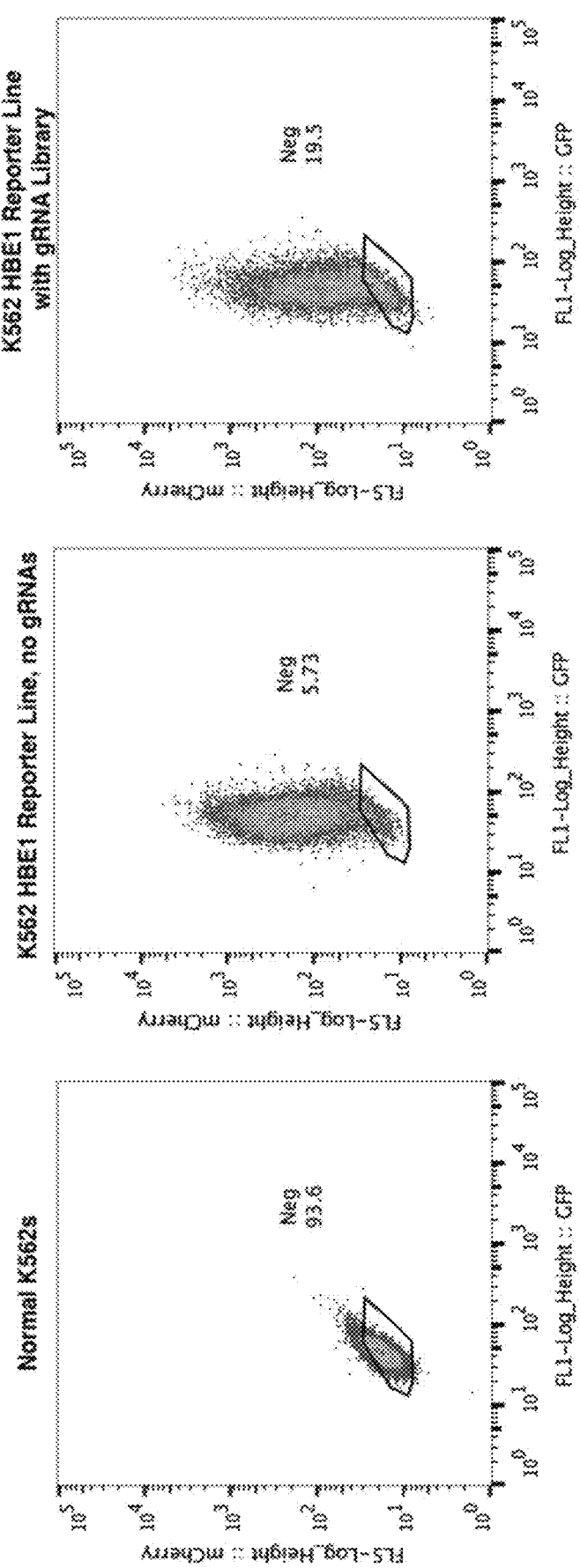
FIGS. 2A-2C show generation of a reporter cell line.
Figure 2B:
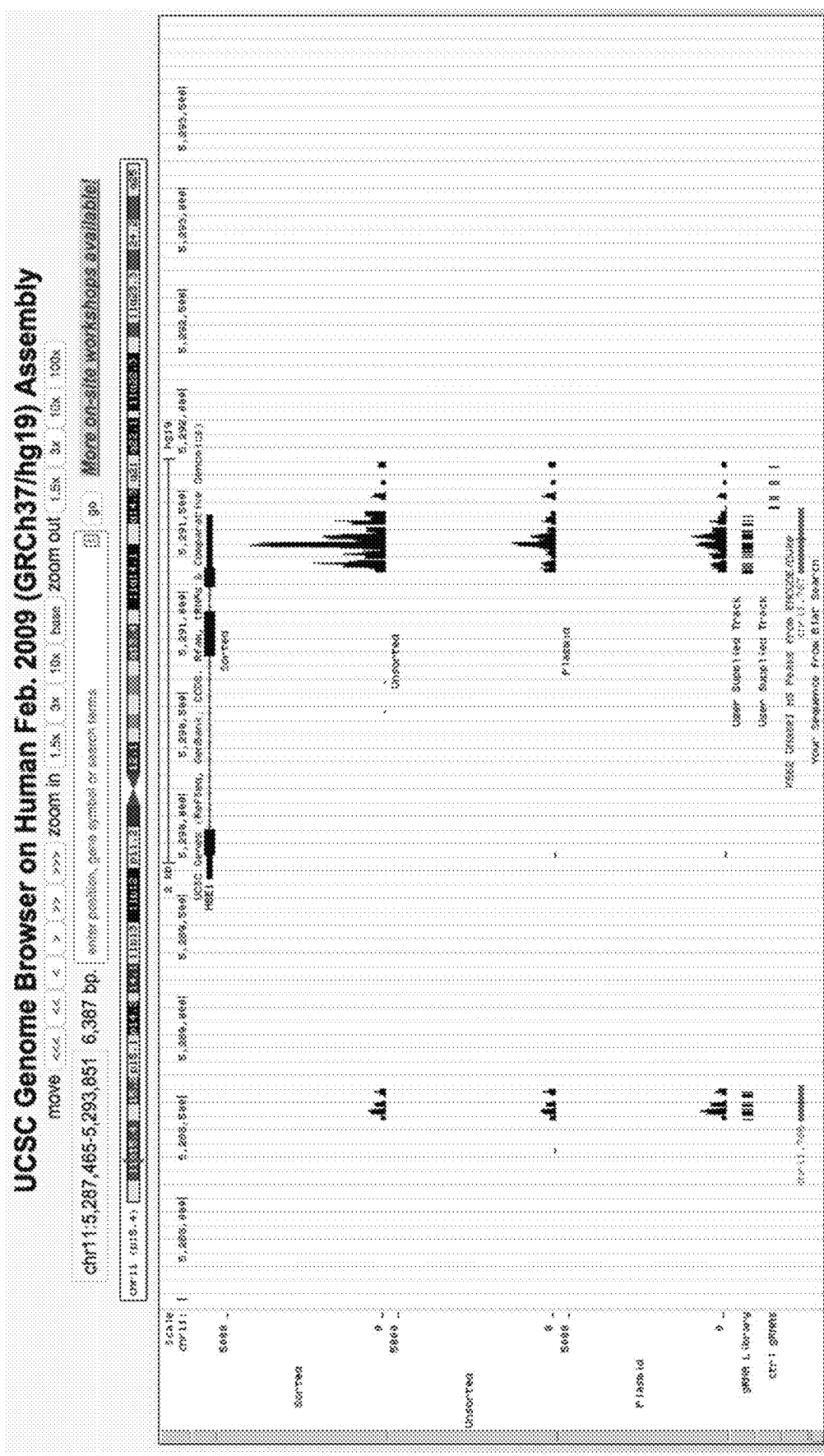
Figure 2C:
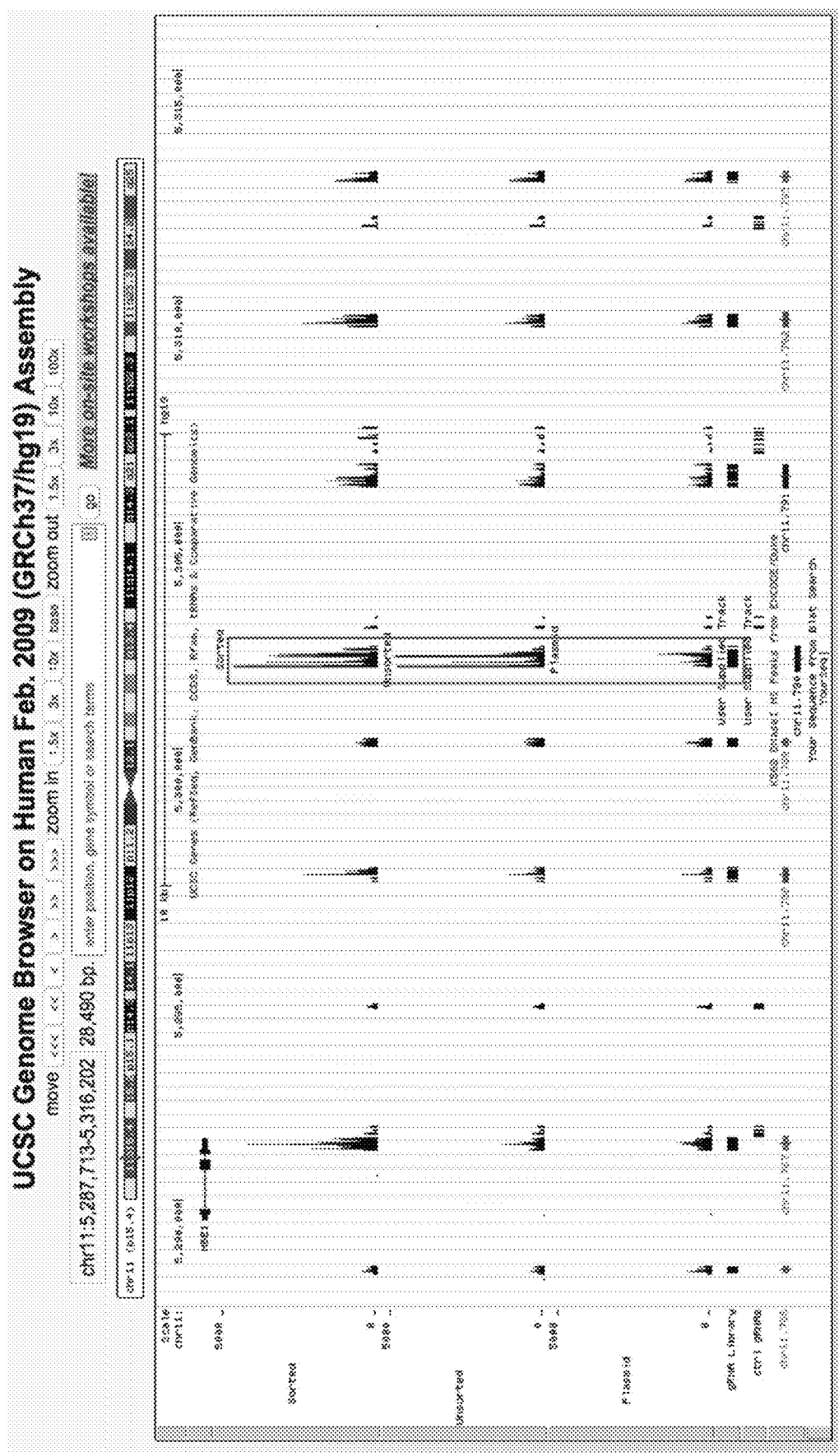
Figure 3A:
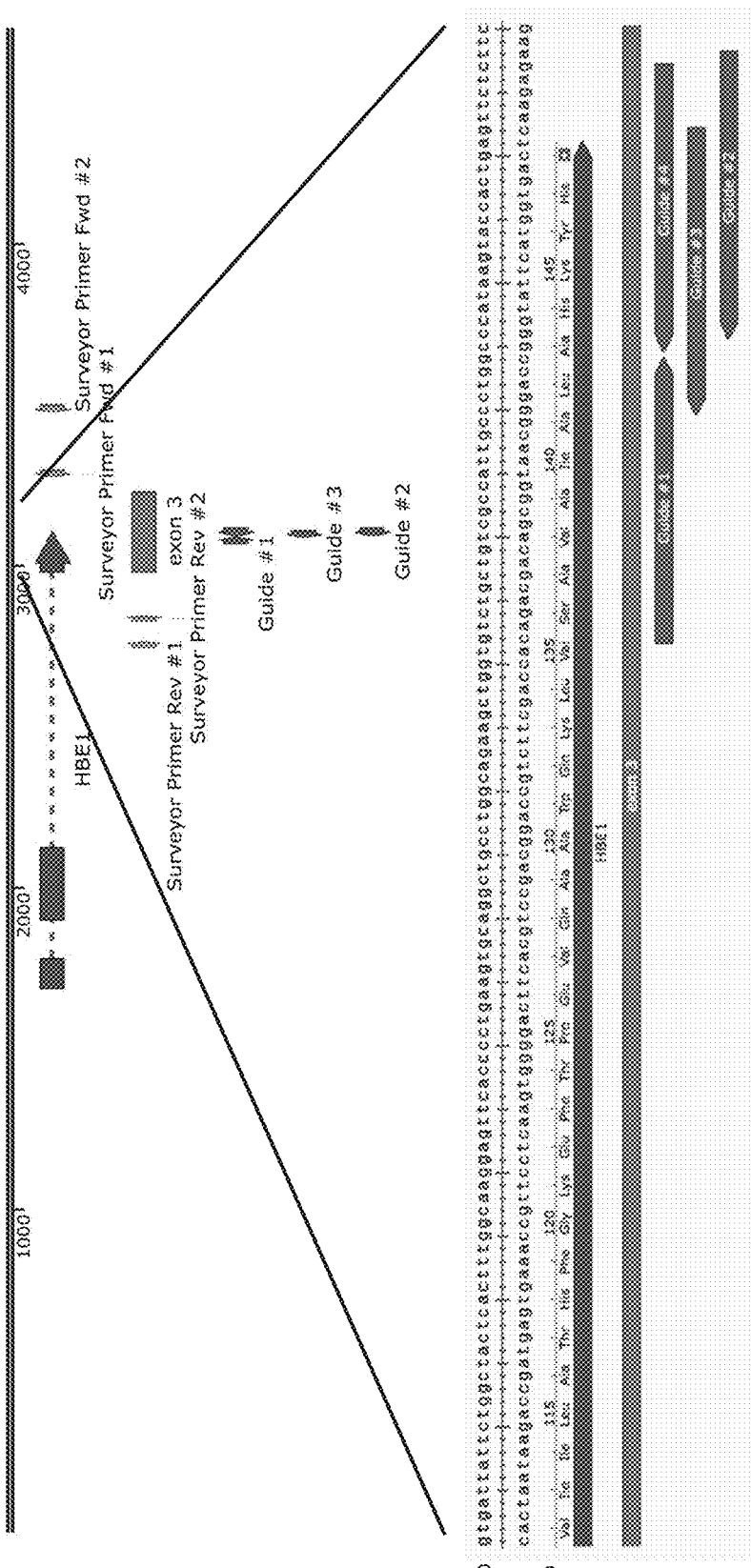
FIGS. 3A-3C show the validation of a human K562 erythroid cell line engineered to express red fluorescence protein (RFP) from the HBE1 (epsilon globin) endogenous gene locus, as well as a CRISPR/dCas9KRAB repressor.
Figure 3B:
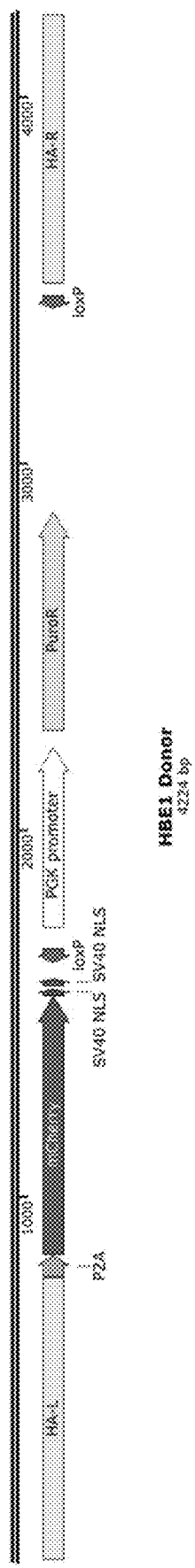
Figure 3C:
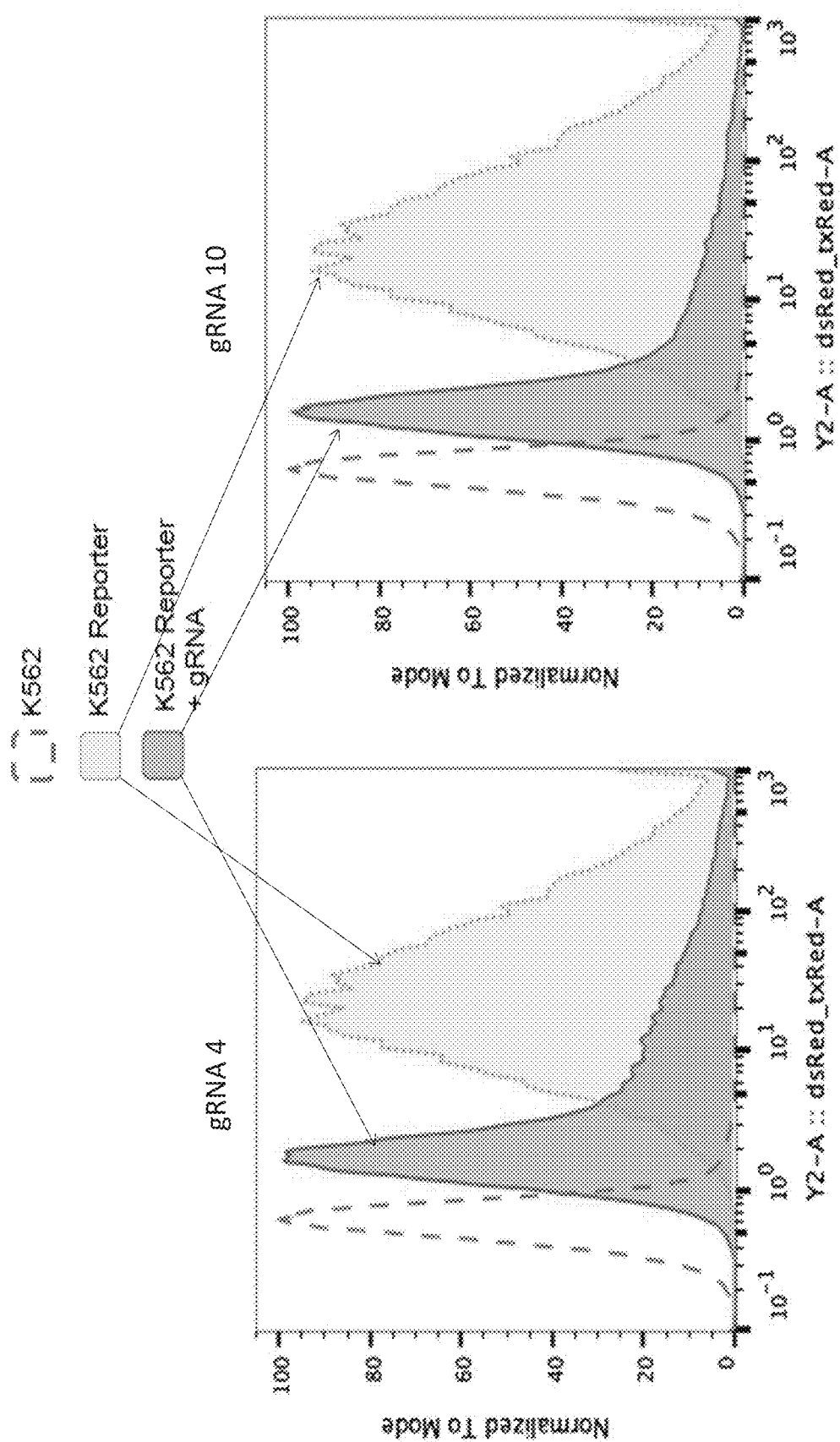
Figure 4:
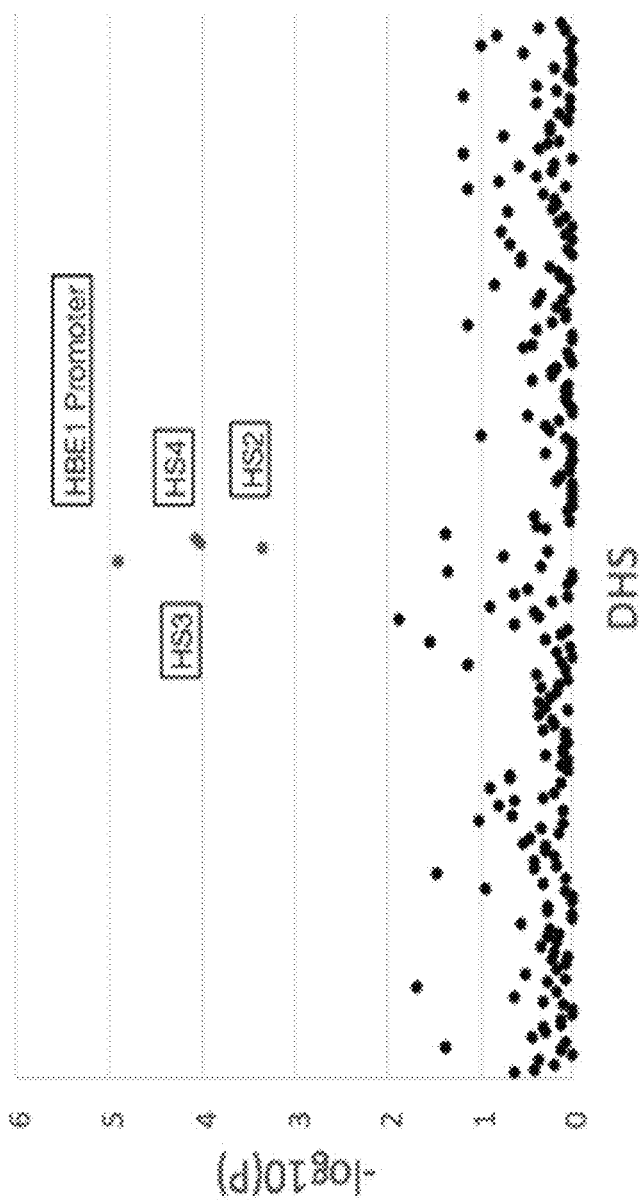
FIG. 4 shows a Manhattan plot showing the results of a high-throughput screen for regulatory elements in the 4.5 Mb surrounding the globin locus using the dCas9$^{KRAB}$ repressor. Every DHS in this region was targeted by up to 50 gRNAs each. Enriched gRNAs following selection for decreased HBE expression were found only in the well-known promoter and enhancers (HS2-4) of this gene.
Figure 5A:
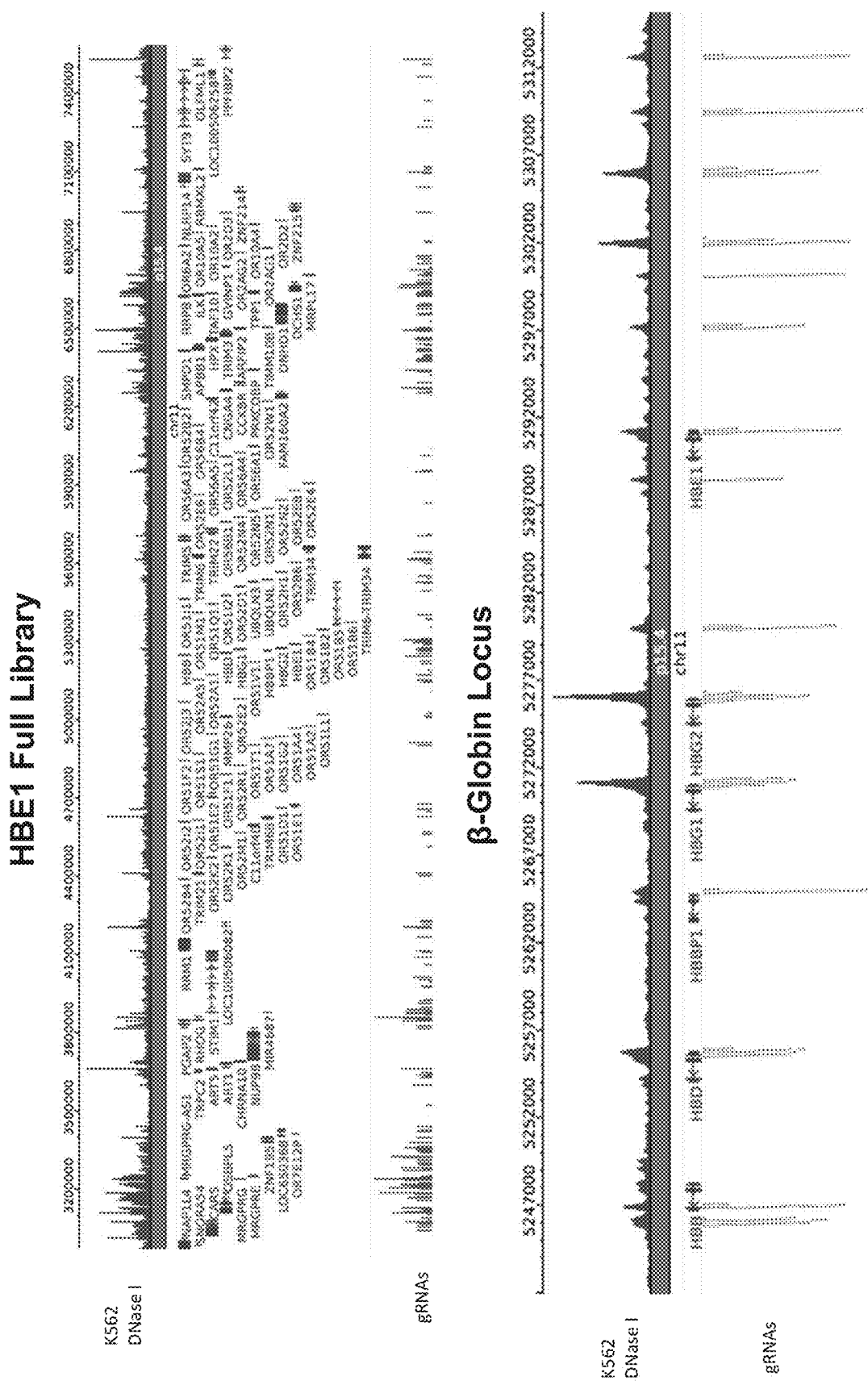
FIGS. 5A-5D show HBE1 dCas9$^{KRAB}$ screening.
Figure 5C:
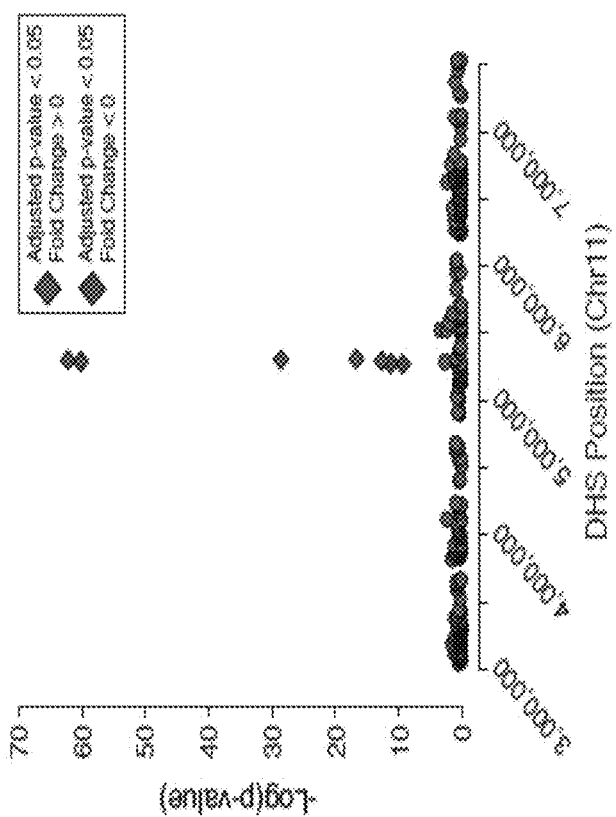
Figure 5B:
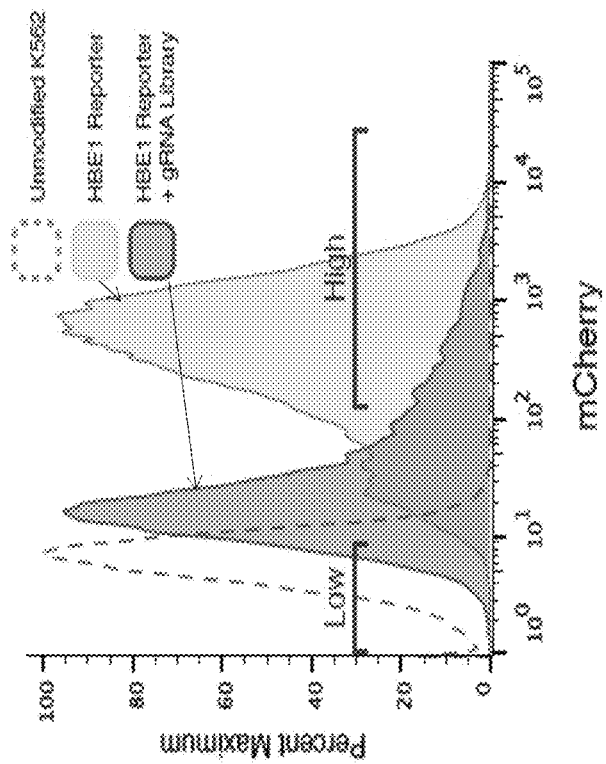
Figure 5D:
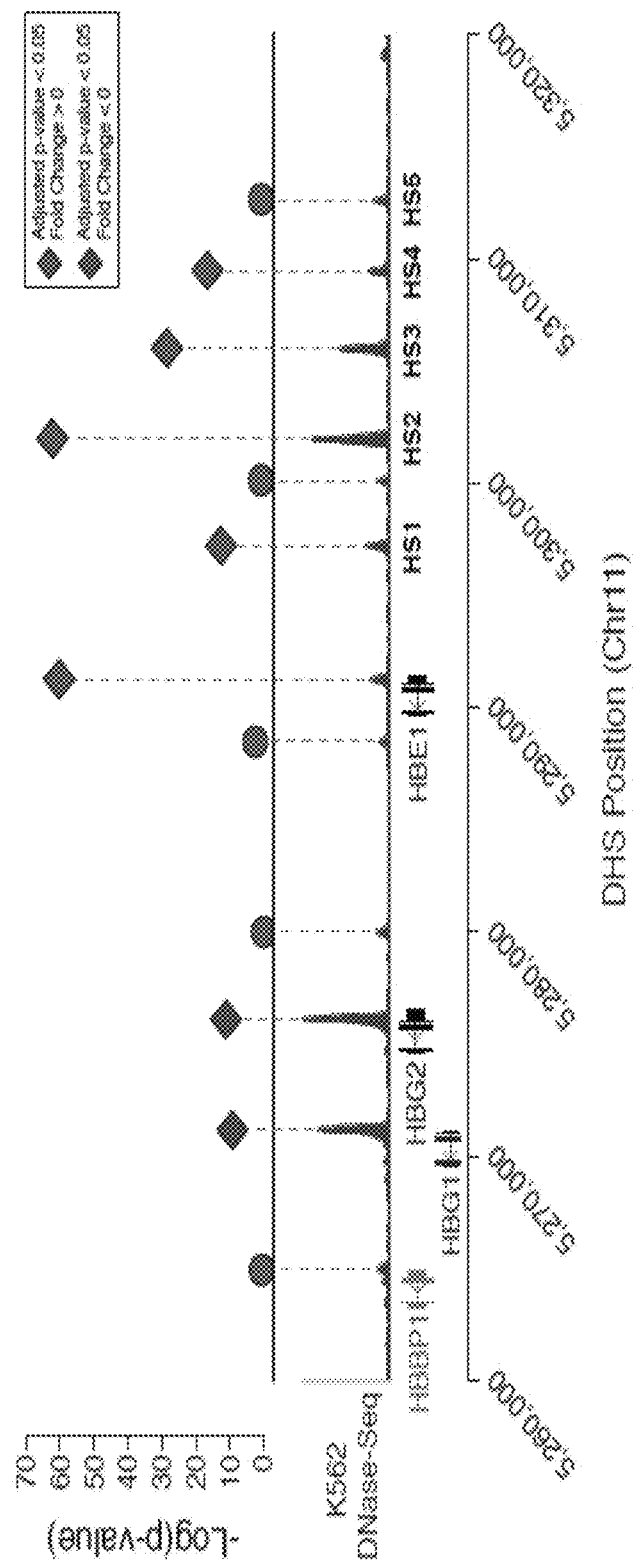

As described above, the human K562 erythroid cell line was engineered to express red fluorescence protein (RFP) from the HBE1 (epsilon globin) endogenous gene locus, as well as a CRISPR/dCas9-KRAB repressor. See FIGS. 2A-2C. FIGS. 3A-3C show the validation of this reporter line. After lentiviral transduction of a library of 10,739 gRNAs targeting all DNase I hypersensitive sites in a 5 megabase window around HBE1 into K562 cells, cells were sorted with diminished HBE1 expression according to a fluorescent reporter that was introduced into the gene by genome editing. These RFP-negative cells were isolated by fluorescence-activated cell sorting, and the gRNAs within in these cells were recovered by PCR from the lentiviral vector. The fraction of RFP-negative cells increased from 6% to 20%. The gRNAs were then recovered from the HBE1-depleted cells and sequenced to determine their identity. High-throughput sequencing of the sgRNA library showed enrichment of sequences targeting known regulatory elements at the HBE1 promoter and the HS1 and HS2 enhancers, demonstrating successful identification of specific known regulator elements in their natural chromosomal location from this complex library (FIGS. 4 and 5C-5C).

Figure 6B:
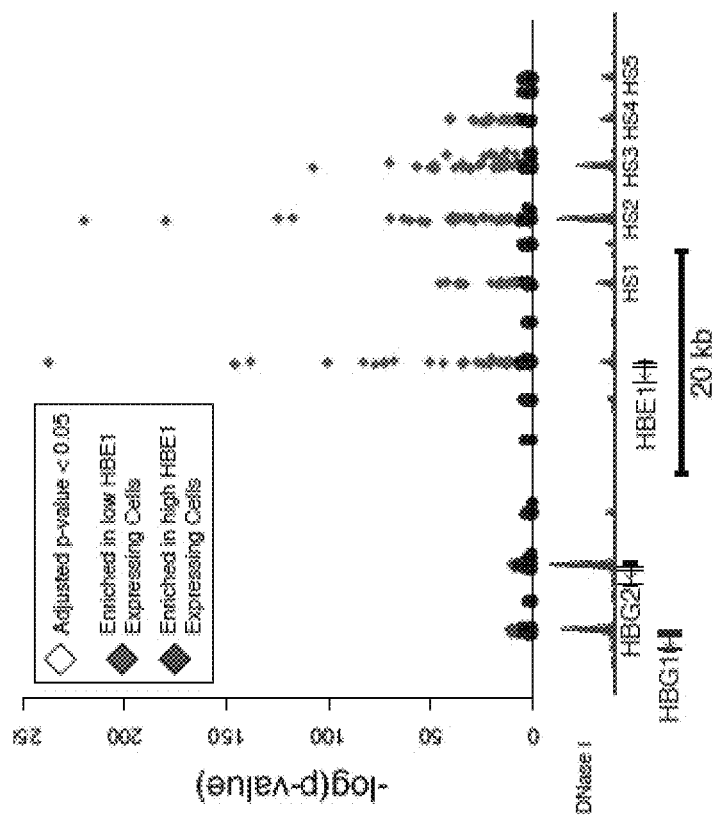
FIGS. 6A-6C show HBE1 screen gRNA enrichment.
Figure 6A:
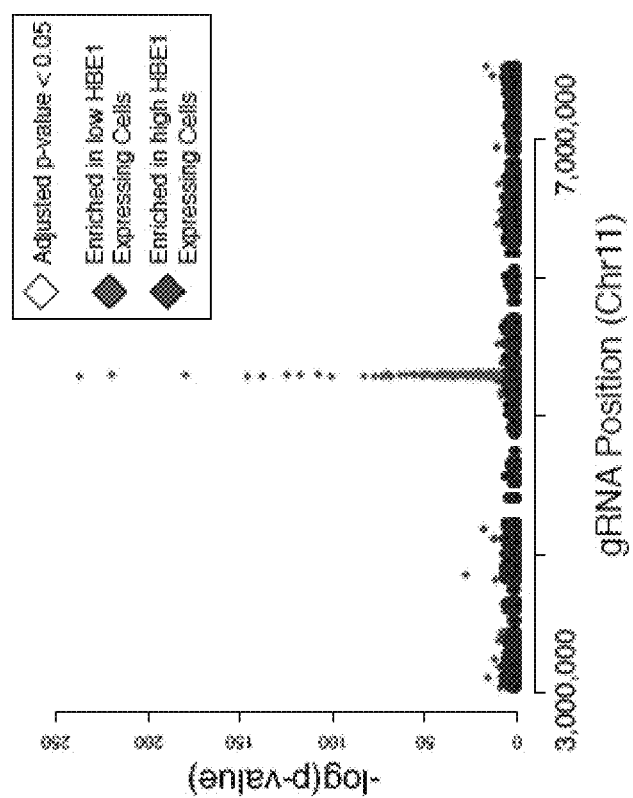
Figure 6C:
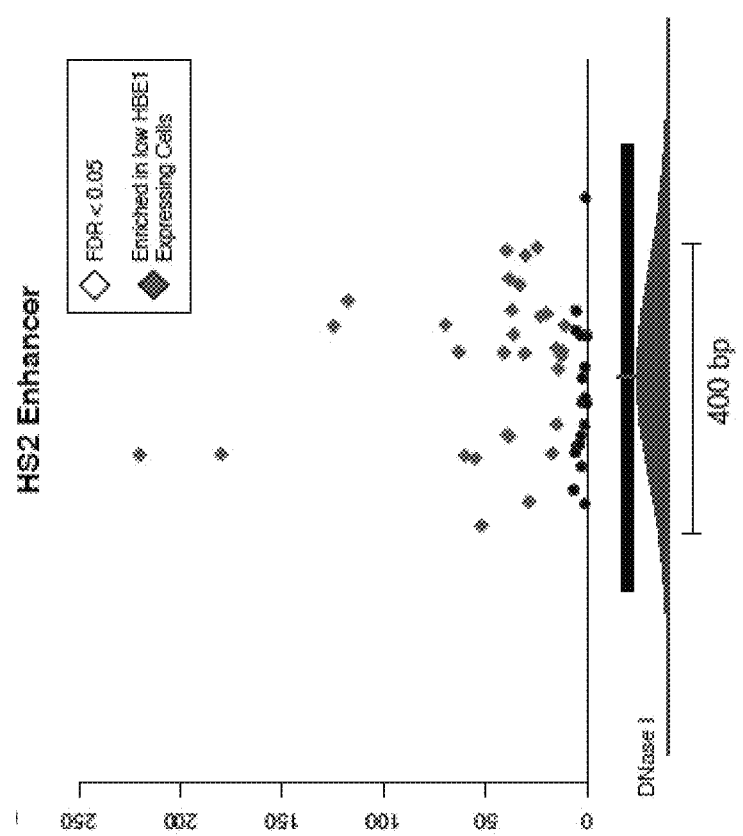

The enrichment of individual gRNAs across the entire library surrounding the 4.5 Mb region surrounding HBE1 is shown in further detail in FIG. 6A. Enriched gRNAs were determined using differential expression analysis instead of grouping gRNAs per DHS and performing linear regression. FIG. 6B shows a closer view of the globin-locus control region (HS1-5). Significant enrichment of gRNAs was found in the promoter region of HBE1 as well as HS1-4. Additionally, gRNAs targeting the promoter of nearby HBG1/2 genes were enriched in the population of cells expressing high levels of HBE1. FIG. 6C shows enriched gRNAs within the HS2 enhancer. Table 2 shows sgRNAs that were identified, wherein the bolded nucleotides indicate the protospacer. dCas9-$^{KRAB}$ directed to the HS2 enhancer with a single gRNA specifically silenced multiple globin genes located 10-150 kb away. FIGS. 41-48 show the enrichment of gRNAs.

Figure 7B:
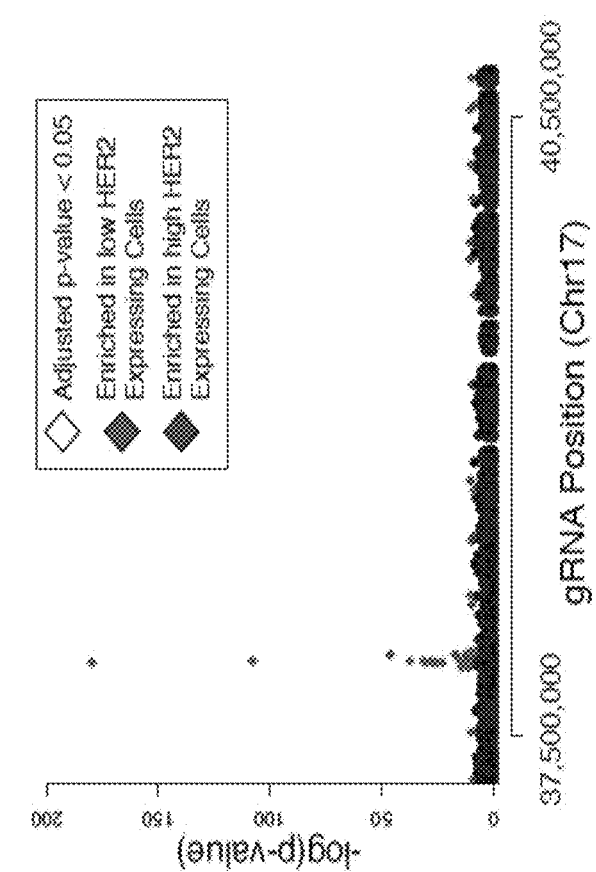
FIGS. 7A-7D shows the screening of HER2 enhancers with HER2 dCas9$^{KRAB}$.
Figure 7A:
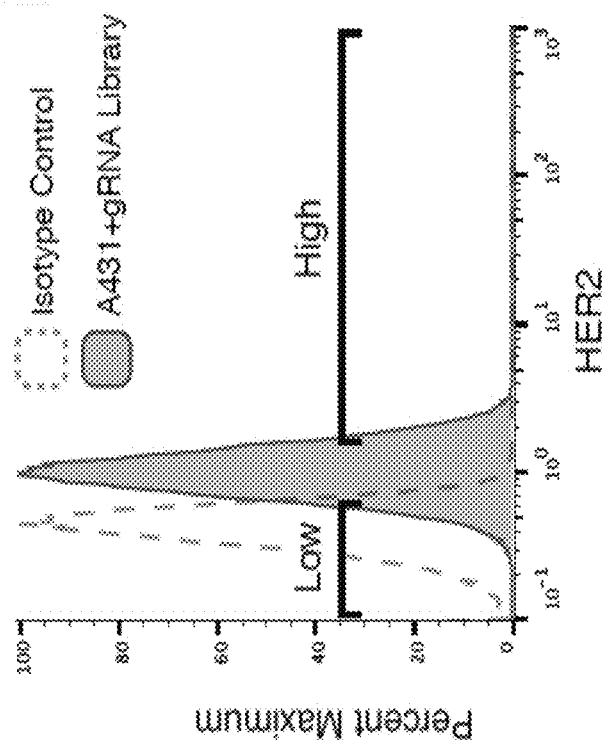
Figure 7C:
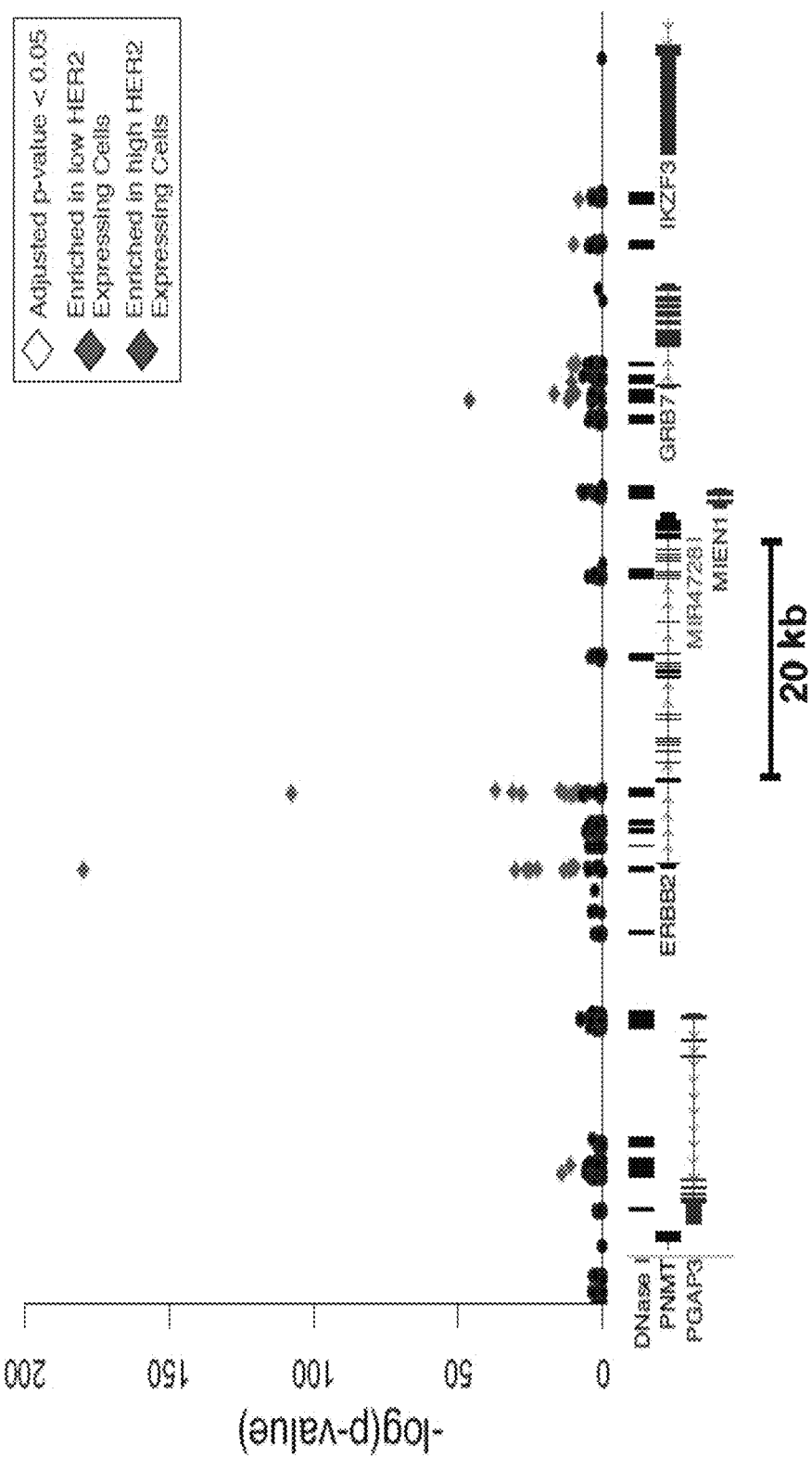
Figure 7D:
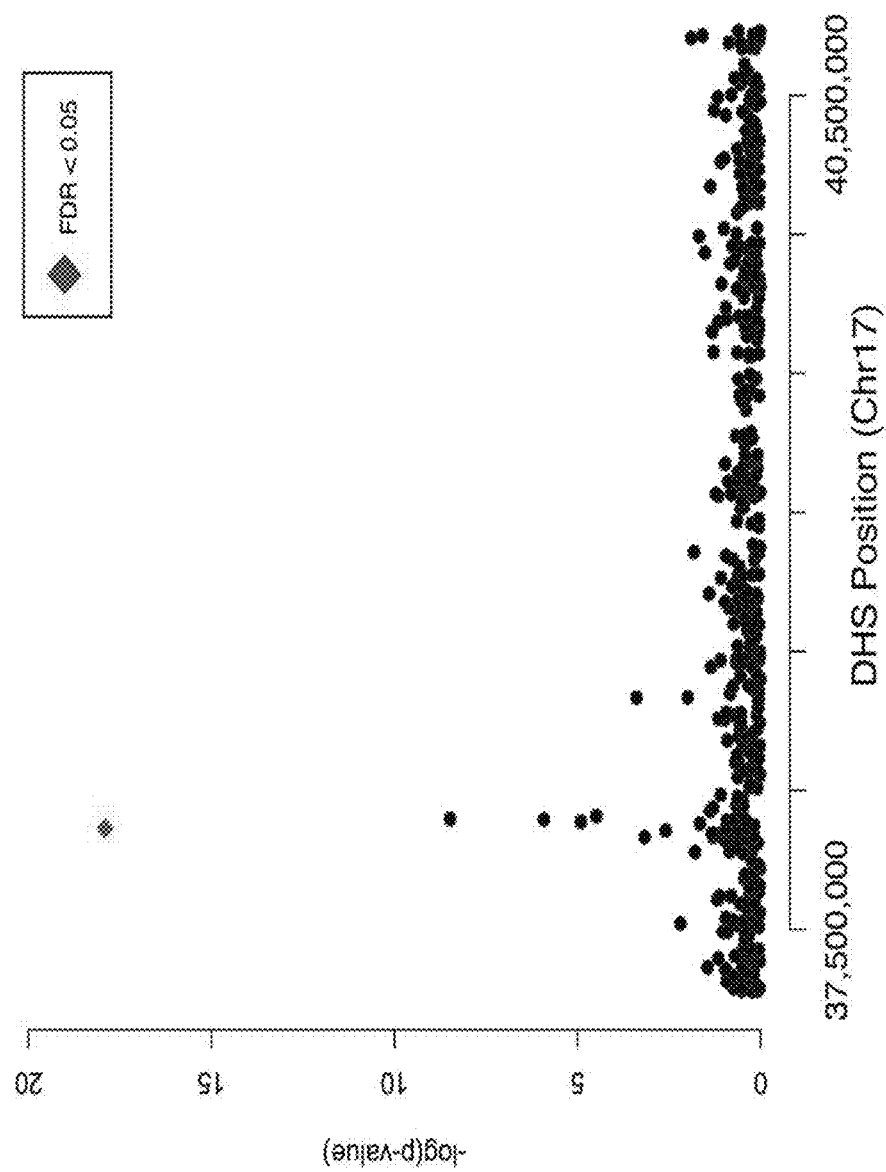

7B shows a Manhattan plot showing the results of a screen for regulatory elements in the 4 Mb surrounding the HER2 gene using the dCas9$^{KRAB}$ repressor. FIG. 7C shows a zoomed view of the HER2 region. When comparing high and low expressing HER2 cell populations, gRNAs are enriched in the promoter and an intronic DHS of HER2, as welling DHSs including the promoter of GRB7, an adapter protein that associates with tyrosine kinases. FIG. 7D shows a Manhattan plot showing the results of a high-throughput screen for regulatory elements in the 4 Mb surrounding the globin locus (HBE1 gene) of 12,189 gRNAs targeting 433 DHSs (limit 30 gRNAs per DHS) using the dCas9$^{KRAB}$ repressor.

Figure 8A:
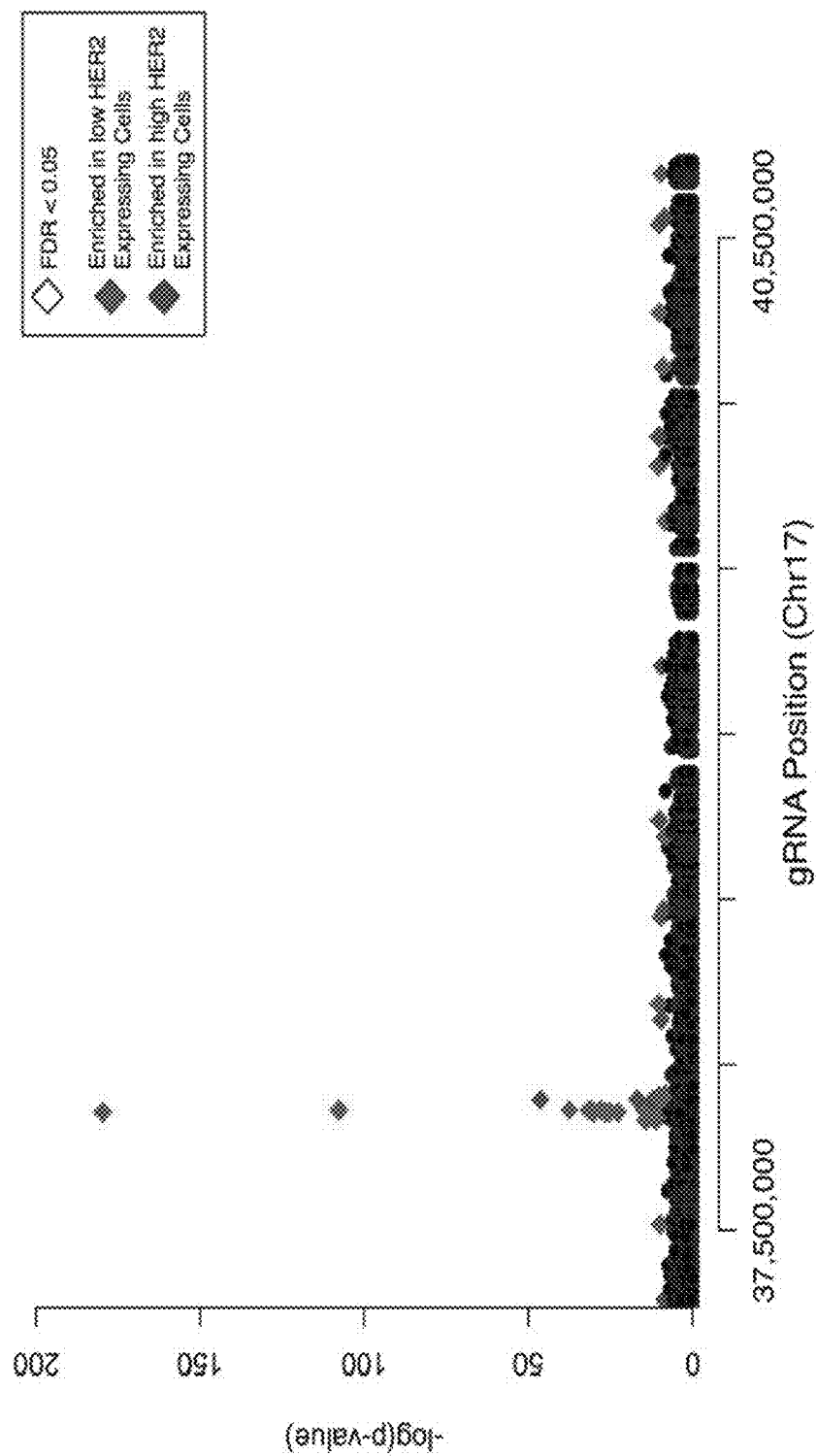
Figure 8B:
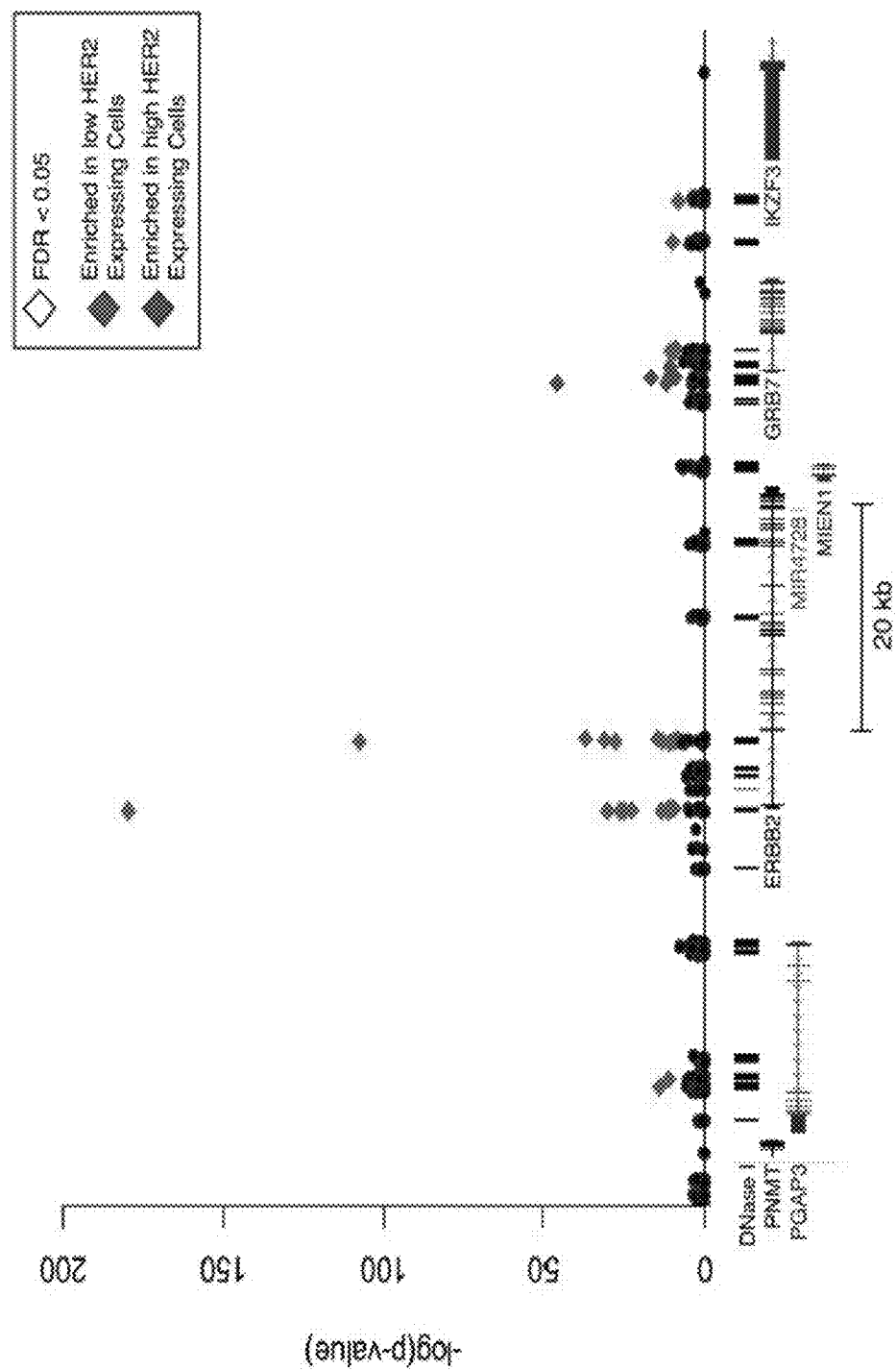

The enrichment of individual gRNAs across the entire library surrounding the 4 Mb region surrounding HER2 is shown in FIG. 8A. FIG. 8B shows enrichment of gRNAs near HER2. FIG. 8C shows enriched gRNAs by the HER2 promoter.

Modulation of HER2 levels by gRNA library members was evaluated by cell surface immunostaining using a cell surface antibody. See Table 3, where the protospacer sequence is bolded. FIGS. 49-58 show enrichment data using combinations of gRNAs (i.e., the combinations of 1549.1 and 1553.1, 1549.1 and 1553.2, 1543.1 and 1544.1, 1553.1 and 1562.1, 1553.2 and 1562.1, 1562.1 and 1562.1, 1553.2, 1543.1, 1544.1, 1561.1, and 1562.1, 1559.2 and 1553.1).

TABLE 2

K562-dCas9$^{KRAB}$ HBE1 Screen Validation sgRNAs

| Name | Target | SEQ ID NO: | sgRNA Sequence |
|---|---|---|---|
| 783_784 | HBG1/2 promoter | 14 | GGCAAGGCTGGCCAACCCATGTTTTAGAGCTAGAAATAGCAAGTTAAAATAAGGCTAGTCCGTTATCAACTTGAAAAAGTGGCACCGAGTCGGTGC |
| 787 | HBE1 promoter | 15 | CGGACCTGACTCCACCCCTGGTTTTAGAGCTAGAAATAGCAAGTTAAAATAAGGCTAGTCCGTTATCAACTTGAAAAAGTGGCACCGAGTCGGTGC |
| 788 | HS1 | 16 | ACTATGCTGAGCTGTGATGAGTTTTAGAGCTAGAAATAGCAAGTTAAAATAAGGCTAGTCCGTTATCAACTTGAAAAAGTGGCACCGAGTCGGTGC |
| 790 | HS2 | 17 | TGCCCTGTAAGCATCCTGCTGTTTTAGAGCTAGAAATAGCAAGTTAAAATAAGGCTAGTCCGTTATCAACTTGAAAAAGTGGCACCGAGTCGGTGC |
| 791 | HS3 | 18 | CCATGAGTAGAGGGCAGACAGTTTTAGAGCTAGAAATAGCAAGTTAAAATAAGGCTAGTCCGTTATCAACTTGAAAAAGTGGCACCGAGTCGGTGC |
| 792 | HS4 | 19 | TACTAGGCTGACTCACTCCAGTTTTAGAGCTAGAAATAGCAAGTTAAAATAAGGCTAGTCCGTTATCAACTTGAAAAAGTGGCACCGAGTCGGTGC |

Example 5

HER2 Regulatory Element Screening with CRISPR/dCas9-$^{KRAB}$ Repressor

The A431 cells were used to screen for HER2 regulatory elements. Modulation of HER2 levels by gRNA library members was evaluated by cell surface immunostaining using a cell surface antibody. FIG. 7A shows flow cytometry data of dCas9$^{KRAB}$ repressing HER2 in A431 cells measured via cell surface staining with a monoclonal antibody. FIG.

TABLE 3

A431-dCas9$^{KRAB}$ HER2 Screen Validation sgRNAs

| Name | SEQ ID NO: | sgRNA Sequence |
|---|---|---|
| 1549.1 | 20 | GGTGCGTCCCTCCTAGCGCCGTTTTAGAGCTAGAAATAGCAAGTTAAAATAAGGCTAGTCCGTTATCAACTTGAAAAAGTGGCACCGAGTCGGTGC |
| 1553.1 | 21 | TACCCCGGCGCCCCTCACCAGTTTTAGAGCTAGAAATAGCAAGTTAAAATAAGGCTAGTCCGTTATCAACTTGAAAAAGTGGCACCGAGTCGGTGC |
| 1553.2 | 22 | CTTTGGCGCATGCTTCACCCGTTTTAGAGCTAGAAATAGCAAGTTAAAATAAGGCTAGTCCGTTATCAACTTGAAAAAGTGGCACCGAGTCGGTGC |
| 1543.1 | 23 | AAGGCCTCAAACATTCCCCTGTTTTAGAGCTAGAAATAGCAAGTTAAAATAAGGCTAGTCCGTTATCAACTTGAAAAAGTGGCACCGAGTCGGTGC |
| 1544.1 | 24 | GCGTTAGGTGGTGTGGTCTAGTTTTAGAGCTAGAAATAGCAAGTTAAAATAAGGCTAGTCCGTTATCAACTTGAAAAAGTGGCACCGAGTCGGTGC |
| 1561.1 | 25 | GTGCCTCCCCCATTCCGCTCGTTTTAGAGCTAGAAATAGCAAGTTAAAATAAGGCTAGTCCGTTATCAACTTGAAAAAGTGGCACCGAGTCGGTGC |
| 1769.1 | 26 | TTCCCACACCCCGTTCCTGGGTTTTAGAGCTAGAAATAGCAAGTTAAAATAAGGCTAGTCCGTTATCAACTTGAAAAAGTGGCACCGAGTCGGTGC |
| 1592.1 | 27 | AACCAGGTGCCCACCCGGGCGTTTTAGAGCTAGAAATAGCAAGTTAAAATAAGGCTAGTCCGTTATCAACTTGAAAAAGTGGCACCGAGTCGGTGC |
| 1856.1 | 28 | TCGCCTGCAGCCTTACGGGCGTTTTAGAGCTAGAAATAGCAAGTTAAAATAAGGCTAGTCCGTTATCAACTTGAAAAAGTGGCACCGAGTCGGTGC |
| 1562.1 | 29 | TCCTTGGCTAACTCCAGGCTGTTTTAGAGCTAGAAATAGCAAGTTAAAATAAGGCTAGTCCGTTATCAACTTGAAAAAGTGGCACCGAGTCGGTGC |

TABLE 3-continued

A431-dCas9<sup>KRAB</sup> HER2 Screen Validation sgRNAs

| Name | SEQ ID NO: | sgRNA Sequence |
|---|---|---|
| 1826.1 | 30 | CGCGGCGCCGCTCTCCGCTGGTTTTAGAGCTAGAAA<br>TAGCAAGTTAAAATAAGGCTAGTCCGTTATCAACTT<br>GAAAAAGTGGCACCGAGTCGGTGC |
| 1559.2 | 31 | AGCCGGGTGTCCTGACGCTCGTTTTAGAGCTAGAAA<br>TAGCAAGTTAAAATAAGGCTAGTCCGTTATCAACTT<br>GAAAAAGTGGCACCGAGTCGGTGC |
| 1560.1 | 32 | GTTTAATTCGGGAAGAATGCGTTTTAGAGCTAGAAA<br>TAGCAAGTTAAAATAAGGCTAGTCCGTTATCAACTT<br>GAAAAAGTGGCACCGAGTCGGTGC |
| 1782.1 | 33 | AGCGCTCGATAAATACTTACGTTTTAGAGCTAGAAA<br>TAGCAAGTTAAAATAAGGCTAGTCCGTTATCAACTT<br>GAAAAAGTGGCACCGAGTCGGTGC |
| 1671.1 | 34 | TGTTGGGCATTAAGAGGGAGGTTTTAGAGCTAGAAA<br>TAGCAAGTTAAAATAAGGCTAGTCCGTTATCAACTT<br>GAAAAAGTGGCACCGAGTCGGTGC |
| 1556.1 | 35 | CATCGCGGCCGGCTCCGCTCGTTTTAGAGCTAGAAA<br>TAGCAAGTTAAAATAAGGCTAGTCCGTTATCAACTT<br>GAAAAAGTGGCACCGAGTCGGTGC |
| 1562.2 | 36 | TGACAGCAATAGTGGCCTACGTTTTAGAGCTAGAAA<br>TAGCAAGTTAAAATAAGGCTAGTCCGTTATCAACTT<br>GAAAAAGTGGCACCGAGTCGGTGC |
| 1612.1 | 37 | CAGGTTAGACTTACAAGGTGGTTTTAGAGCTAGAAA<br>TAGCAAGTTAAAATAAGGCTAGTCCGTTATCAACTT<br>GAAAAAGTGGCACCGAGTCGGTGC |
| 1535.1 | 38 | CTACTCCTTCCTCTTGAGACGTTTTAGAGCTAGAAA<br>TAGCAAGTTAAAATAAGGCTAGTCCGTTATCAACTT<br>GAAAAAGTGGCACCGAGTCGGTGC |

Figure 11A:
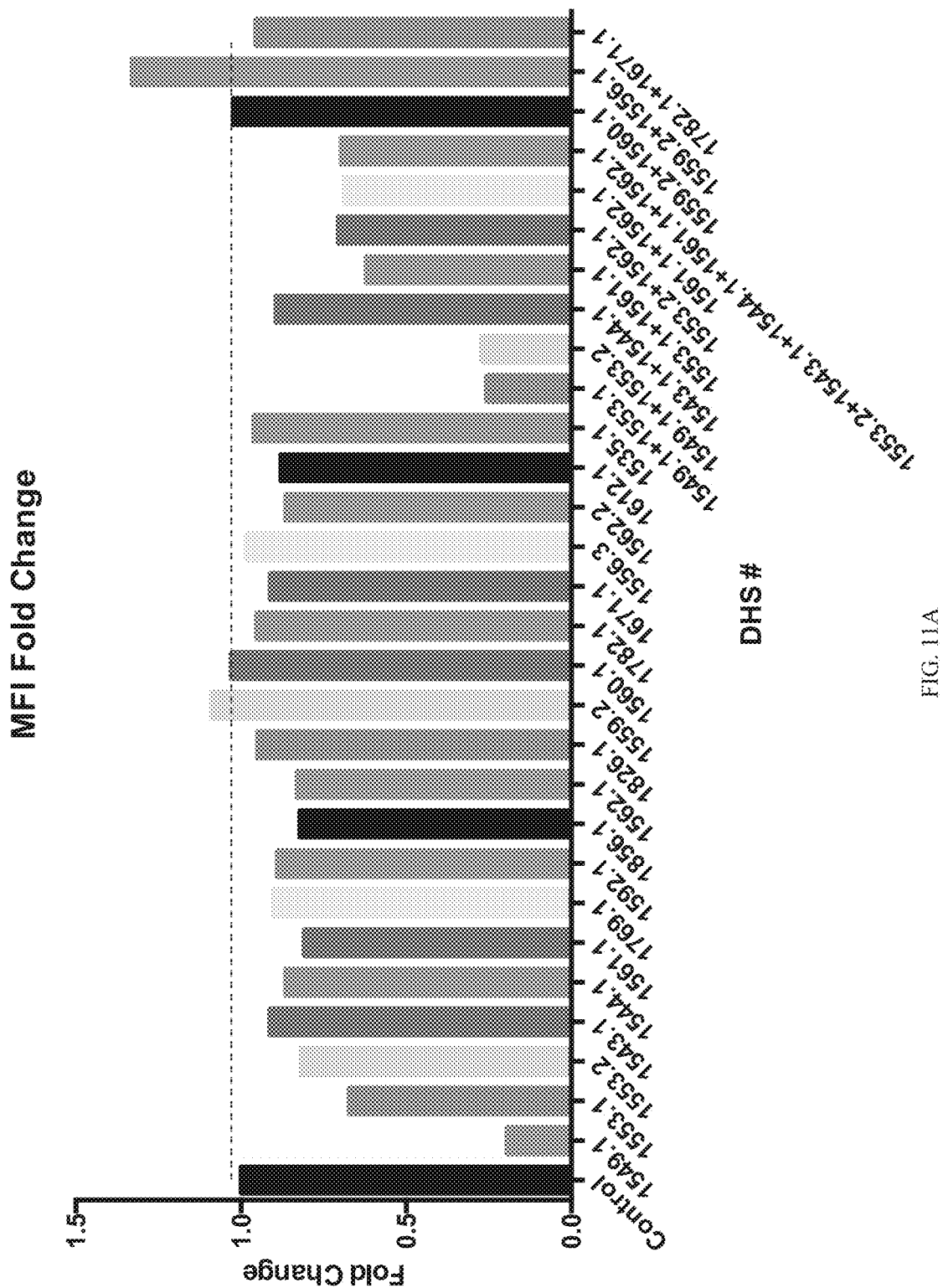
FIGS. 11A and 11B show the fold change in mean fluorescent intensity (FIG. 11A) and expression of HER2 mRNA (FIG. 11B) for individual hits (gRNAs 1549.1, 1553.1, 1553.2, 1543.1, 1544.1, 1561.1, 1769.1, 1592.1, 1856.1, 1562.1, 1826.1, 1559.2, 1560.1, 1782.1, 1671.1, 1556.1 ("1556.3"), 1562.2, 1612.1, and 1535.1) that were identified using the CRISPR/dCas9$^{KRAB}$ repression system and combinations of gRNAs (i.e., the combinations of 1549.1 and 1553.1, 1549.1 and 1553.2, 1543.1 and 1544.1, 1553.1 and 1562.1, 1553.2 and 1562.1, 1562.1 and 1562.1, 1553.2, 1543.1, 1544.1, 1561.1, and 1562.1, 1559.2 and 1553.1).
Figure 11C:
FIG. 11C shows flow cytometry data of dCas9$^{KRAB}$ repressing HER2 in control A431 cells measured via cell surface staining with a monoclonal antibody (Monoclonal Mouse IgG2B Clone #191924, R&D Systems).
Figure 11B:
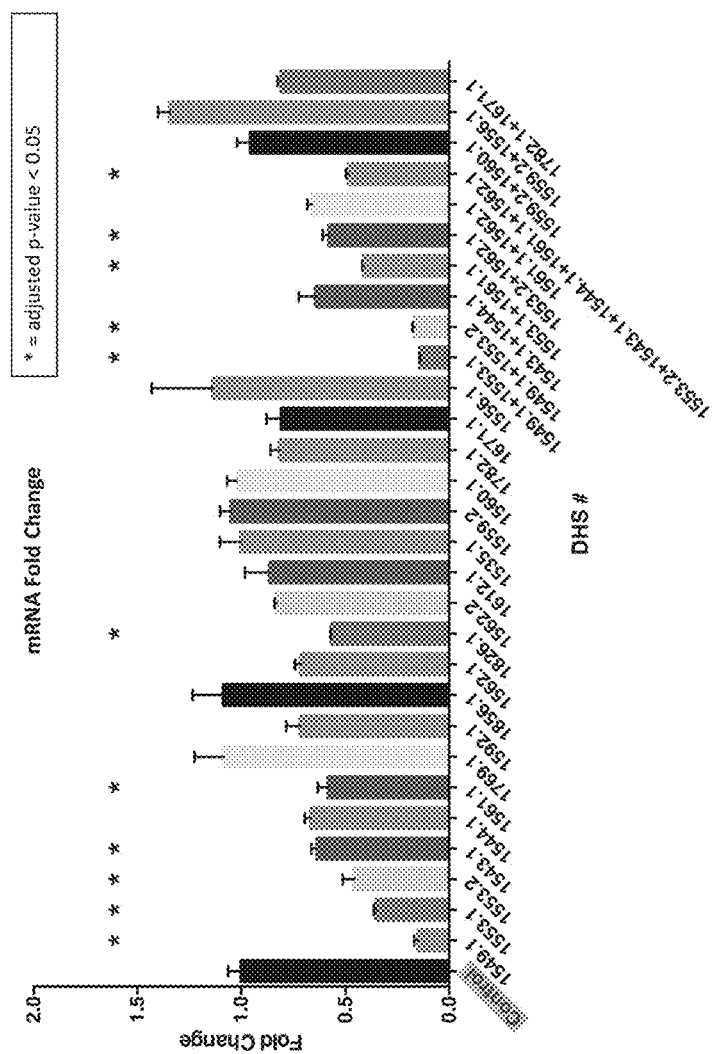

The fold change in expression of HER2 mRNA individual hits (gRNAs 1549, 1553, 1543, 1544, 1561, 1769, 1592, 1856, 1562, 1826, 1559, 1560, 1782, 1671, 1556, 1612, and 1535) that were identified using the CRISPR/dCas9$^{KRAB}$ repression system are shown in FIG. 11A. FIG. 11B shows flow cytometry data of dCas9$^{KRAB}$ repressing HER2 in control SKBR3 cells measured via cell surface staining with a monoclonal antibody.

Figure 12A:
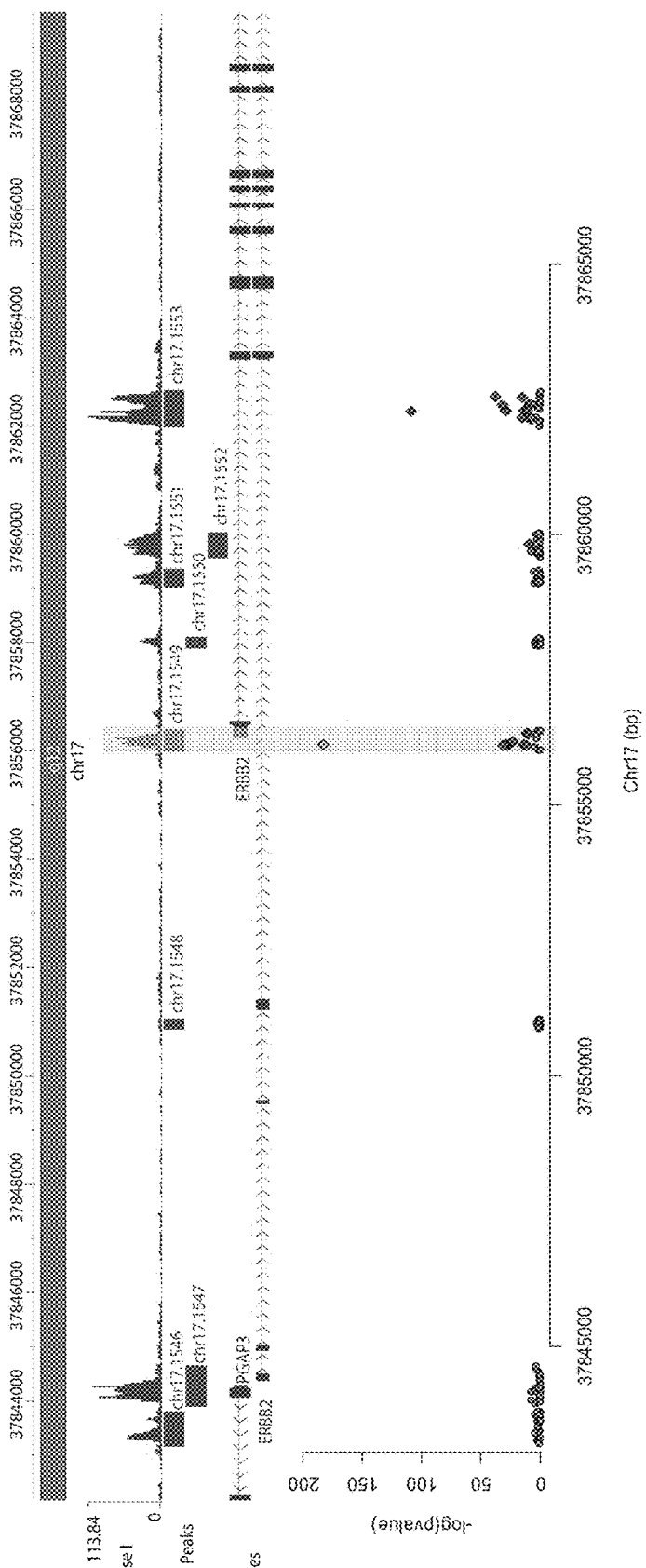
FIGS. 12A-12C show enrichment of gRNA 1549.1 ("1549").
Figure 12B:
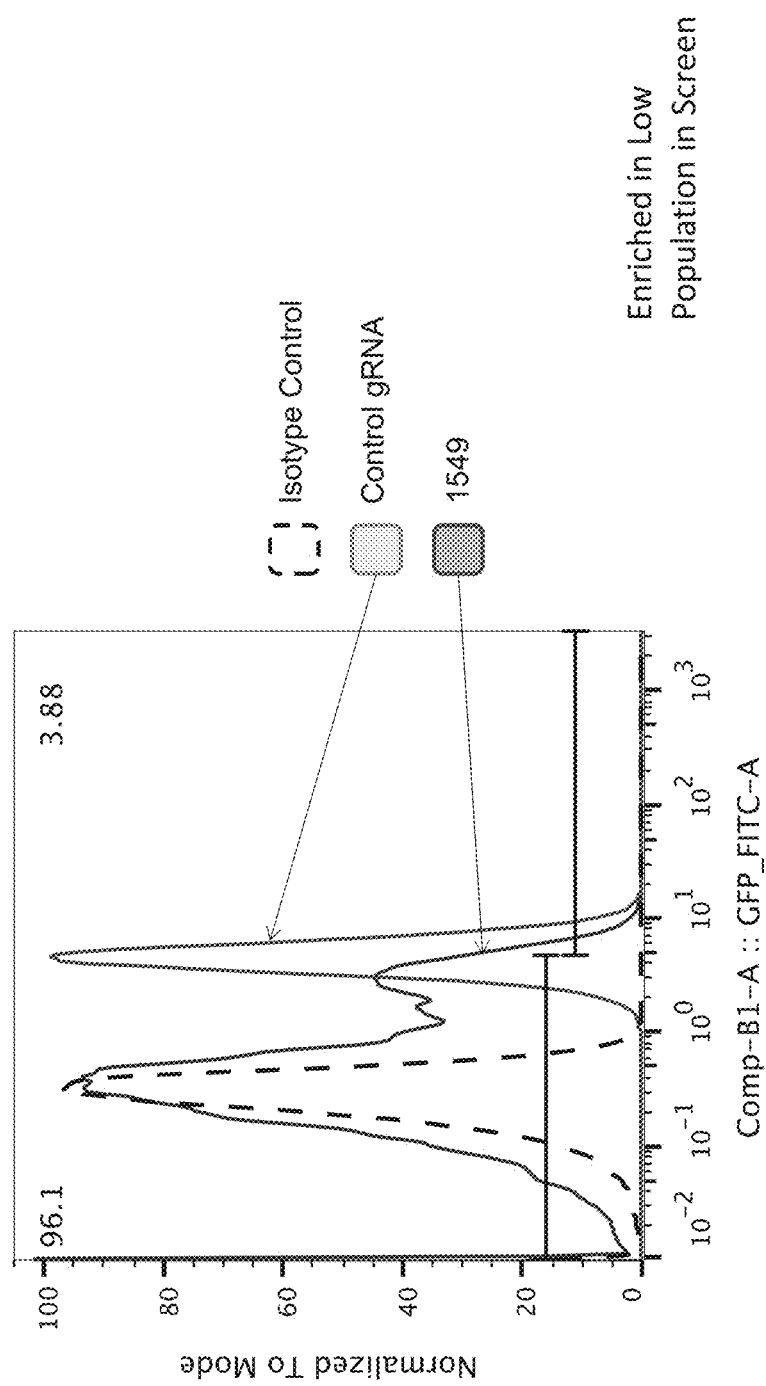
Figure 12C:
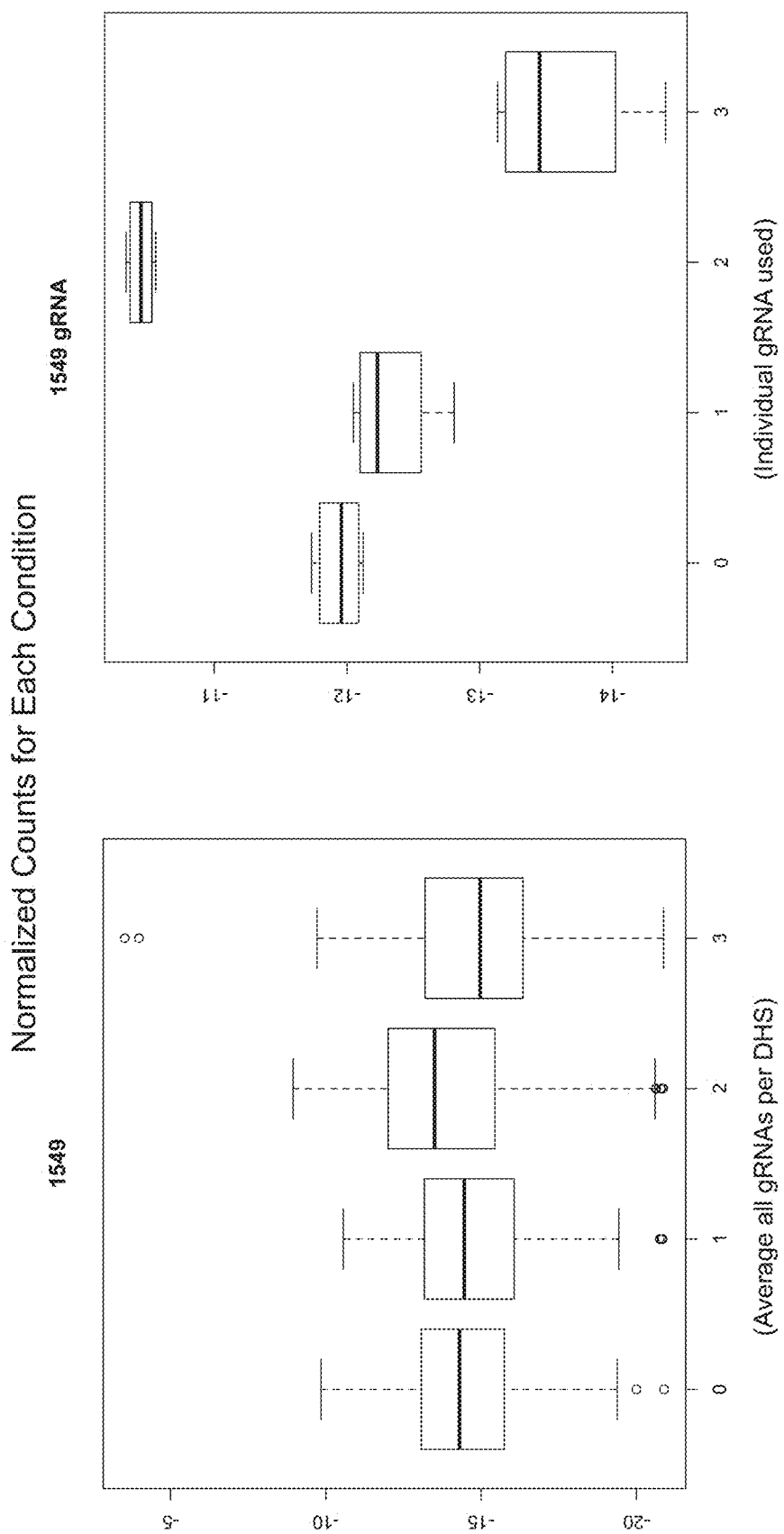
Figure 13A:
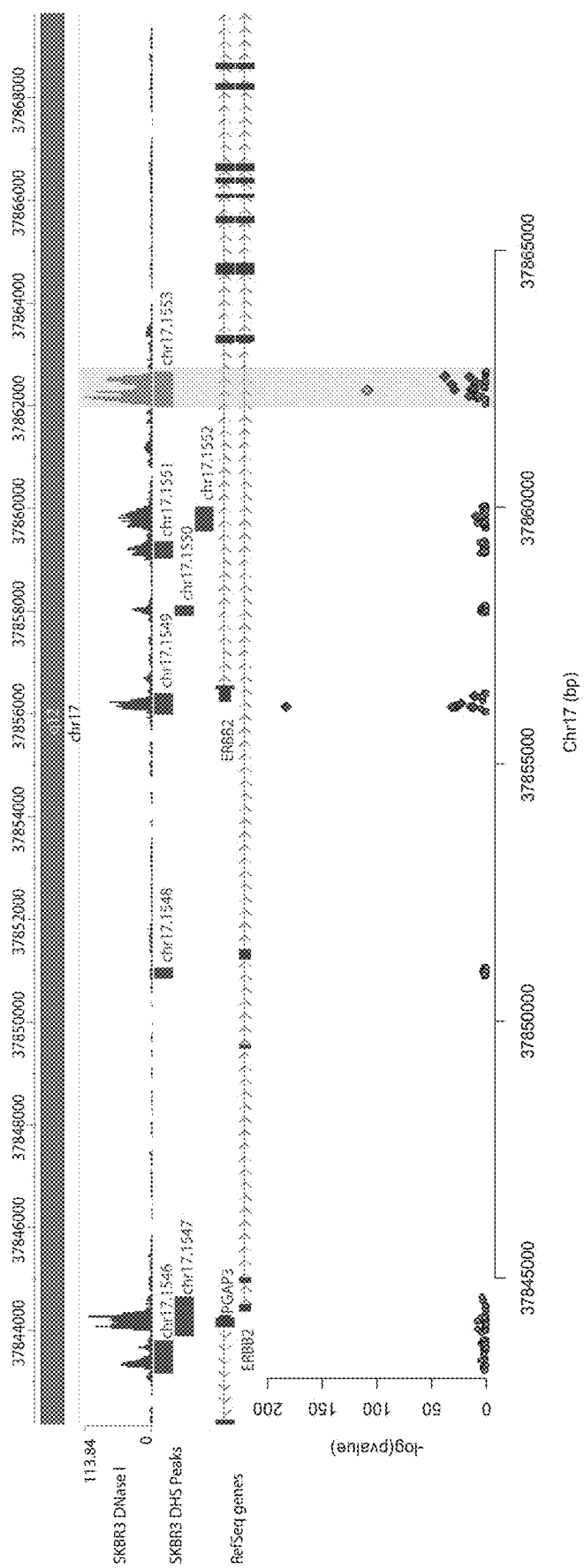
FIGS. 13A-13F show enrichment of gRNA 1553.1 and 1553.2.
Figure 13B:
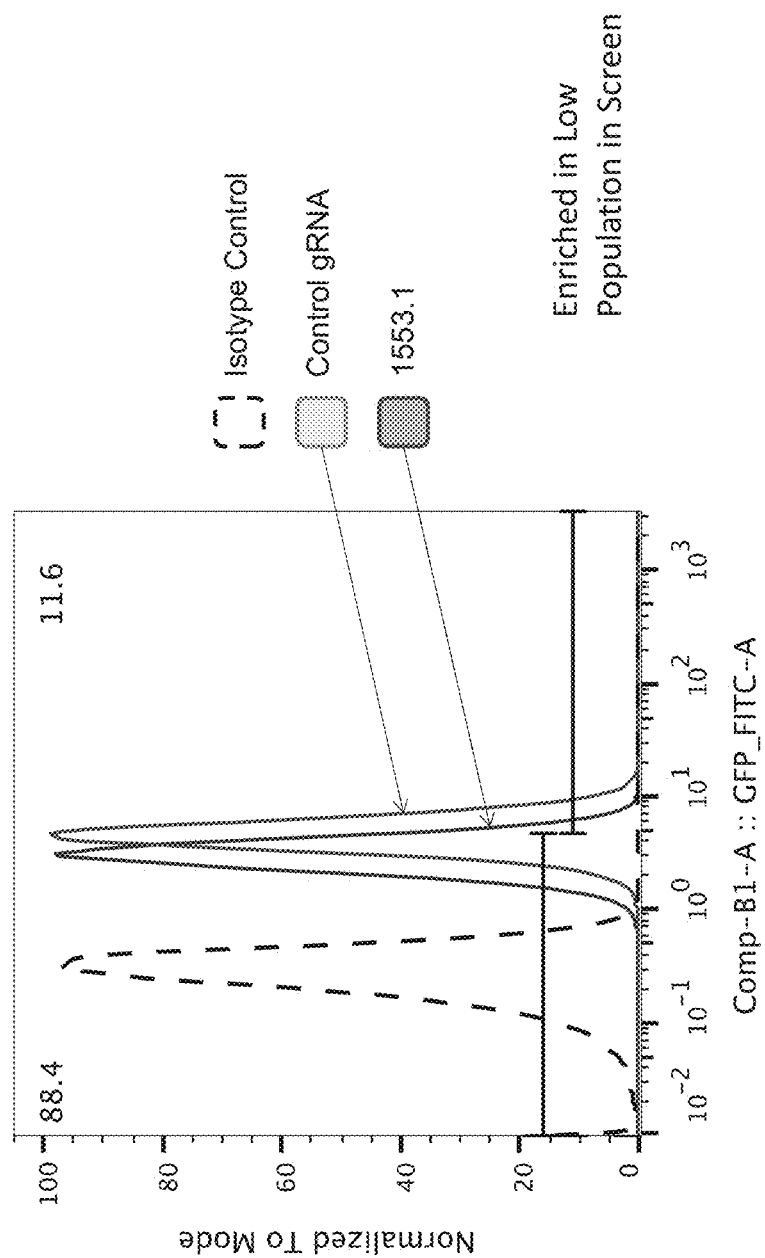
Figure 13C:
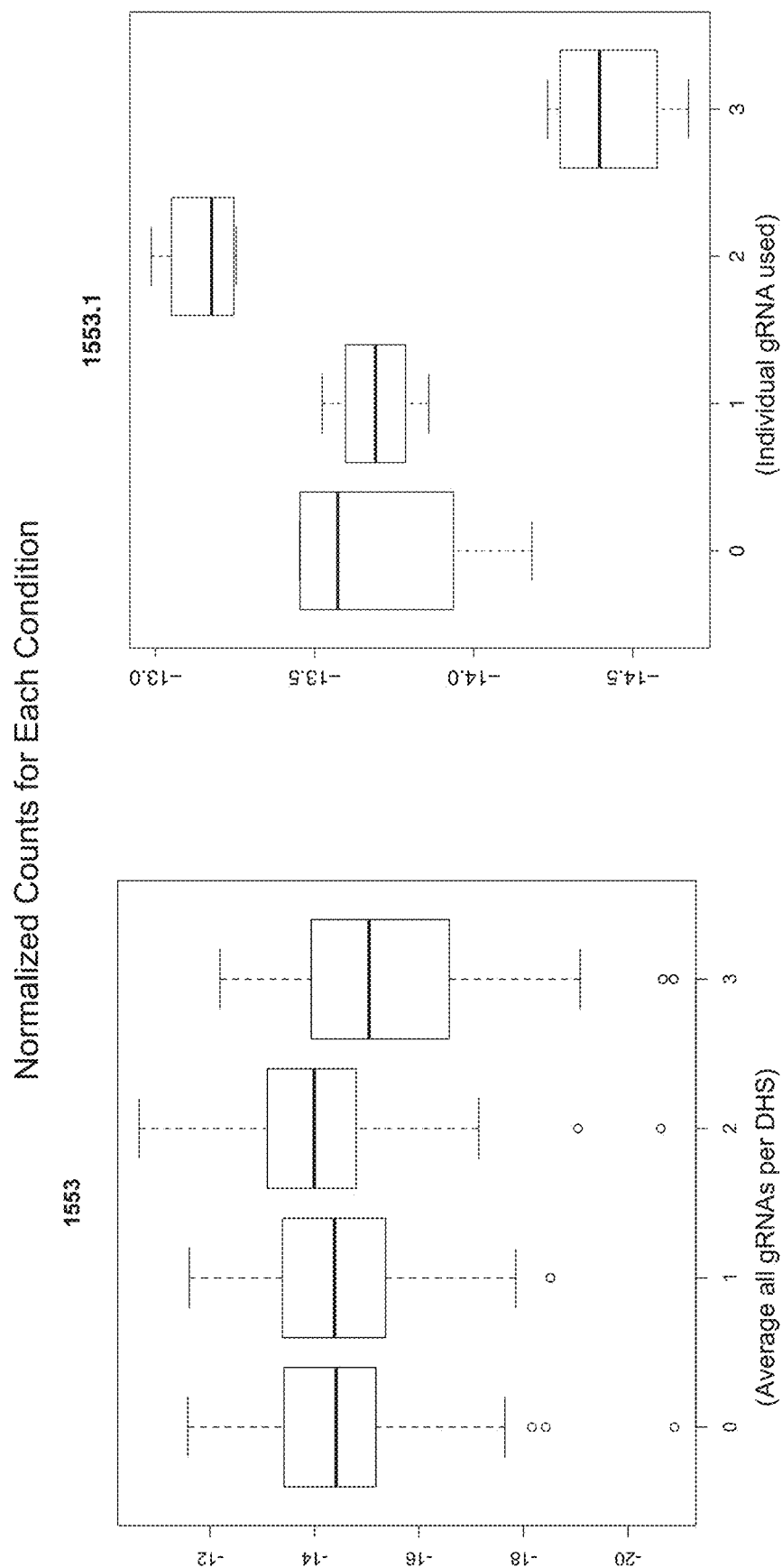
Figure 13D:
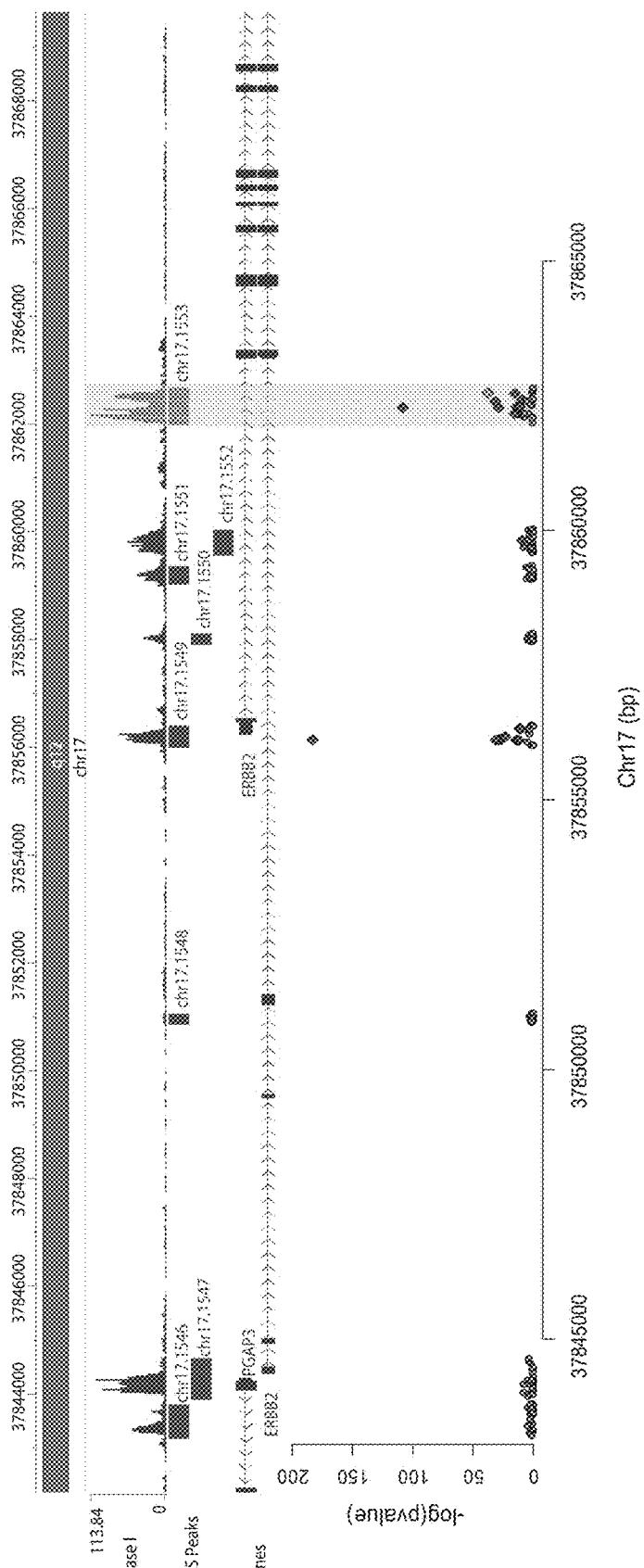
Figure 13E:
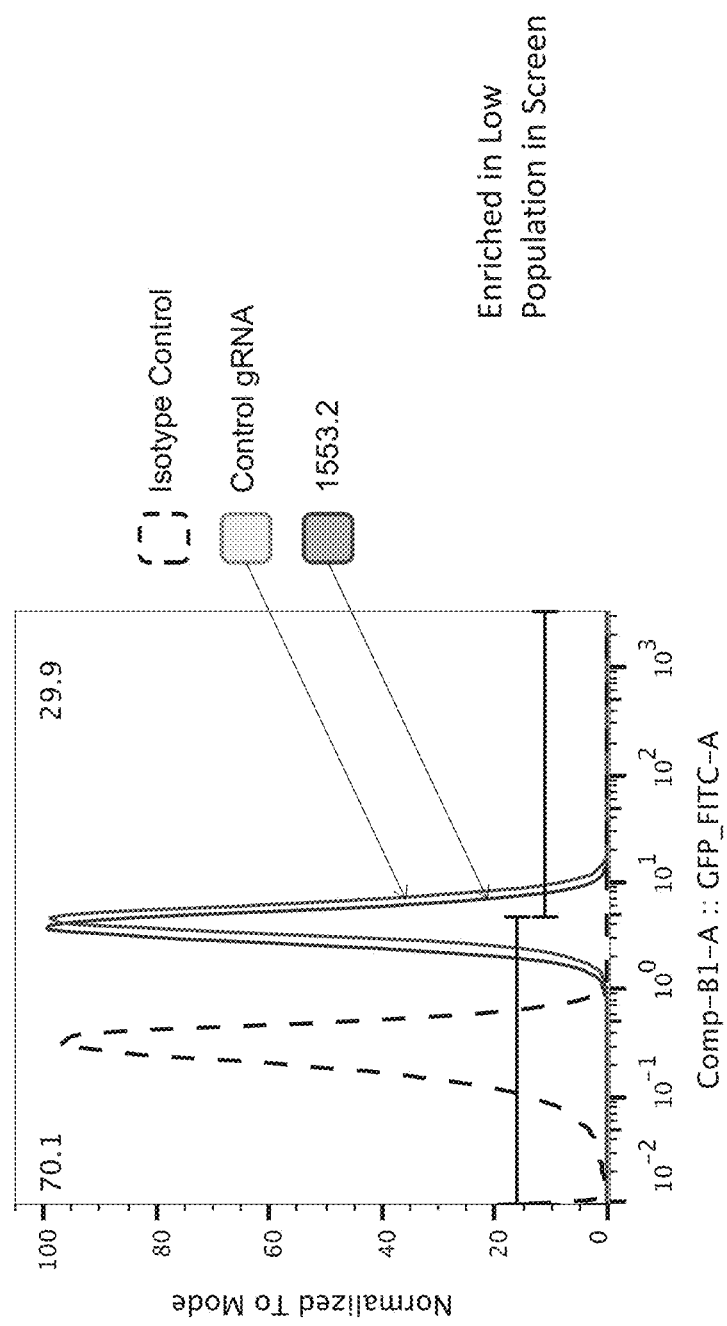
Figure 13F:
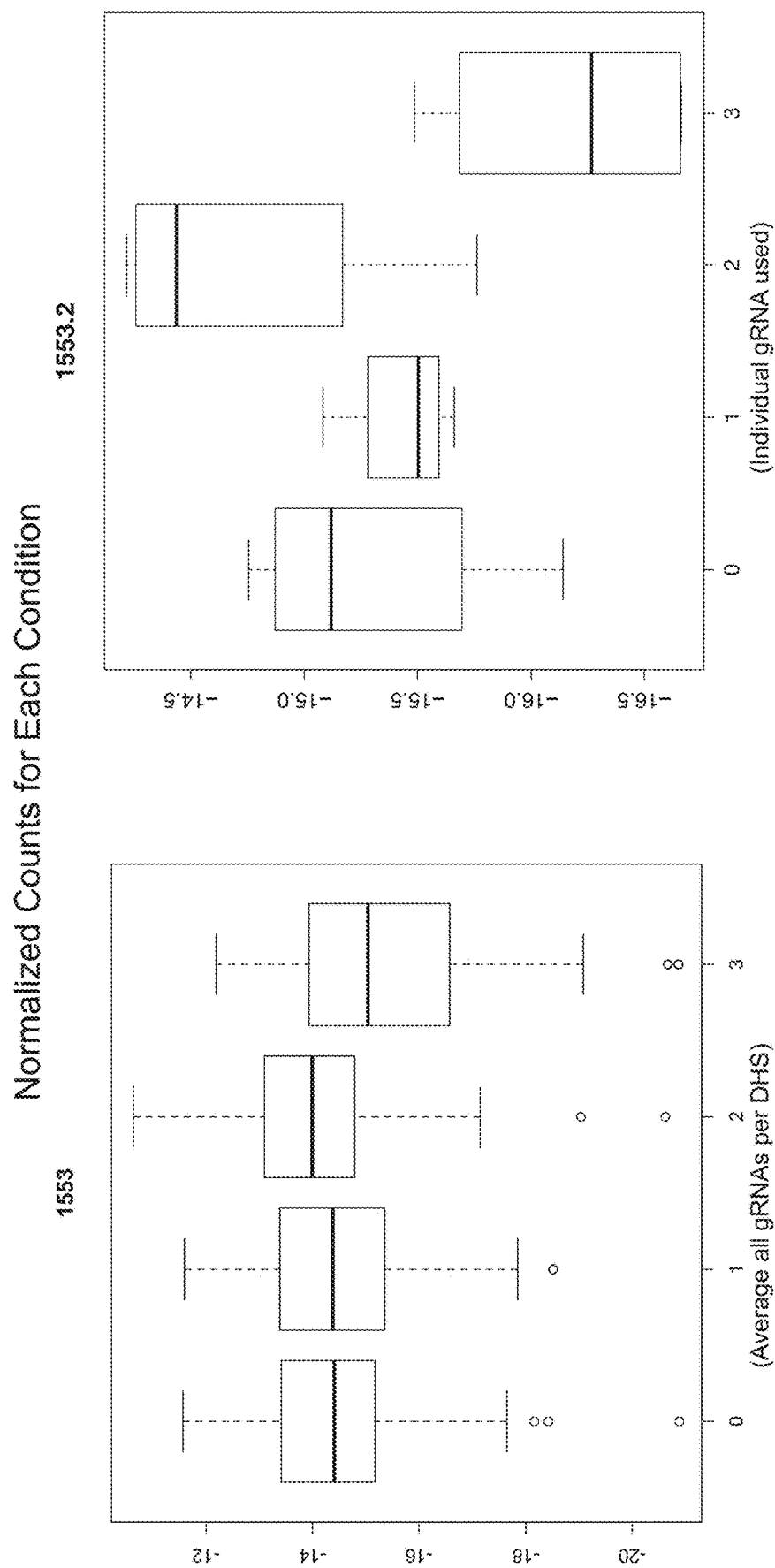
Figure 14A:
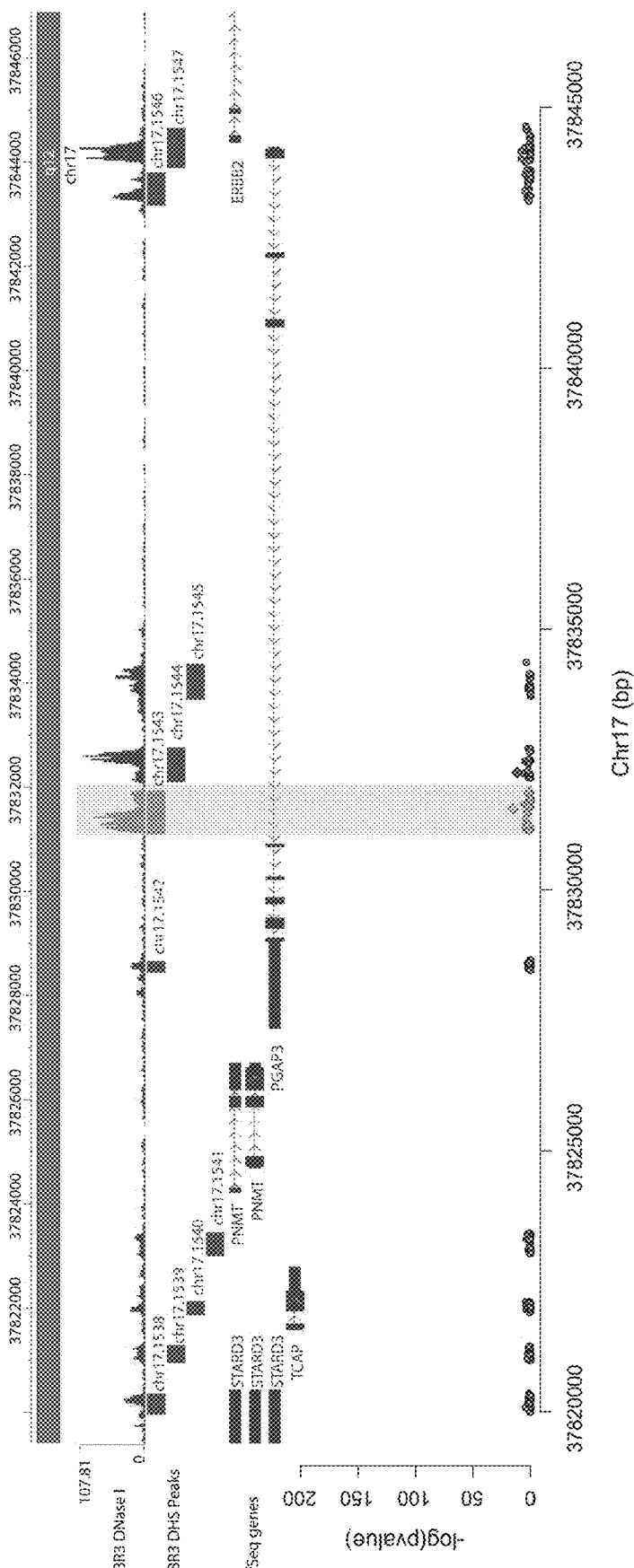
FIGS. 14A-14C show enrichment of gRNA 1543.1 ("1543").
Figure 14B:
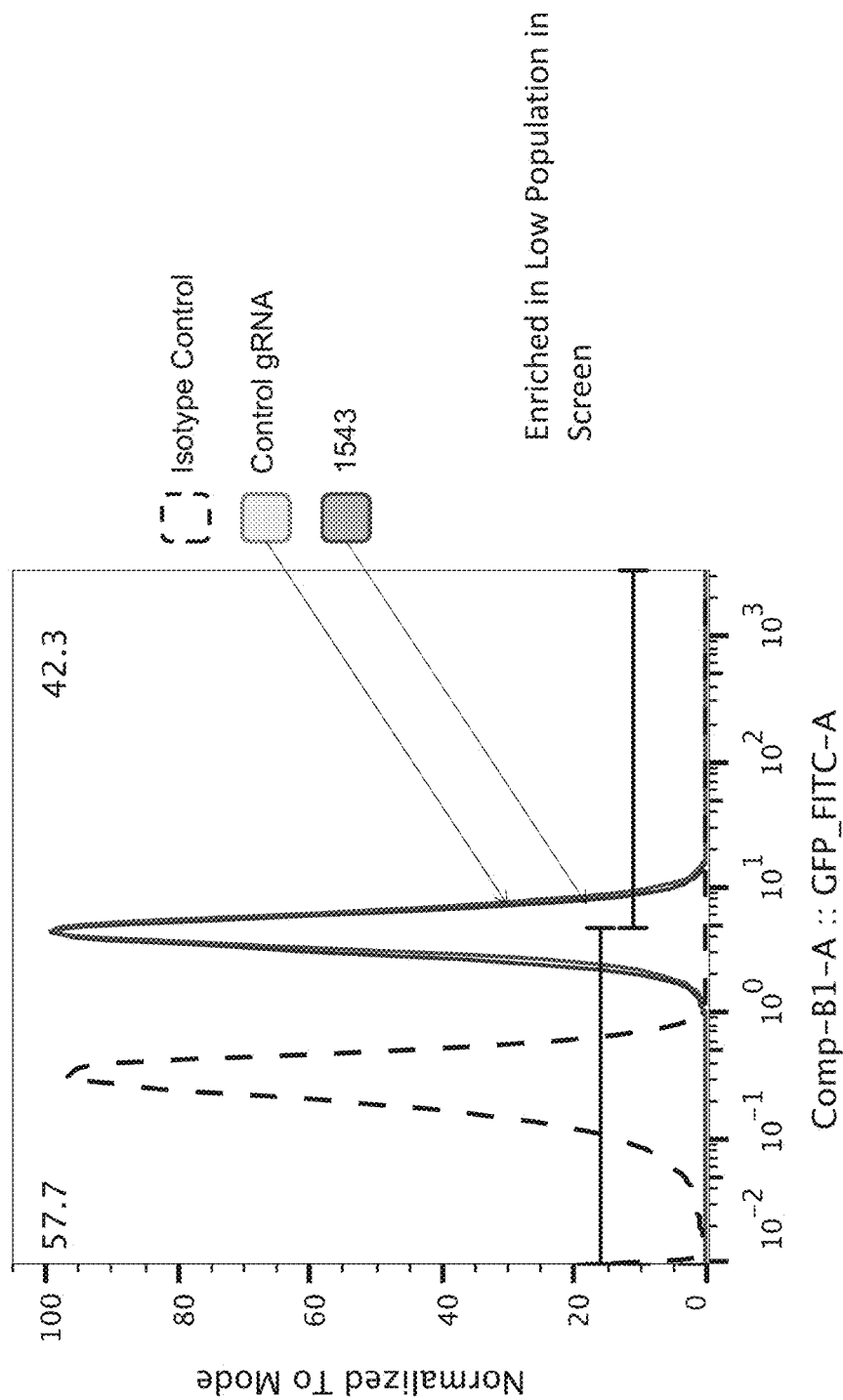
Figure 14C:
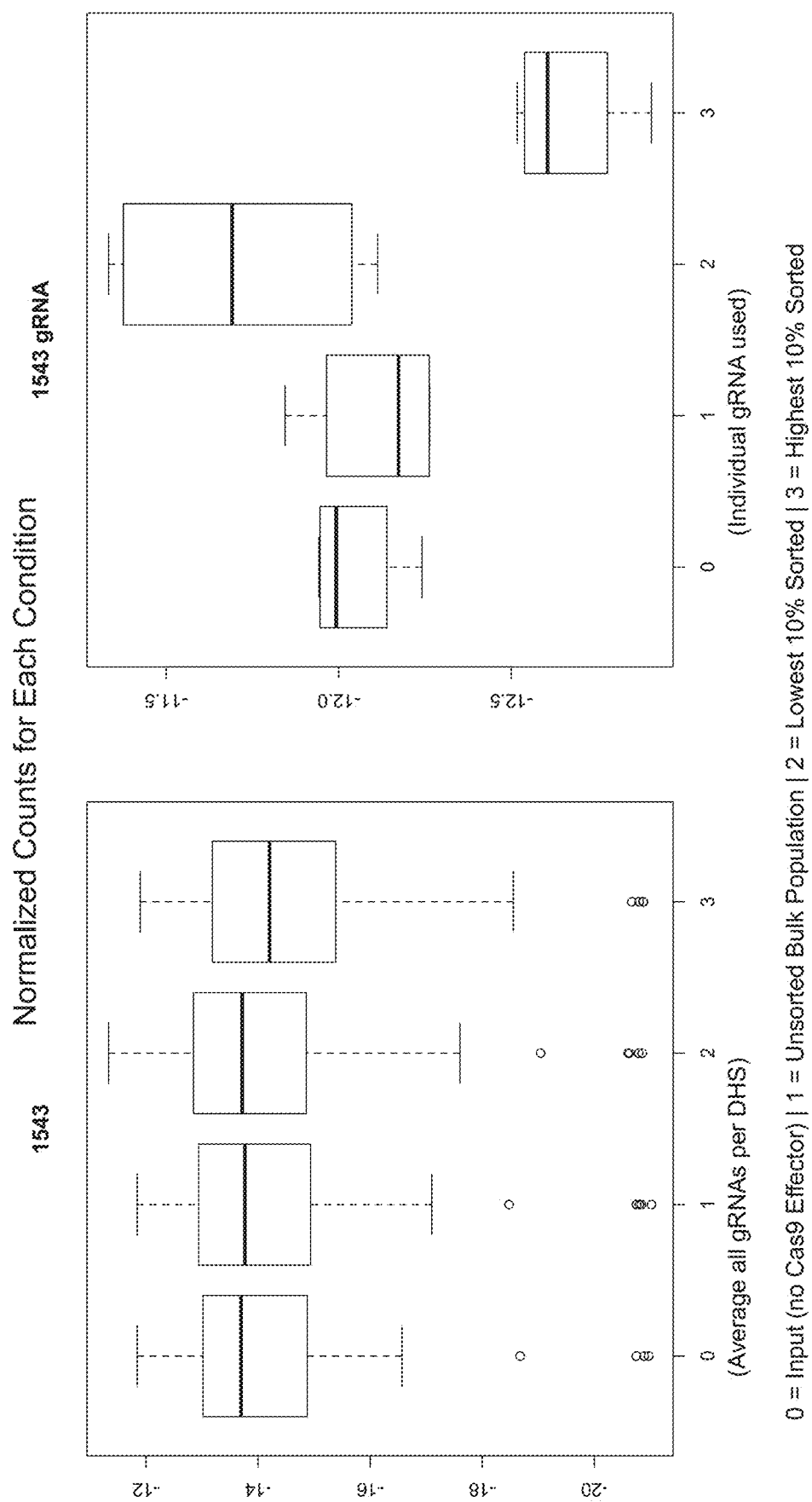
Figure 15A:
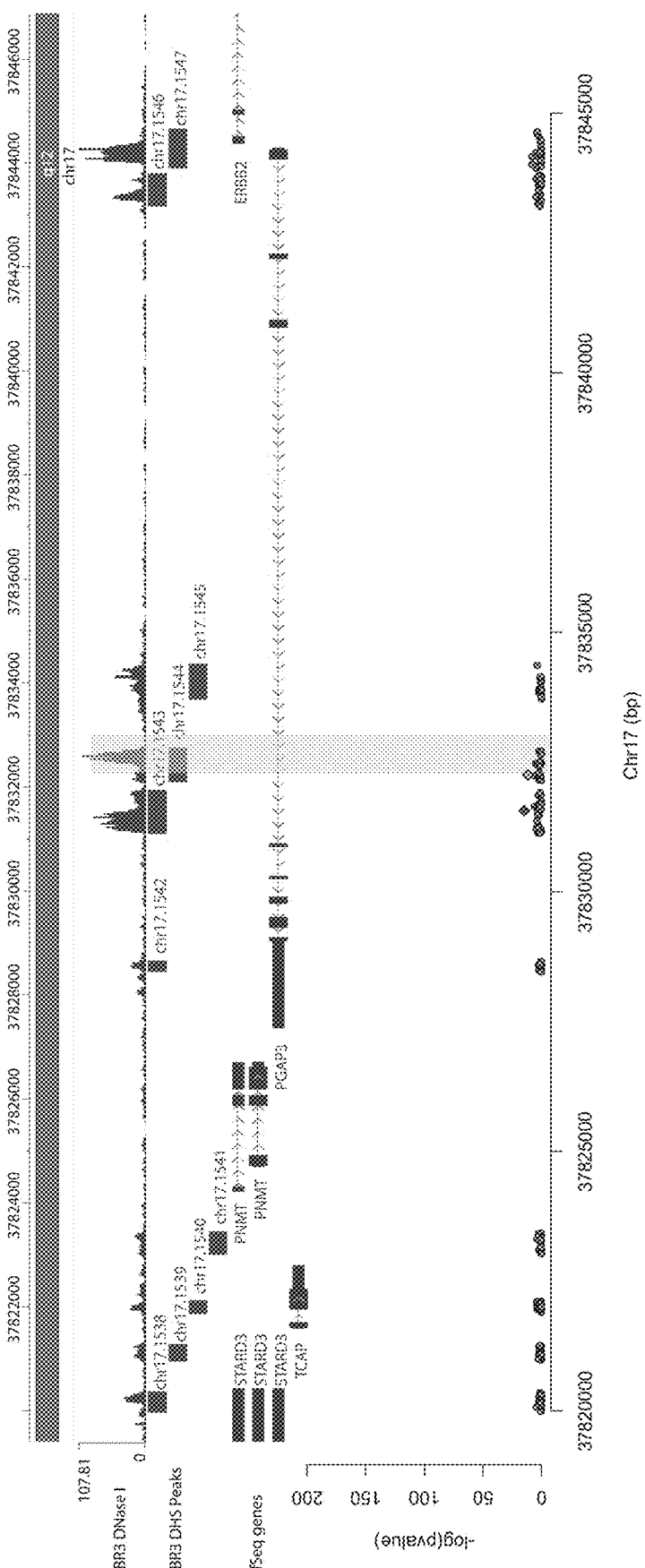
FIGS. 15A-15C show enrichment of gRNA 1544.1 ("1544").
Figure 15B:
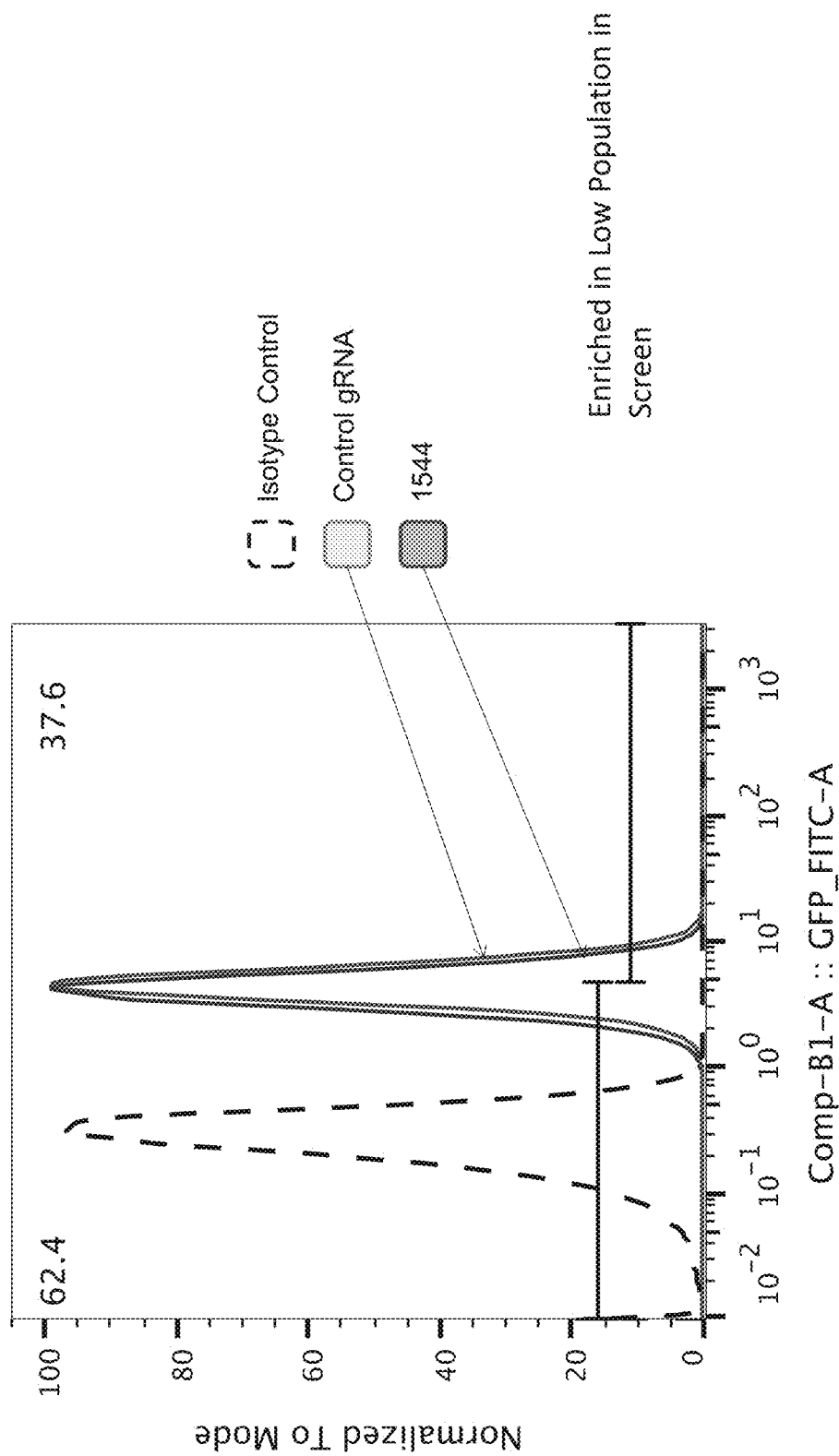
Figure 15C:
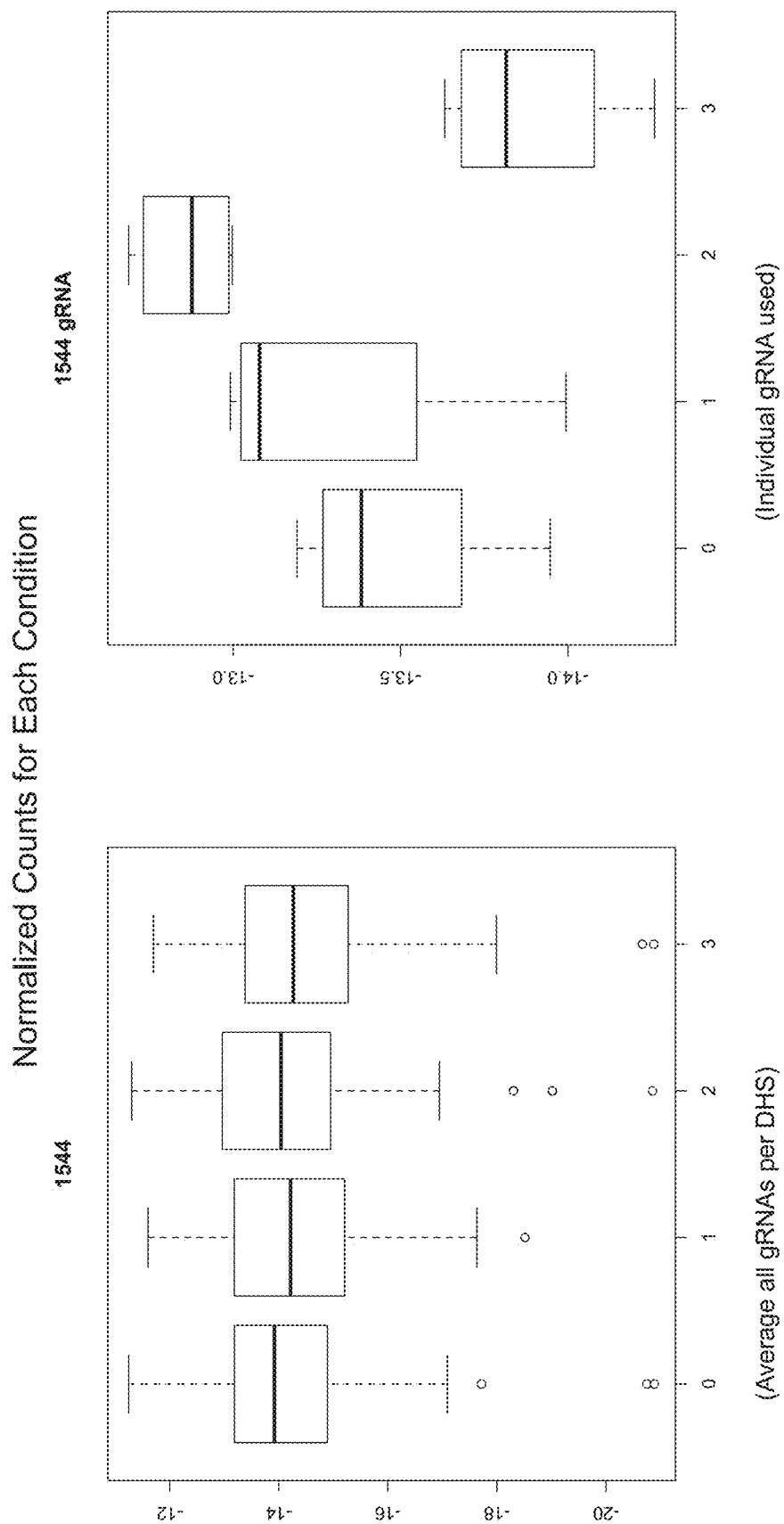
Figure 16A:
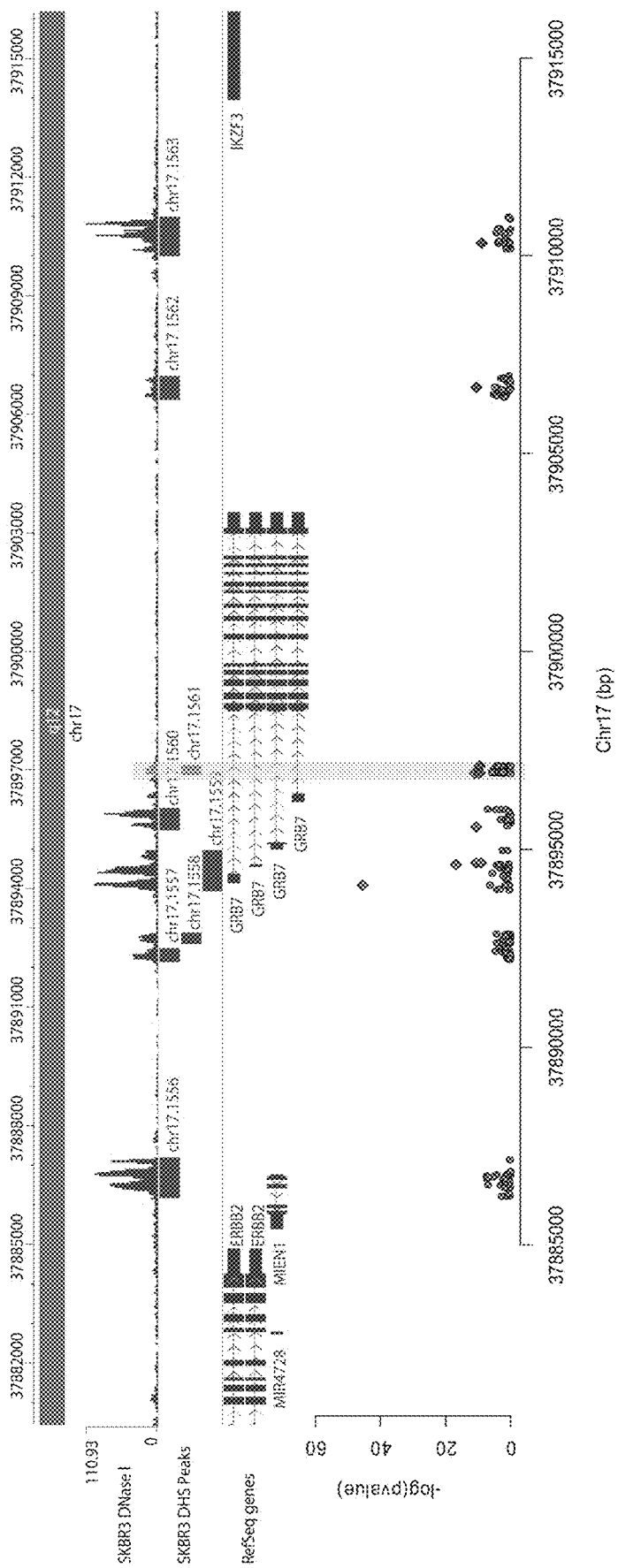
FIGS. 16A-16C show enrichment of gRNA 1561.1 ("1561").
Figure 16B:
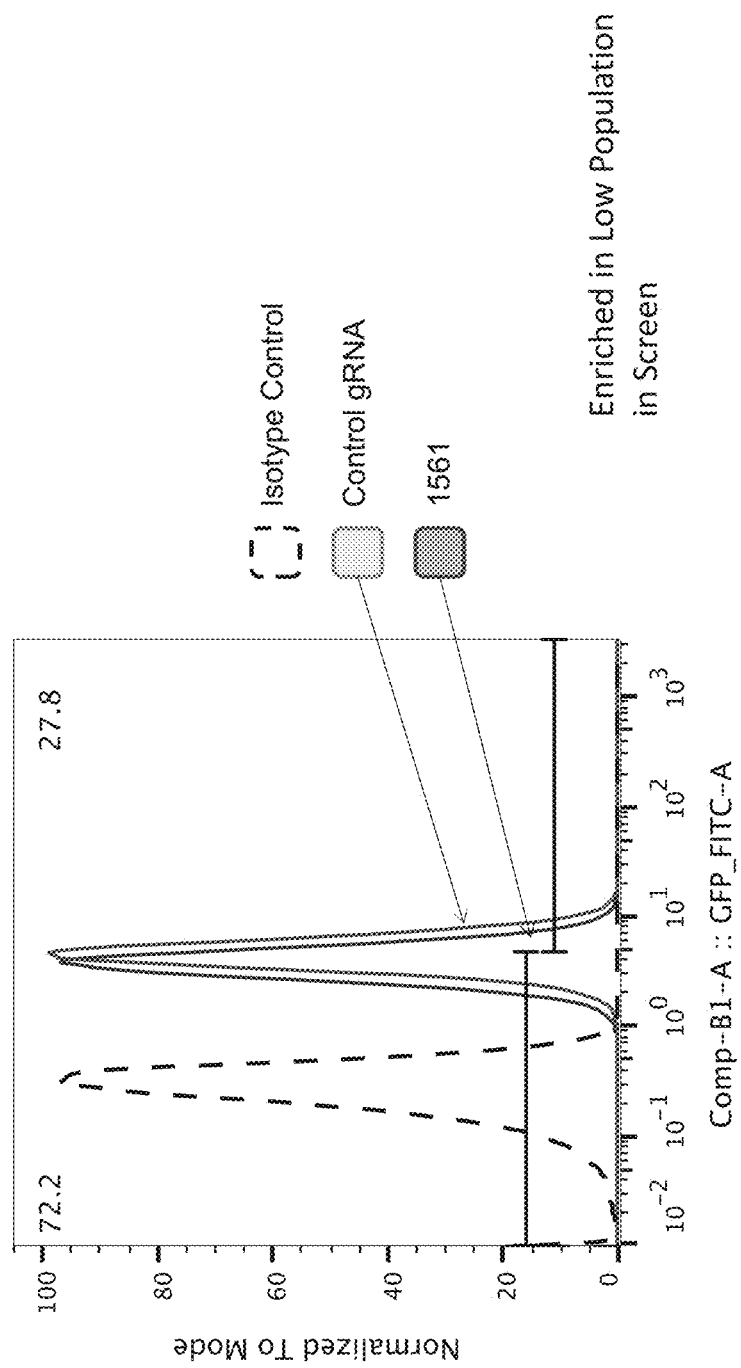
Figure 16C:
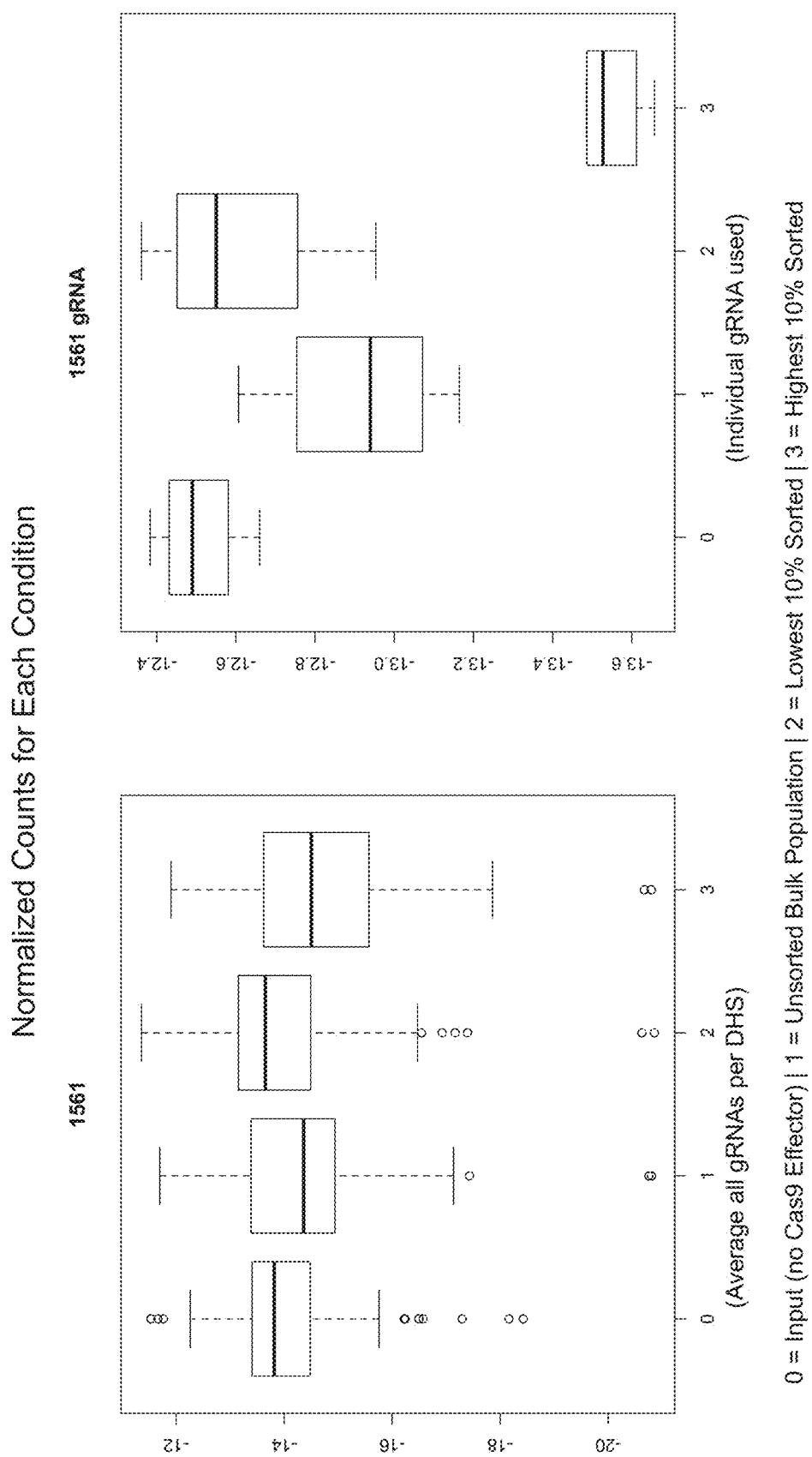
Figure 17A:
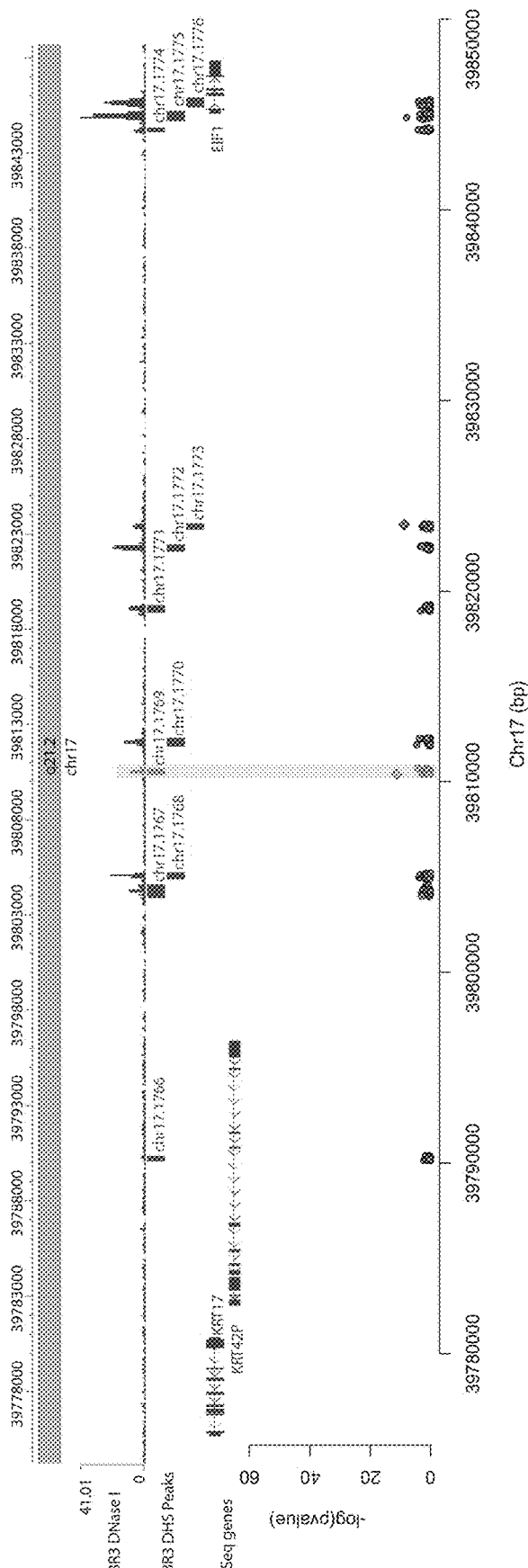
FIGS. 17A-17C show enrichment of gRNA 1769.1 ("1769").
Figure 17B:
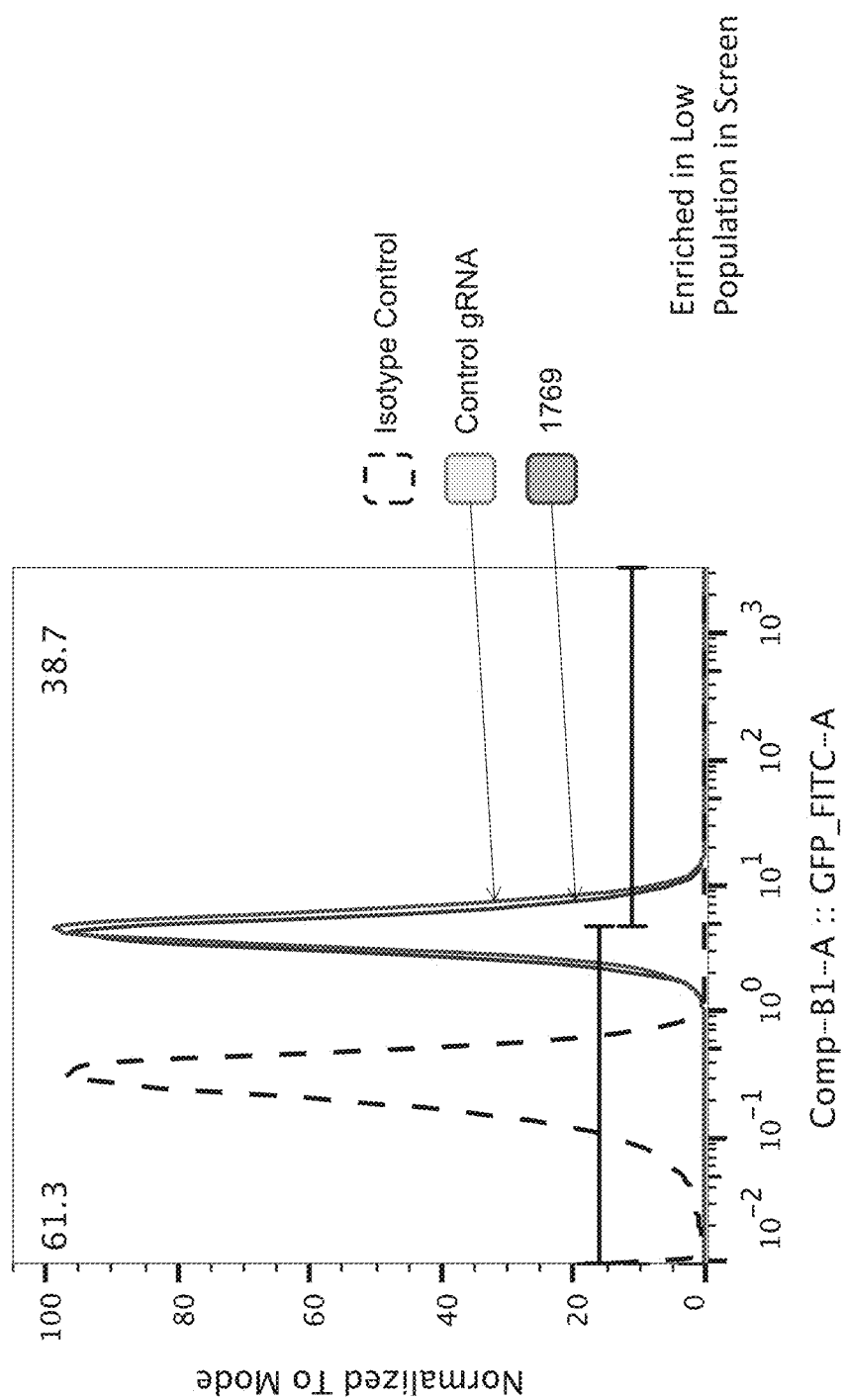
Figure 17C:
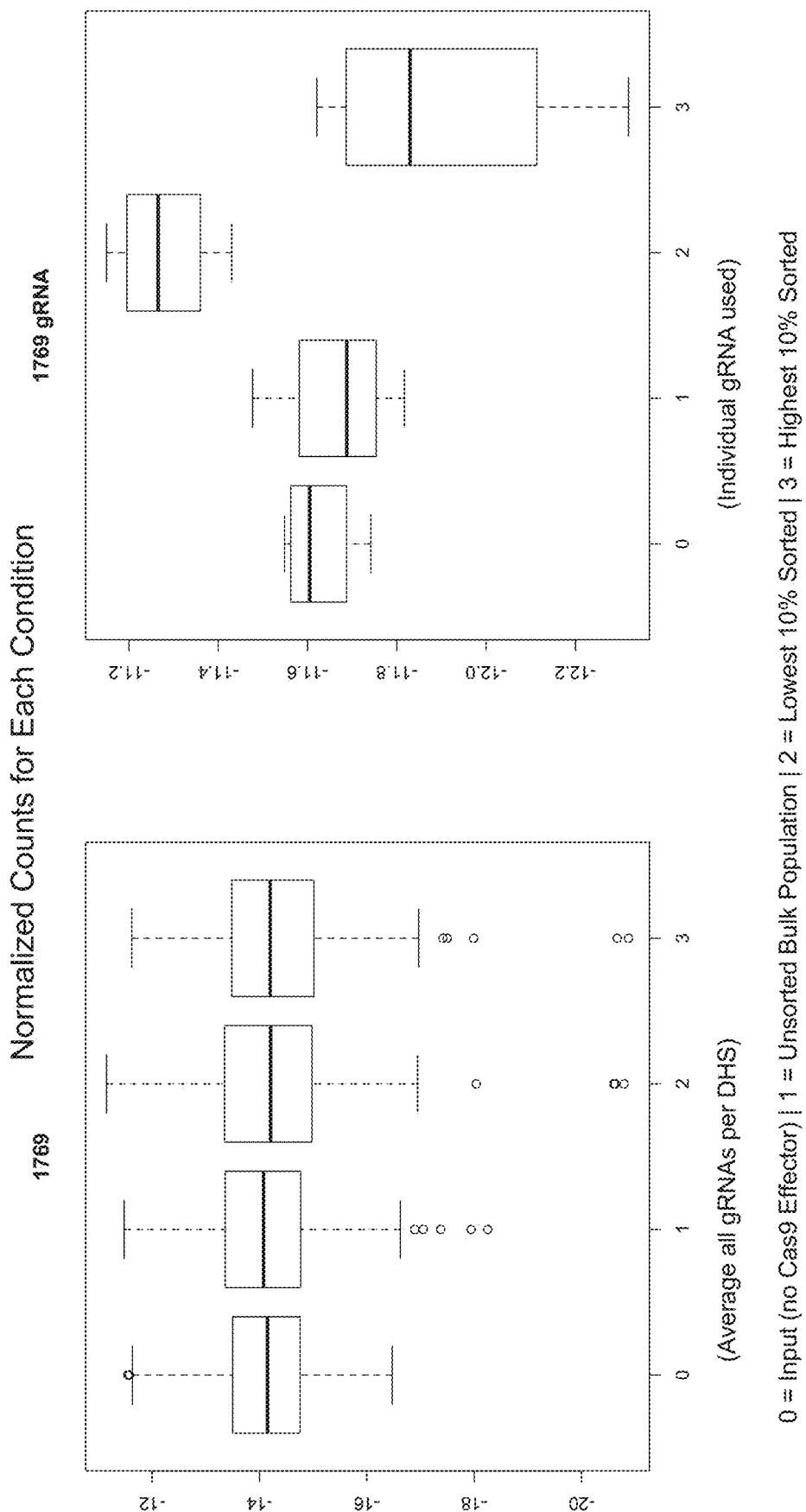
Figure 18A:
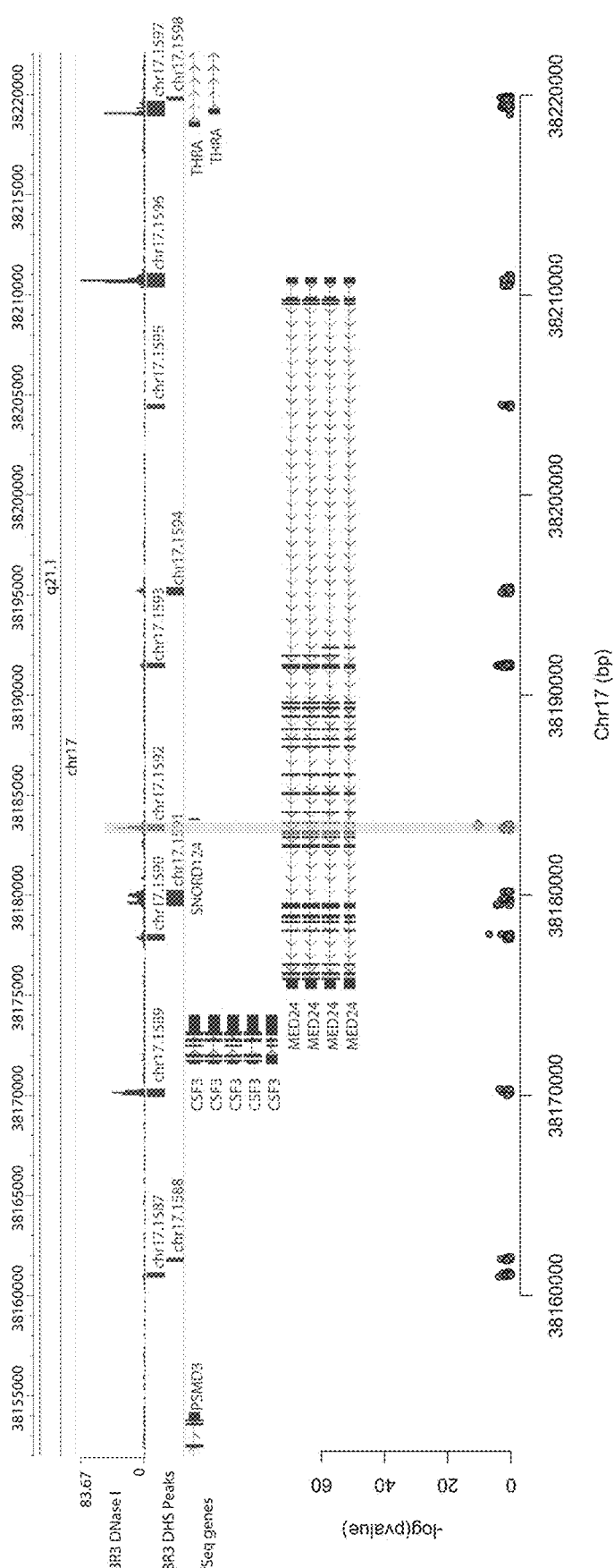
FIGS. 18A-18C show enrichment of gRNA 1592.1 ("1592").
Figure 18B:
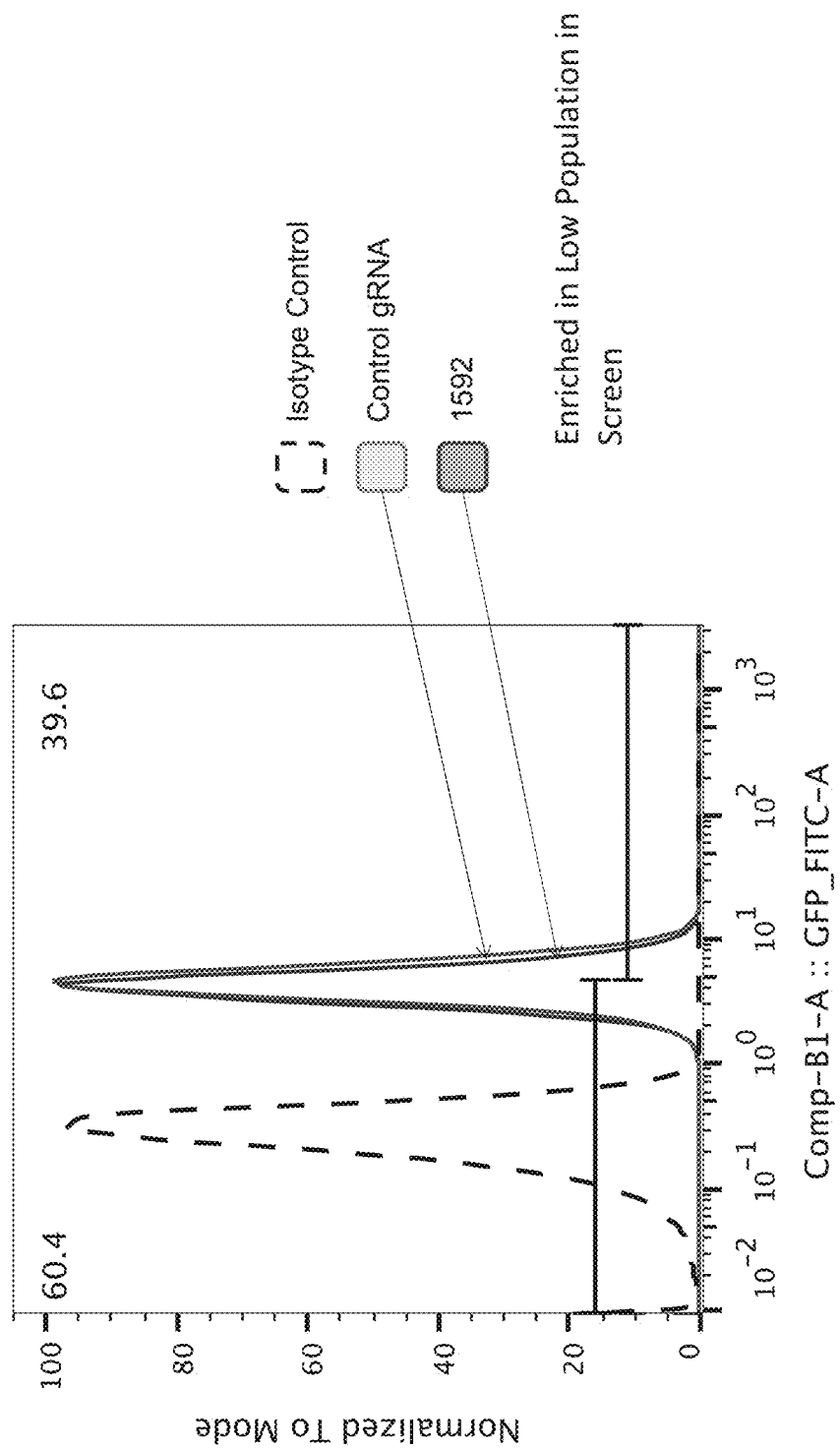
Figure 18C:
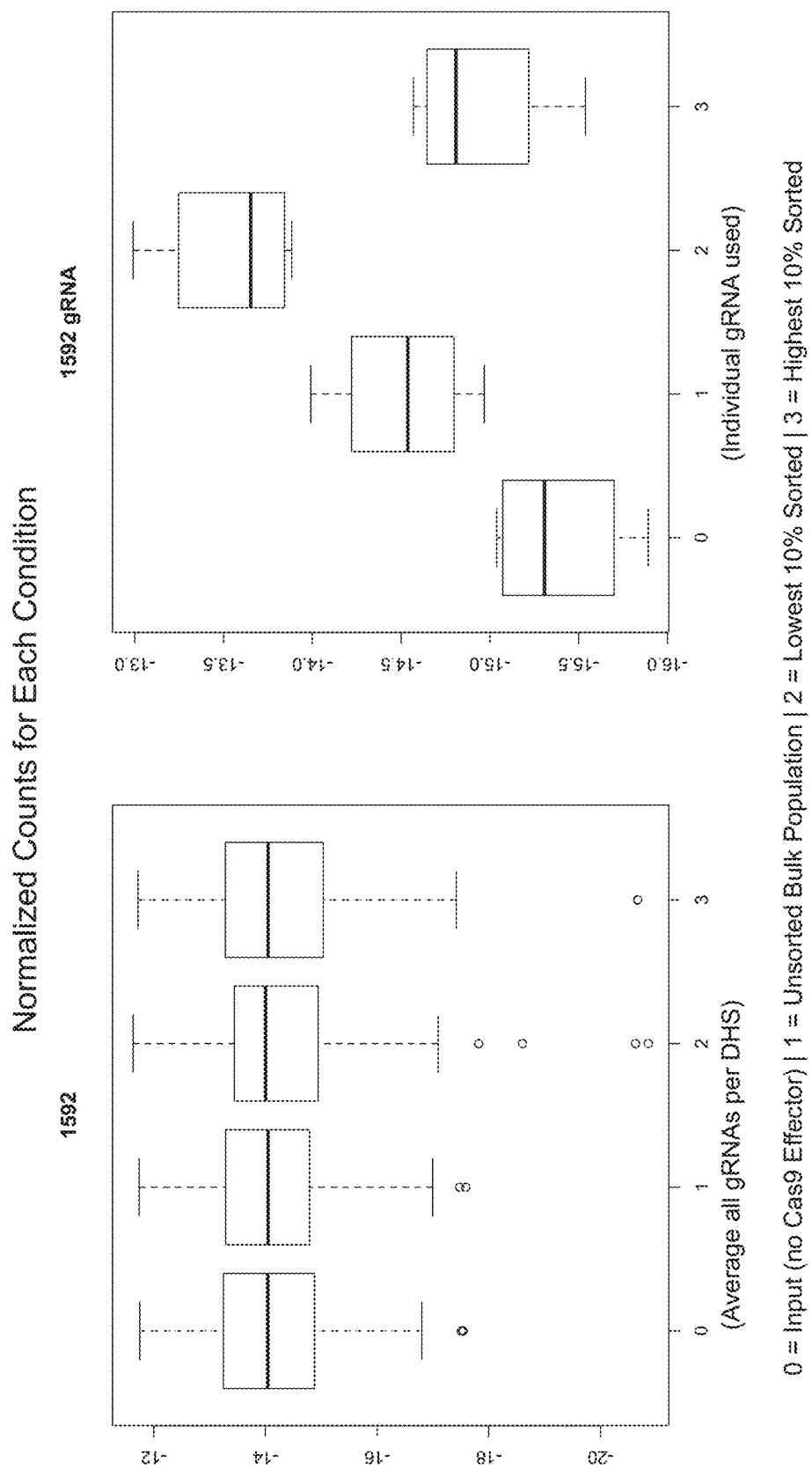
Figure 19A:
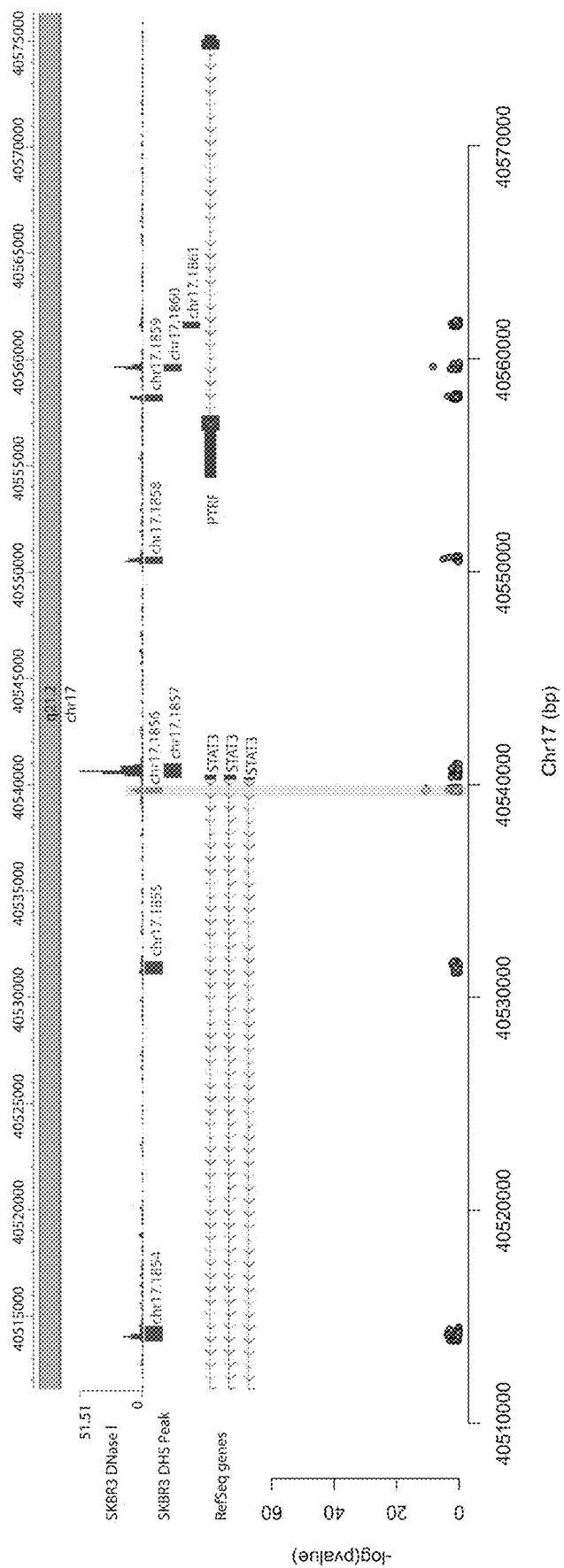
FIGS. 19A-19C show enrichment of gRNA 1856.1 ("1856").
Figure 19B:
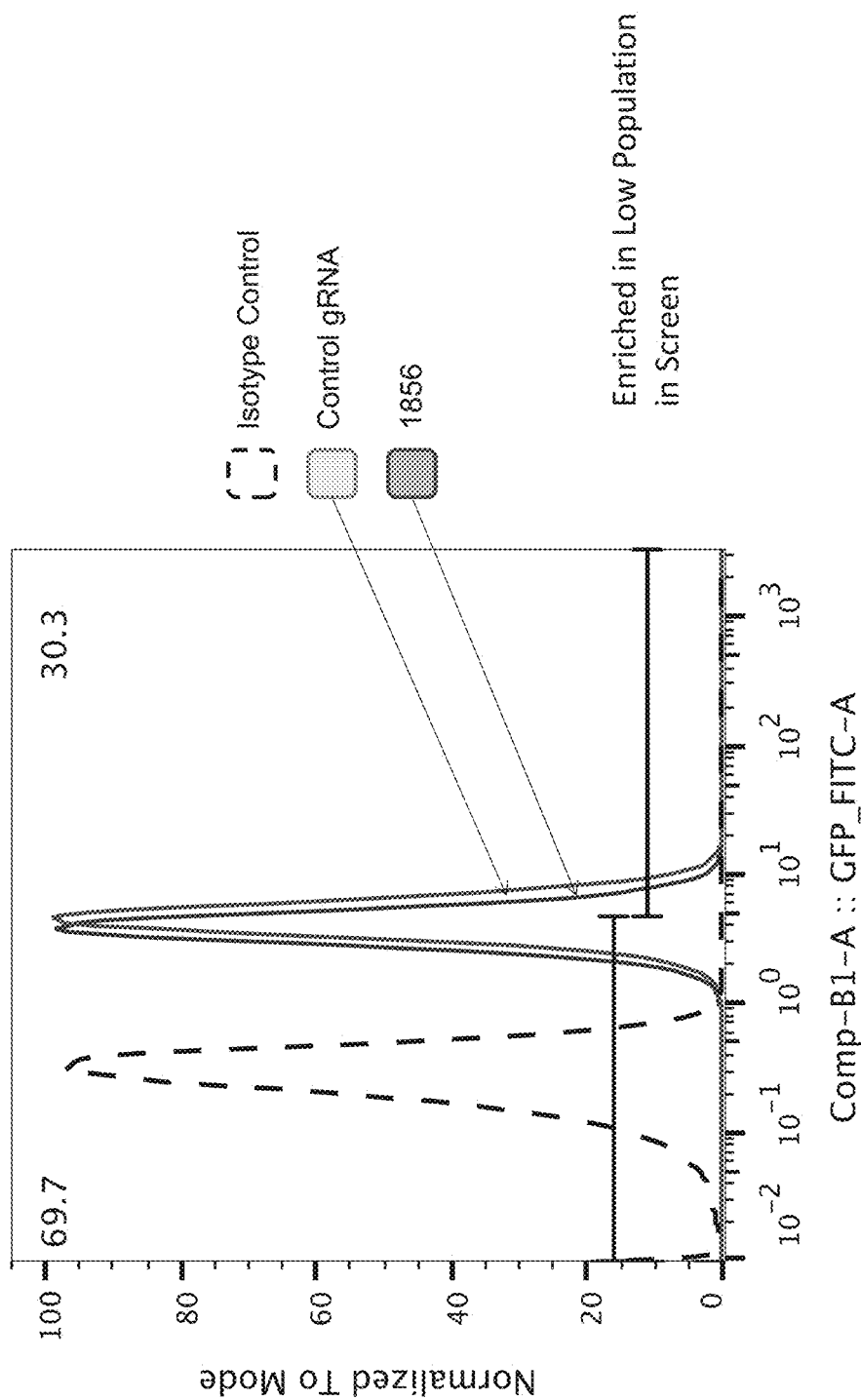
Figure 19C:
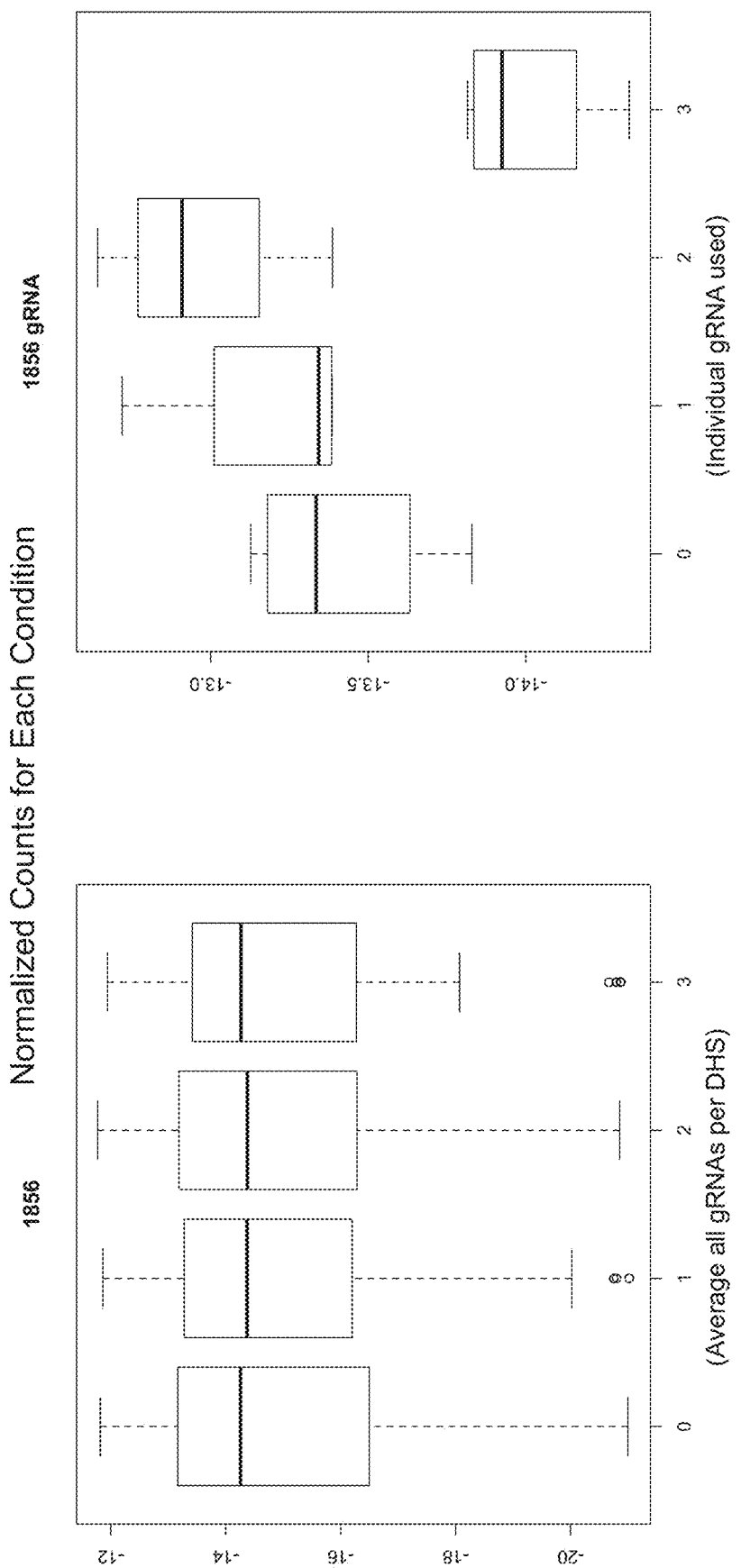
Figure 20A:
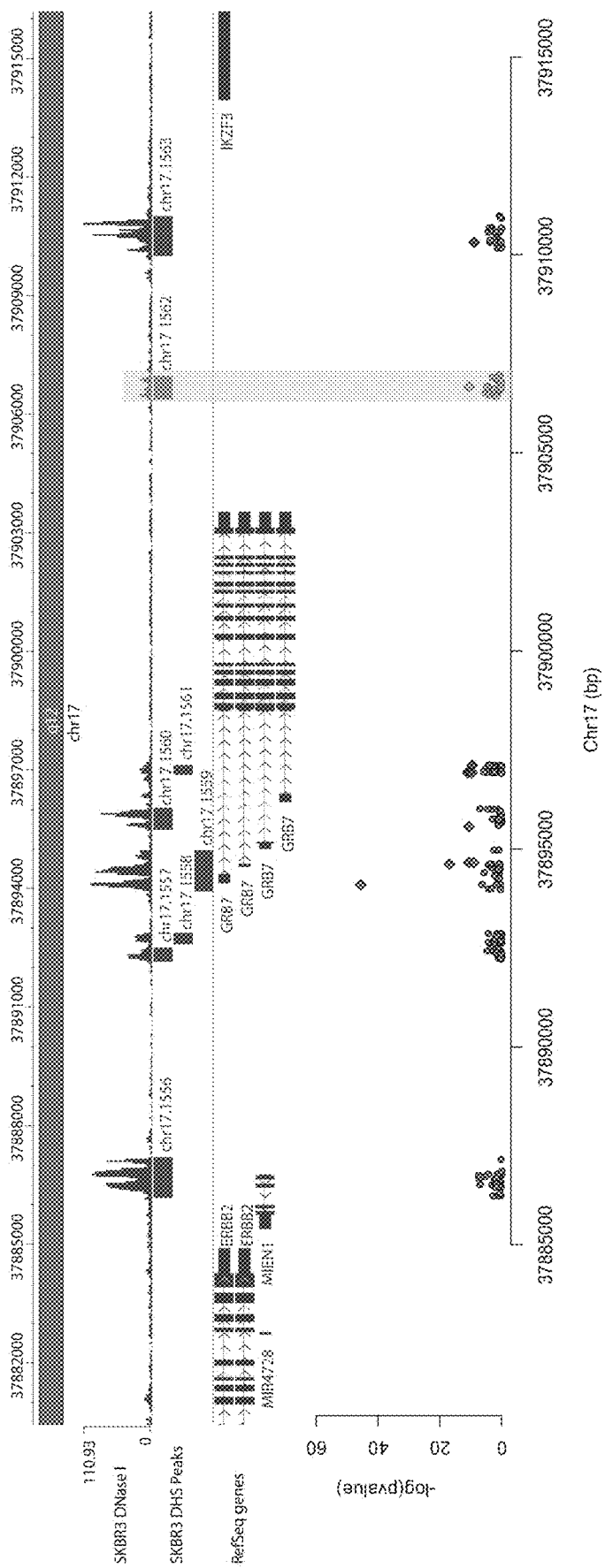
FIGS. 20A-20C show enrichment of gRNA 1562.1 ("1562").
Figure 20B:
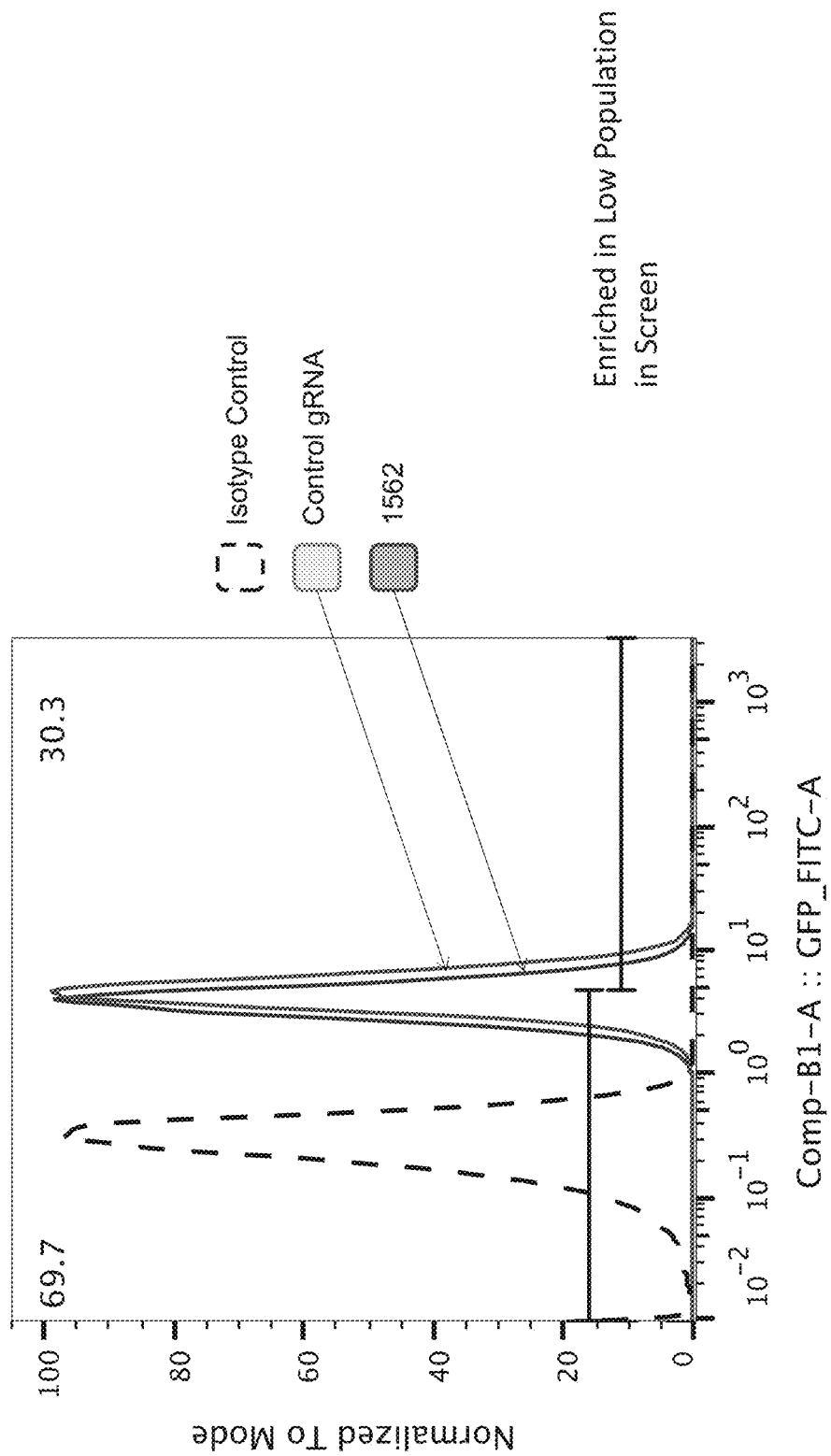
Figure 20C:
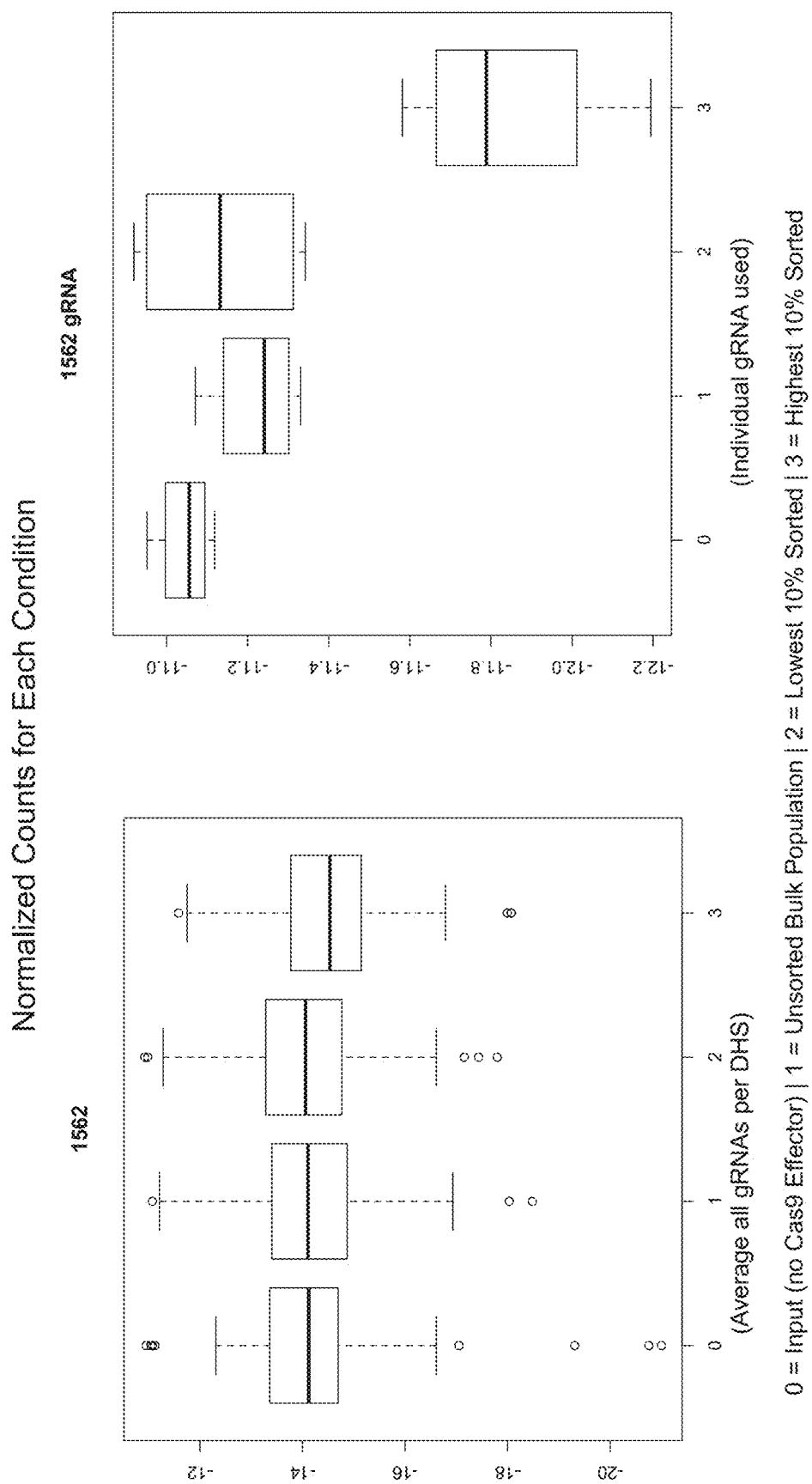
Figure 21A:
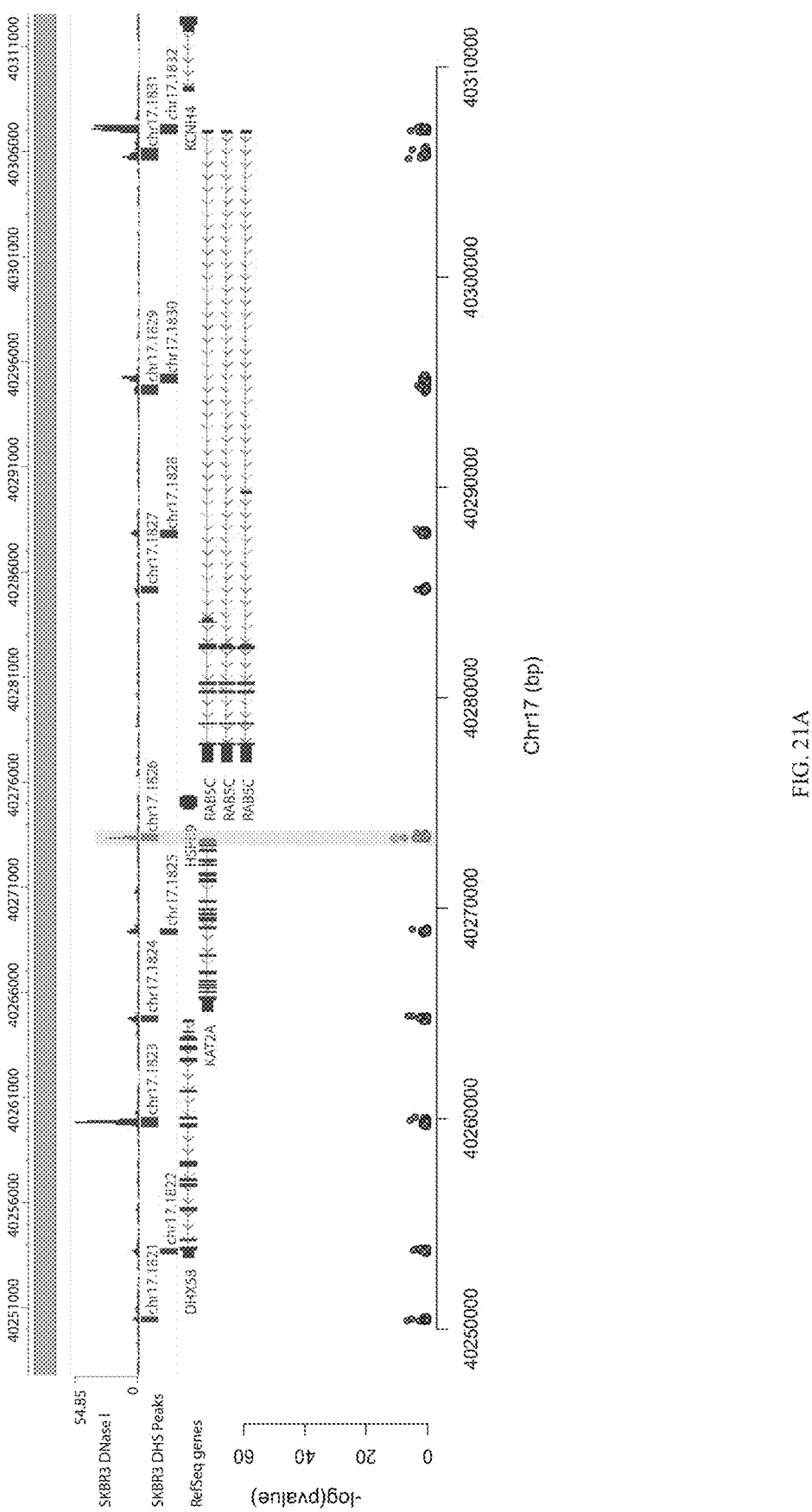
FIGS. 21A-21C show enrichment of gRNA 1826.1 ("1826").
Figure 21B:
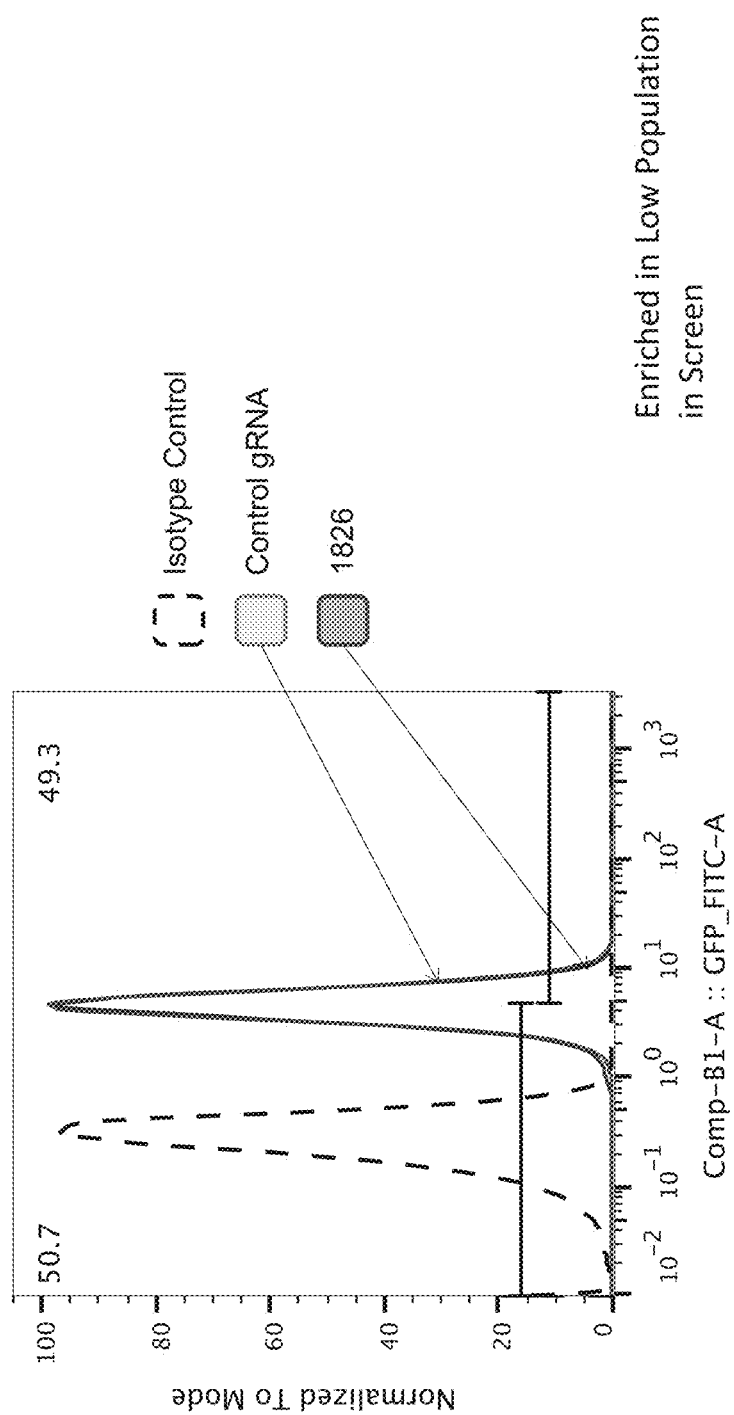
Figure 21C:
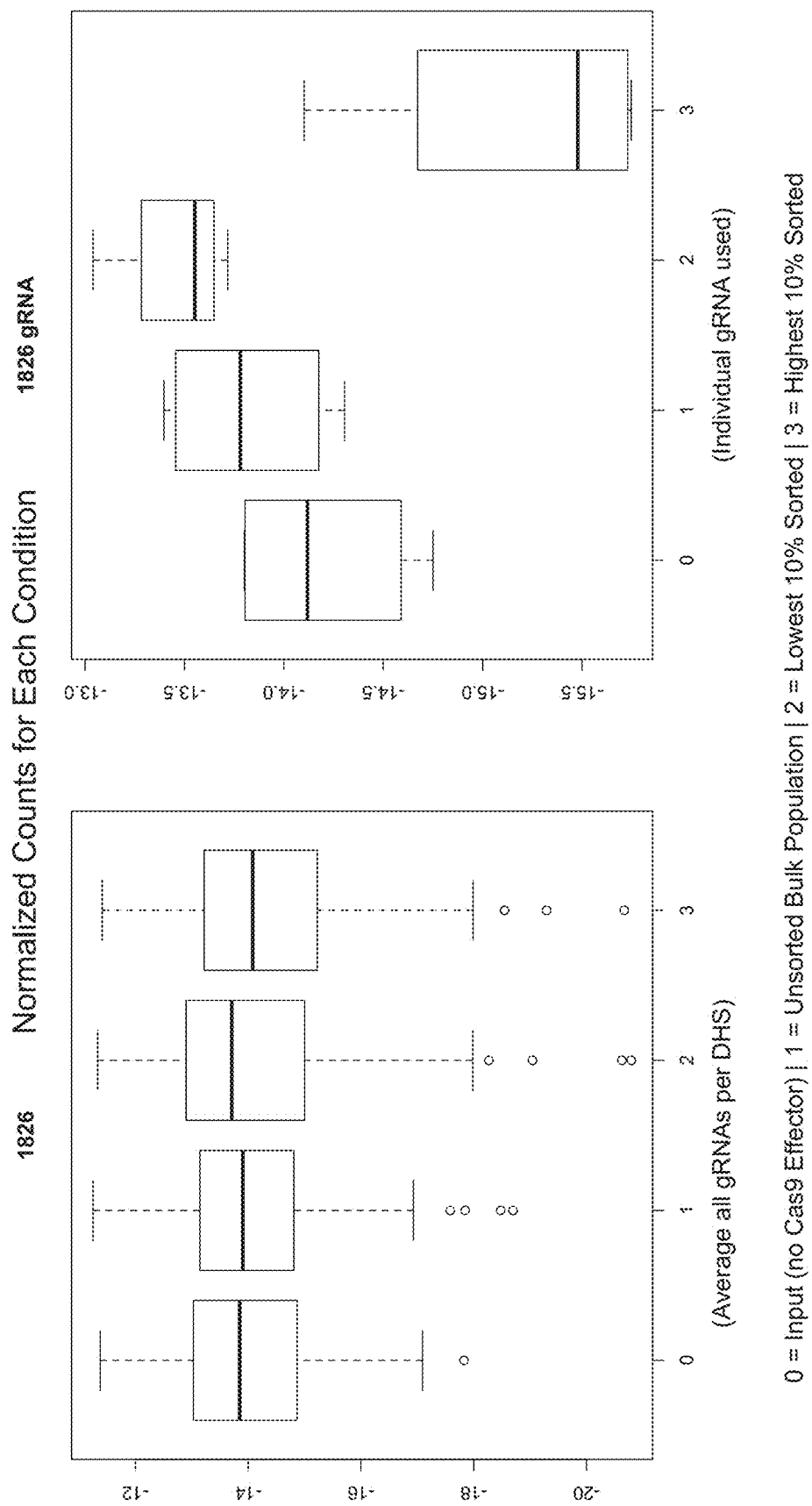
Figure 22A:
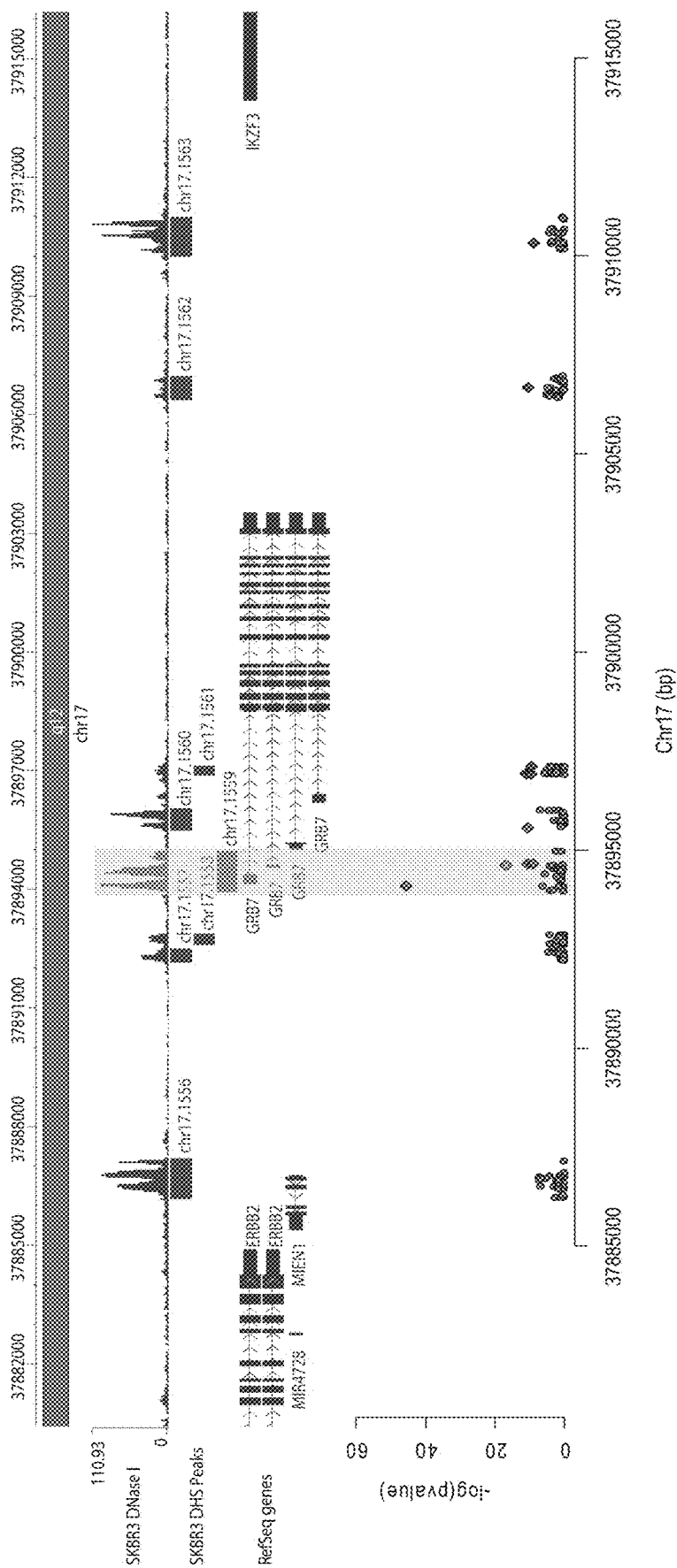
FIGS. 22A-22C show enrichment of gRNA 1559.1 ("1559").
Figure 22B:
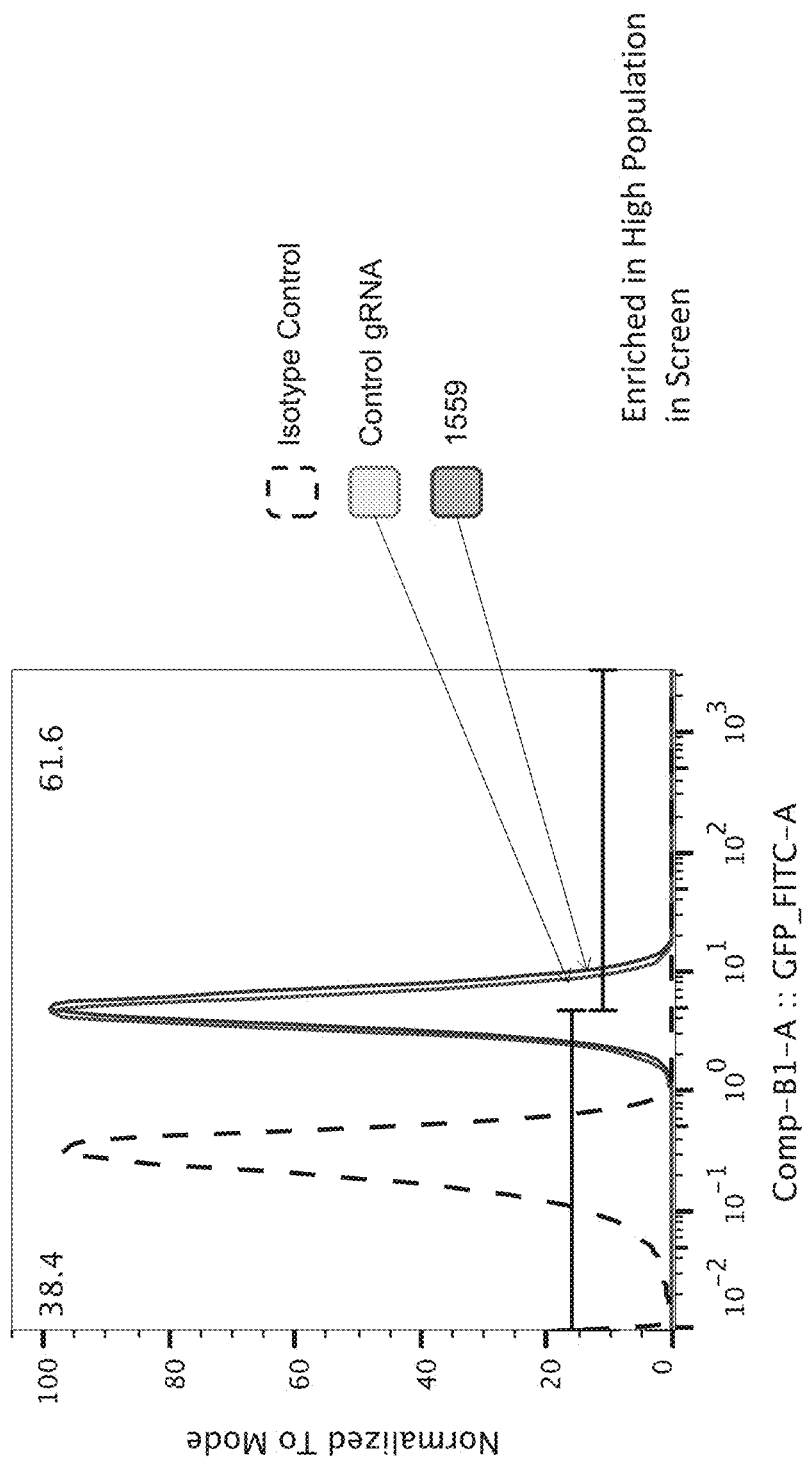
Figure 22C:
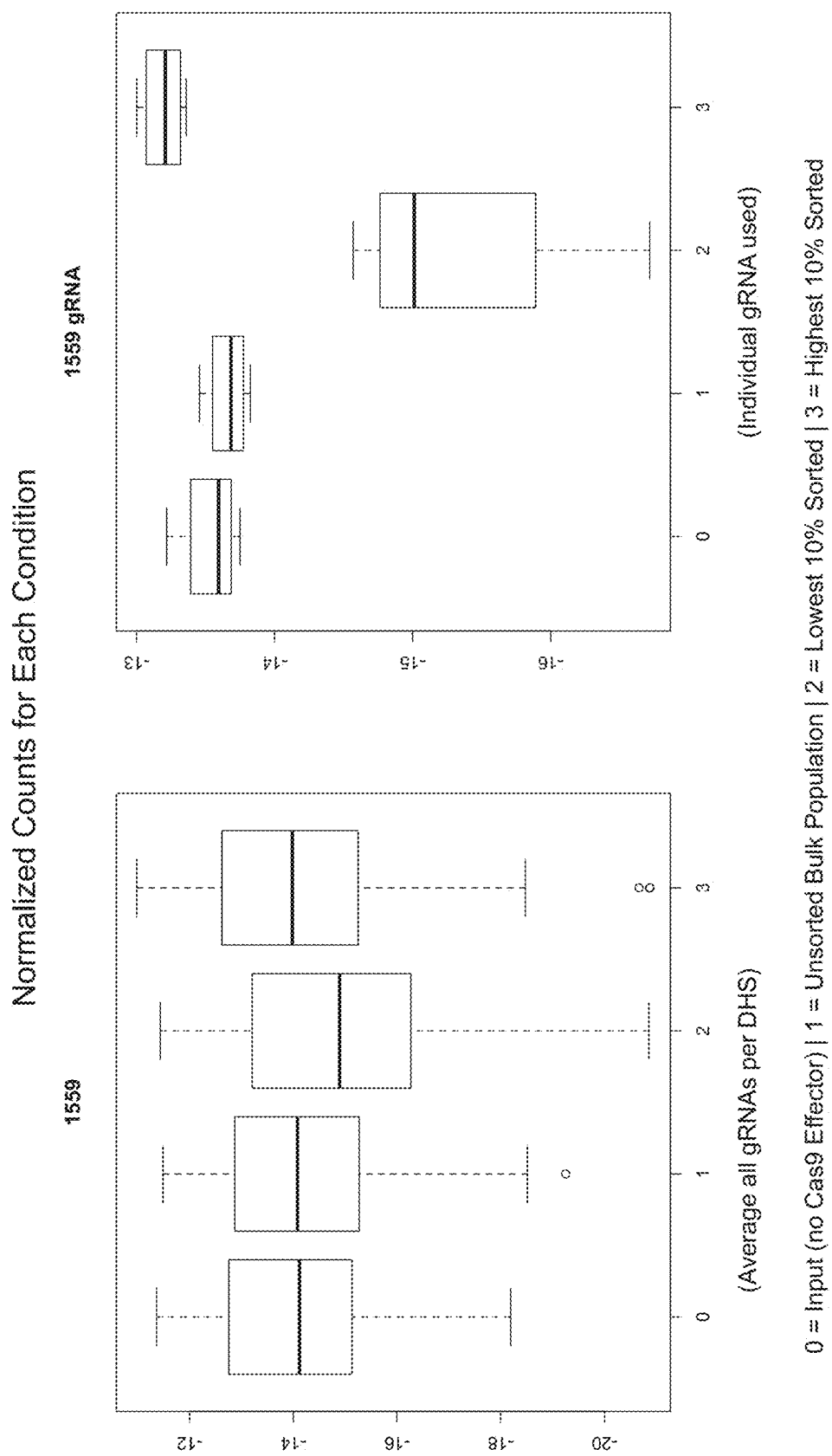
Figure 23A:
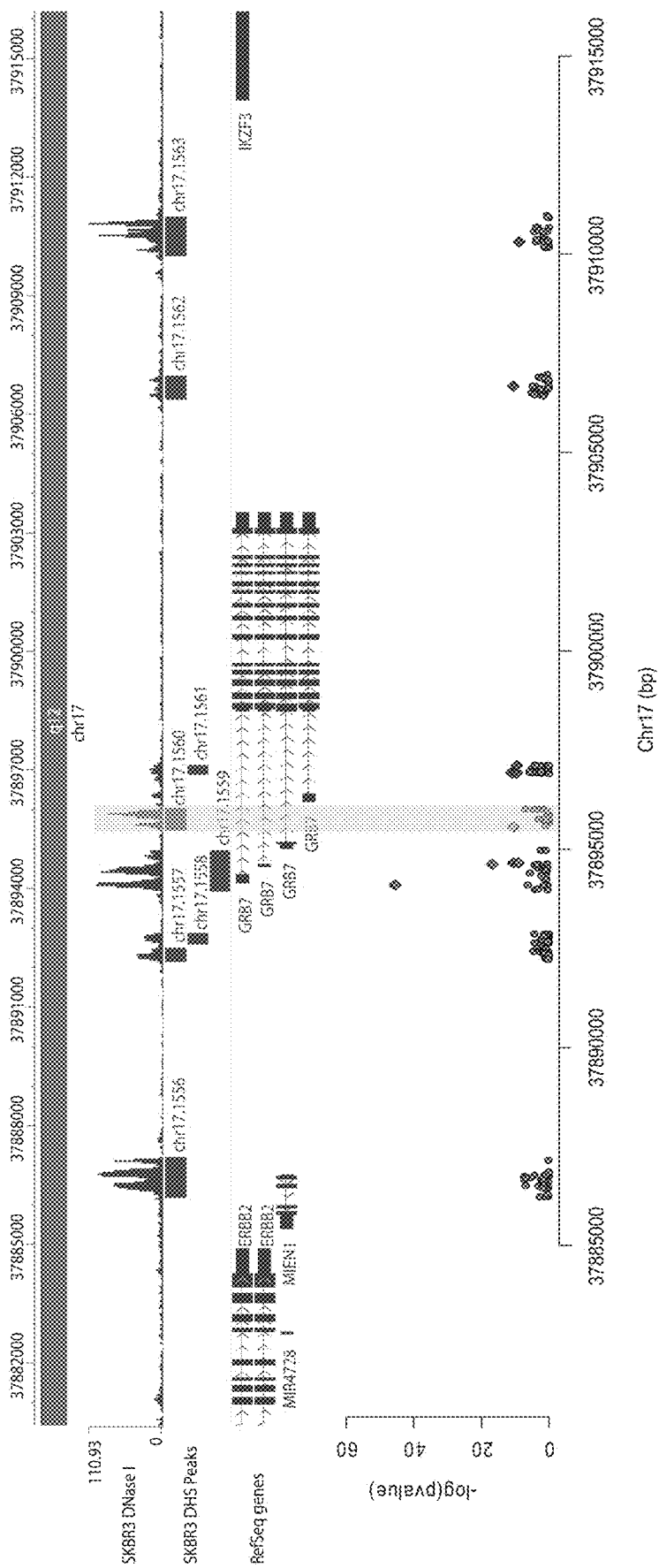
FIGS. 23A-23C show enrichment of gRNA 1560.1 ("1560").
Figure 23B:
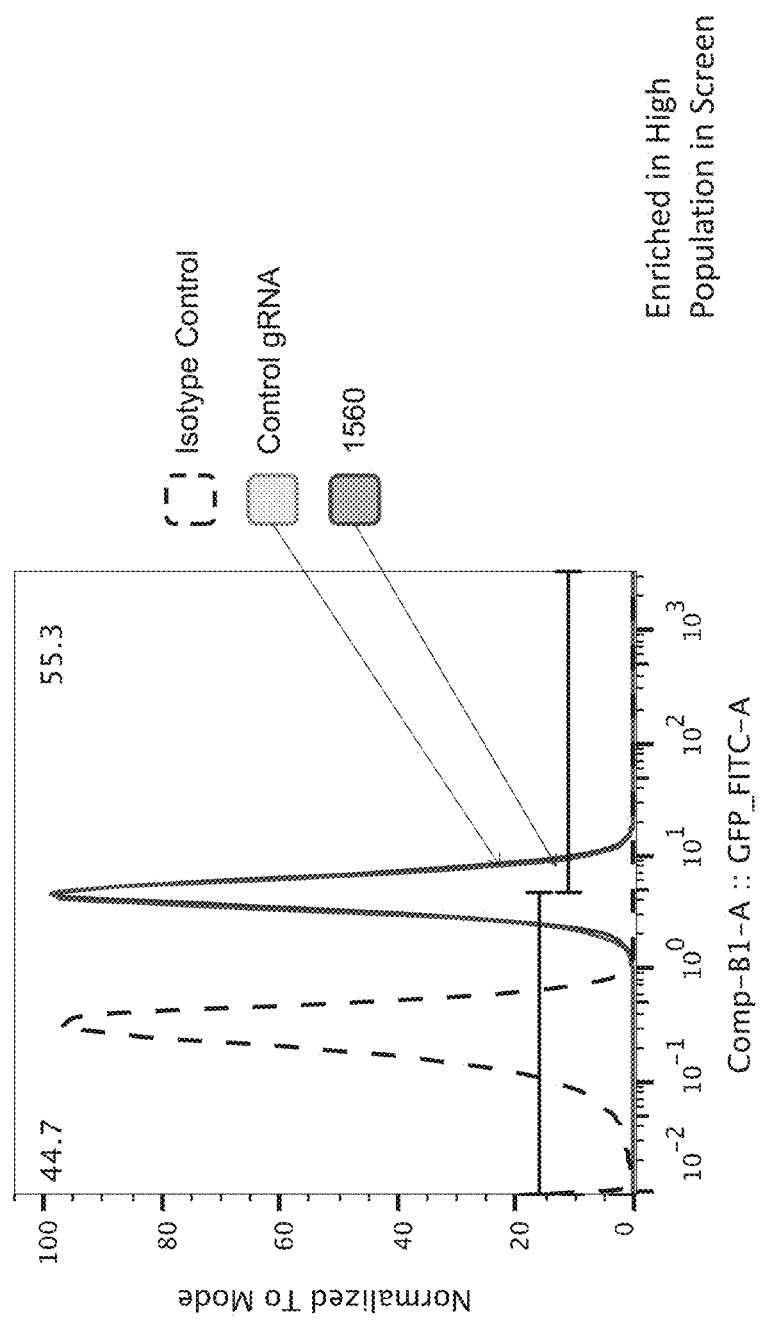
Figure 23C:
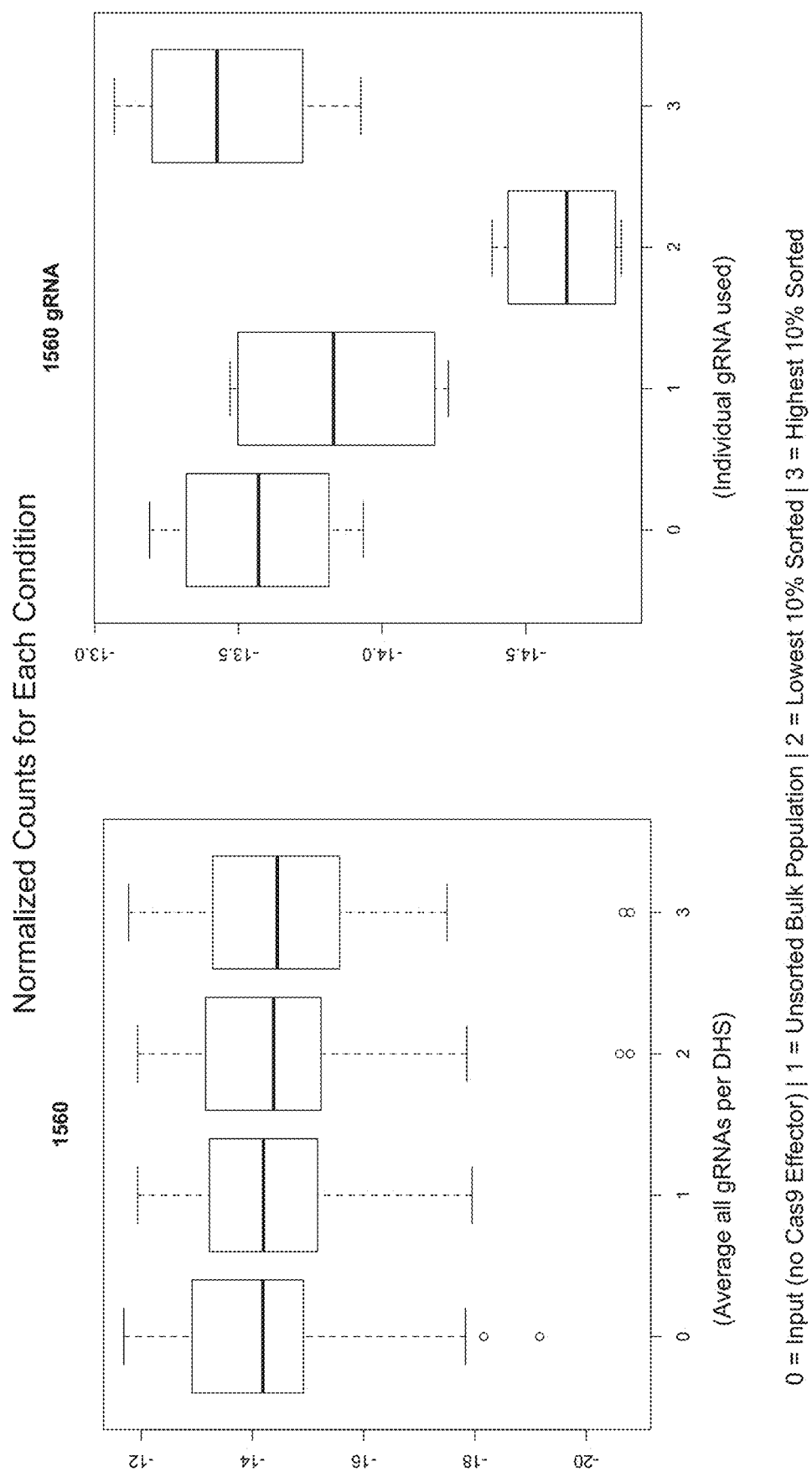
Figure 24A:
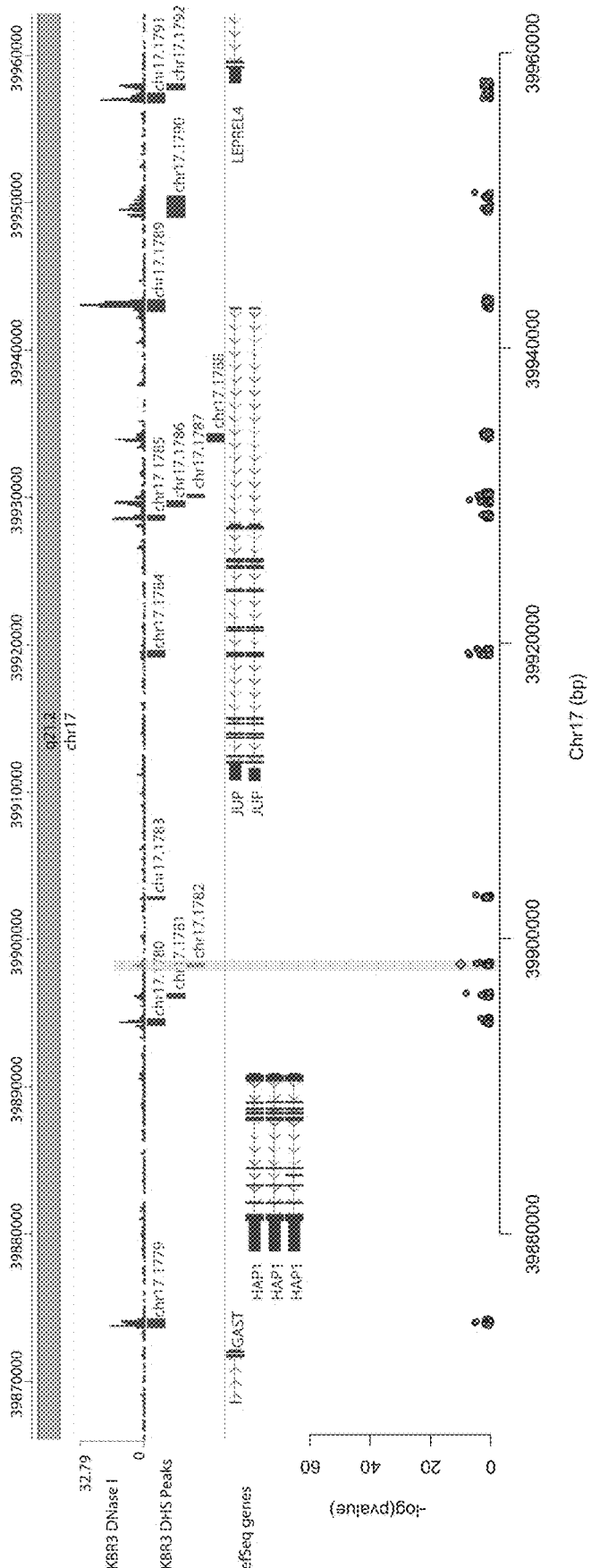
FIGS. 24A-24C show enrichment of gRNA 1782.1 ("1782").
Figure 24B:
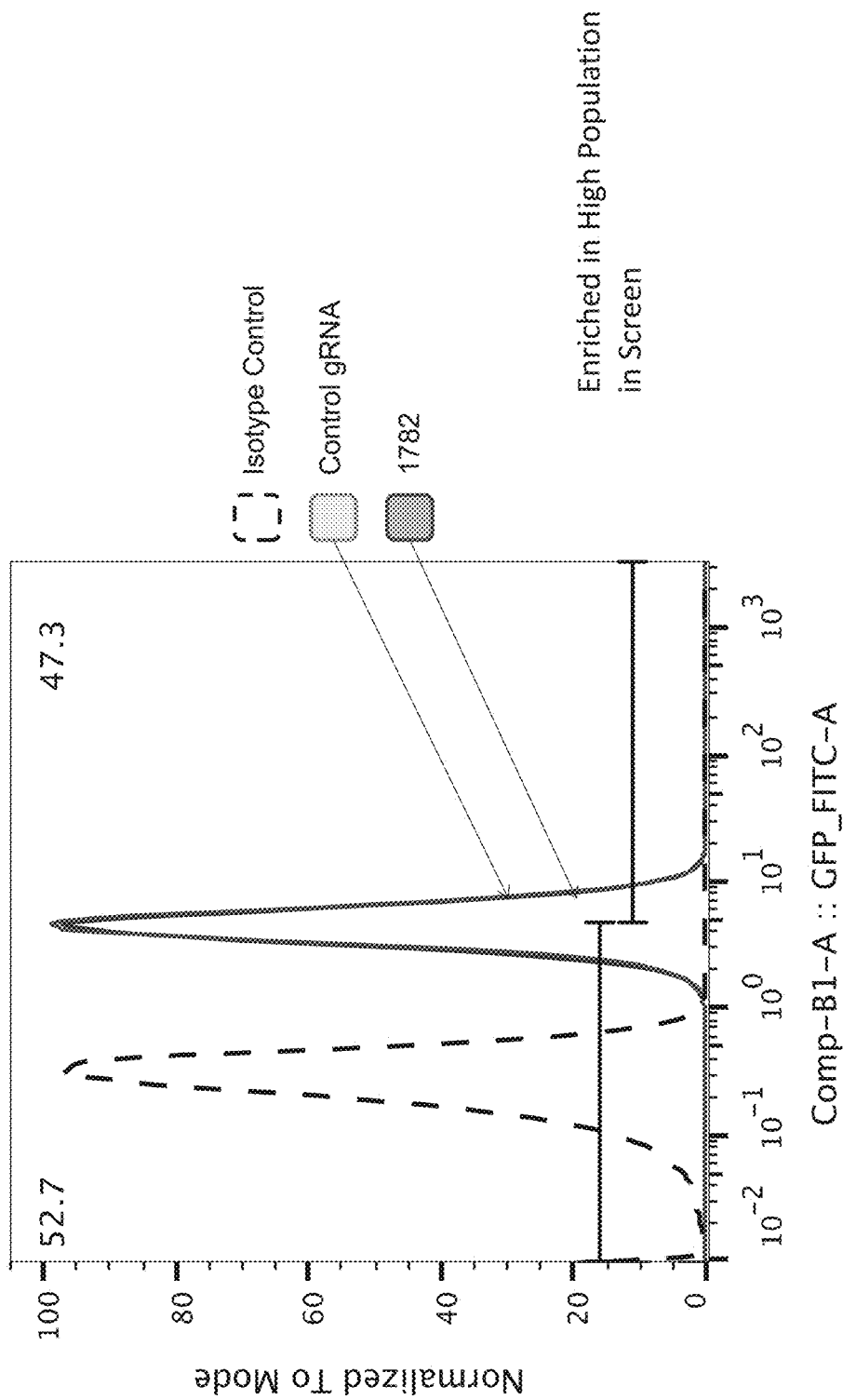
Figure 24C:
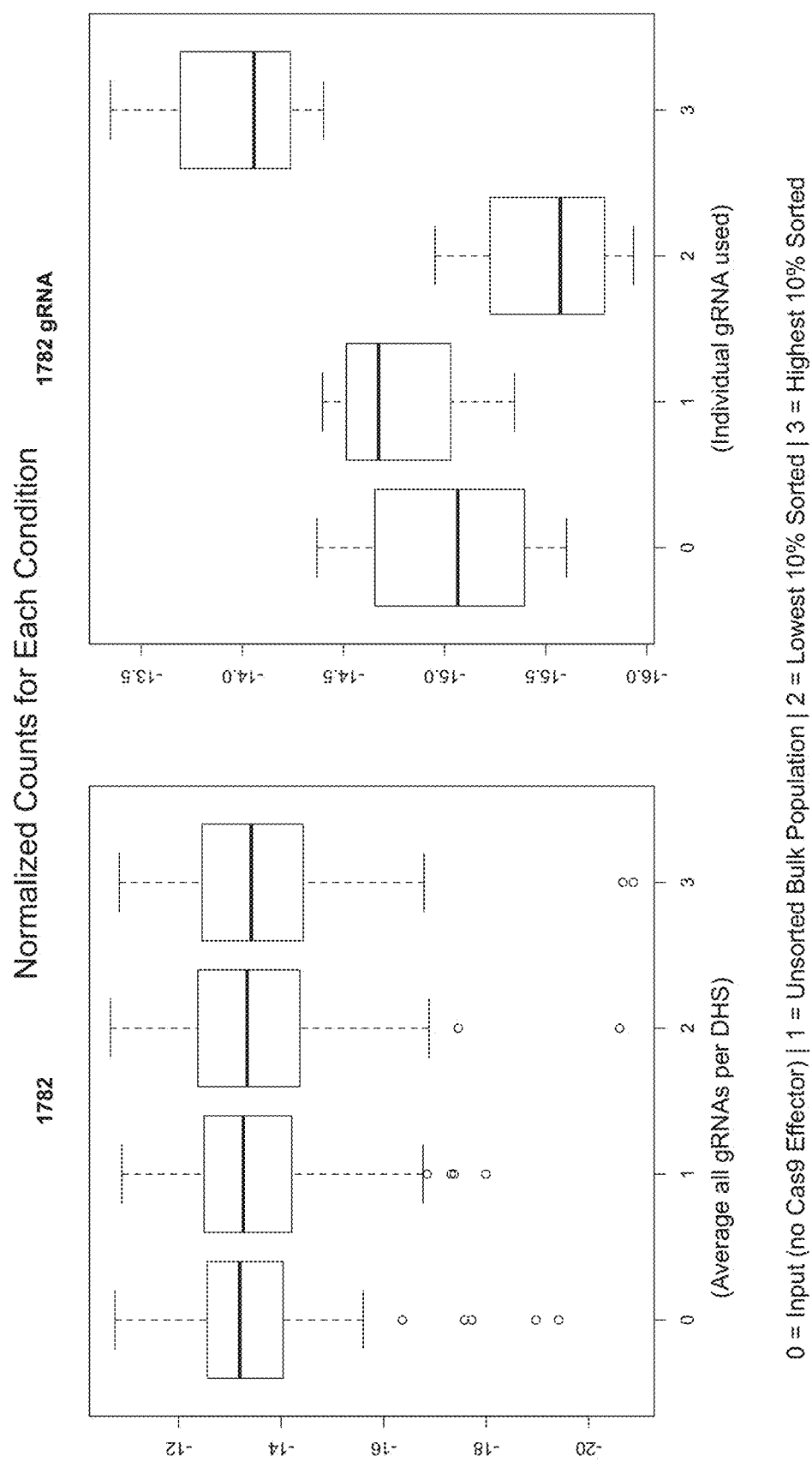
Figure 25A:
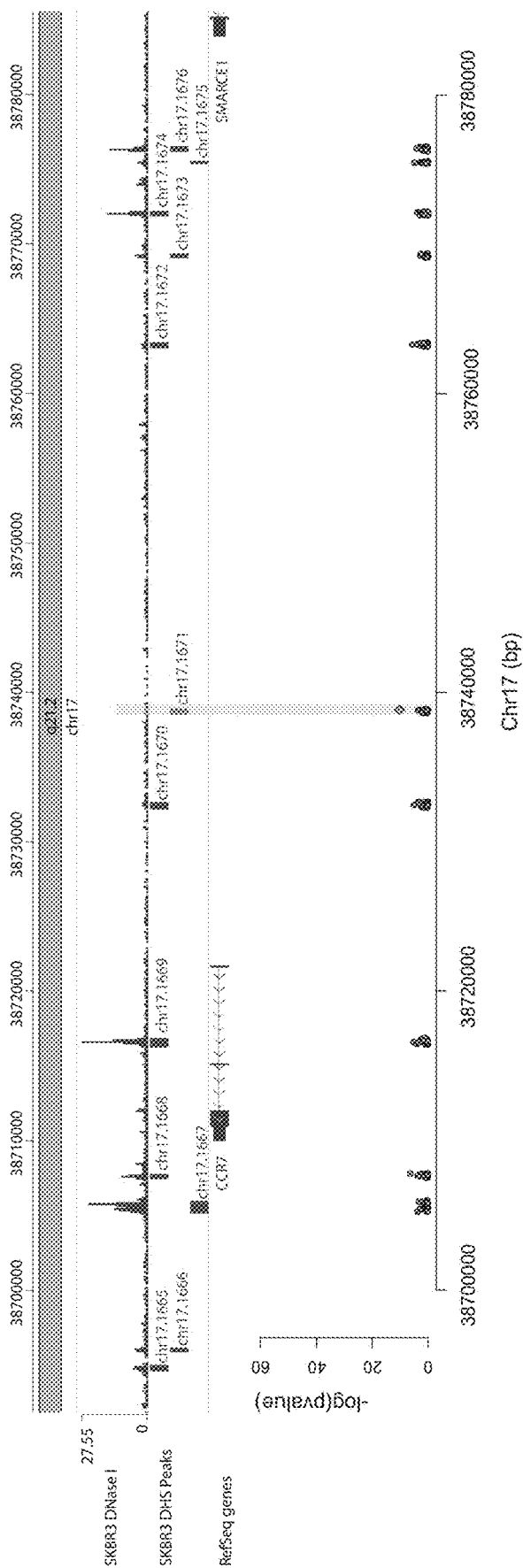
FIGS. 25A-25C show enrichment of gRNA 1671.1 ("1671").
Figure 25B:
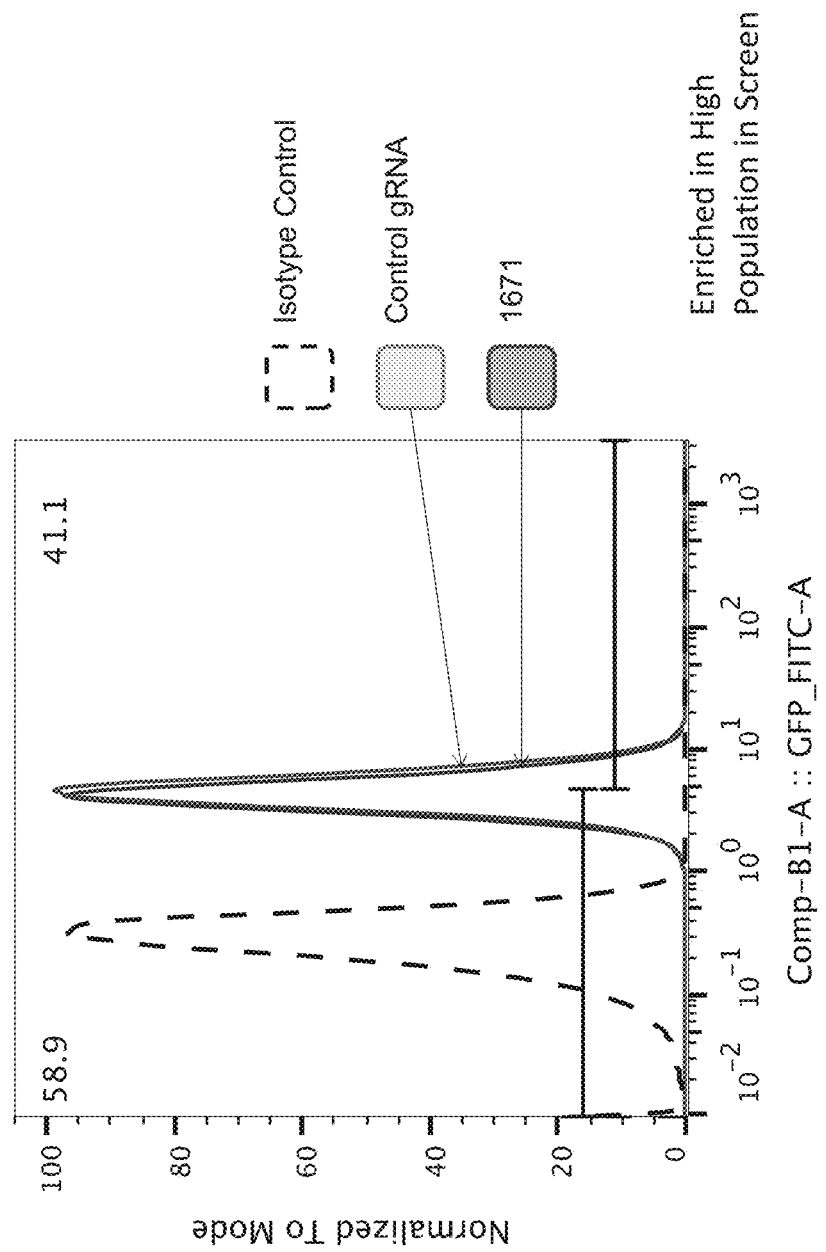
Figure 25C:
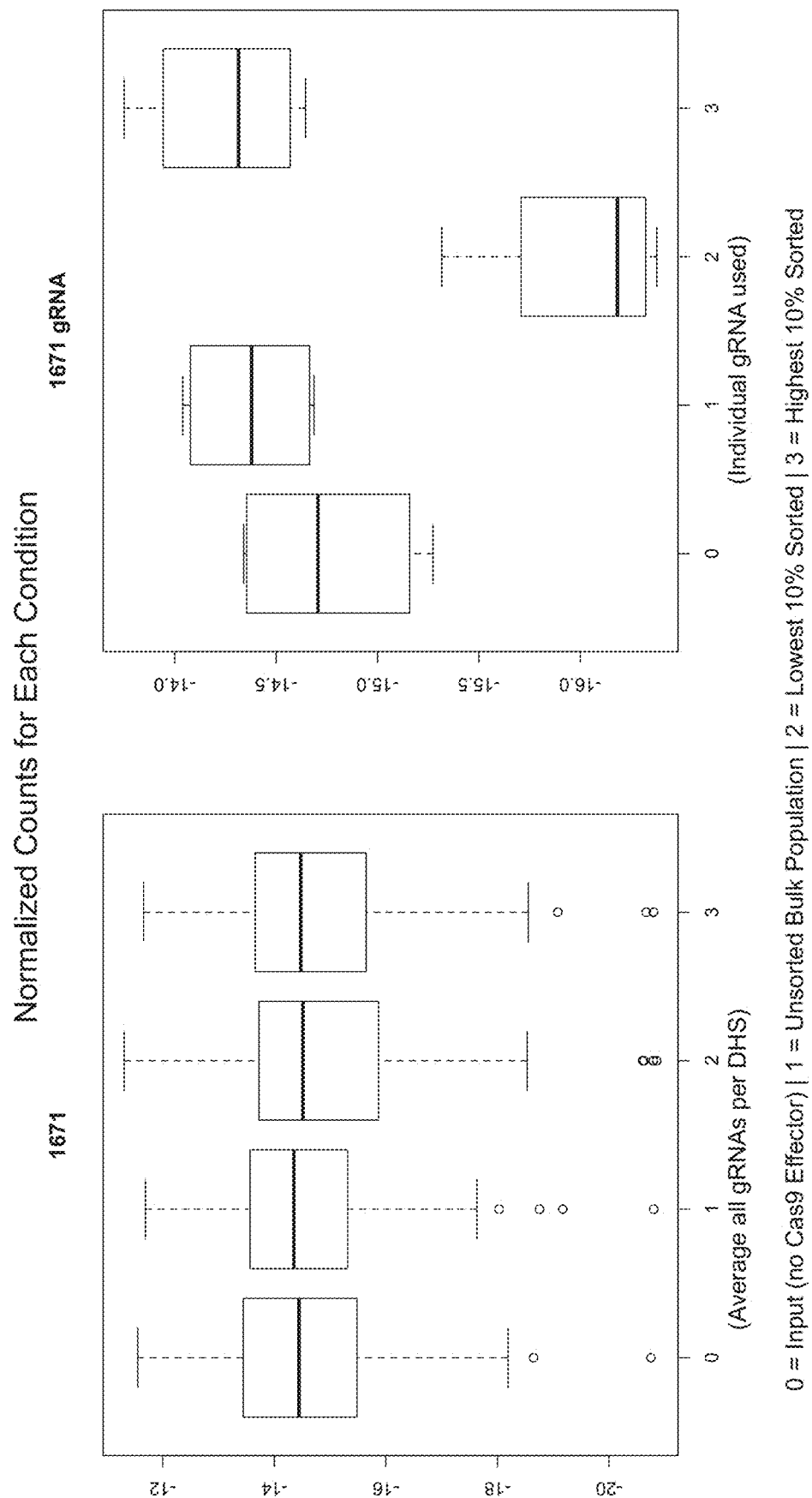
Figure 26A:
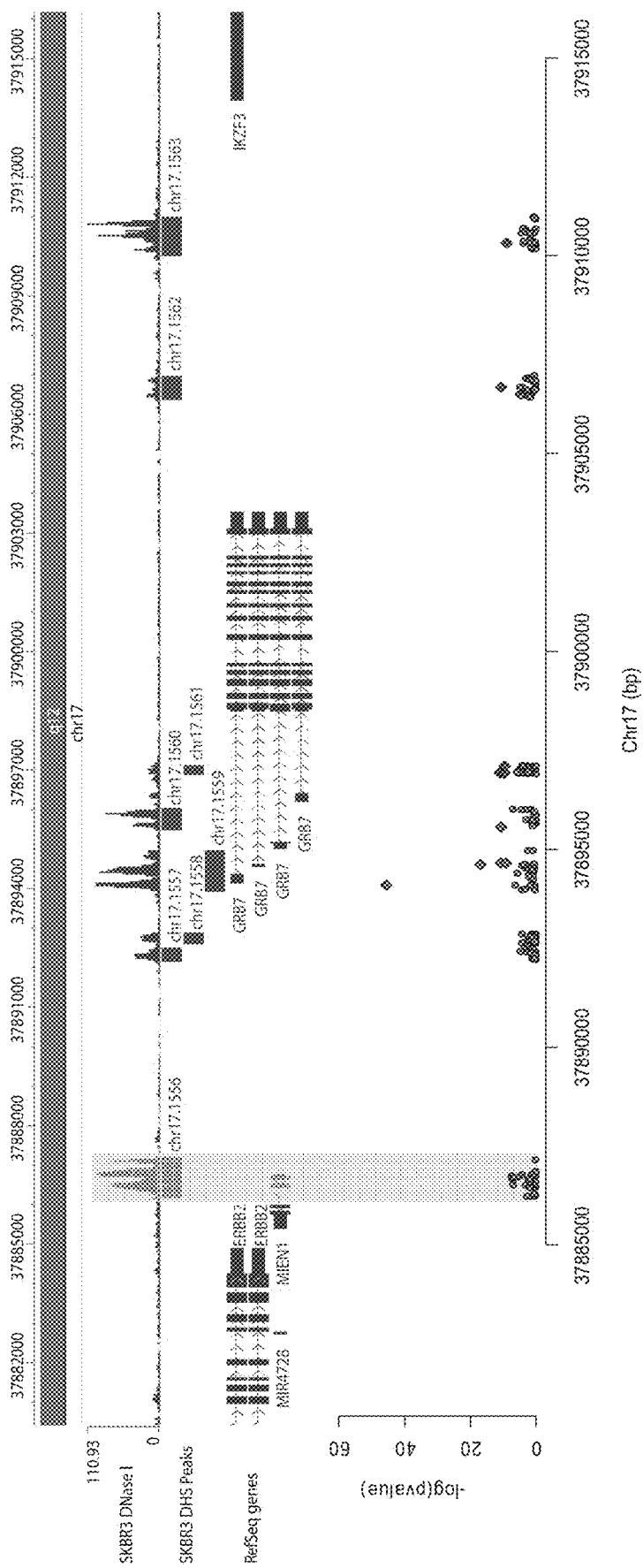
FIGS. 26A-26C show enrichment of gRNA 1556.1 ("1556").
Figure 26B:
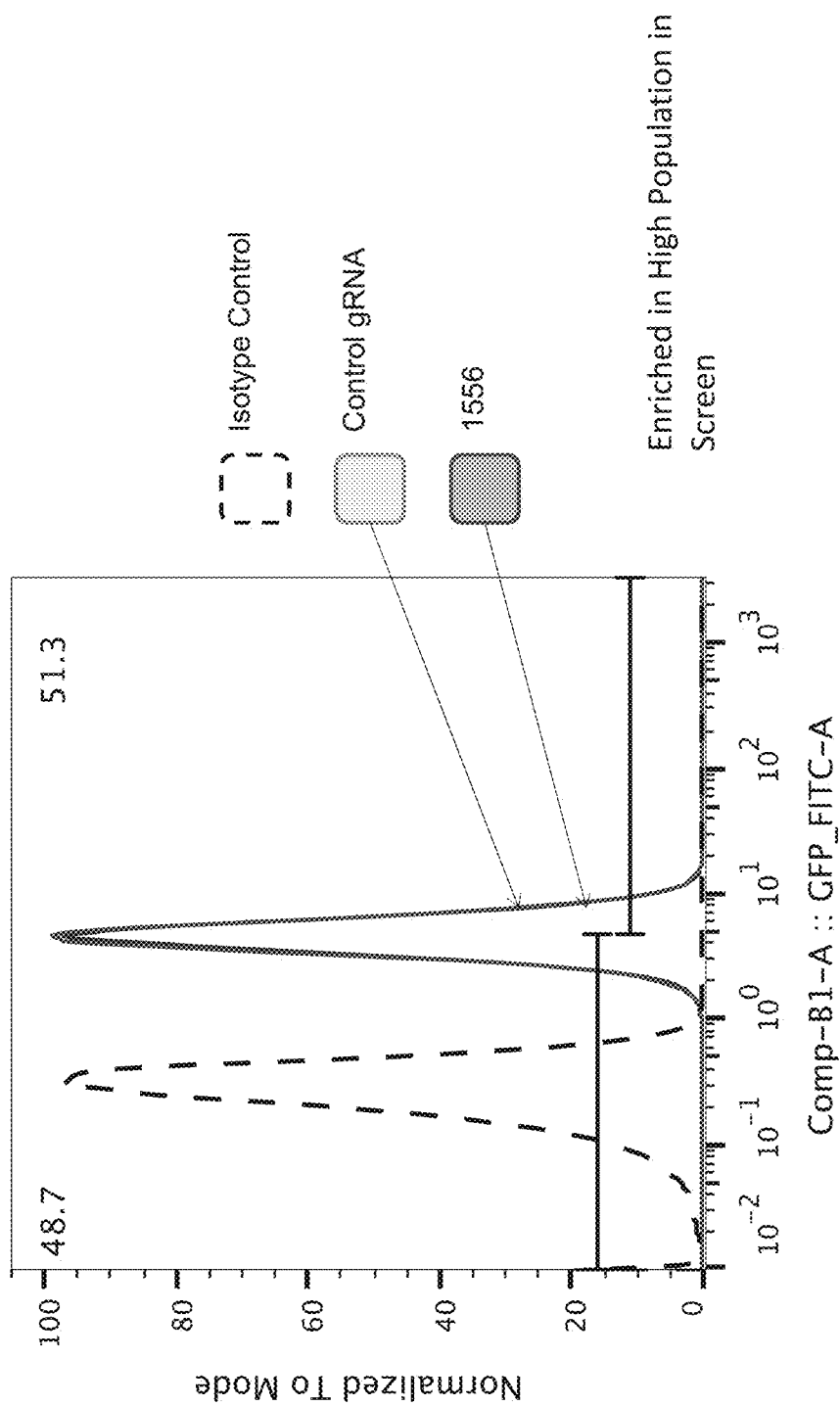
Figure 26C:
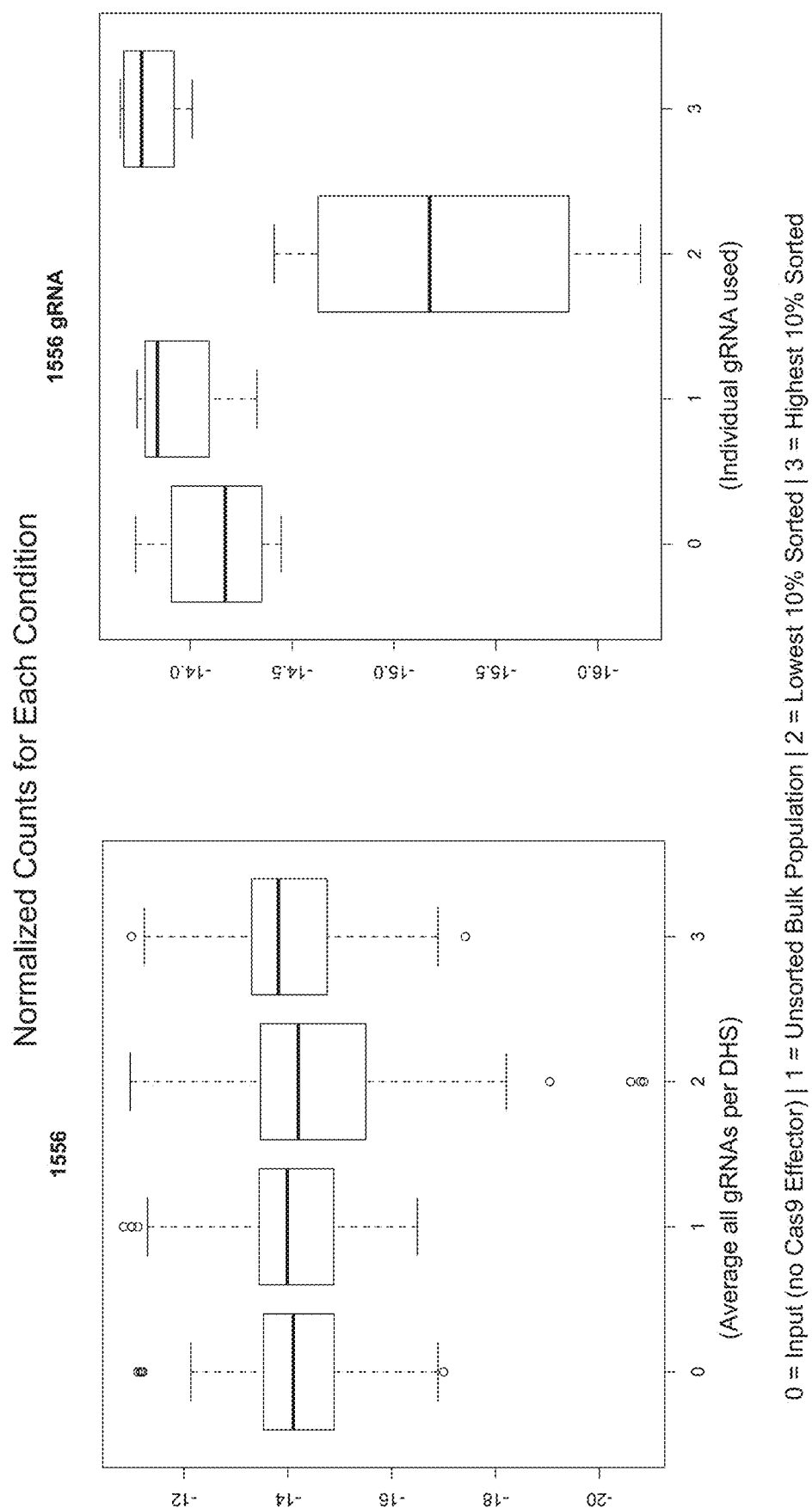
Figure 27A:
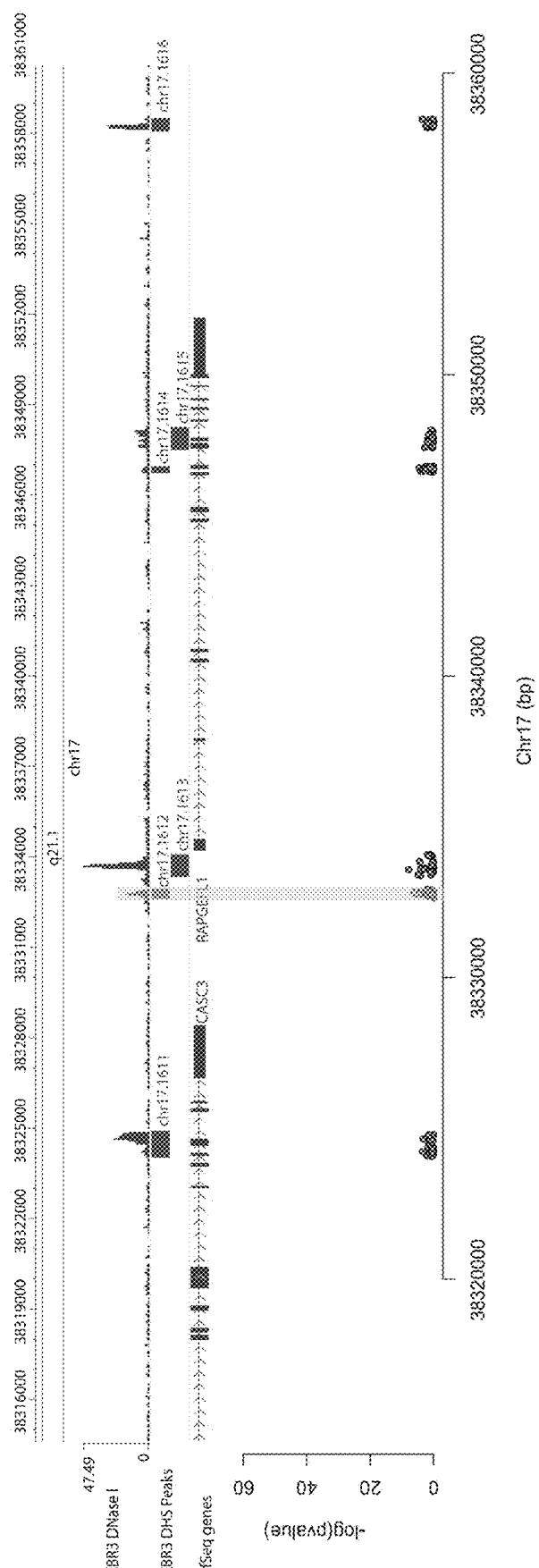
FIGS. 27A-27C show enrichment of gRNA 1612.1 ("1612").
Figure 27B:
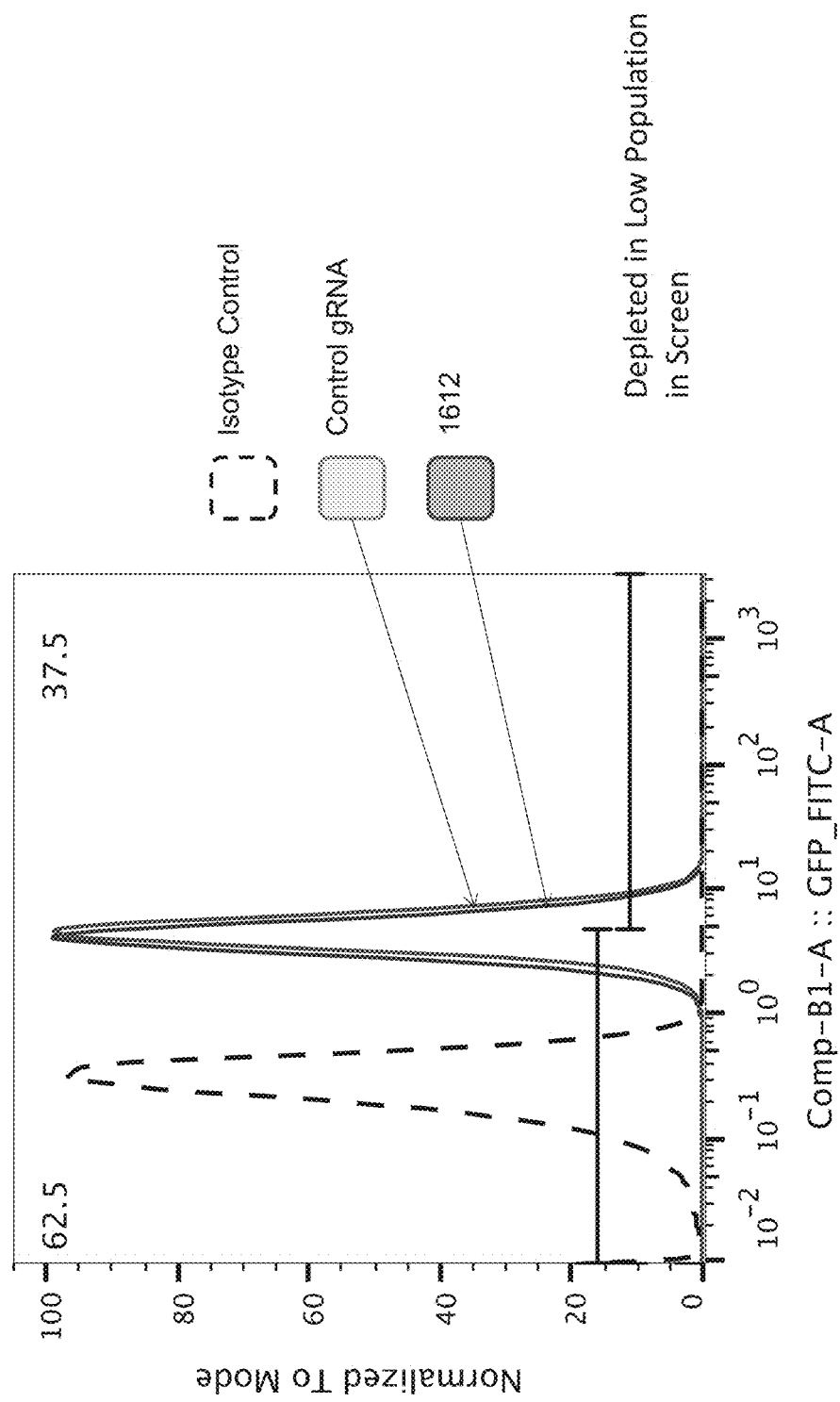
Figure 27C:
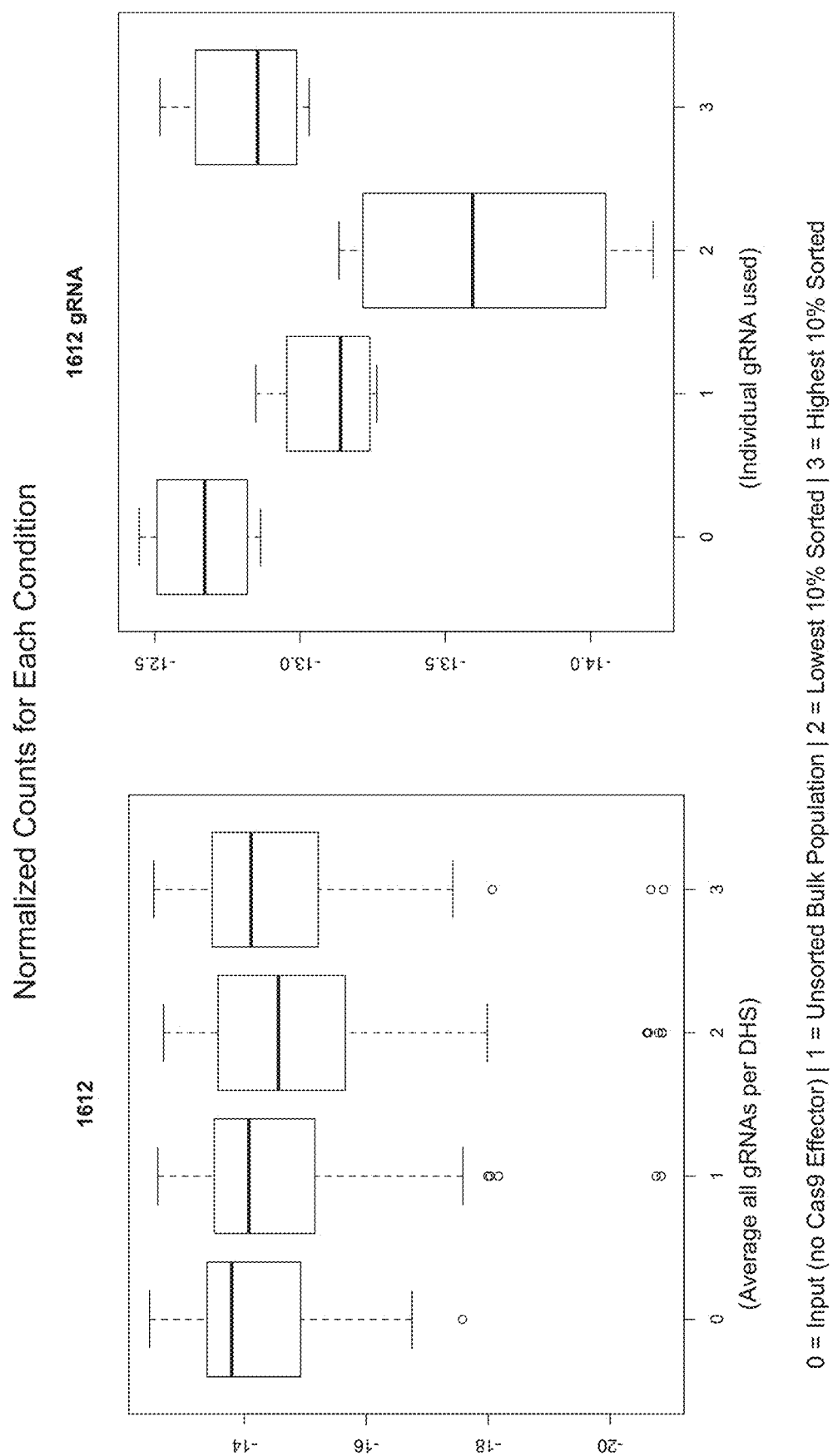
Figure 28A:
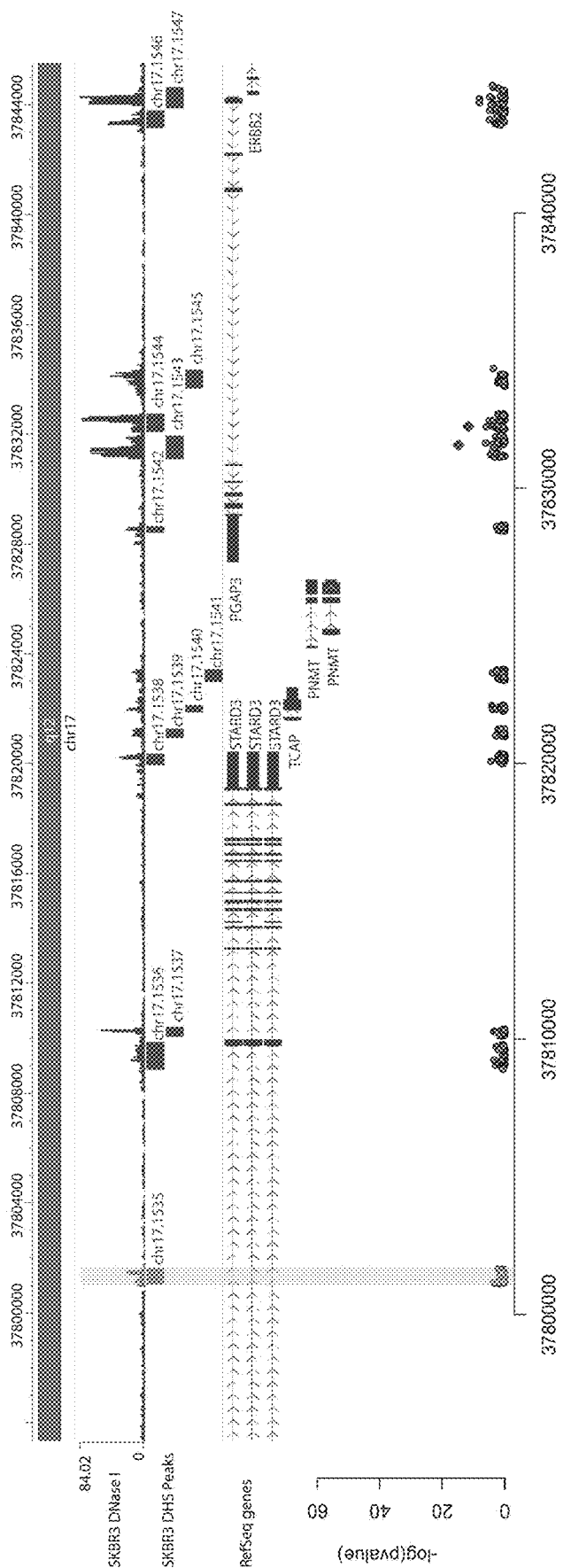
FIGS. 28A-28C show enrichment of gRNA 1535.1 ("1535").
Figure 28B:
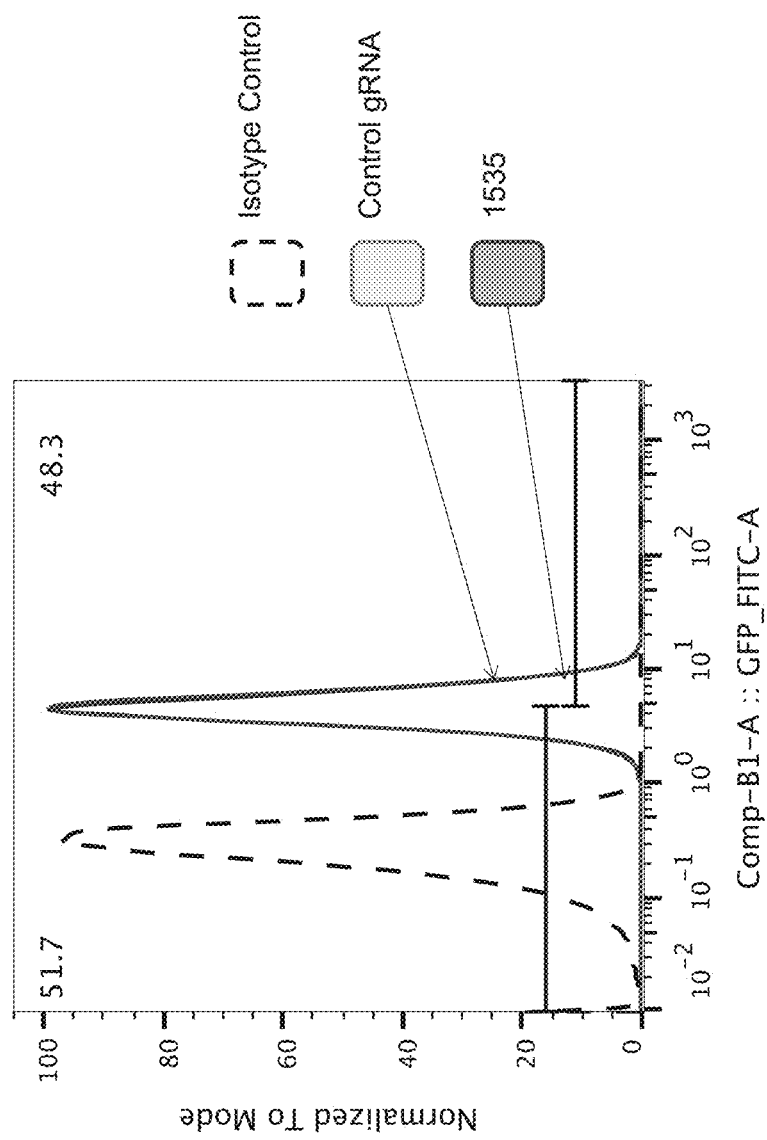
Figure 28C:
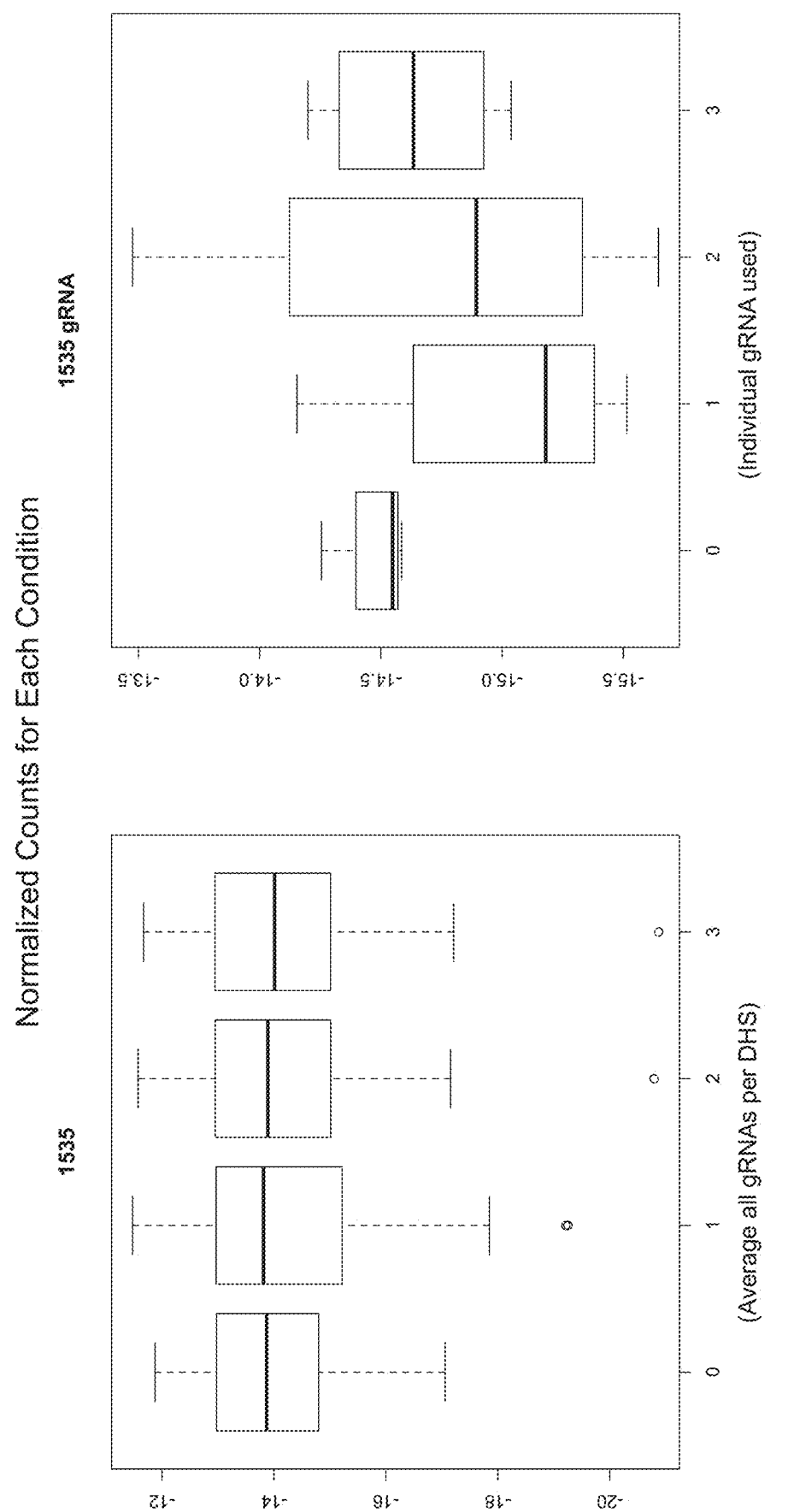

The enrichment of gRNA 1549 is shown in FIGS. 12A-12C. The enrichment of gRNA 1553 is shown in FIGS. 13A-13C. The enrichment of gRNA 1543 is shown in FIGS. 14A-14C. The enrichment of gRNA 1544 is shown in FIGS. 15A-15C. The enrichment of gRNA 1561 is shown in FIGS. 16A-16C. The enrichment of gRNA 1769 is shown in FIGS. 17A-17C. The enrichment of gRNA 1592 is shown in FIGS. 18A-18C. The enrichment of gRNA 1856 is shown in FIGS. 19A-19C. The enrichment of gRNA 1562 is shown in FIGS. 20A-20C. The enrichment of gRNA 1826 is shown in FIGS. 21A-21C. The enrichment of gRNA 1559 is shown in FIGS. 22A-22C. The enrichment of gRNA 1560 is shown in FIGS. 23A-23C. The enrichment of gRNA 1782 is shown in FIGS. 24A-24C. The enrichment of gRNA 1671 is shown in FIGS. 25A-25C. The enrichment of gRNA 1556 is shown in FIGS. 26A-26C. The enrichment of gRNA 1612 is shown in FIGS. 27A-27C. The enrichment of gRNA 1535 is shown in FIGS. 28A-28C.

Example 6

HER2 Regulatory Element Screening with CRISPR/dCas9$^{p300}$ Screen

Figure 9C:
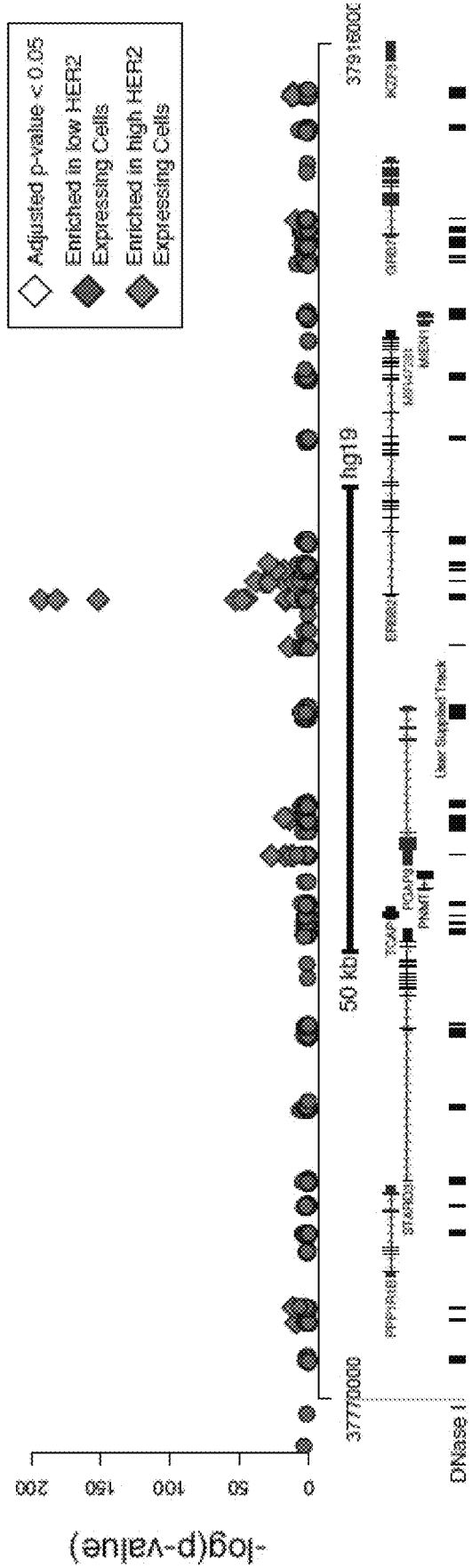
Figure 9D:
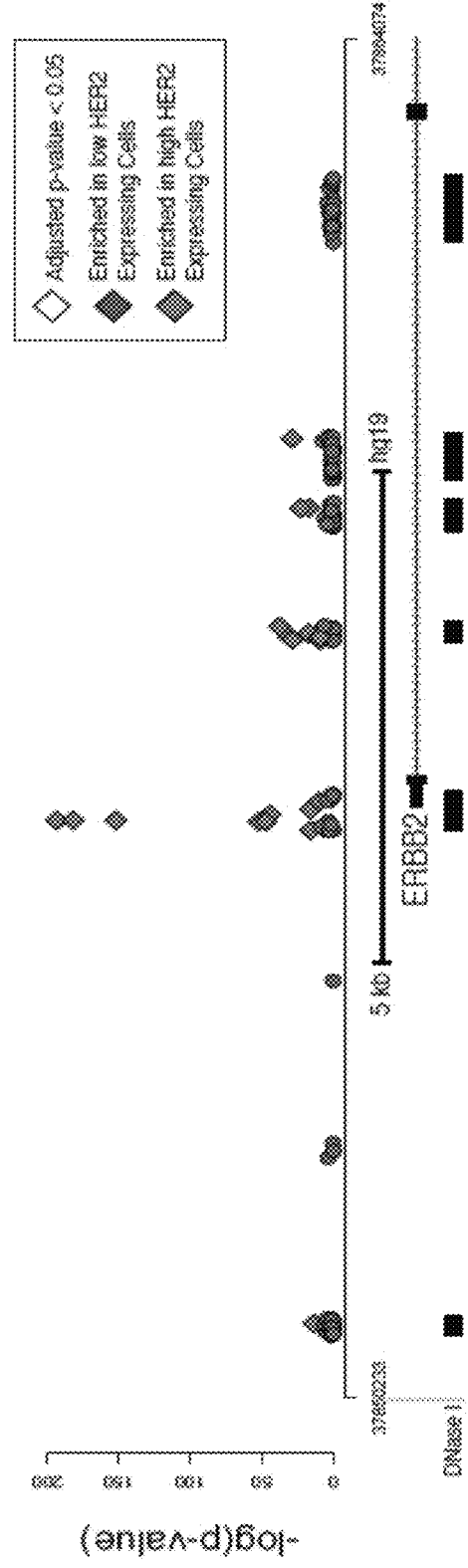

The HER2 gRNA library was also screened with HER2 dCas9$^{p300}$ for enhancers. FIG. 9A shows flow cytometry data of dCas9$^{p300}$ activating HER2 in 293Tcells measured via cell surface staining with a monoclonal antibody. FIG. 9B shows a Manhattan plot showing results of a screen for regulatory elements in the 4 Mb surrounding the HER2 gene using the dCas9$^{p300}$ activator. FIG. 9C shows a zoomed view of the HER2 region. When comparing high and low expressing HER2 cell populations, gRNAs are enriched in the promoter and three intronic DHSs of HER2 as well as several nearby DHSs. FIG. 9D shows a closer view of the beginning of the HER2 gene. Interestingly, the intronic DHS enriched in the dCas9$^{KRAB}$ screen did not appear enriched in the p300 screen.

Figure 29:
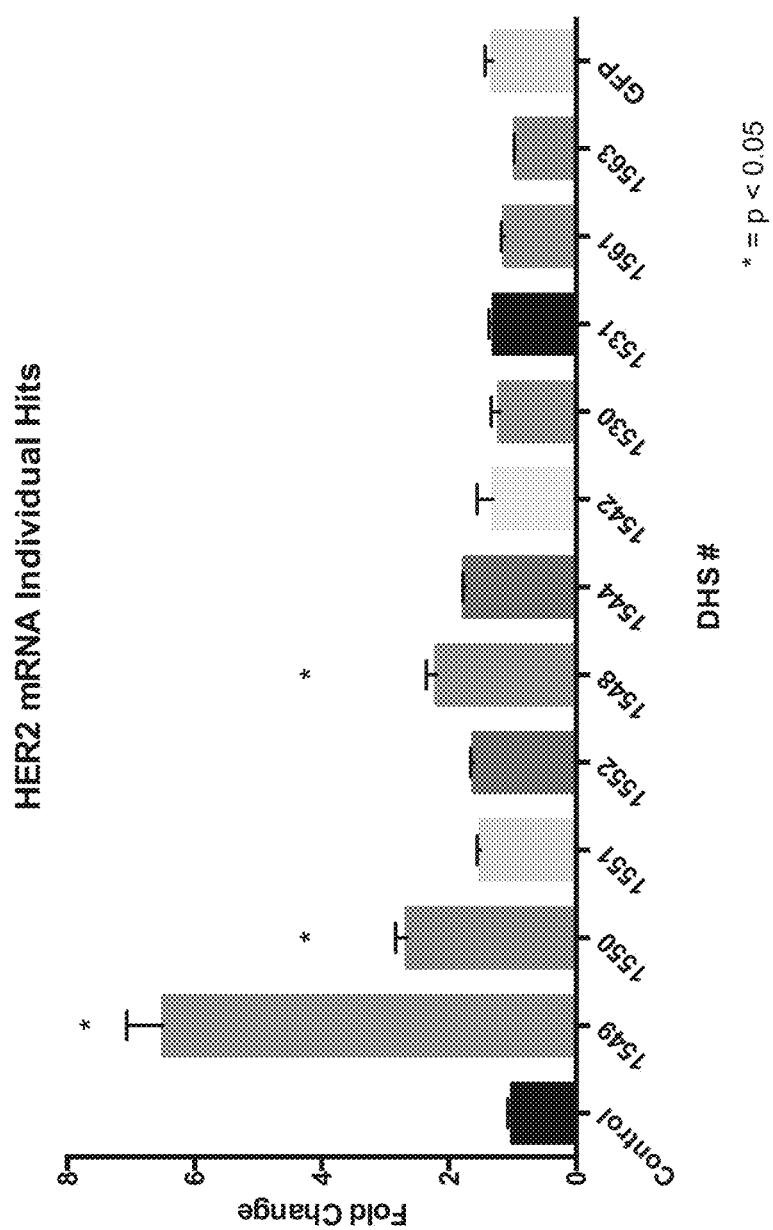
FIG. 29 shows the fold change in expression of HER2 mRNA individual hits (gRNAs 1549, 1550, 1551, 1552, 1548, 1544, 1542, 1530, 1531, 1561, and 1563) that were identified using the CRISPR/dCas9$^{p300\ Core}$ activation system compared with Control and GFP control.

The fold change in expression of HER2 mRNA individual hits (gRNAs 1549, 1550, 1551, 1552, 1548, 1544, 1542, 1530, 1531, 1561, and 1563) that were identified using the CRISPR/dCas9$^{p300\ Core}$ activation system compared with Control and GFP control is shown in FIG. 29. See Table 4, where the protospacer sequence is bolded.

TABLE 4

293T-dCas9$^{p300}$ HER2 Screen Validation sgRNAs

| Name | SEQ ID NO: | sgRNA Sequence |
|---|---|---|
| 1549 | 39 | GGGTGCGTCCCTCCTAGCGCGTTTTAGAGCTAGAAAT<br>AGCAAGTTAAAATAAGGCTAGTCCGTTATCAACTTGA<br>AAAAGTGGCACCGAGTCGGTGC |
| 1550 | 40 | GGATGTACTCCCTGGAAGAGGTTTTAGAGCTAGAAAT<br>AGCAAGTTAAAATAAGGCTAGTCCGTTATCAACTTGA<br>AAAAGTGGCACCGAGTCGGTGC |
| 1551 | 41 | GTAGAAAGTGGAGCTGAGCTGTTTTAGAGCTAGAAAT<br>AGCAAGTTAAAATAAGGCTAGTCCGTTATCAACTTGA<br>AAAAGTGGCACCGAGTCGGTGC |
| 1552 | 42 | TCAGGCCTGACATCAGACCAGTTTTAGAGCTAGAAAT<br>AGCAAGTTAAAATAAGGCTAGTCCGTTATCAACTTGA<br>AAAAGTGGCACCGAGTCGGTGC |
| 1548 | 43 | GCTGGAGGTATAGACCACTGGTTTTAGAGCTAGAAAT<br>AGCAAGTTAAAATAAGGCTAGTCCGTTATCAACTTGA<br>AAAAGTGGCACCGAGTCGGTGC |
| 1544 | 44 | GACTGCAGGACTGAGCTAAGGTTTTAGAGCTAGAAAT<br>AGCAAGTTAAAATAAGGCTAGTCCGTTATCAACTTGA<br>AAAAGTGGCACCGAGTCGGTGC |
| 1542 | 45 | AGGGACCAAGCTGCTGGGATGTTTTAGAGCTAGAAAT<br>AGCAAGTTAAAATAAGGCTAGTCCGTTATCAACTTGA<br>AAAAGTGGCACCGAGTCGGTGC |
| 1530 | 46 | GACTGAGGCTACCCCTGCTGGTTTTAGAGCTAGAAAT<br>AGCAAGTTAAAATAAGGCTAGTCCGTTATCAACTTGA<br>AAAAGTGGCACCGAGTCGGTGC |
| 1531 | 47 | TTCCTGATAGCCCTTGACCGGTTTTAGAGCTAGAAAT<br>AGCAAGTTAAAATAAGGCTAGTCCGTTATCAACTTGA<br>AAAAGTGGCACCGAGTCGGTGC |
| 1561 | 48 | TGCTAGCCAGAGCGGAATGGGTTTTAGAGCTAGAAAT<br>AGCAAGTTAAAATAAGGCTAGTCCGTTATCAACTTGA<br>AAAAGTGGCACCGAGTCGGTGC |

TABLE 4-continued 293T-dCas9$^{p300}$ HER2 Screen Validation sgRNAs

| Name | SEQ ID NO: | sgRNA Sequence |
|---|---|---|
| 1563 | 49 | CGATGGCGCGTCCCCTCGTGGTTTTAGAGCTAGAAAT AGCAAGTTAAAATAAGGCTAGTCCGTTATCAACTTGA AAAAGTGGCACCGAGTCGGTGC |

Figure 30A:
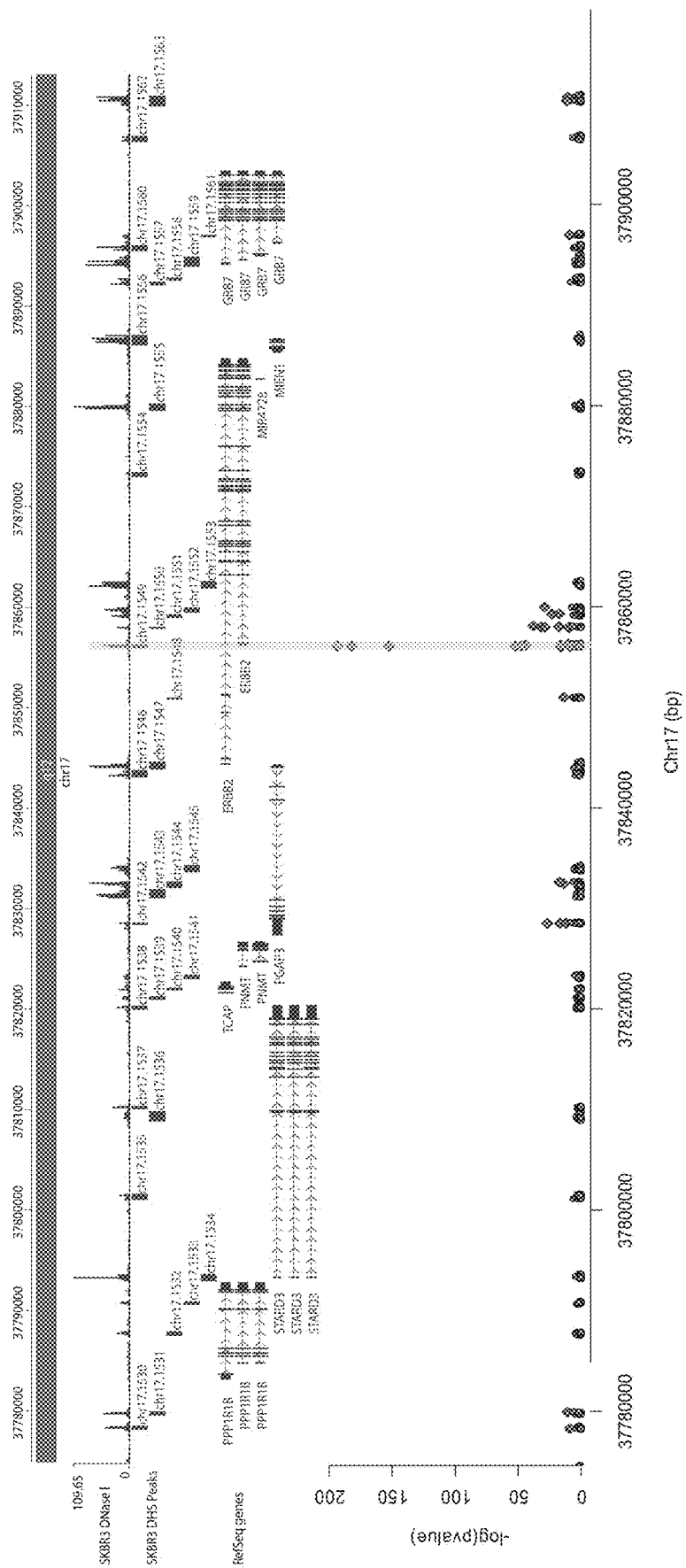
FIGS. 30A-30C show the enrichment of gRNA 1549.
Figure 30B:
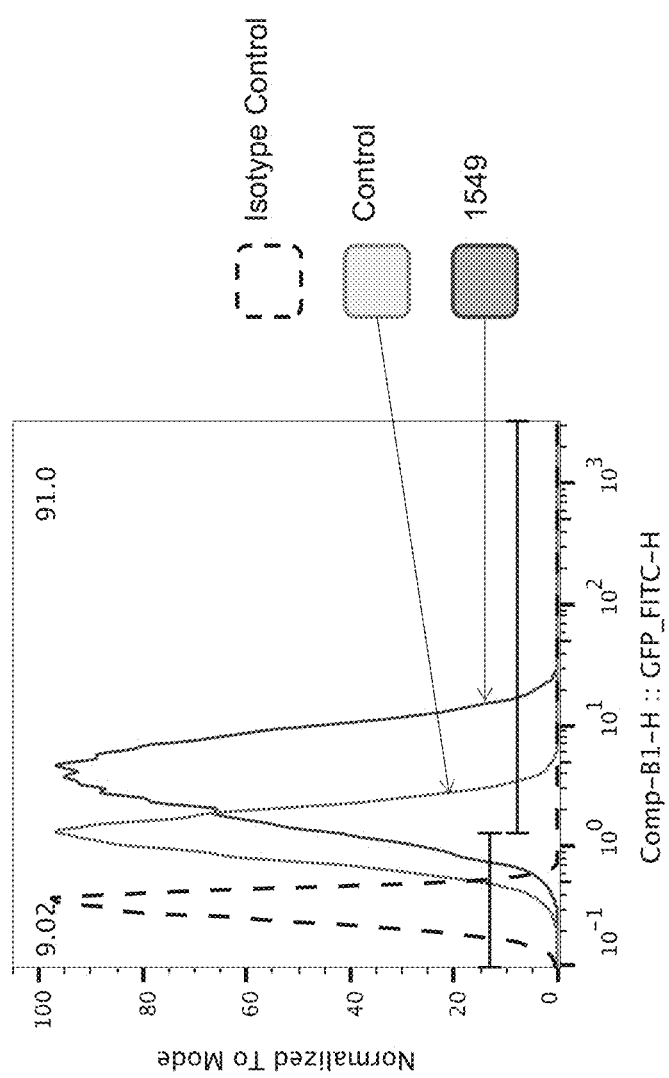
Figure 30C:
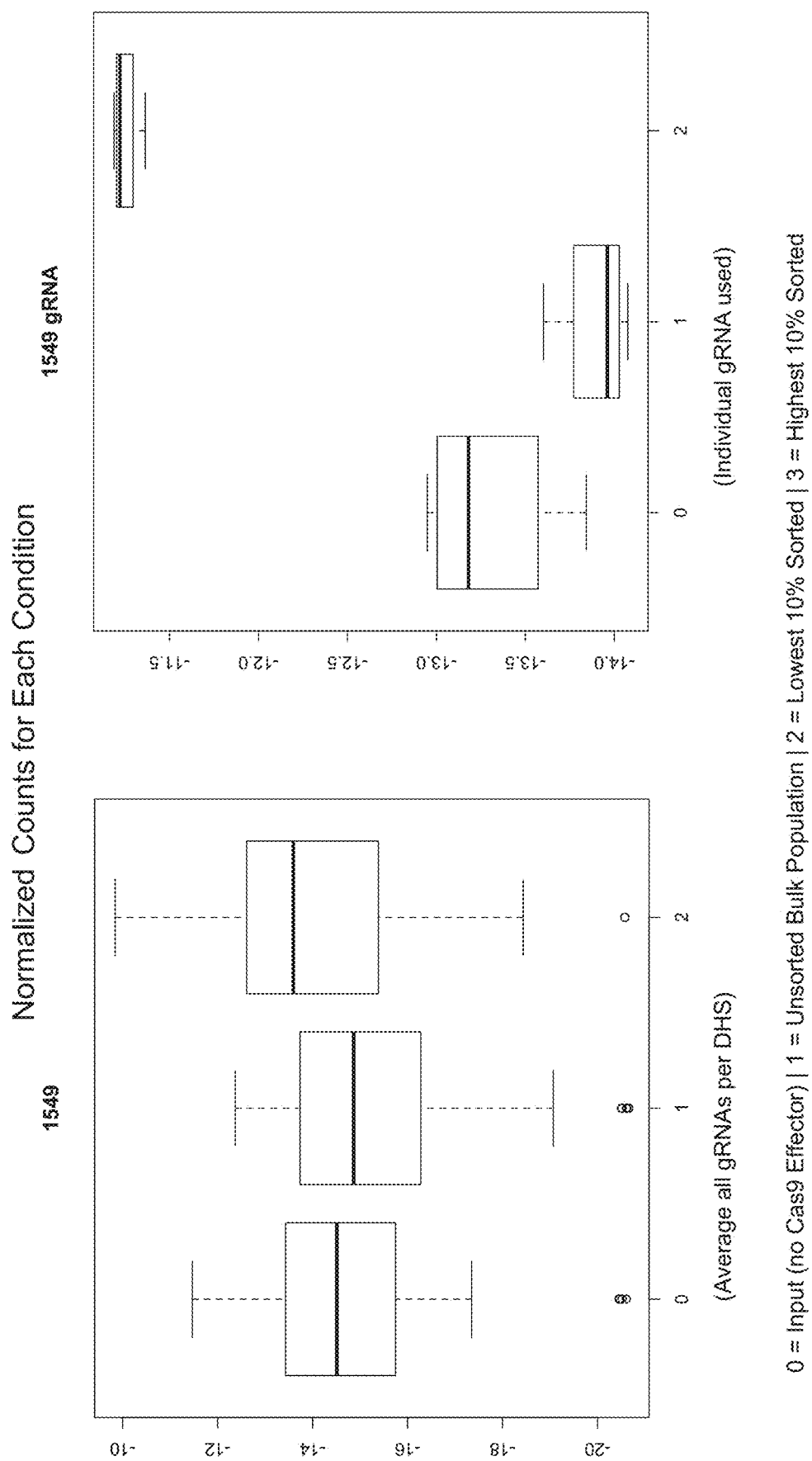
Figure 31A:
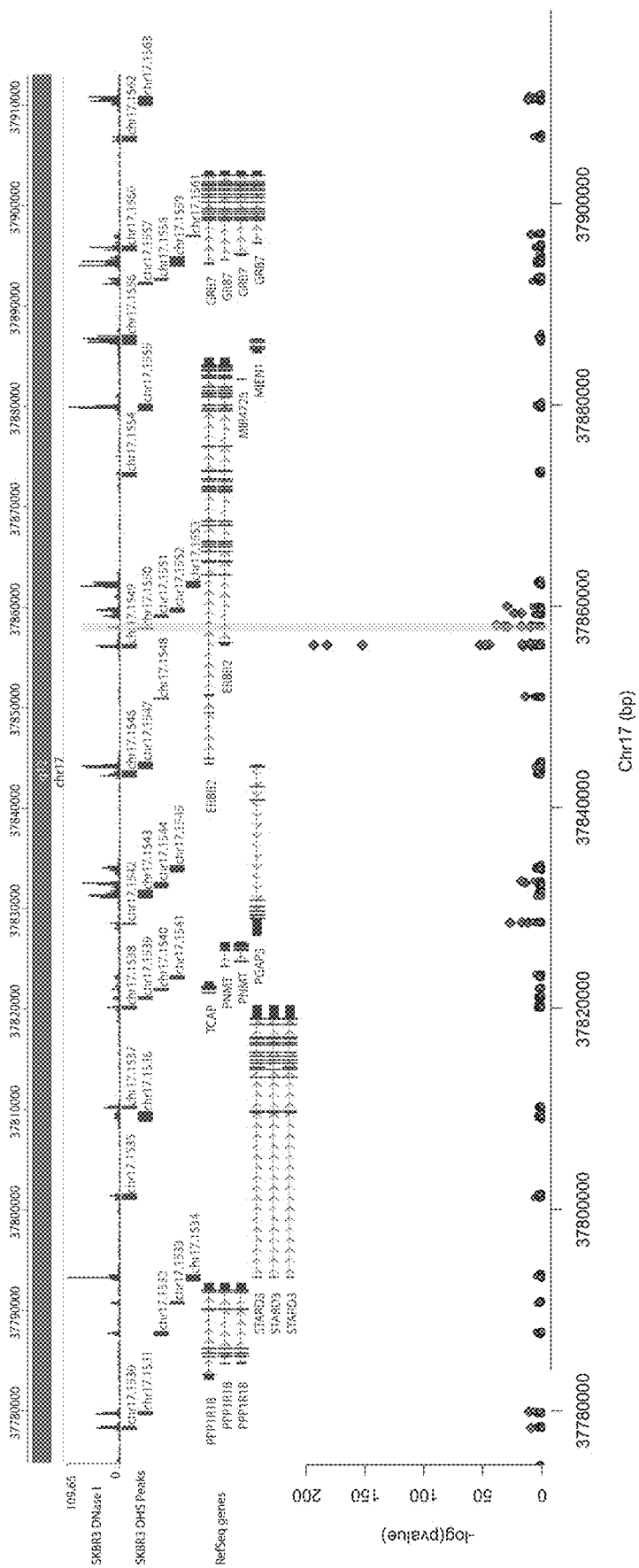
FIGS. 31A-31C show the enrichment of gRNA 1550.
Figure 31B:
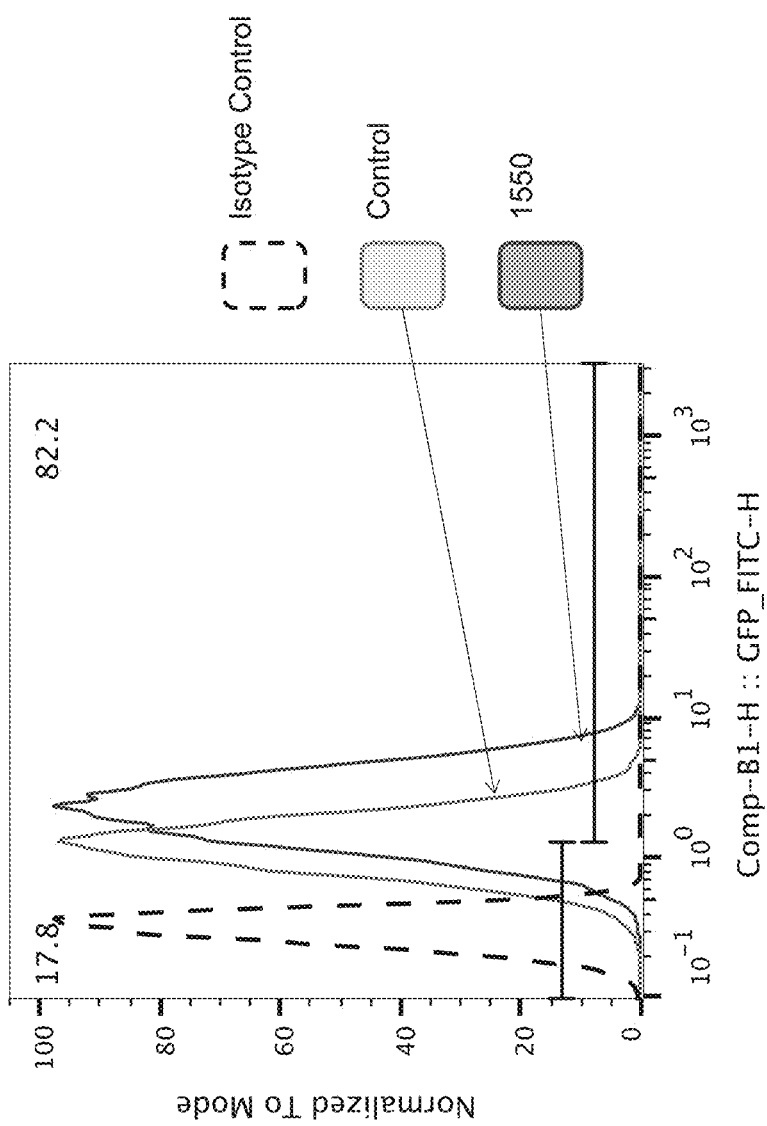
Figure 31C:
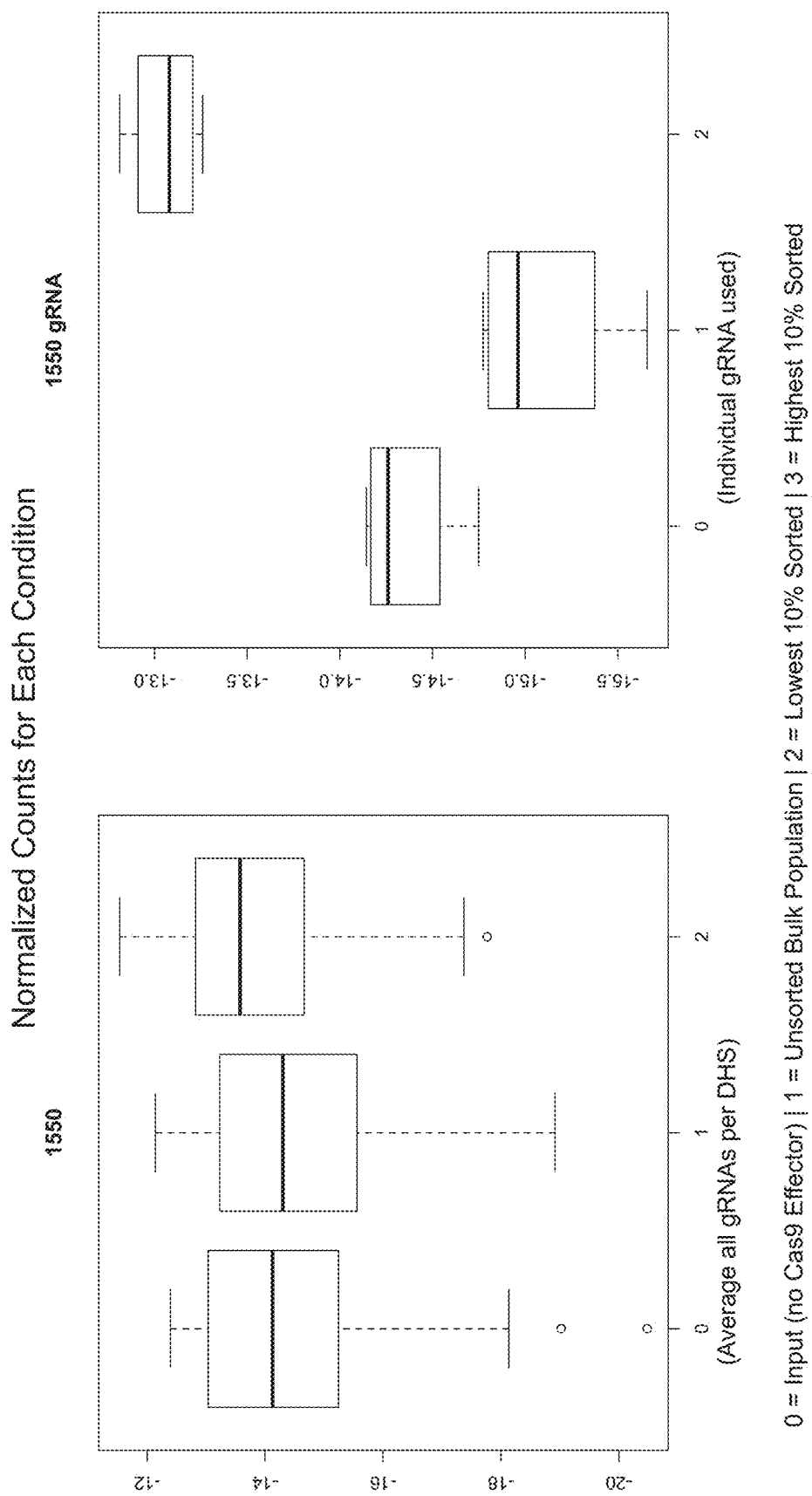
Figure 32A:
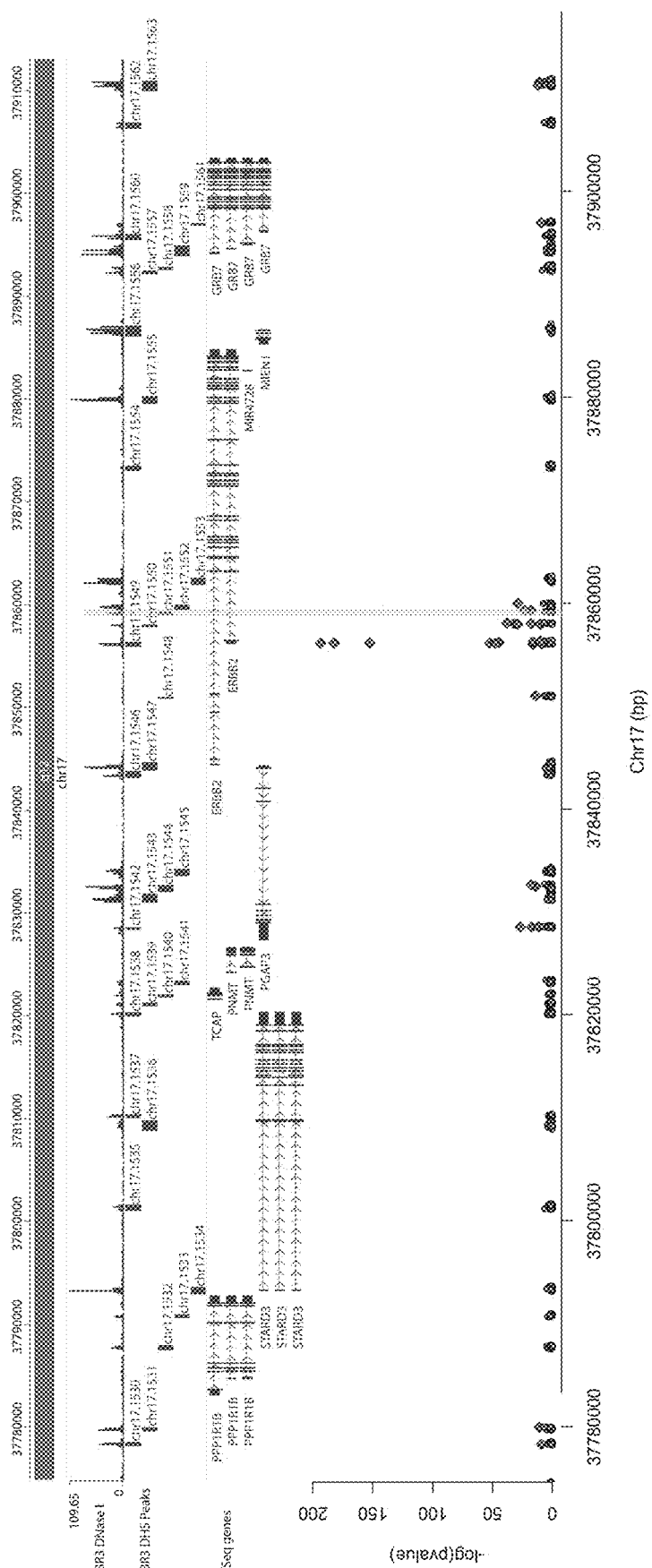
FIGS. 32A-32C show the enrichment of gRNA 1551.
Figure 32B:
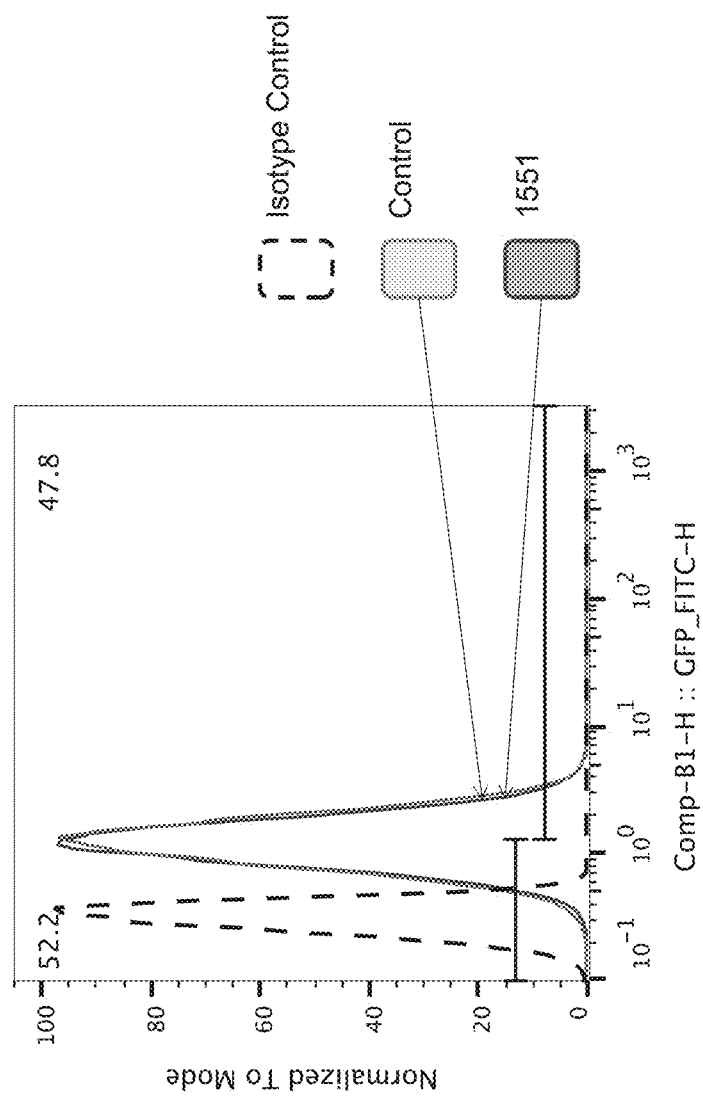
Figure 32C:
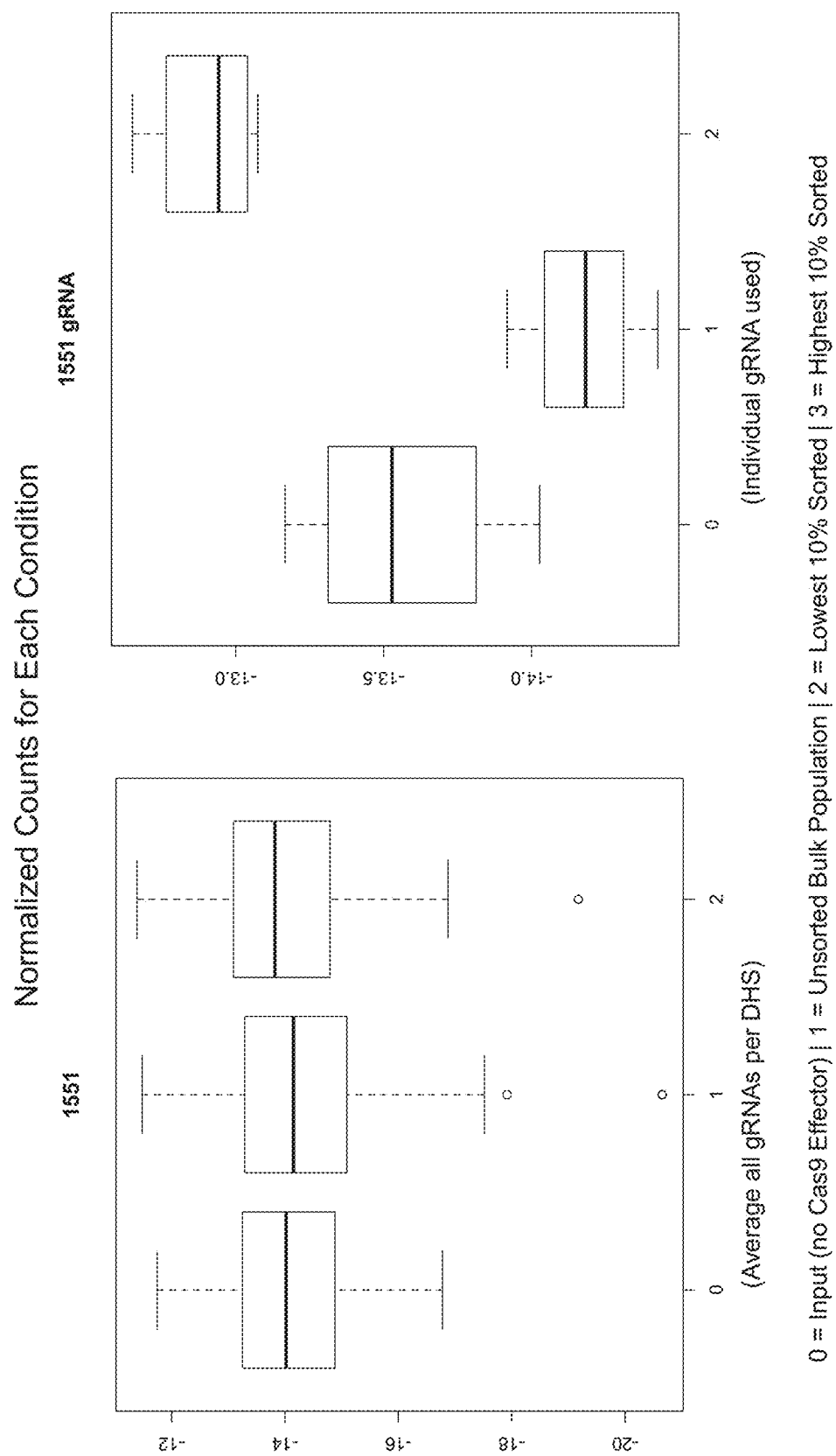
Figure 33A:
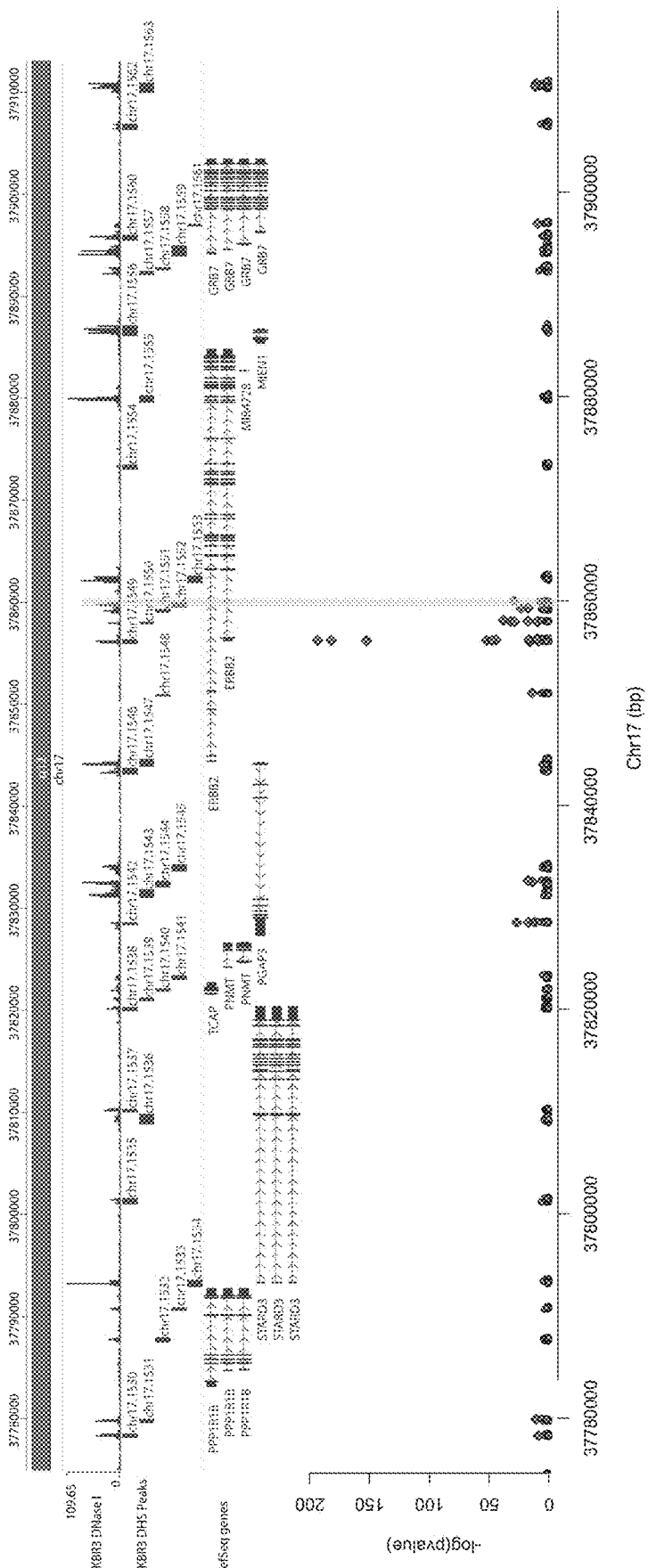
FIGS. 33A-33C show the enrichment of gRNA 1552.
Figure 33B:
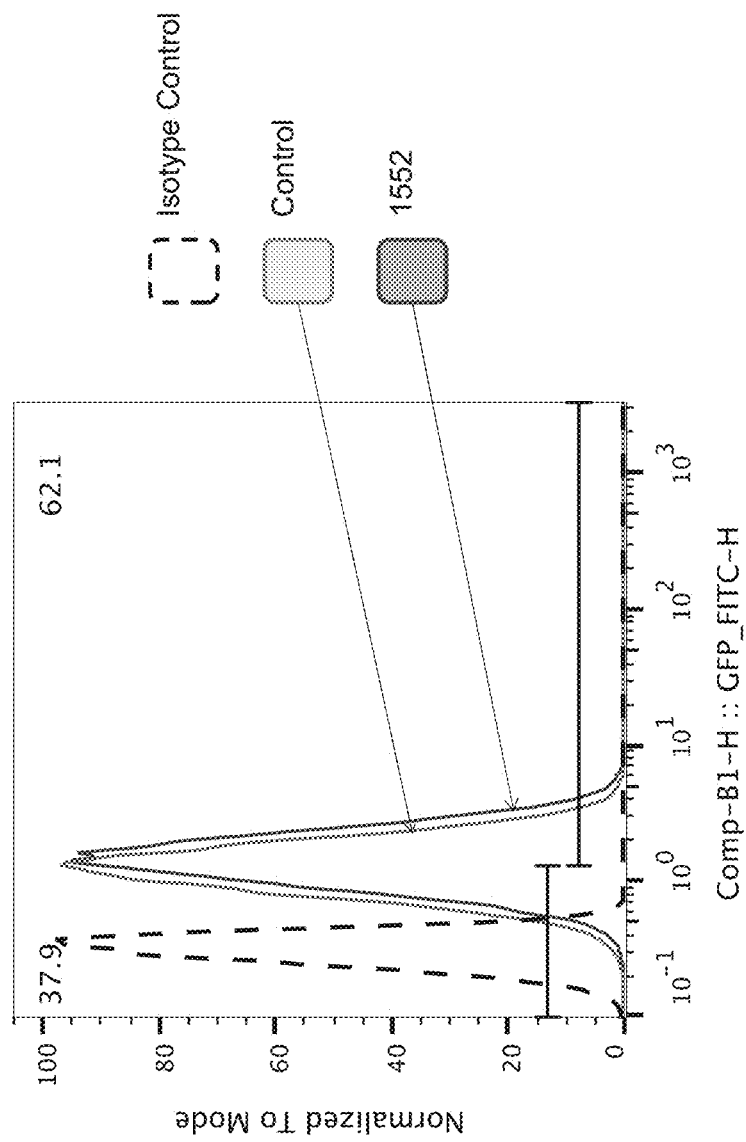
Figure 33C:
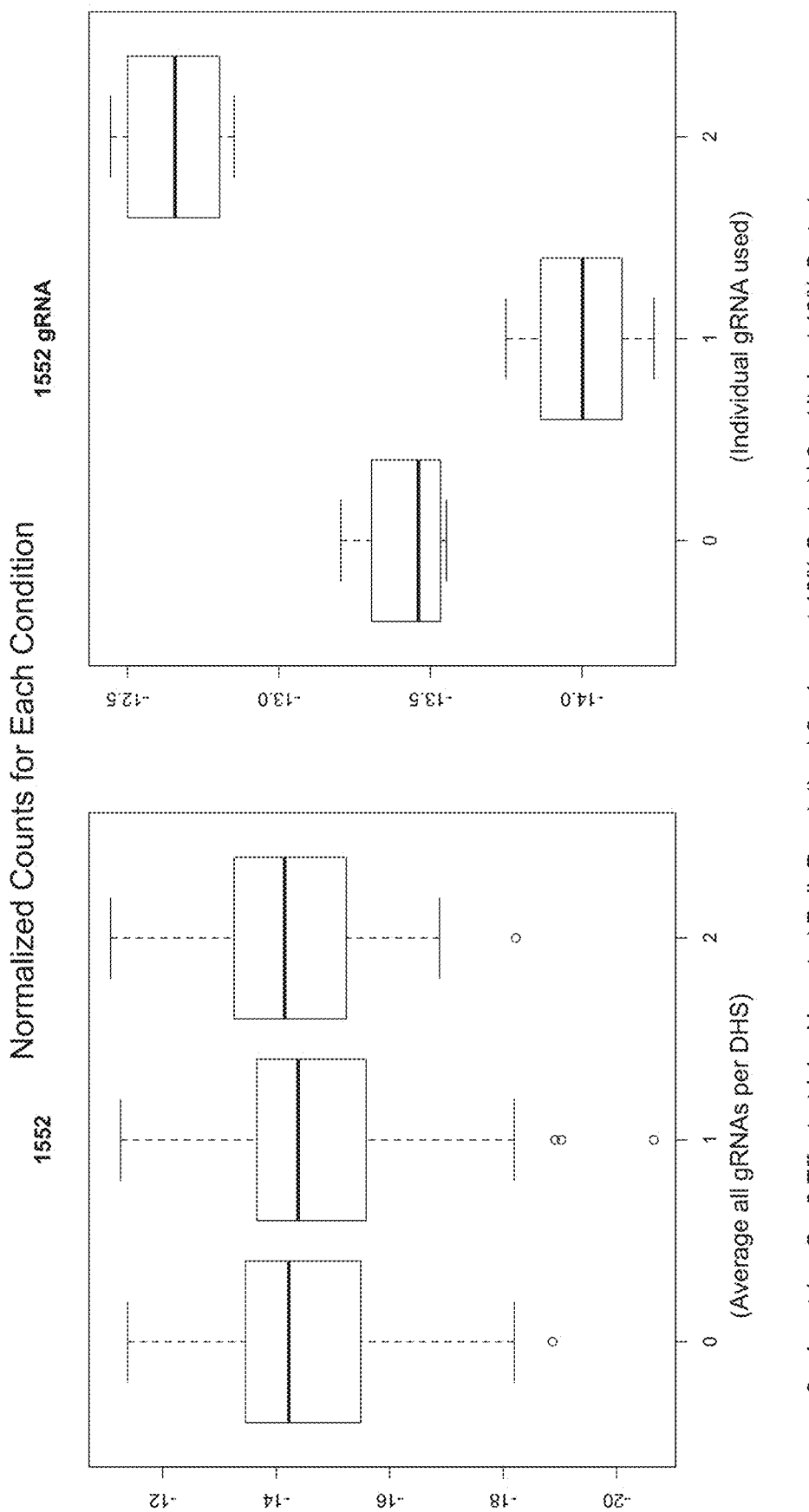
Figure 34A:
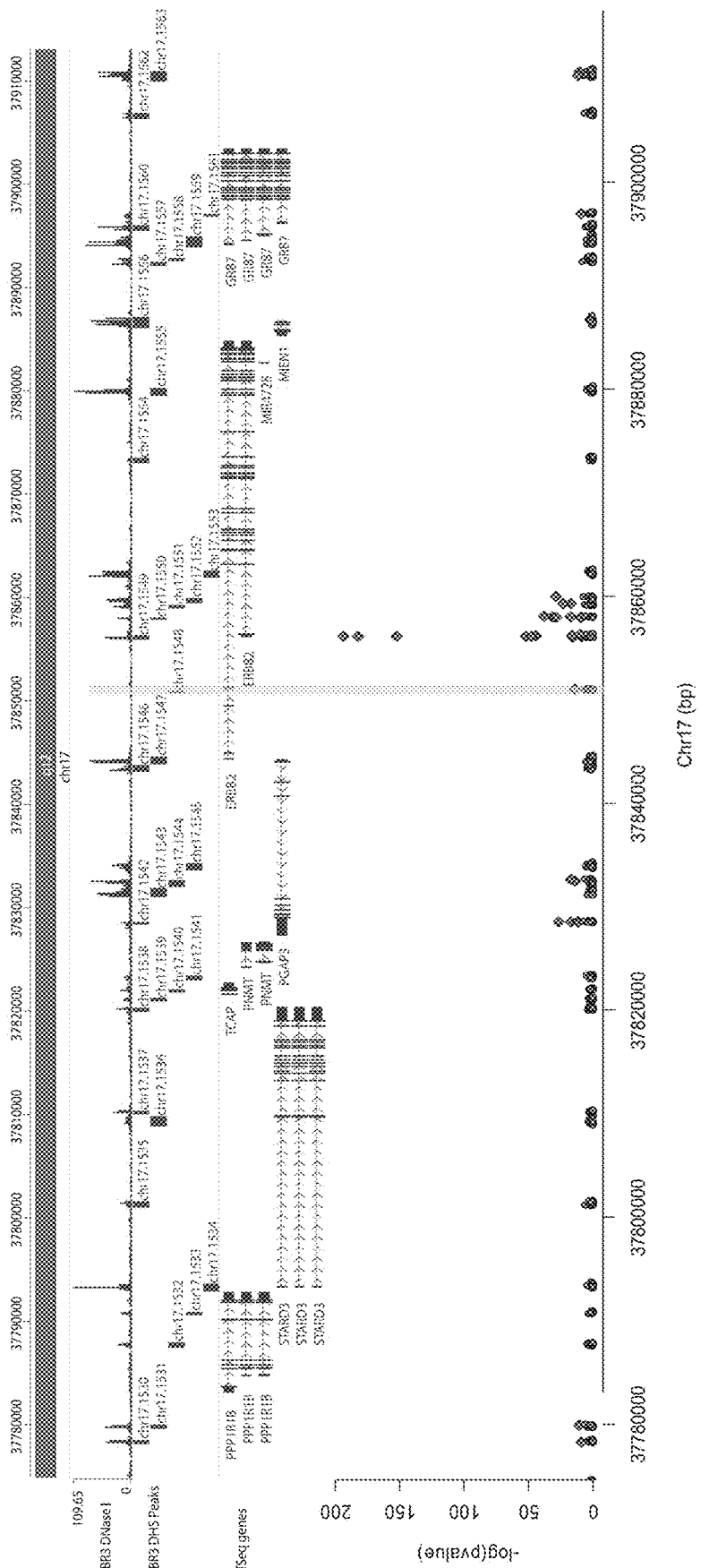
FIGS. 34A-34C show the enrichment of gRNA 1548.
Figure 34B:
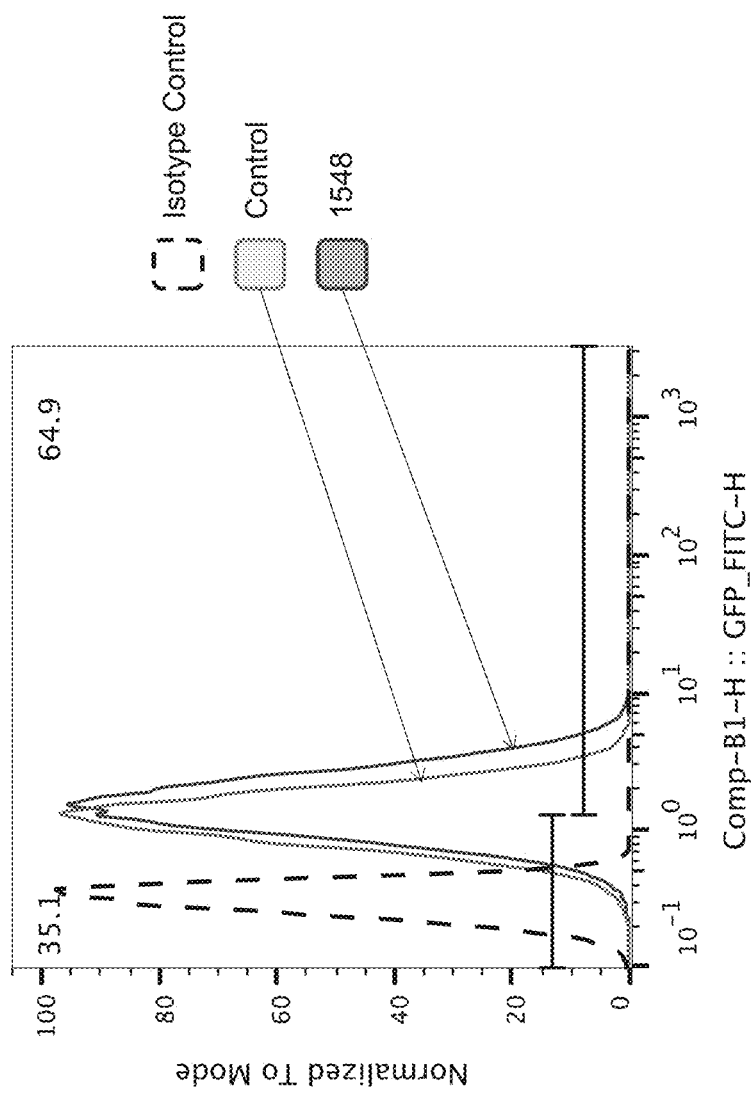
Figure 34C:
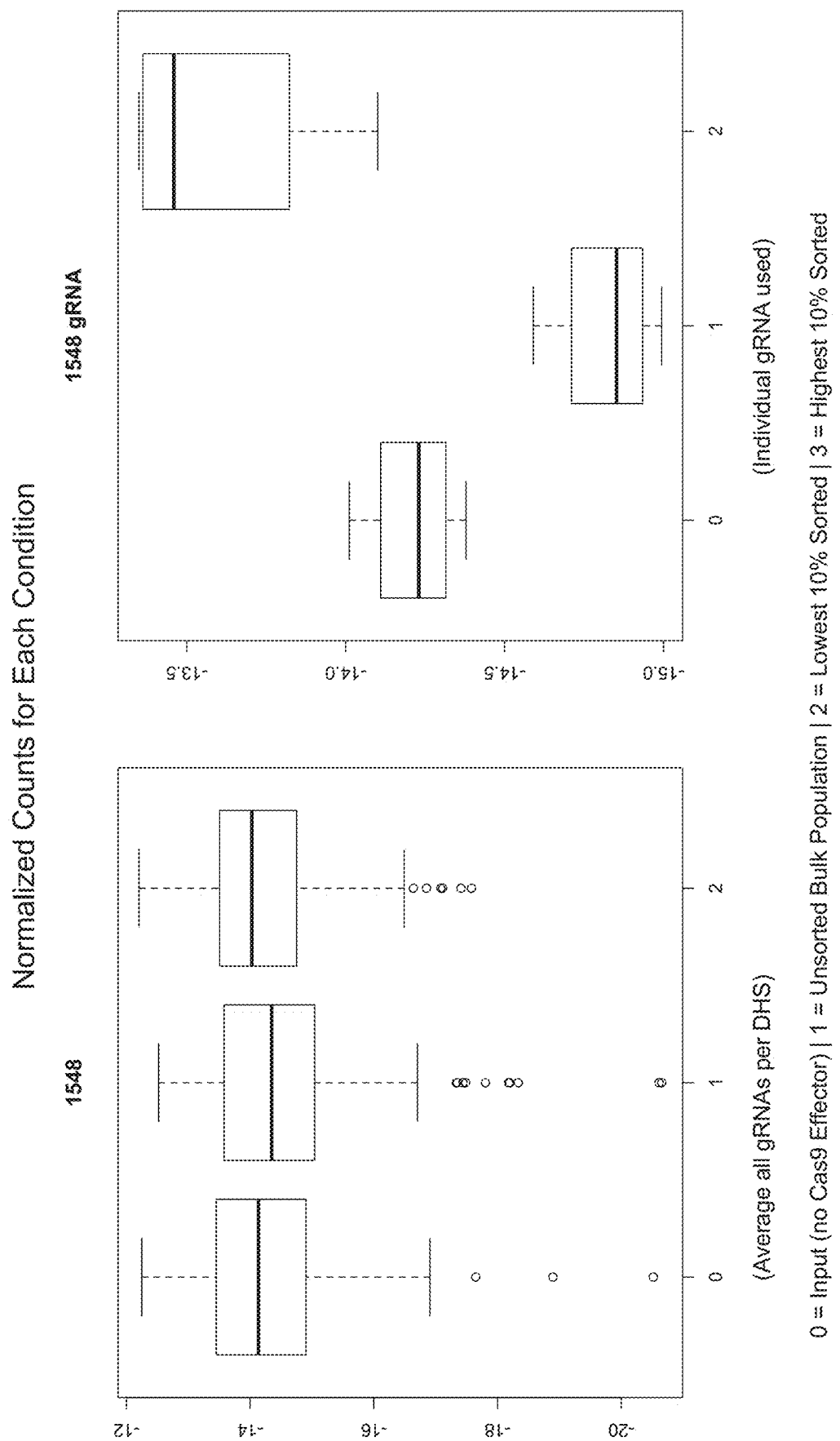
Figure 35A:
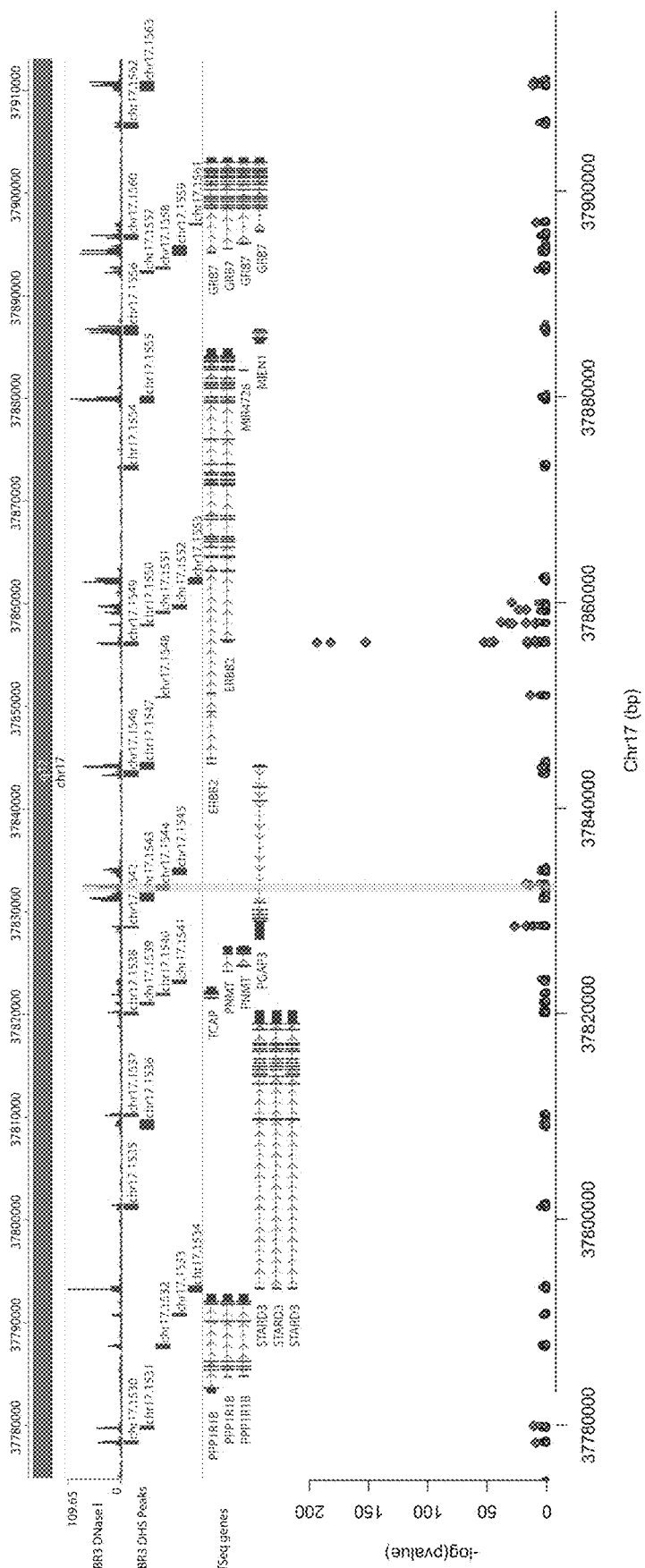
FIGS. 35A-35C show the enrichment of gRNA 1544.
Figure 35B:
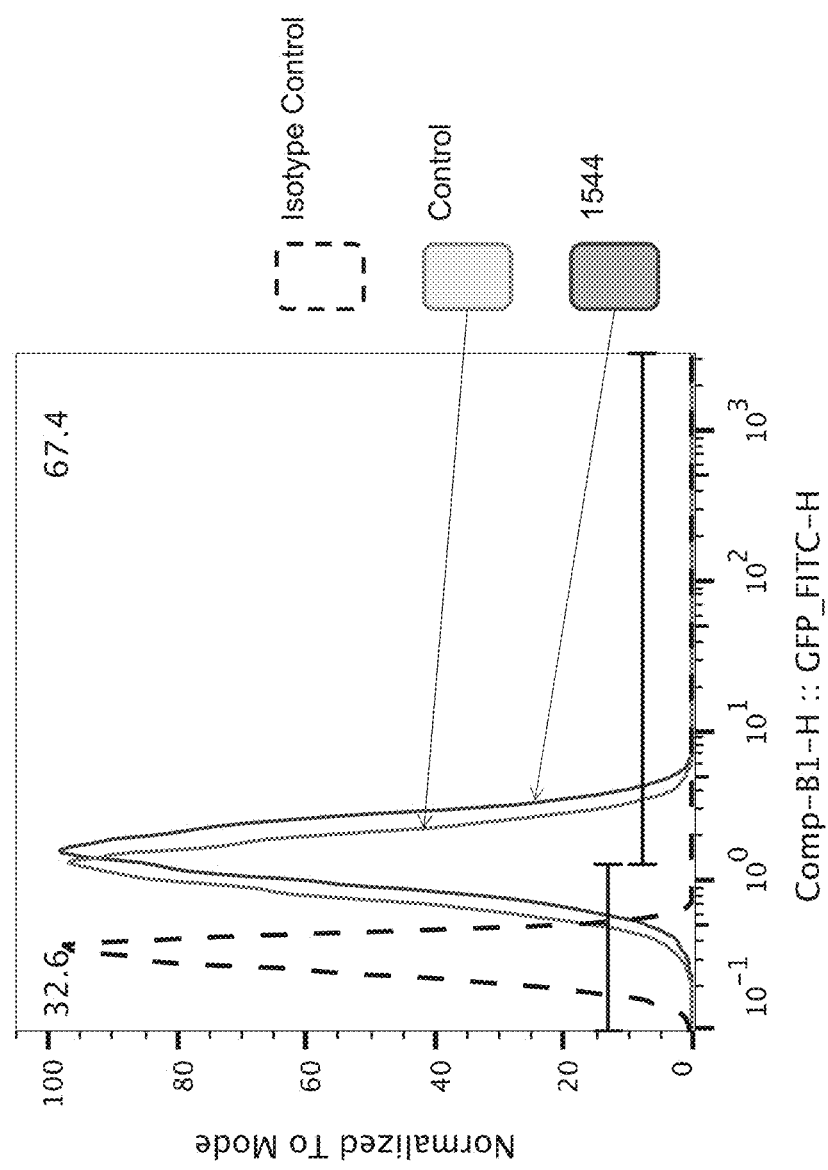
Figure 35C:
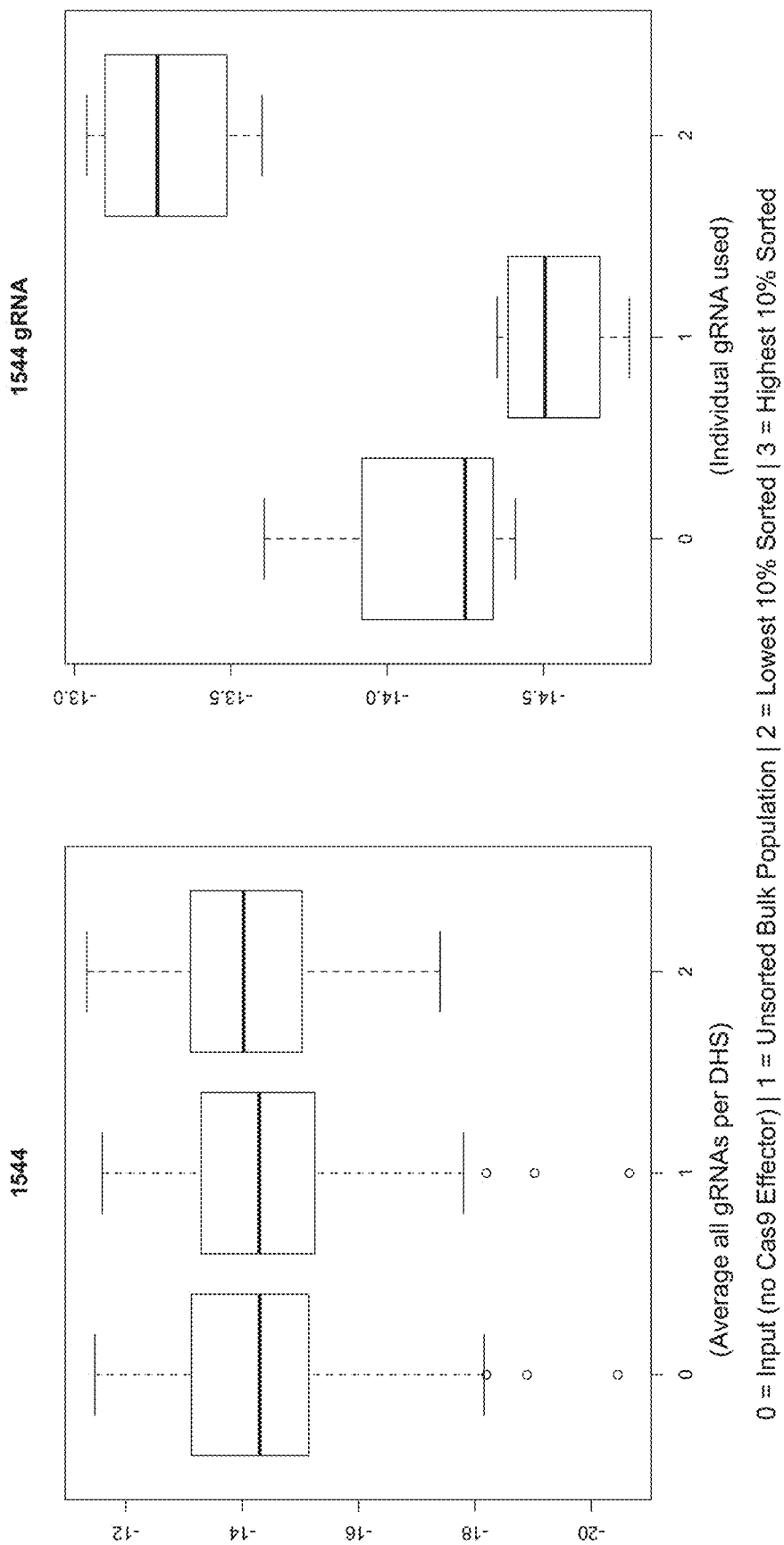
Figure 36A:
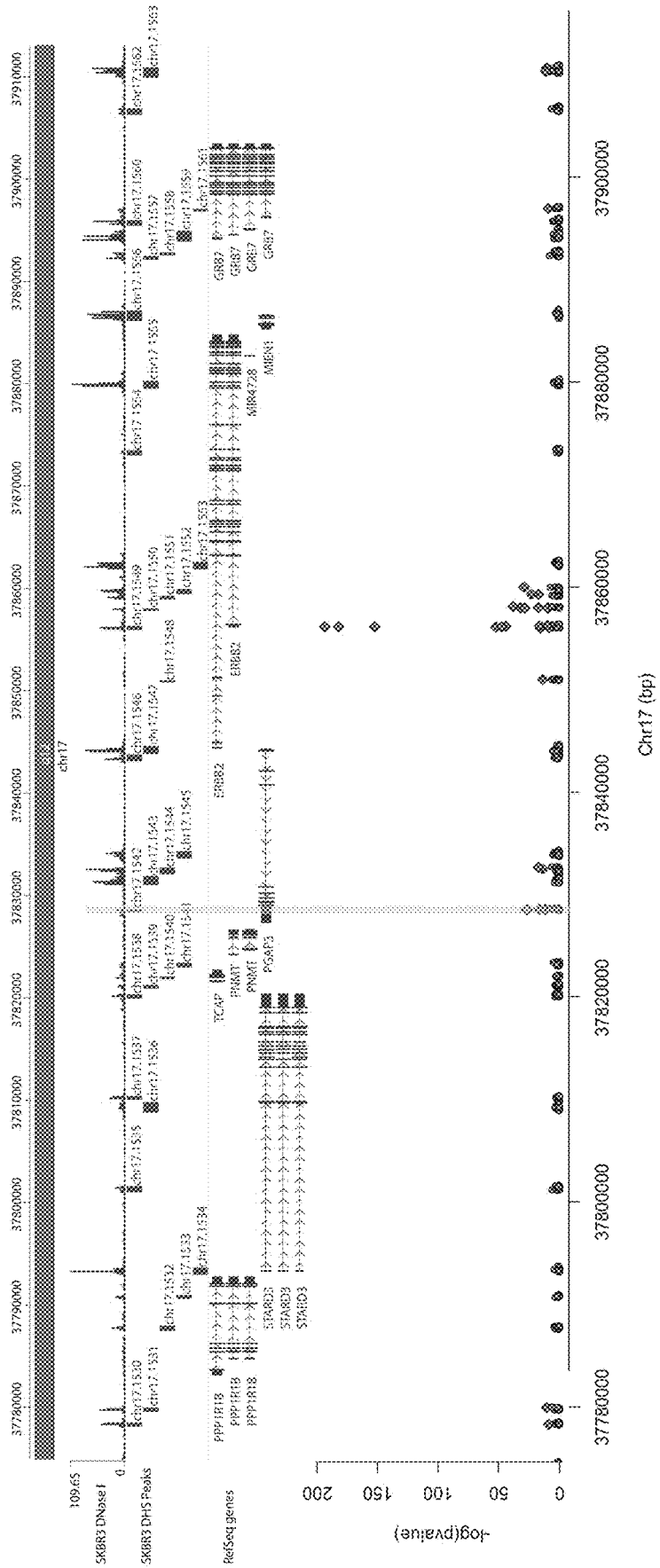
FIGS. 36A-36C show the enrichment of gRNA 1542.
Figure 36B:
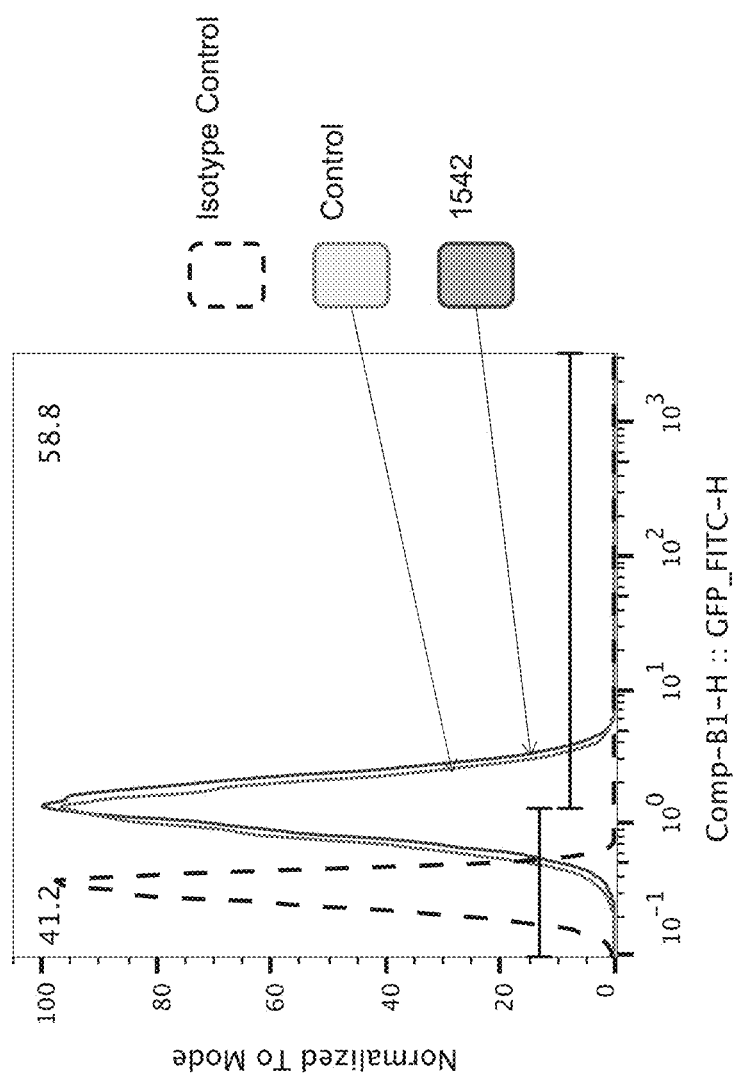
Figure 36C:
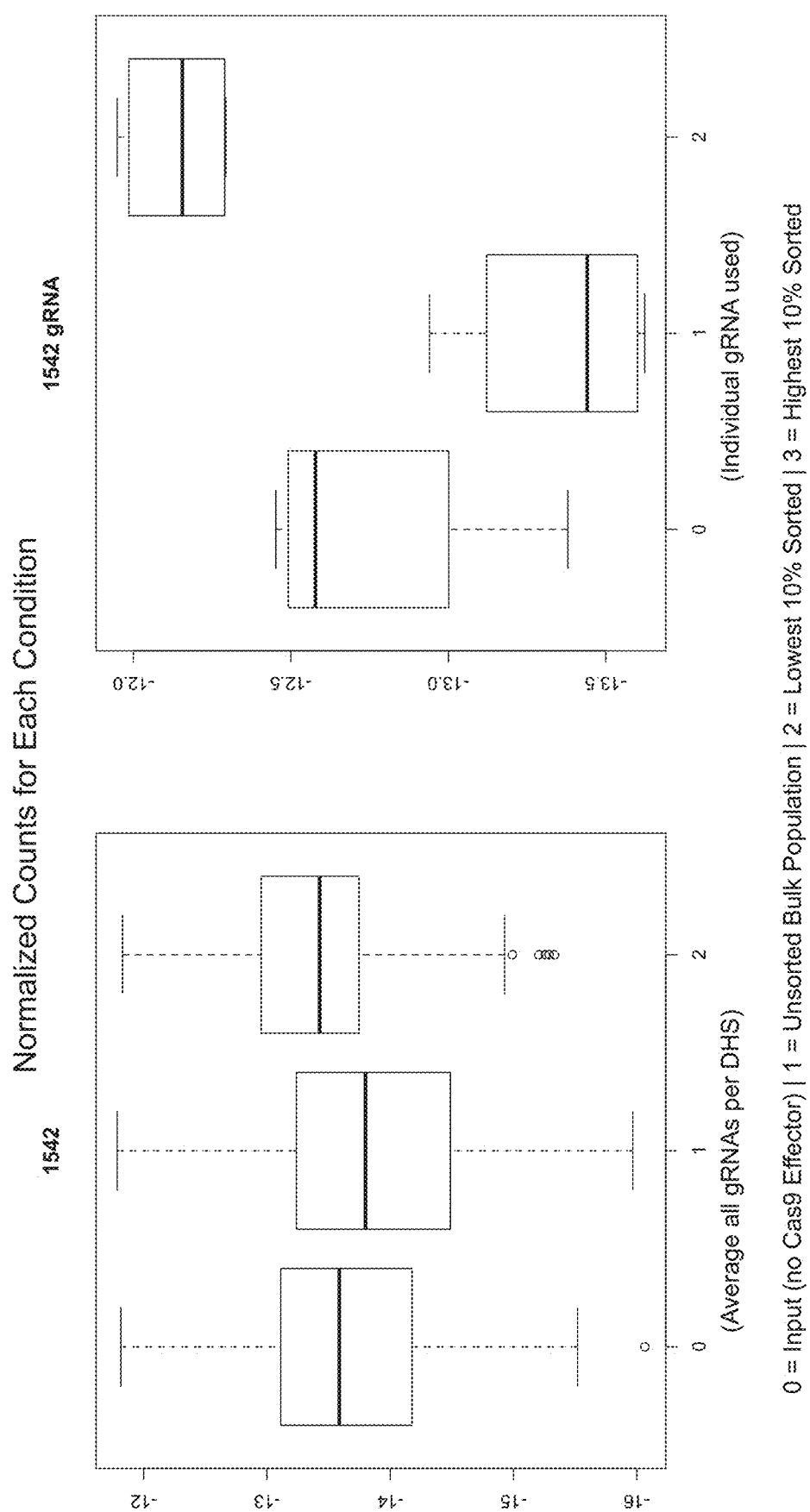
Figure 37A:
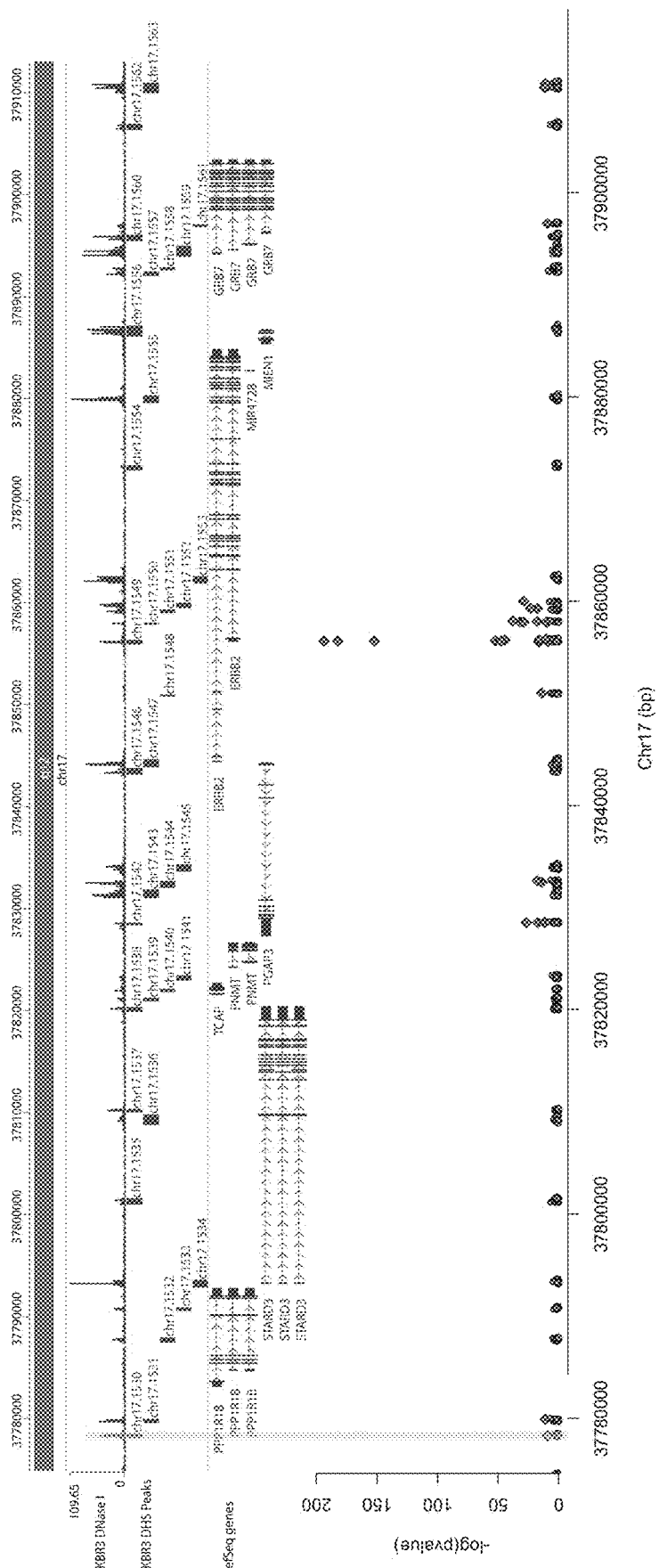
FIGS. 37A-37C show the enrichment of gRNA 1530.
Figure 37B:
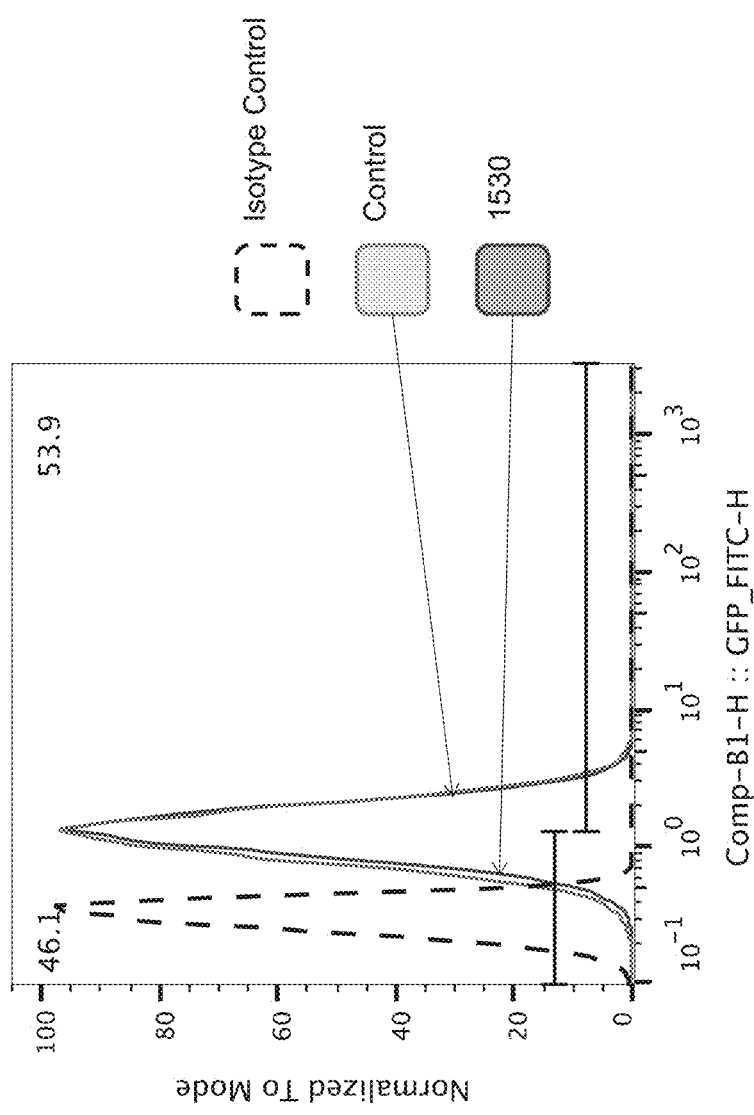
Figure 37C:
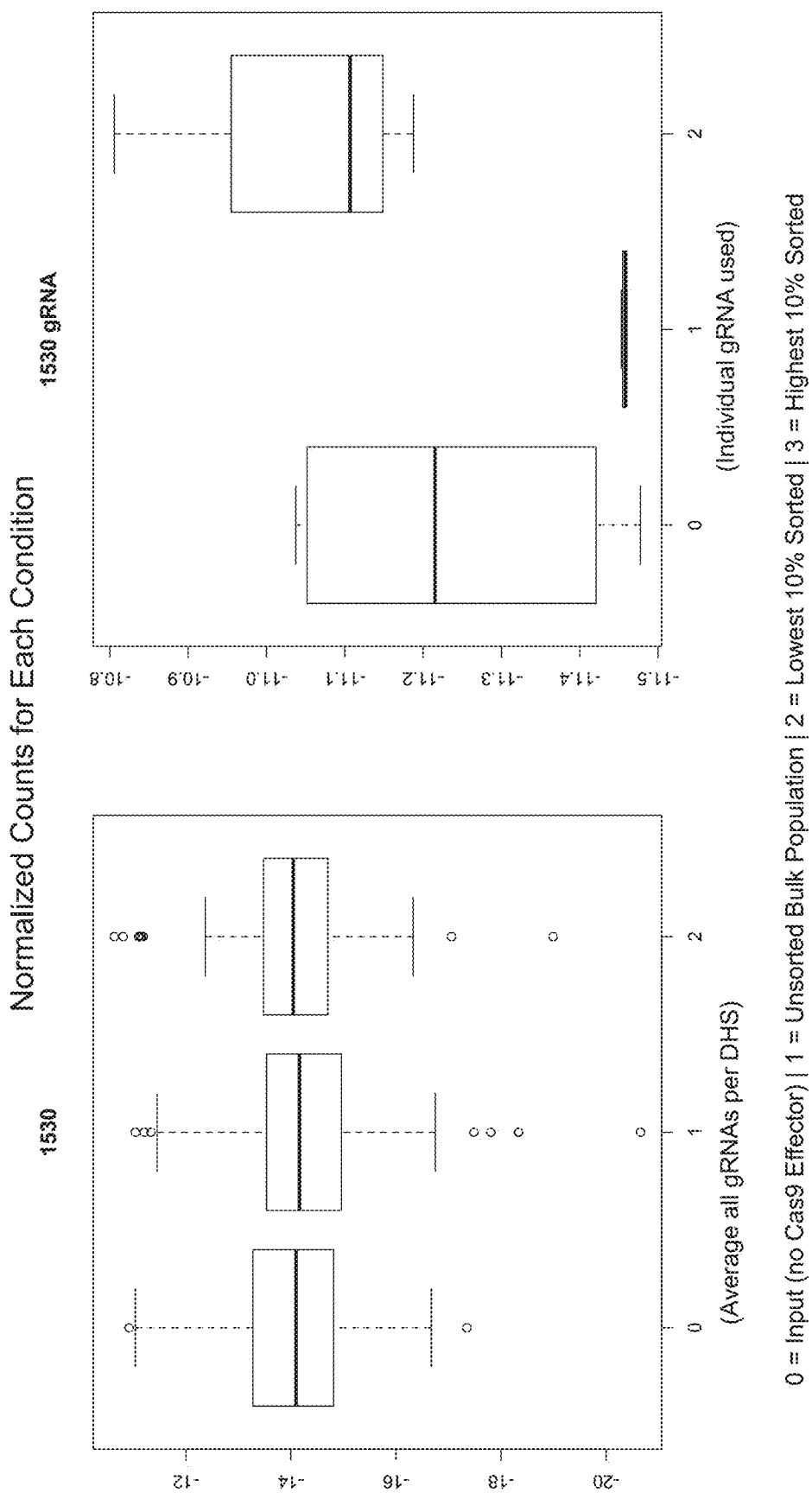
Figure 38A:
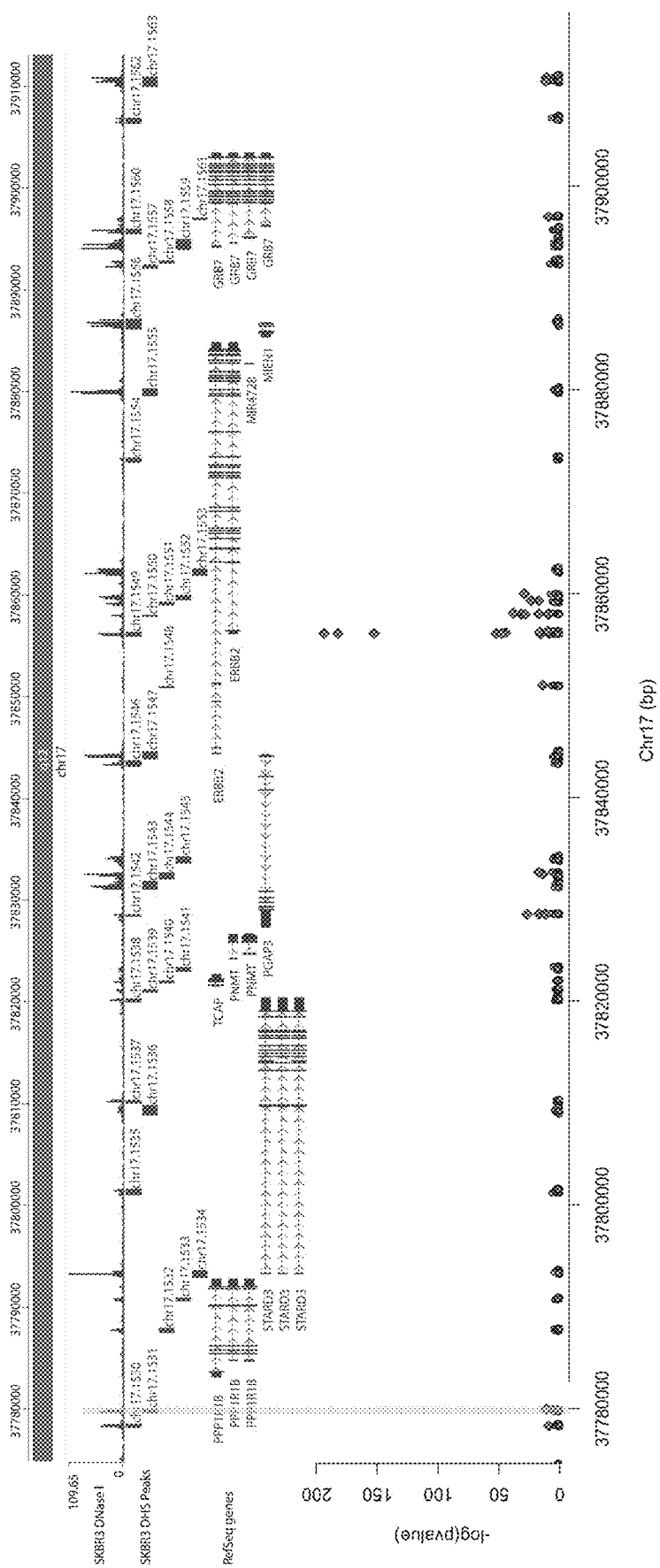
FIGS. 38A-38C show the enrichment of gRNA 1531.
Figure 38B:
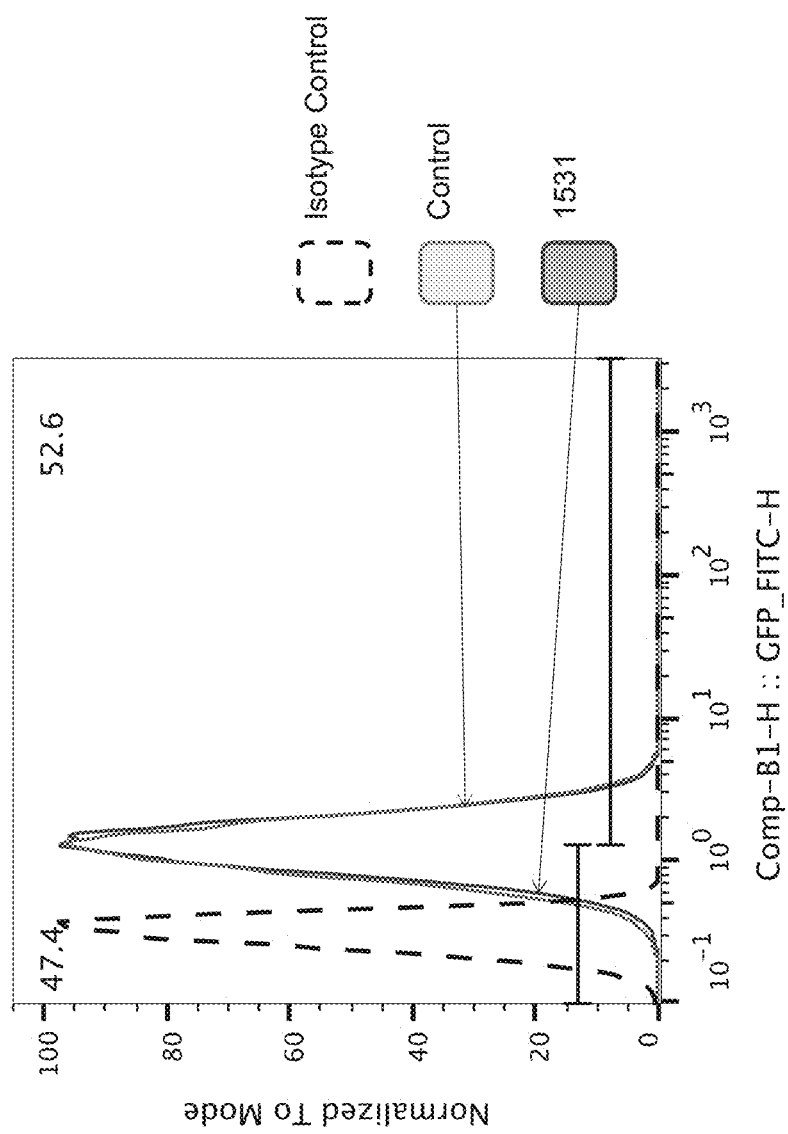
Figure 38C:
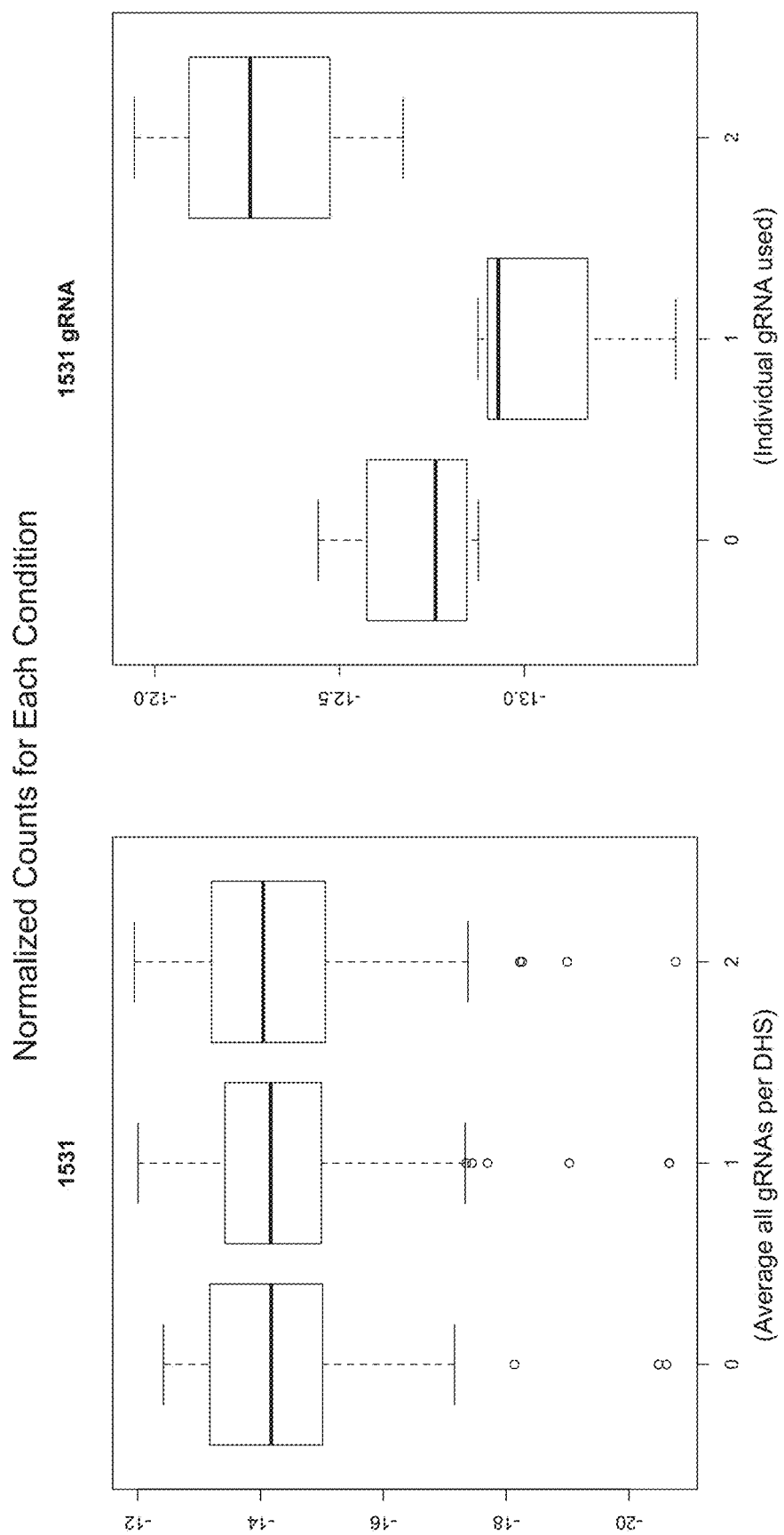
Figure 39A:
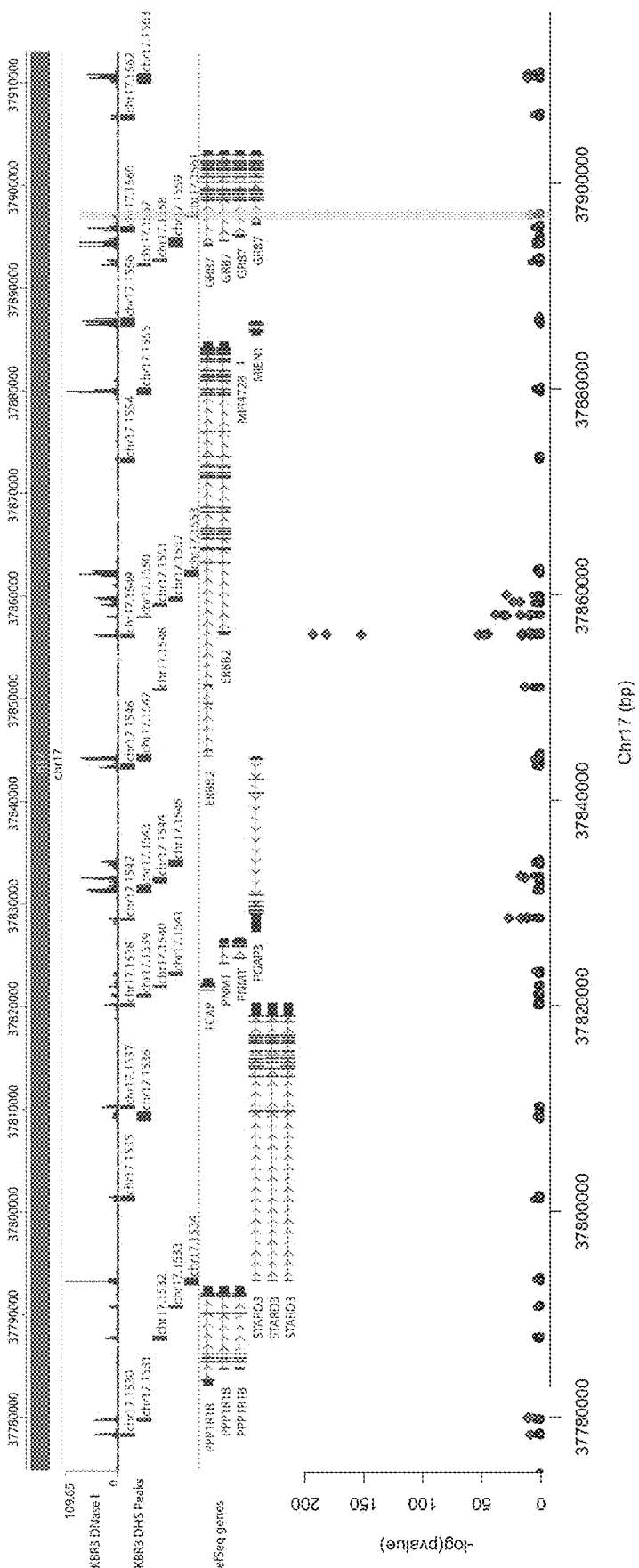
FIGS. 39A-39C show the enrichment of gRNA 1561.
Figure 39B:
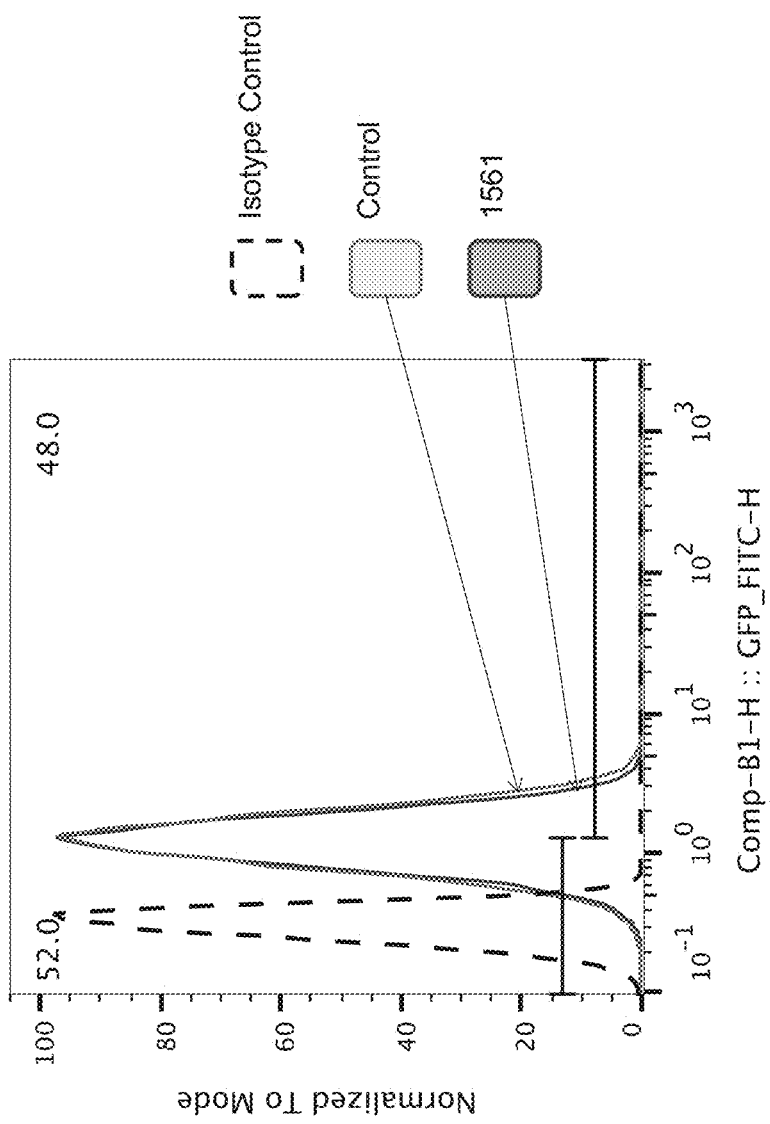
Figure 39C:
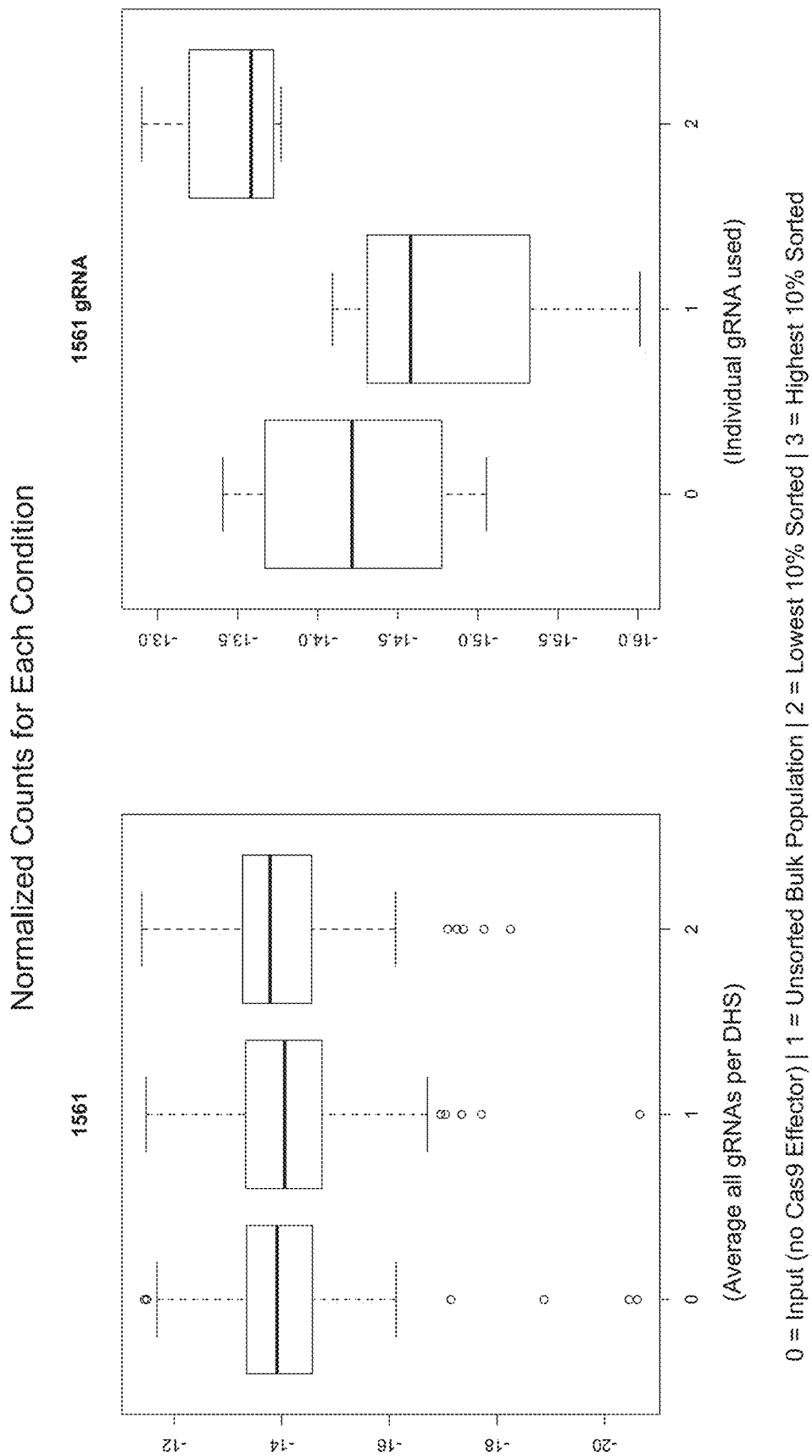
Figure 40A:
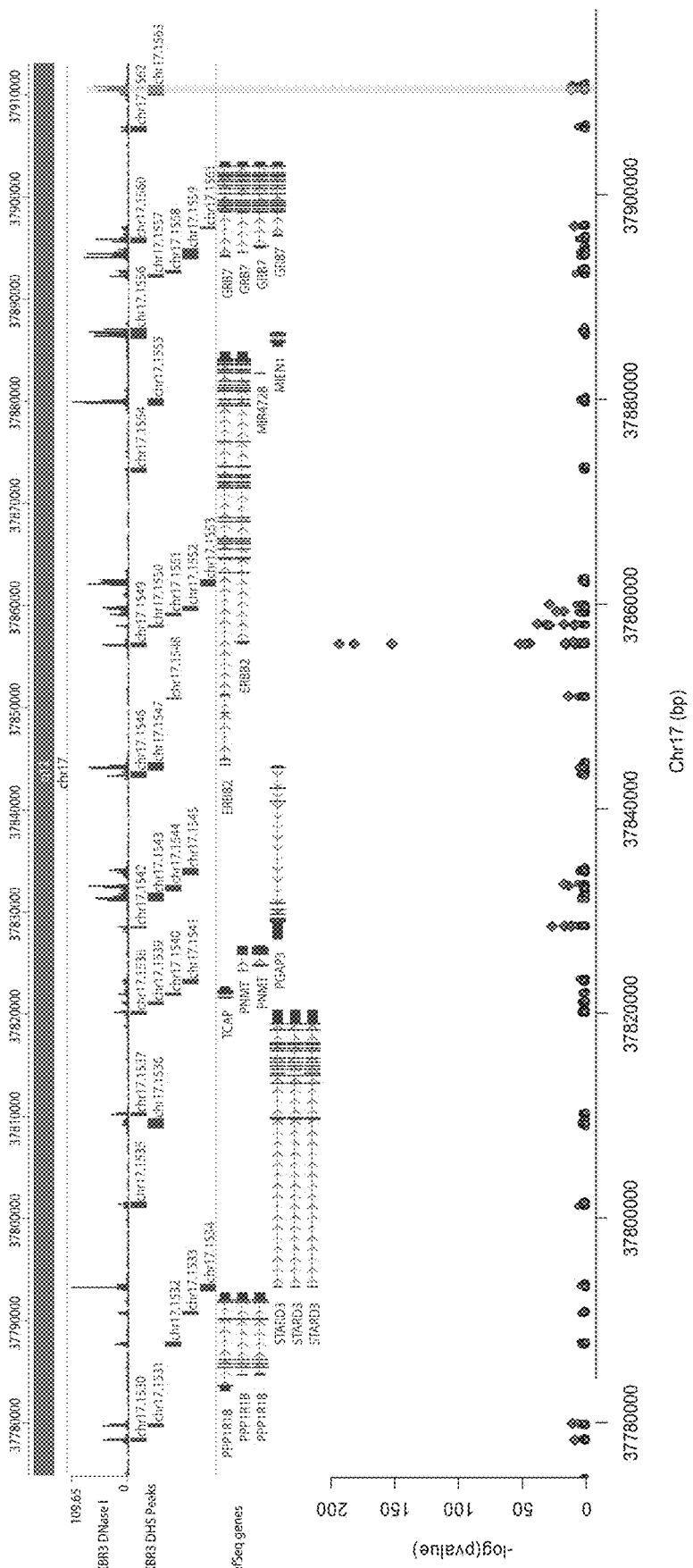
FIGS. 40A-40C show the enrichment of gRNA 1563.
Figure 40B:
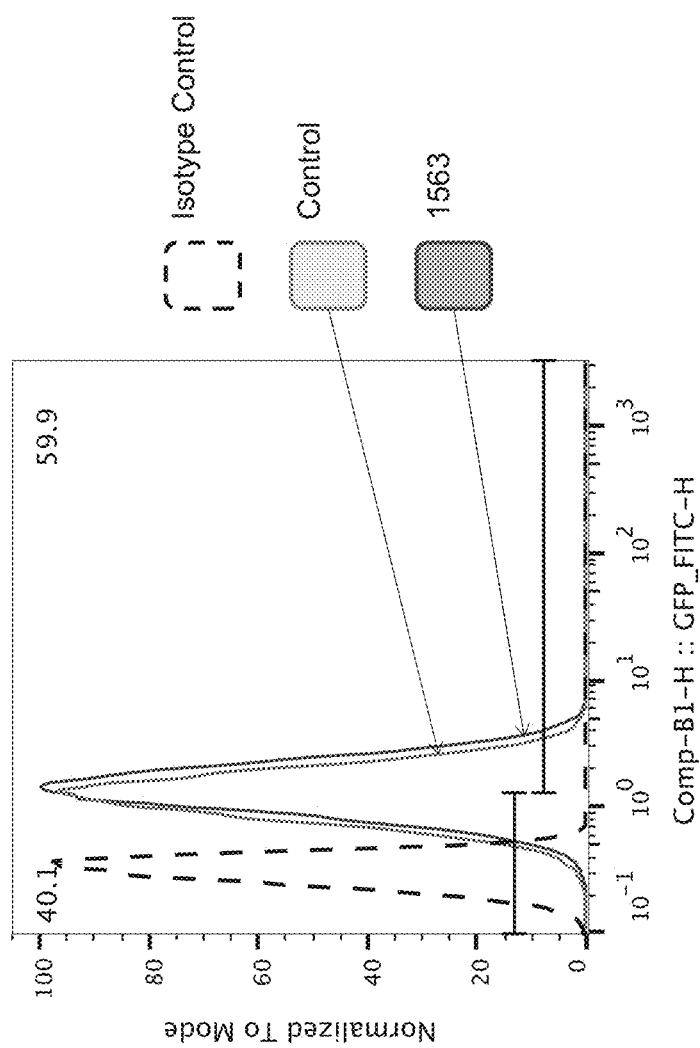
Figure 40C:
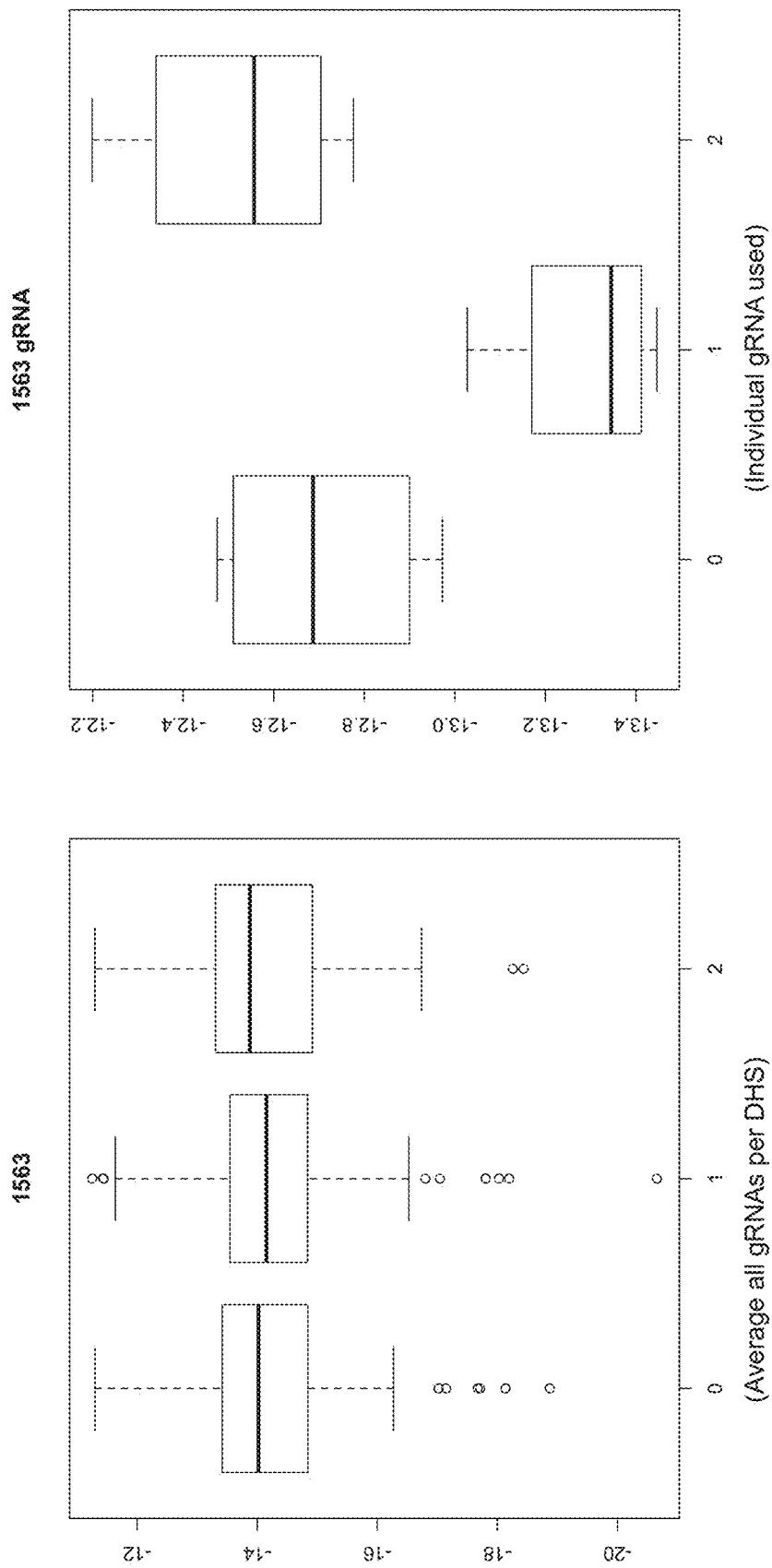
Figure 41B:
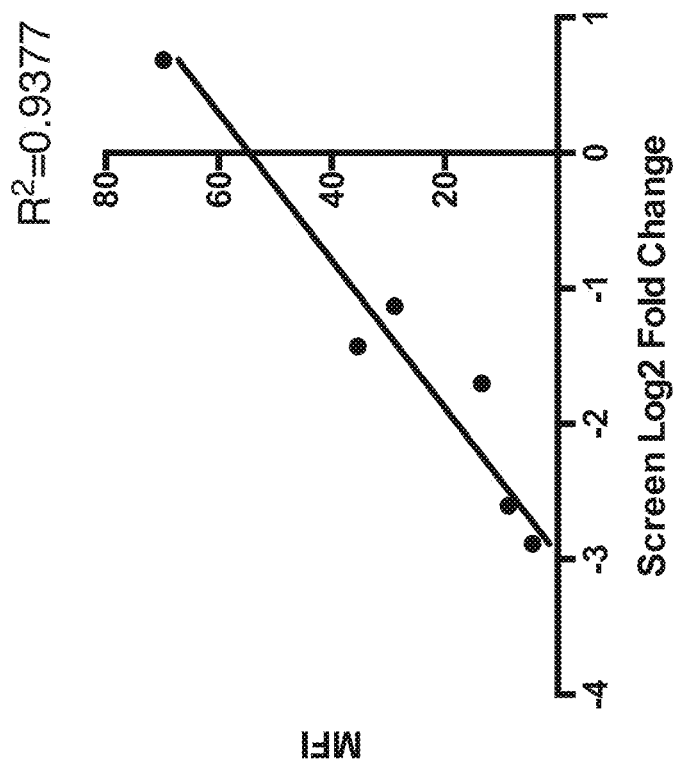
FIG. 41B shows HBE1 mean fluorescence intensity (MFI) versus log 2 fold change in the screen for dCas9$^{KRAB}$ hits.
Figure 41A:
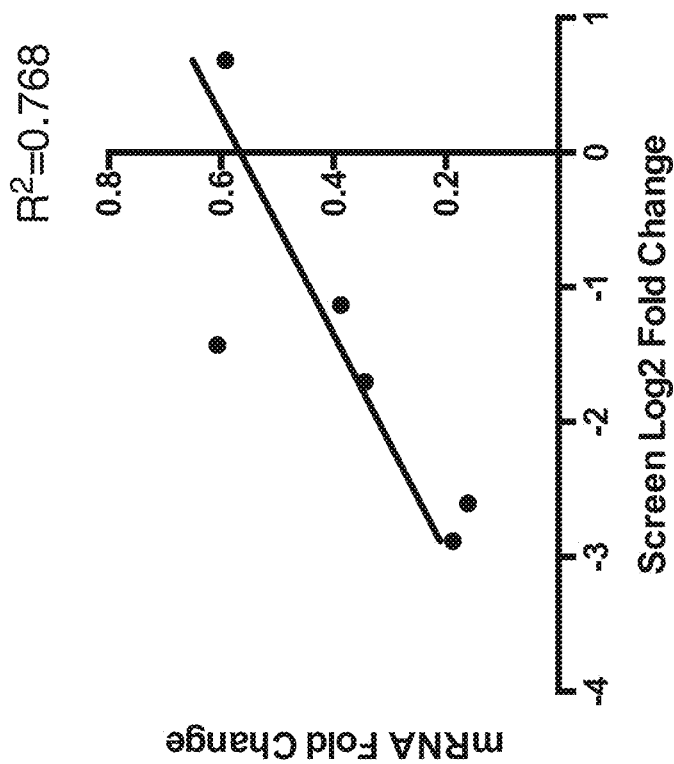
FIG. 41A shows HBE1 mRNA fold change versus log 2 fold change in the screen for dCas9$^{KRAB}$ hits.
Figure 42B:
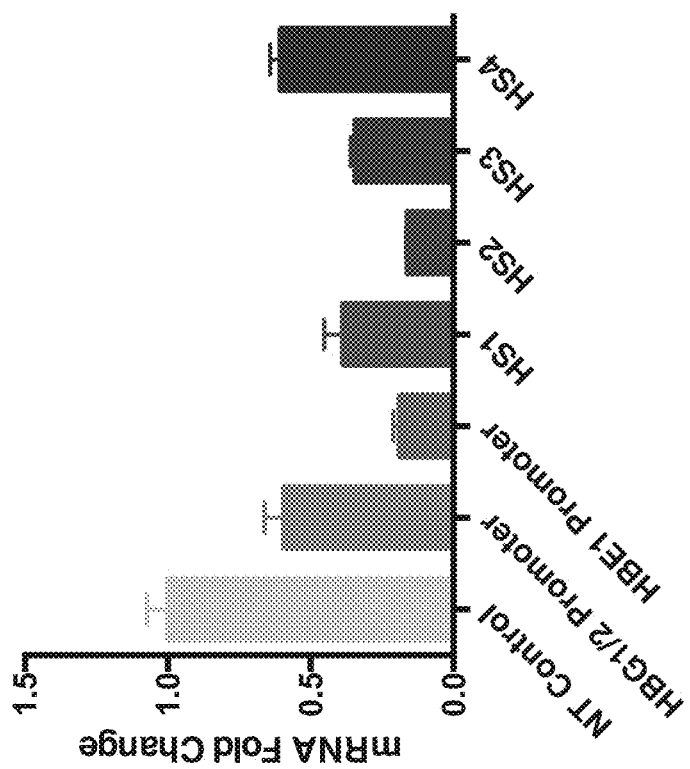
FIGS. 42A and 42B show mean fluorescent intensity fold change (FIG. 42A) and mRNA fold change (FIG. 42B) for sgRNAs targeting HBG1/2 promoter, HBE1 promoter, HS1, HS2, HS3, and HS4.
Figure 42A:
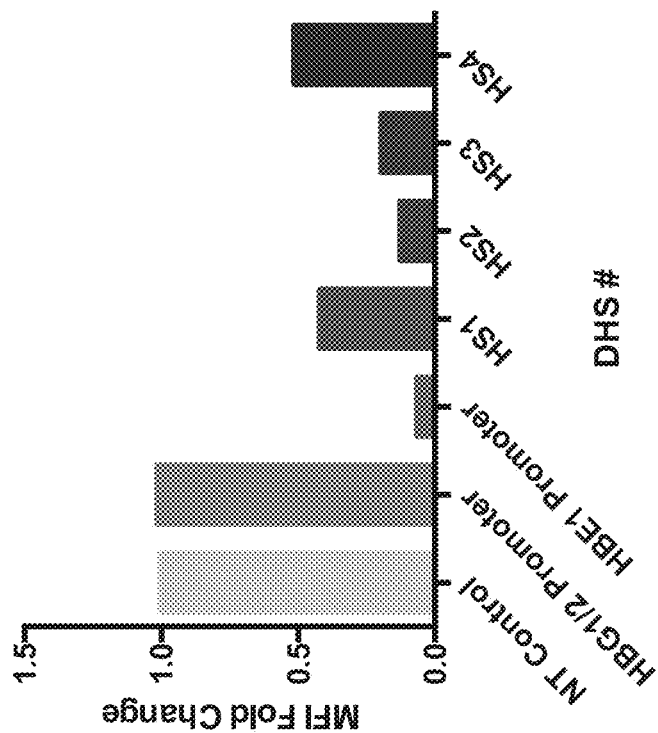
Figure 43A:
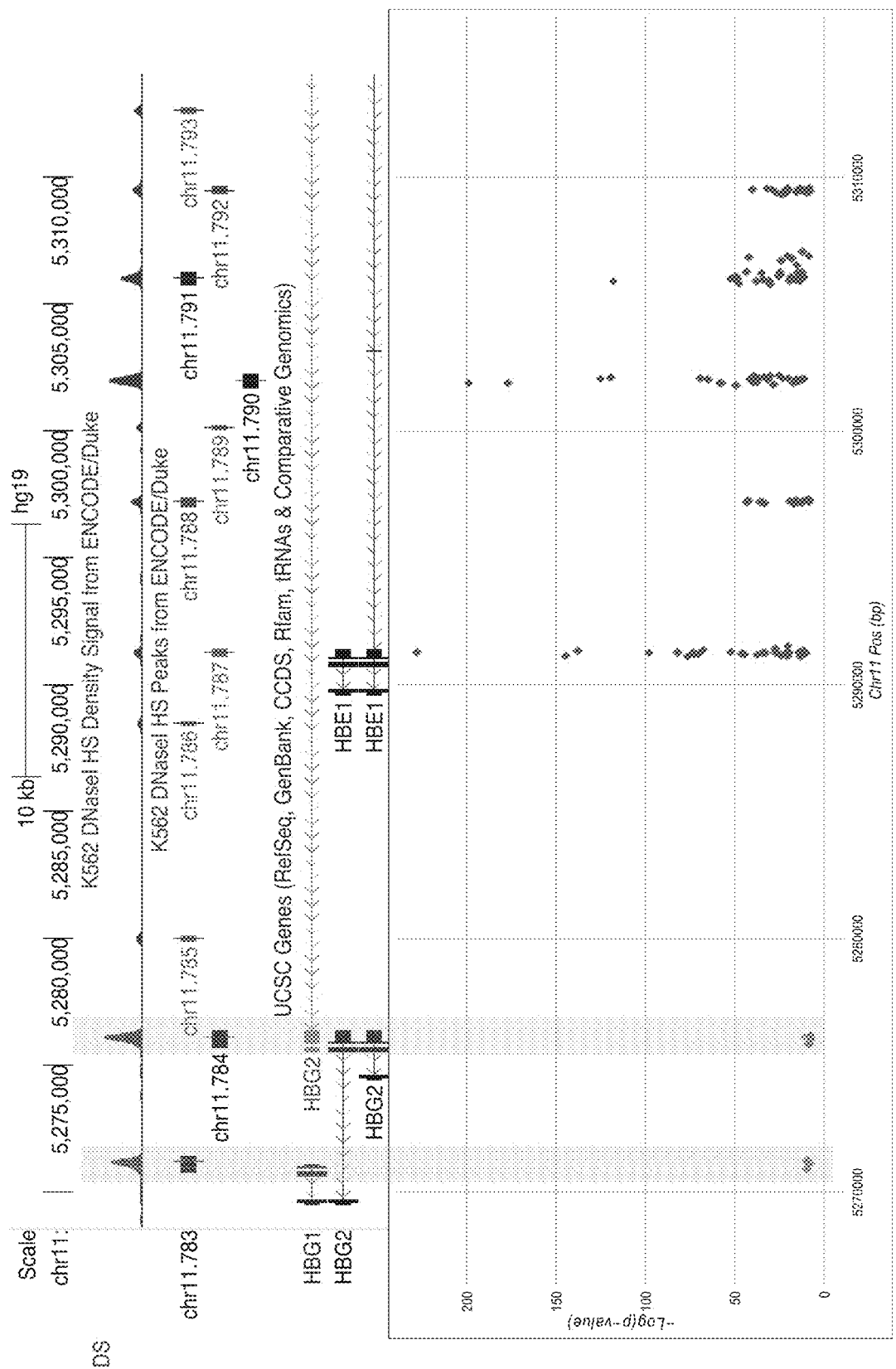
FIGS. 43A-43C show enrichment of gRNA targeting HBG1/2 promoter (gRNA 783_784).
Figure 43B:
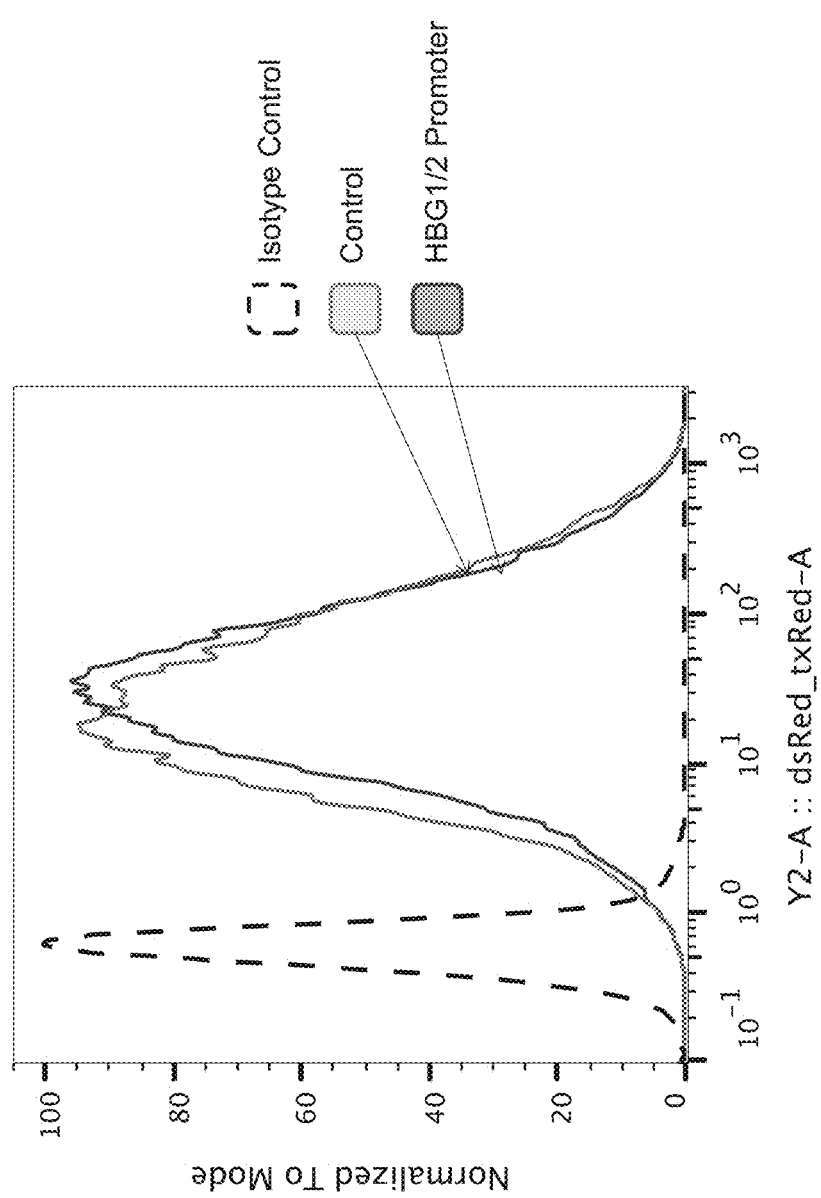
Figure 43C:
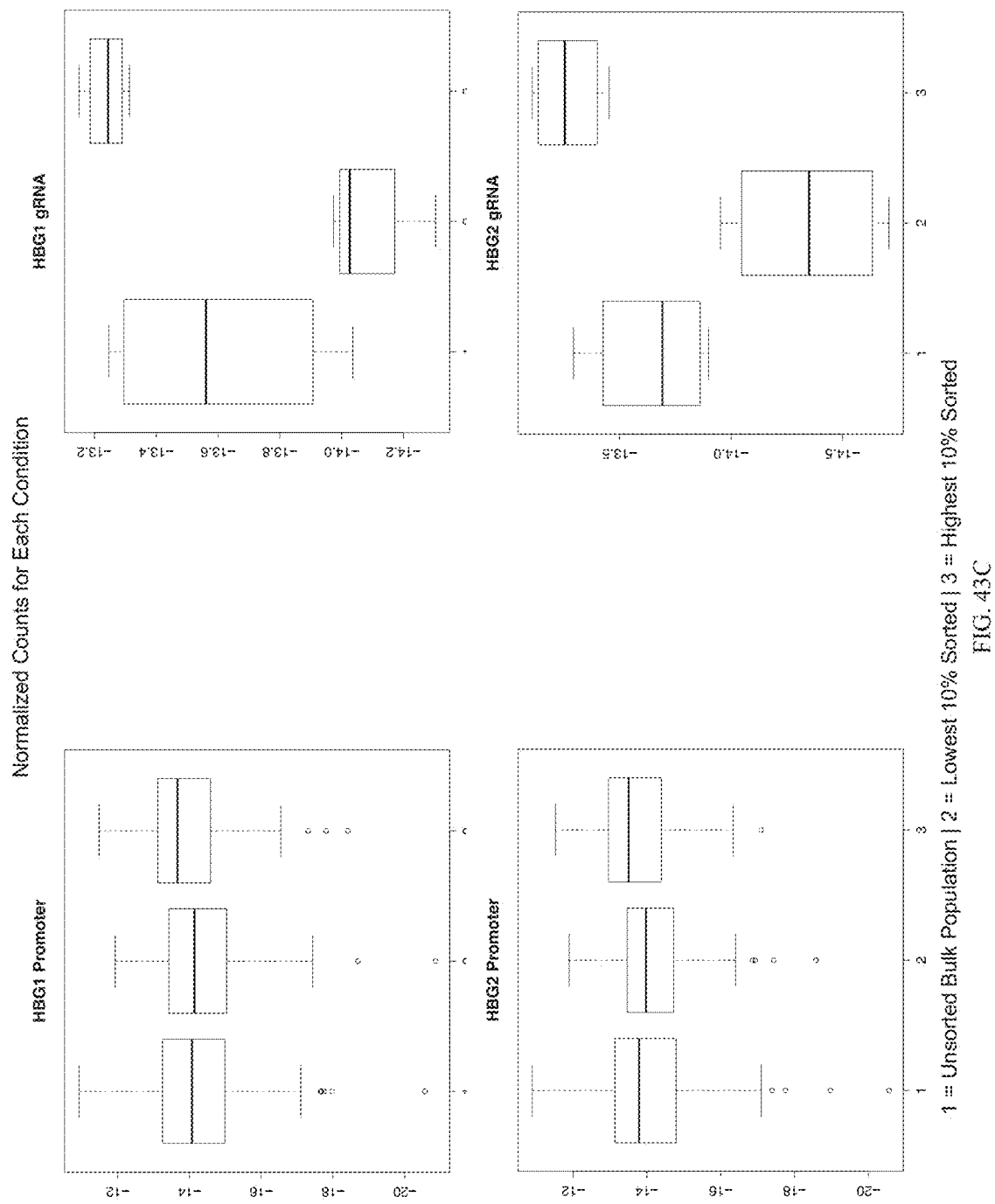
Figure 44A:
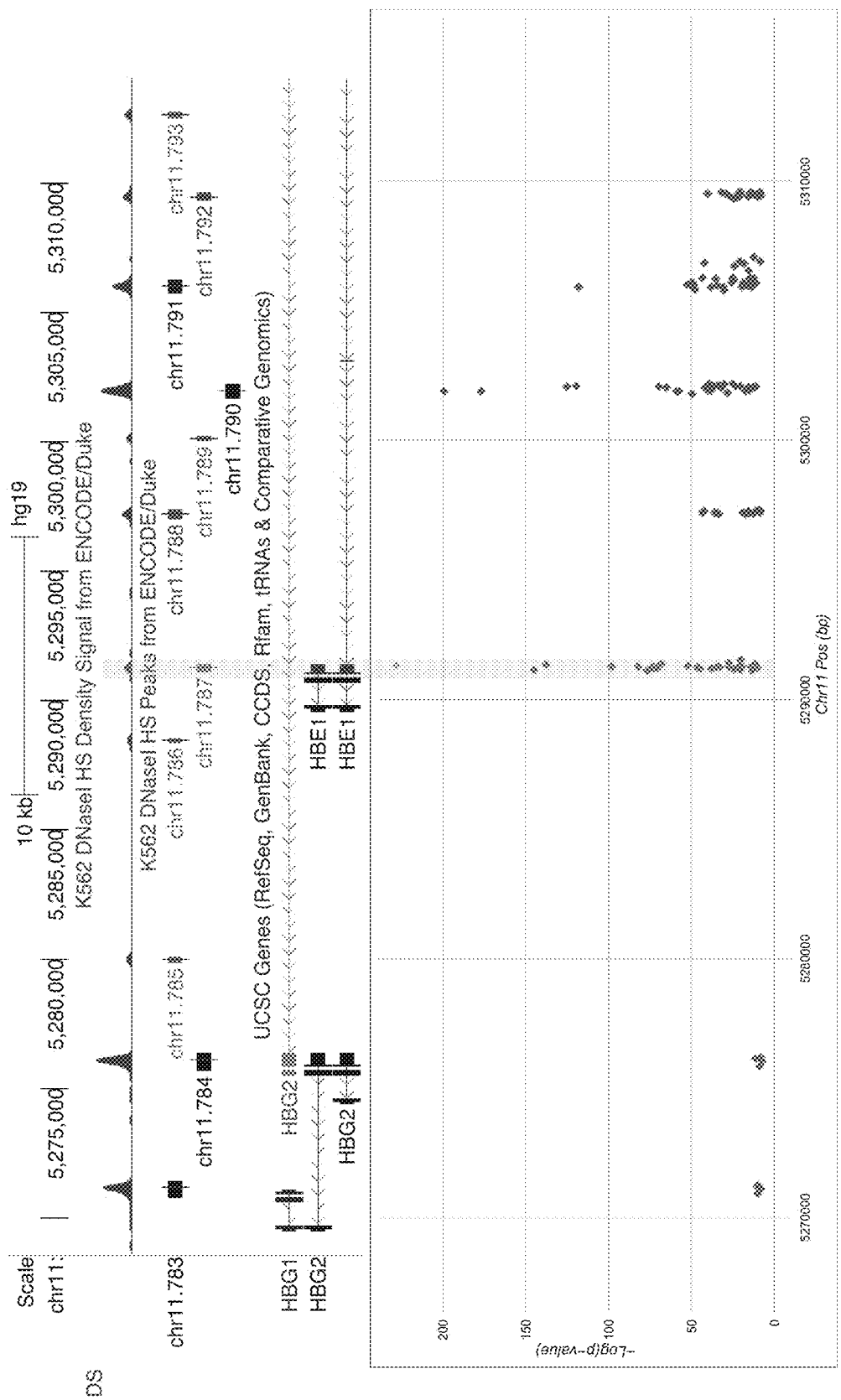
FIGS. 44A-44C show enrichment of gRNA targeting HBE1 promoter (gRNA 787).
Figure 44B:
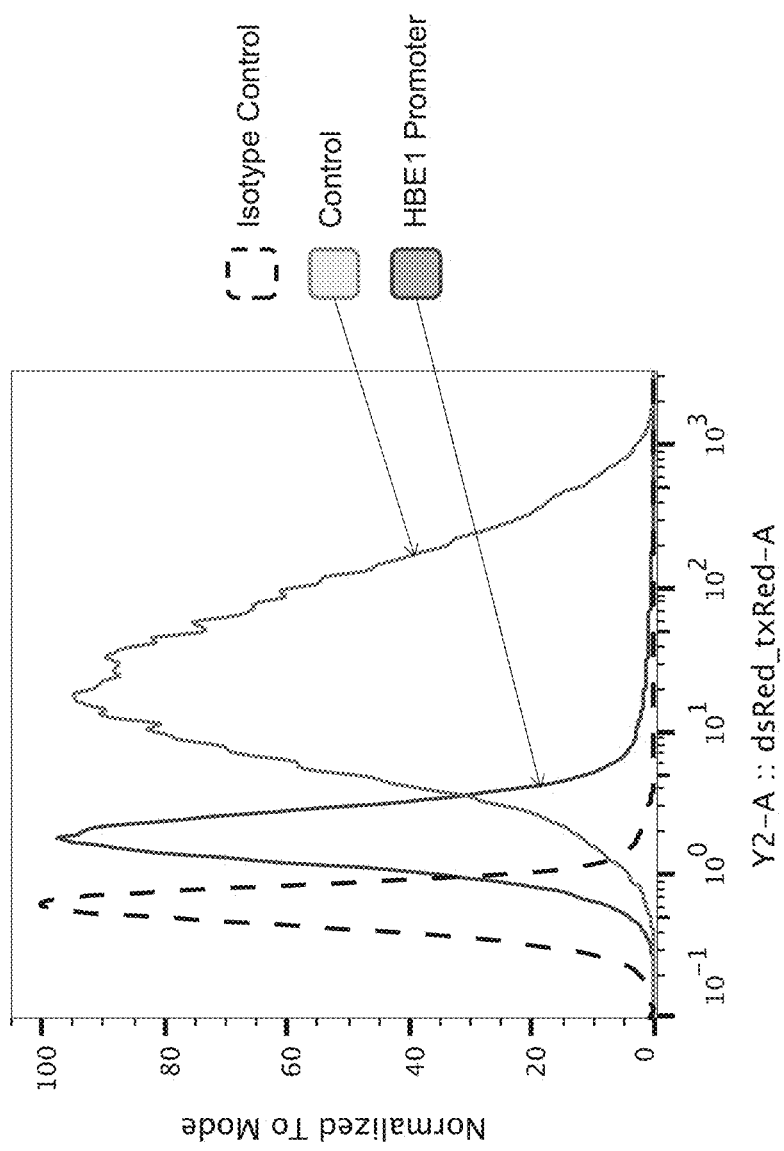
Figure 44C:
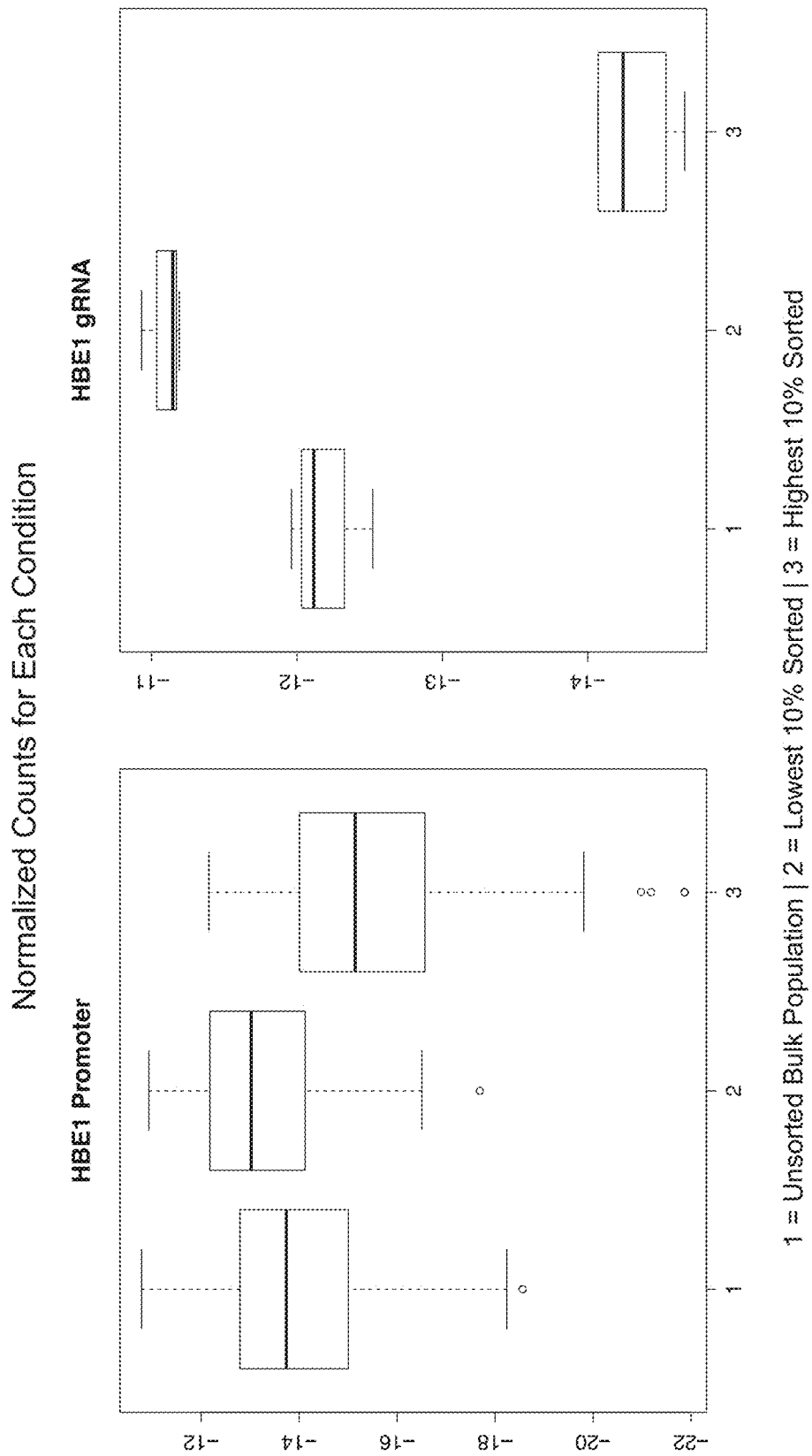
Figure 45A:
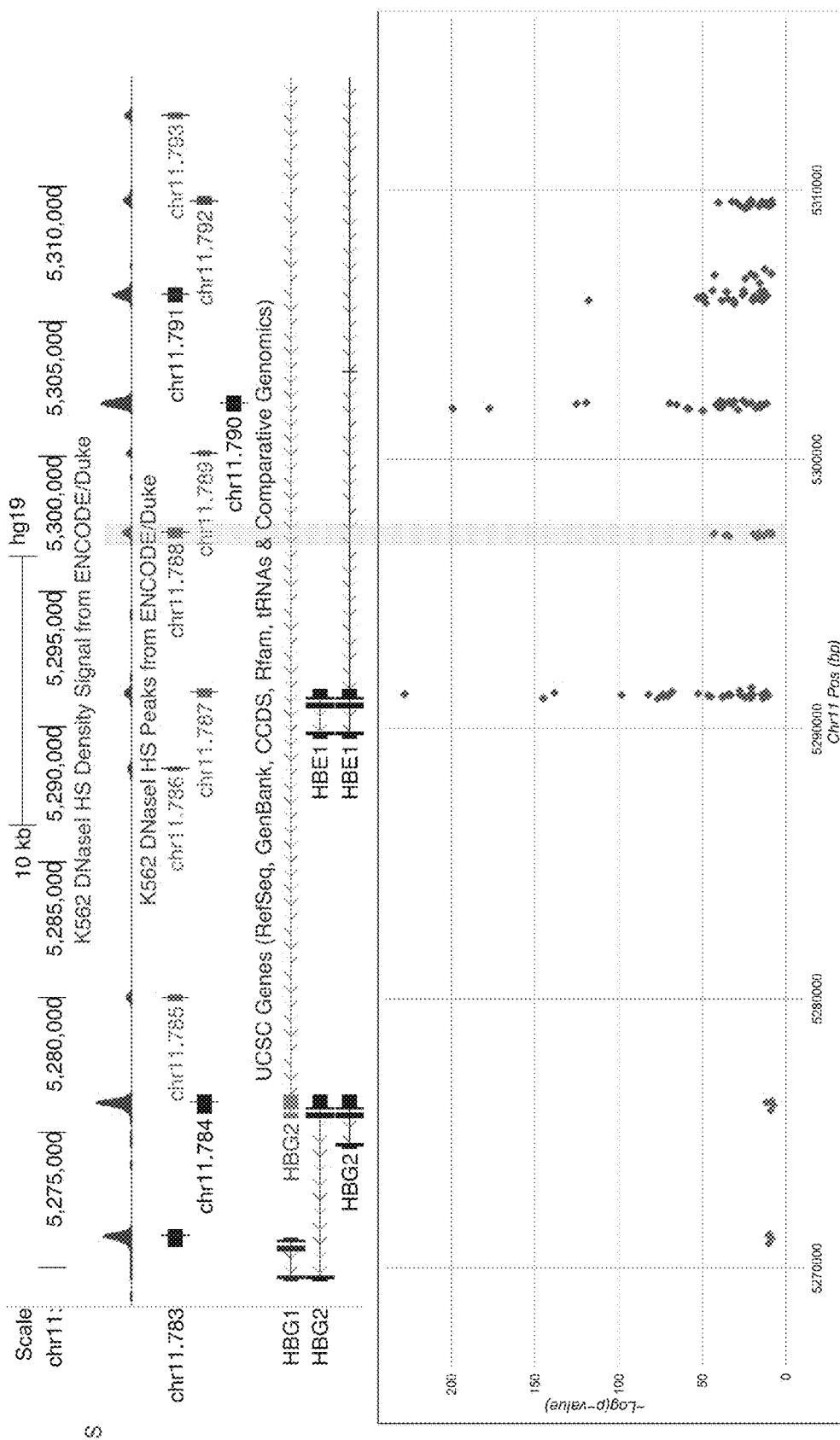
FIGS. 45A-45C show enrichment of gRNA targeting HS1 (gRNA 788).
Figure 45B:
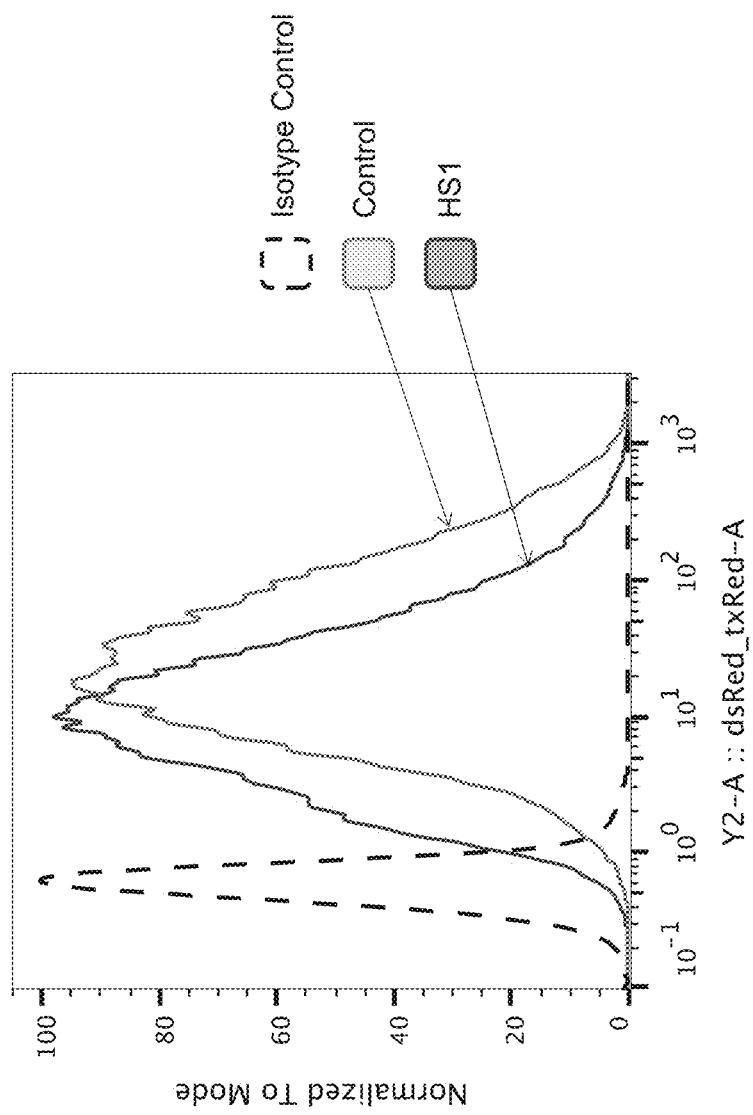
Figure 45C:
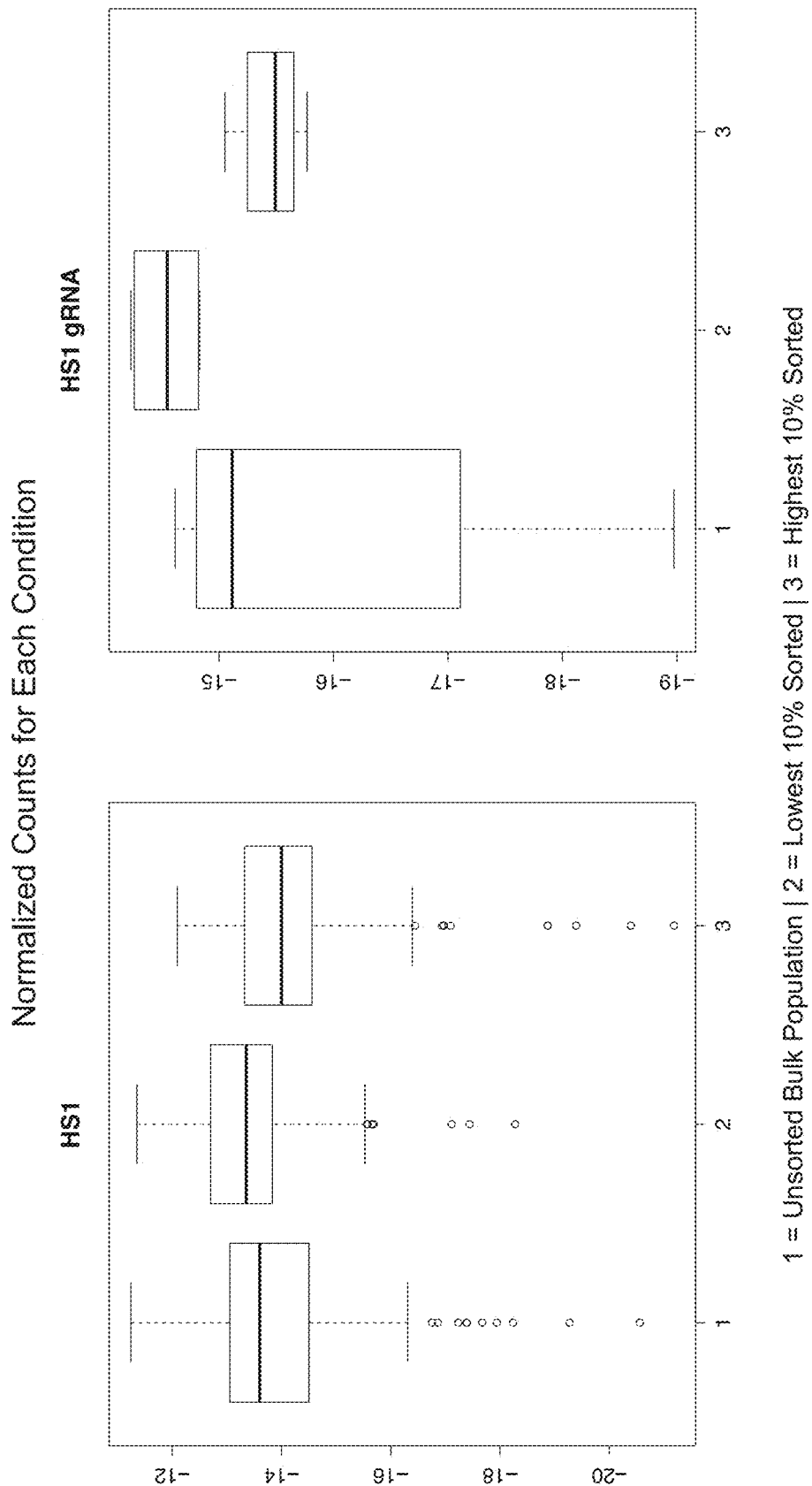
Figure 46A:
FIGS. 46A-46C show enrichment of gRNA targeting HS2 (gRNA 790).
Figure 46B:
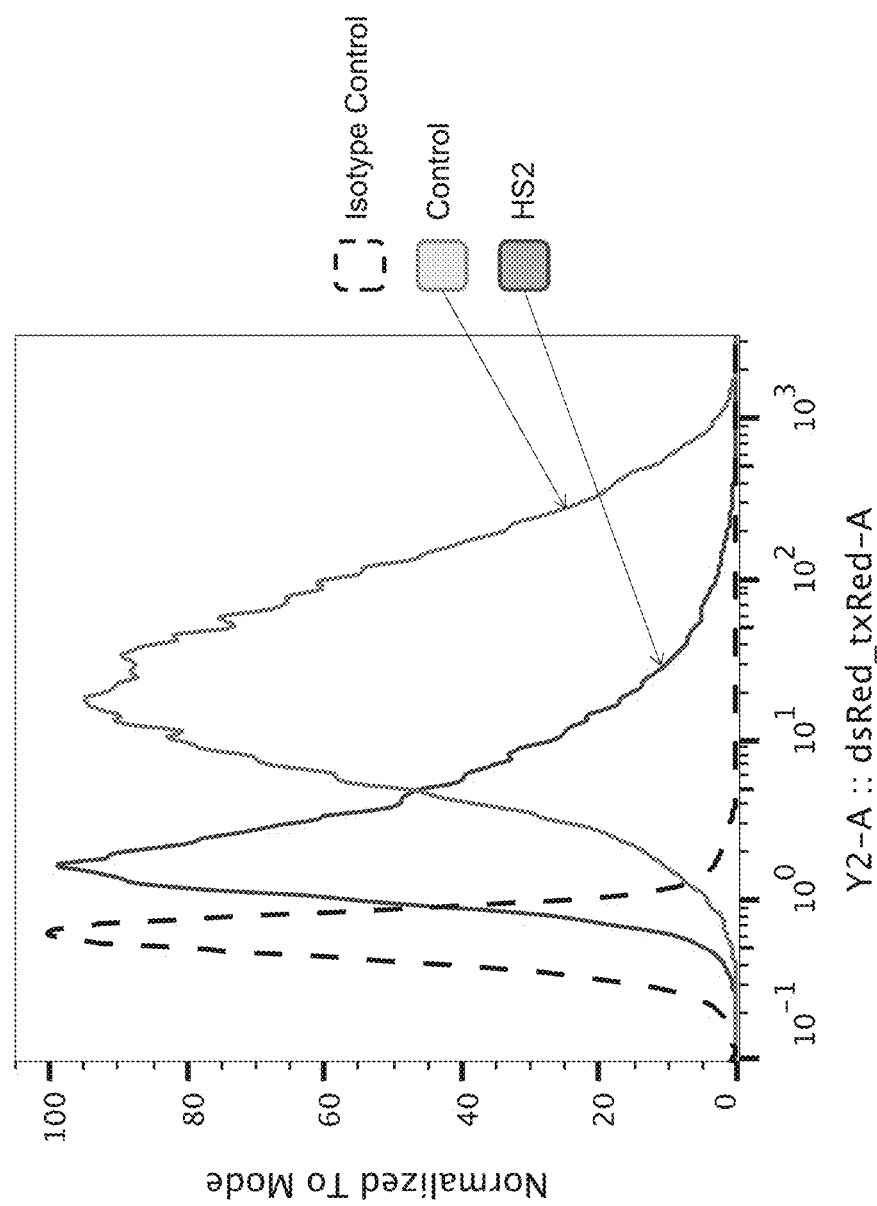
Figure 46C:
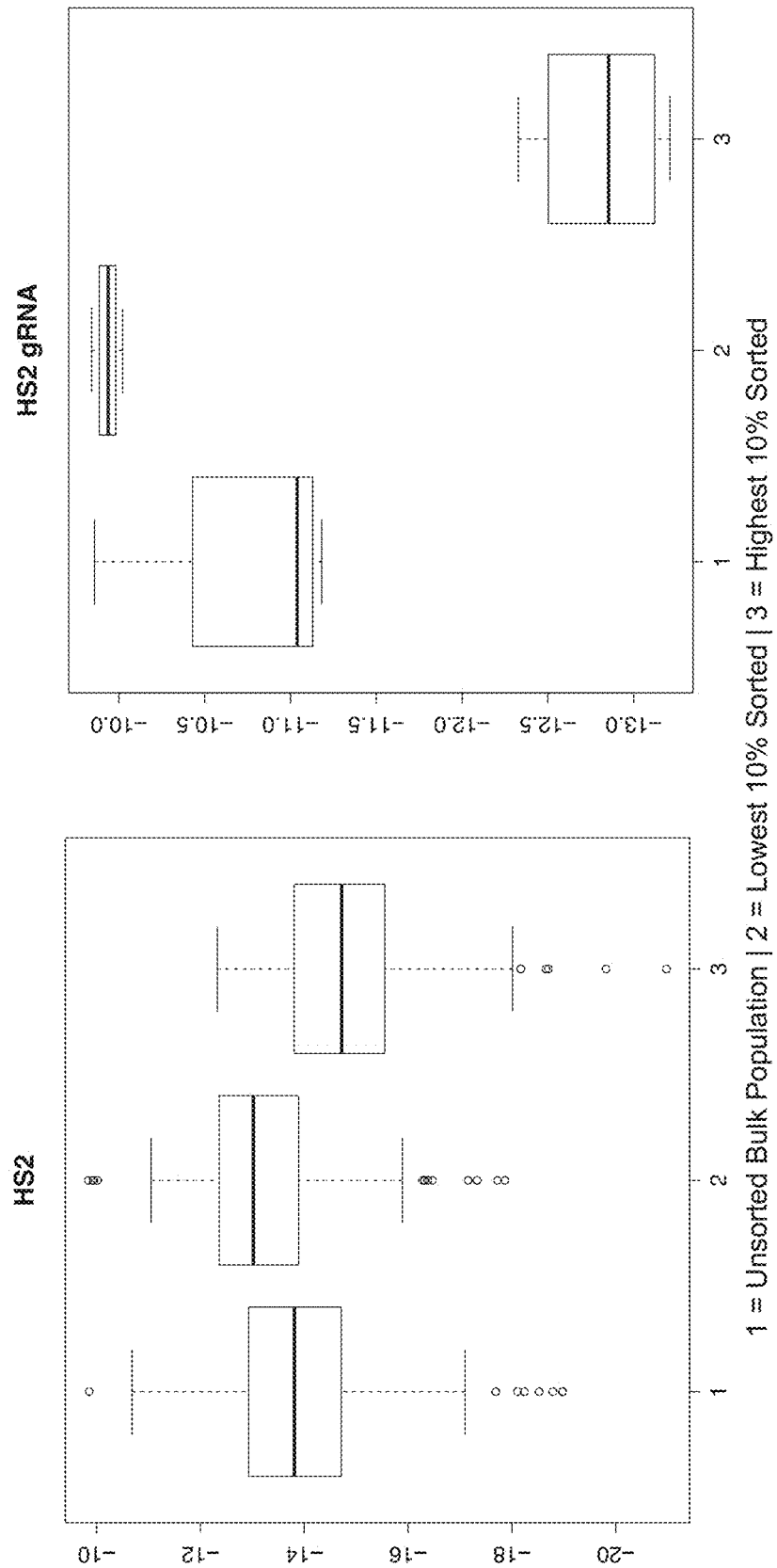
Figure 47A:
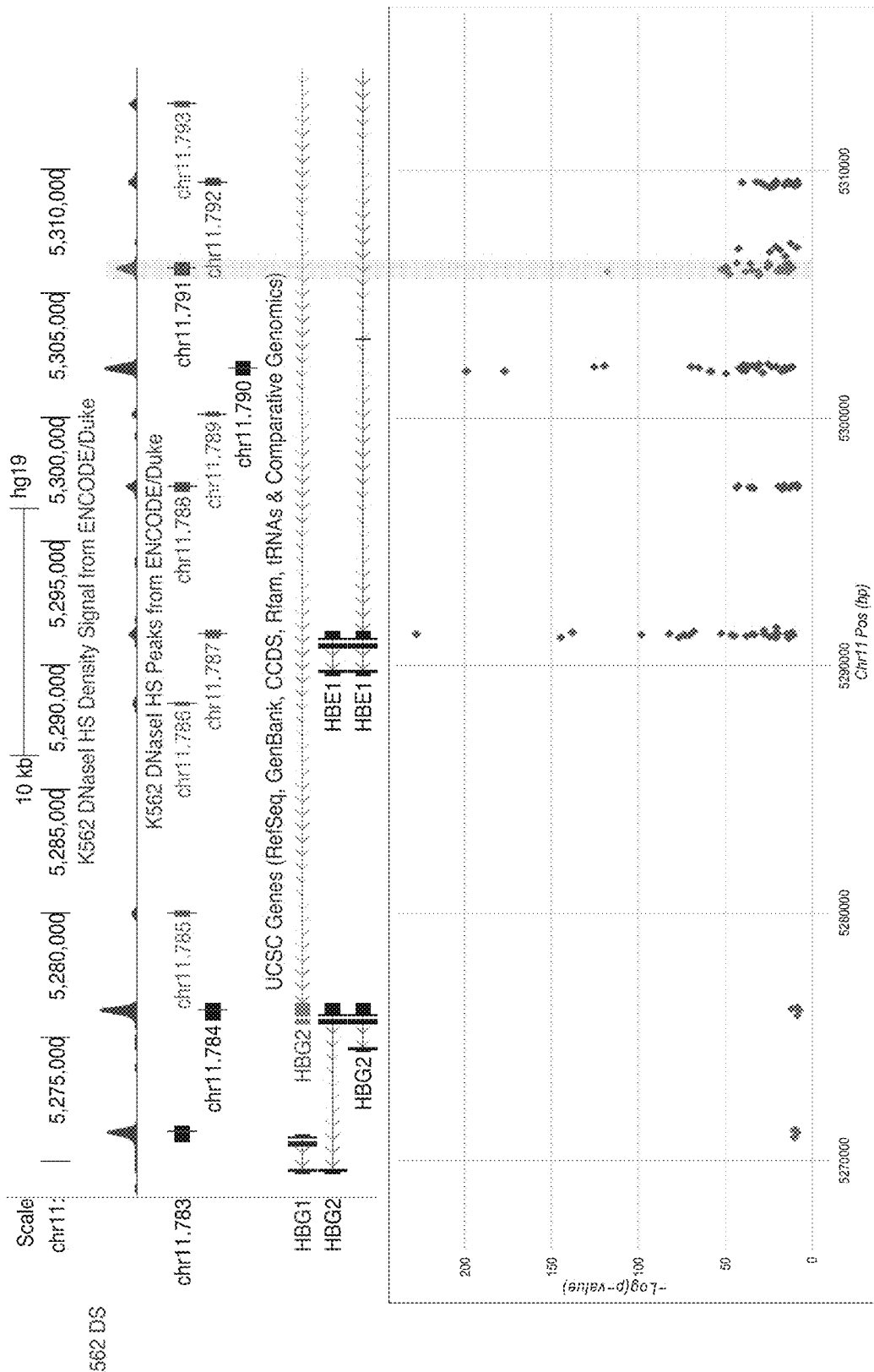
FIGS. 47A-47C show enrichment of gRNA targeting HS3 (gRNA 791).
Figure 47B:
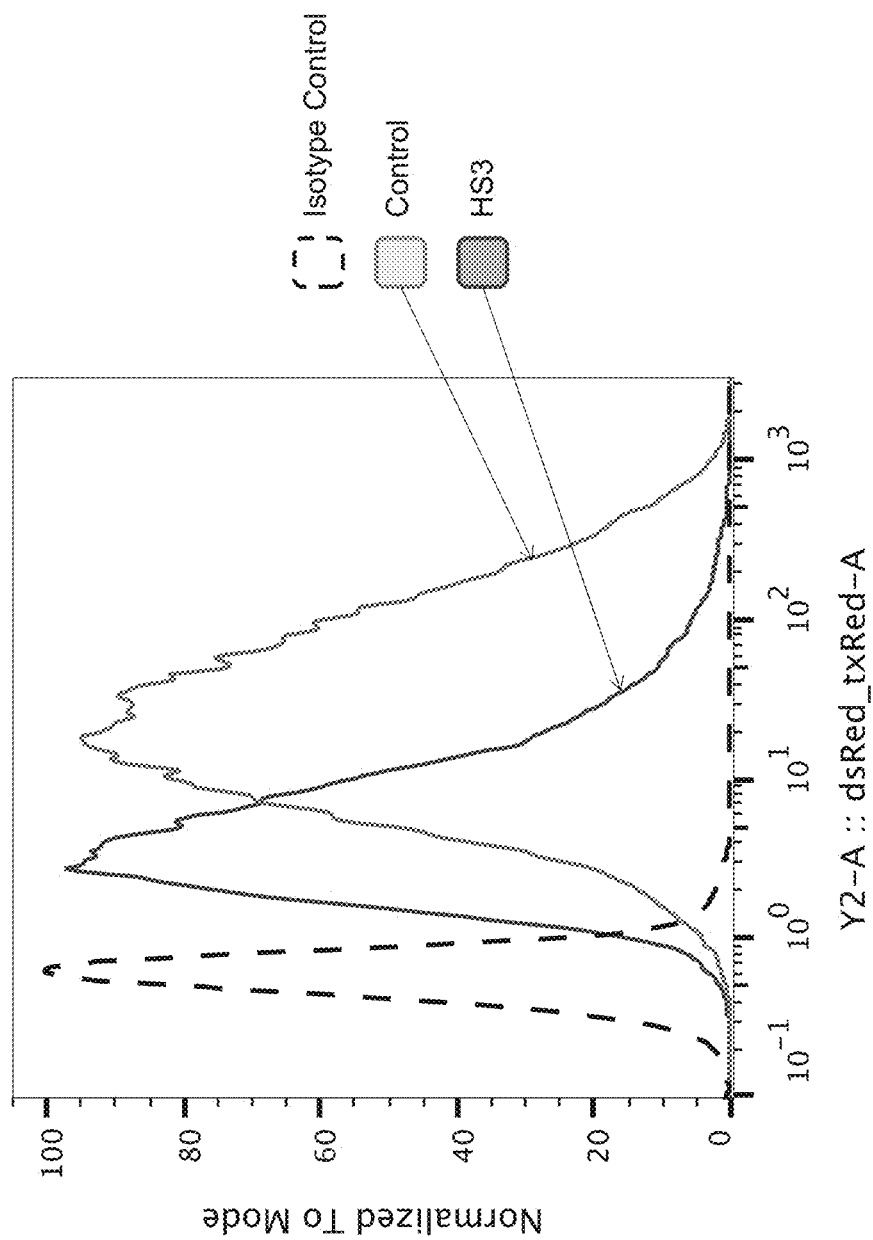
Figure 47C:
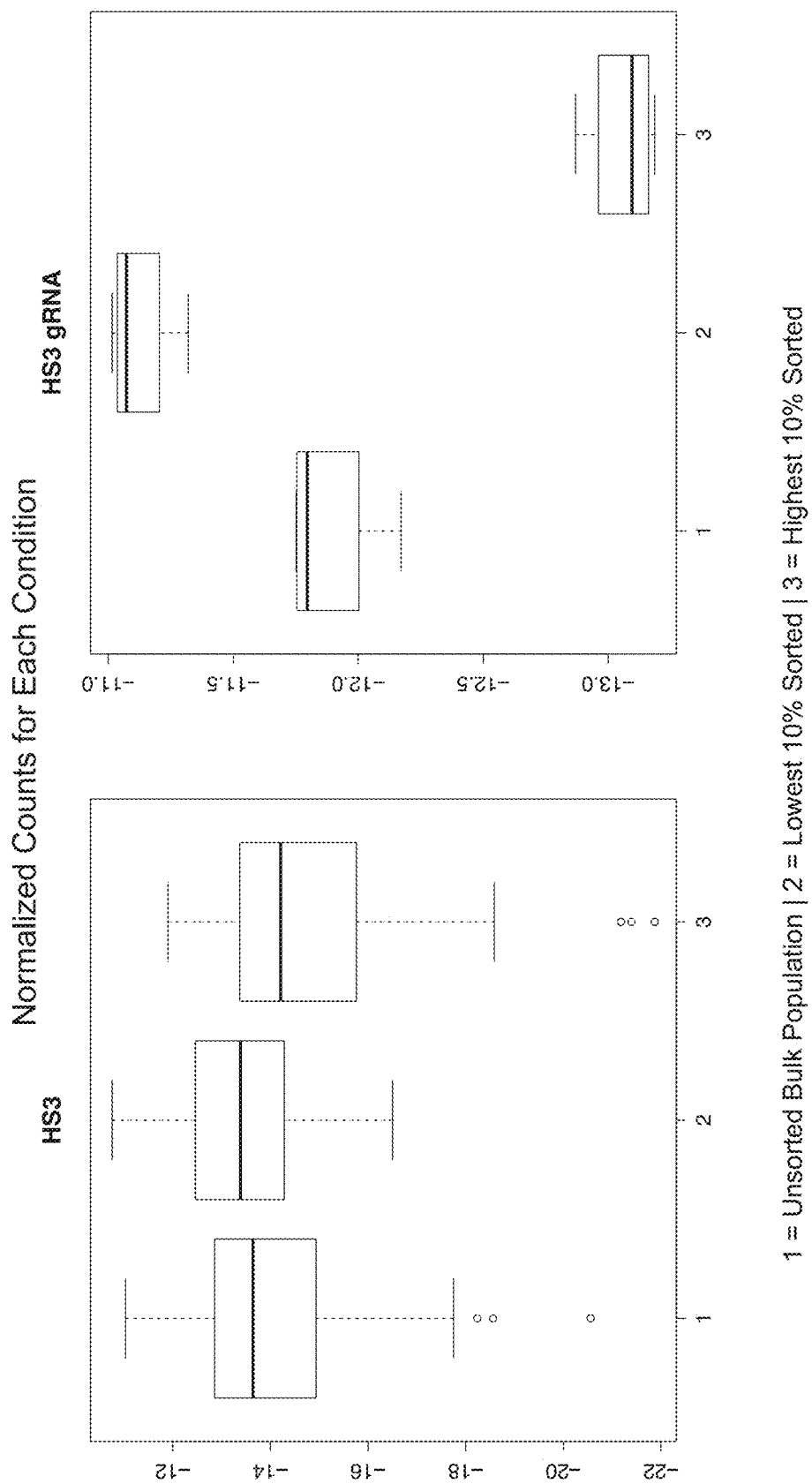
Figure 48A:
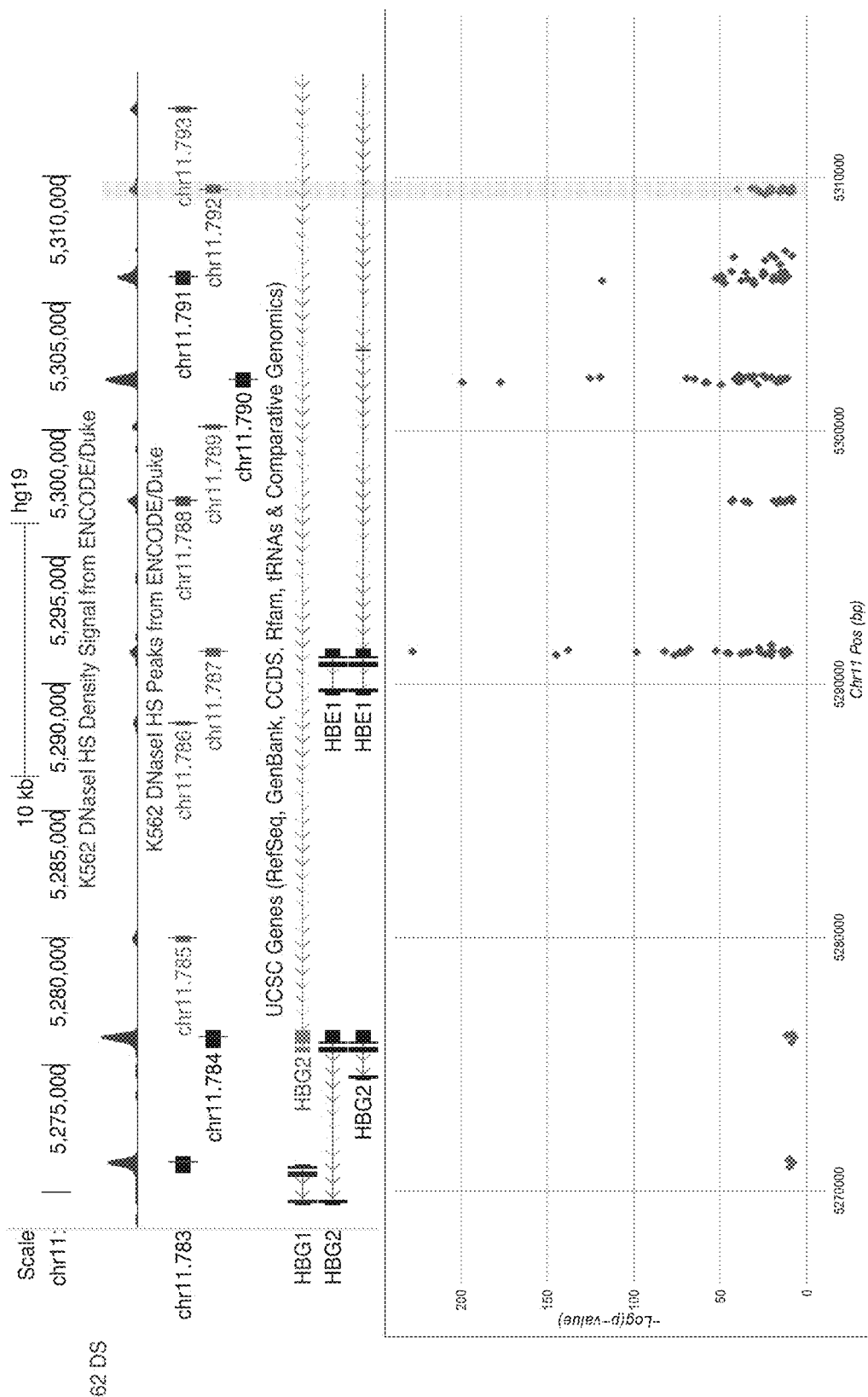
FIGS. 48A-48C show enrichment of gRNA targeting HS4 (gRNA 792).
Figure 48B:
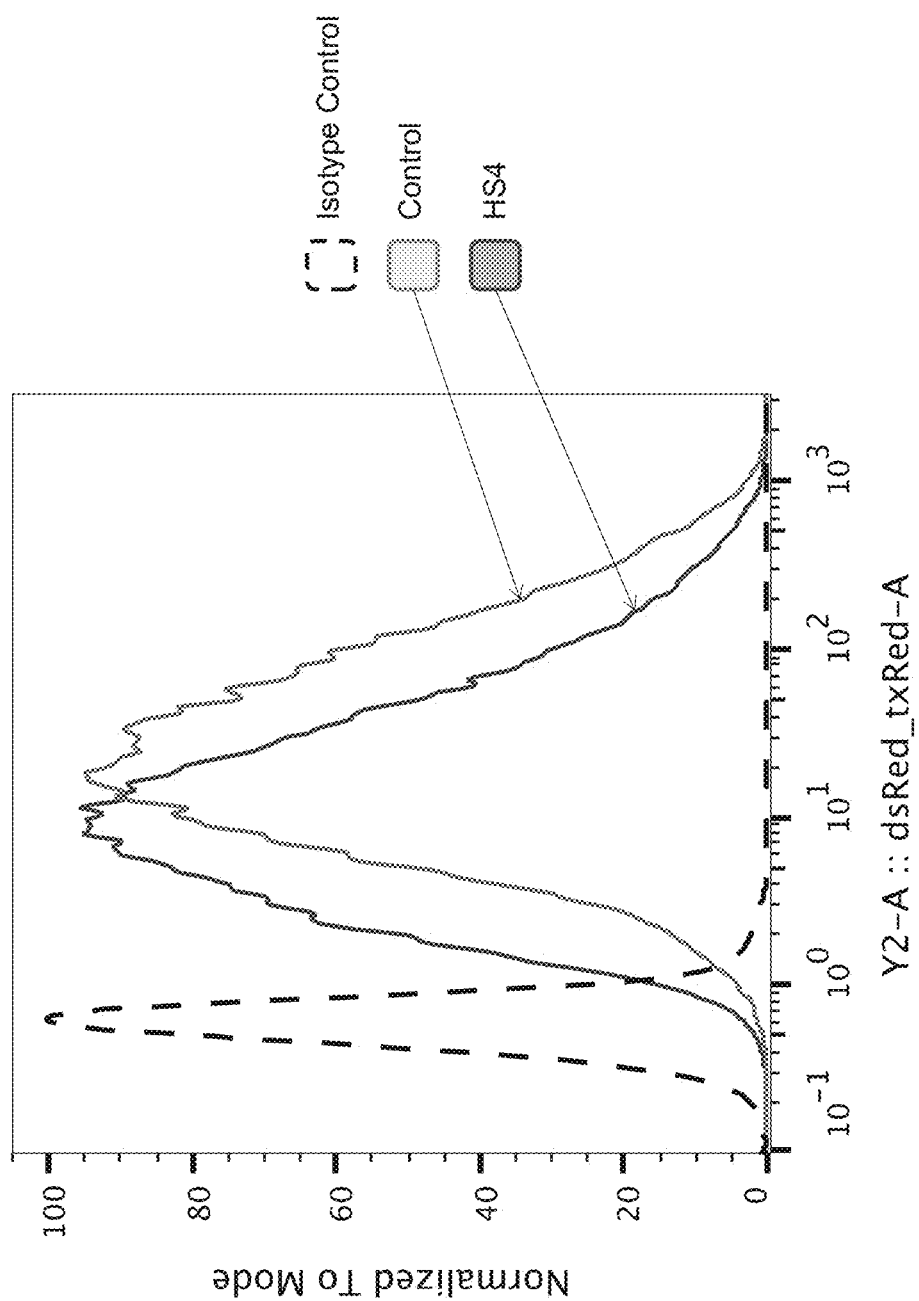
Figure 48C:
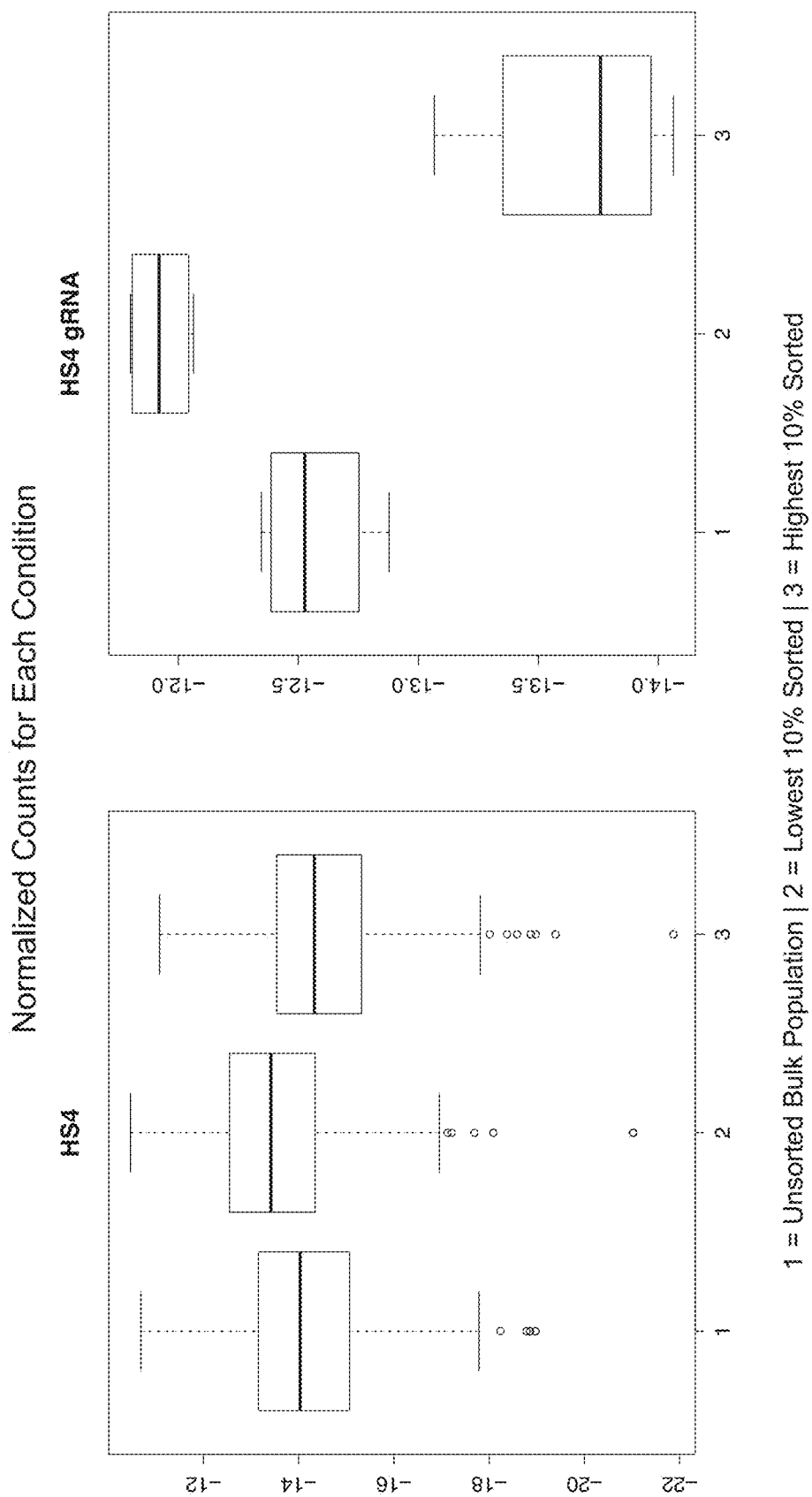
Figure 49A:
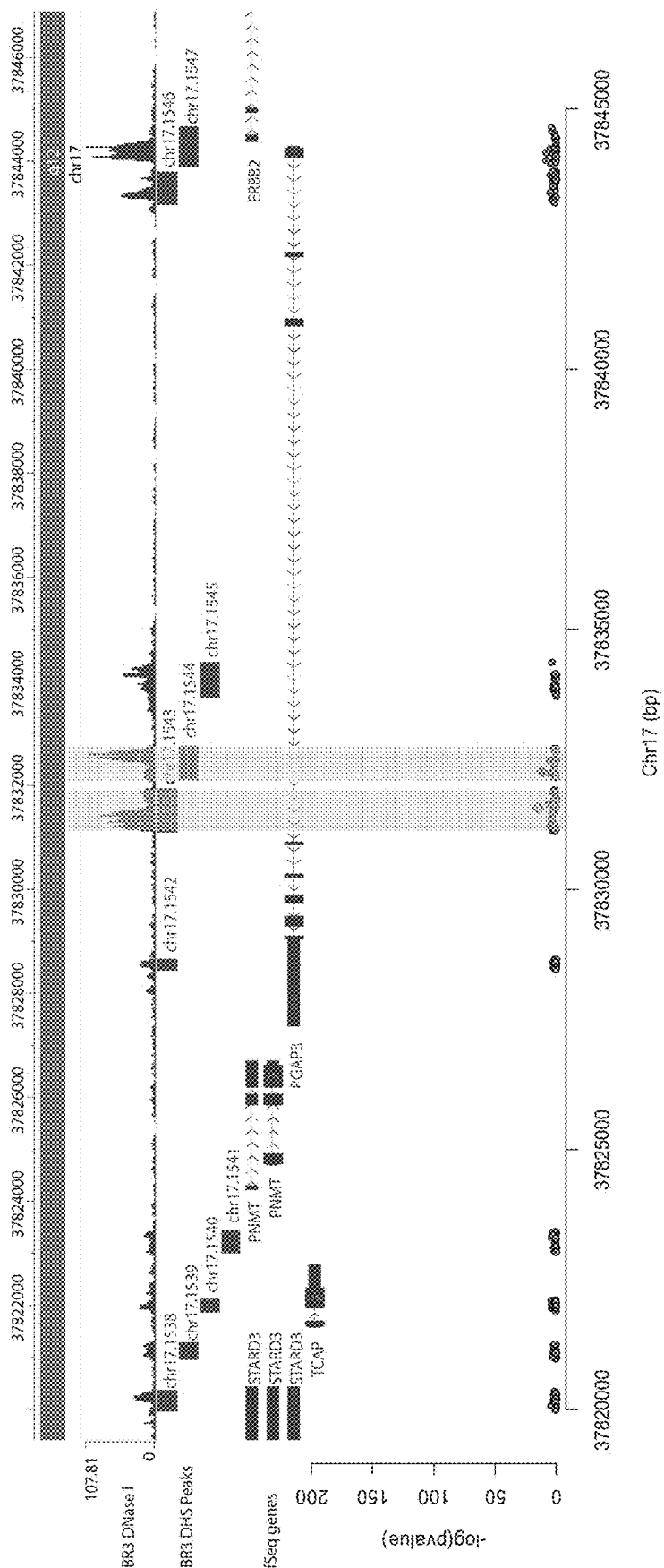
FIGS. 49A-49B show enrichment of combinations of 1543.1 and 1544.1 gRNAs identified in HER2 screen.
Figure 49B:
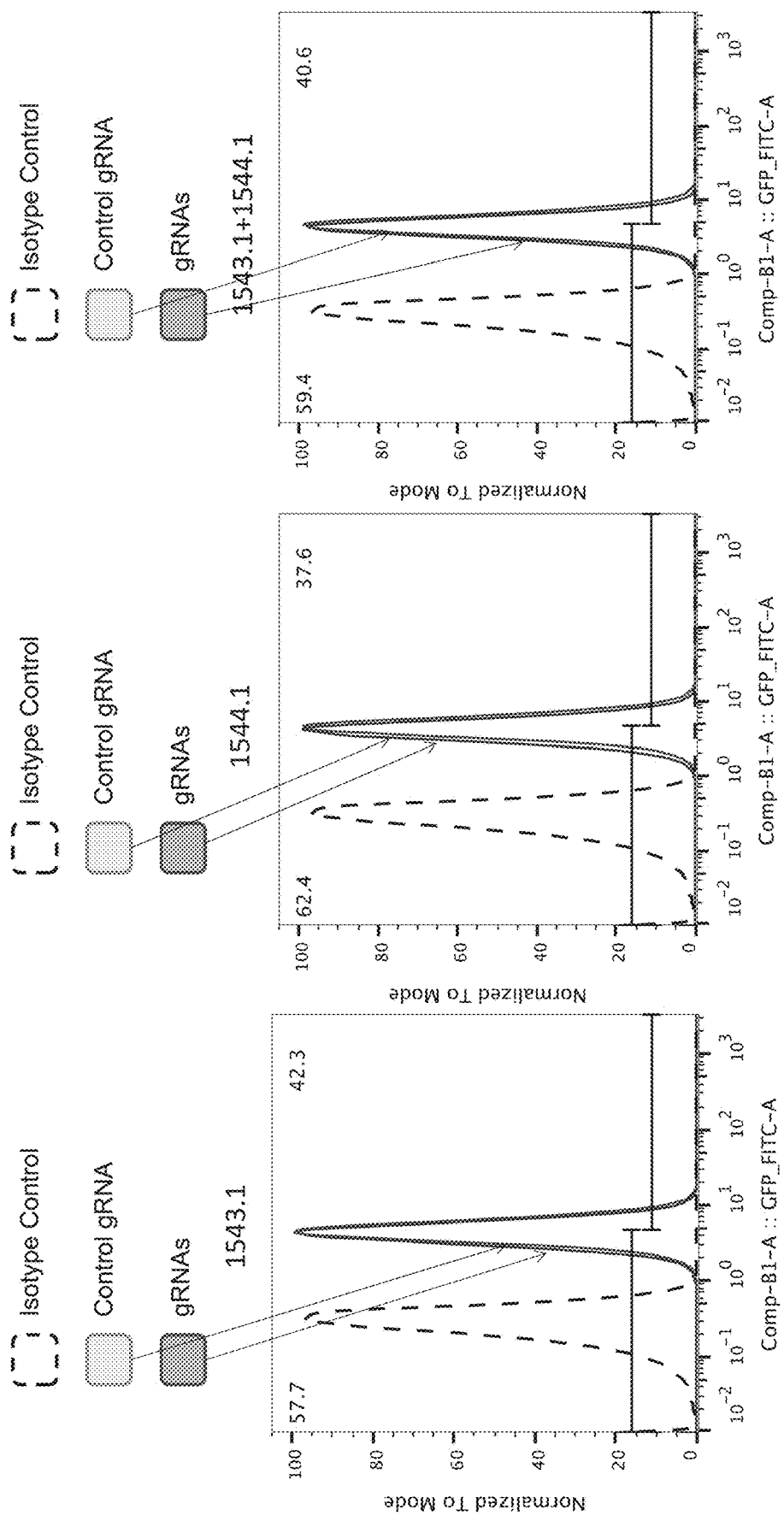
Figure 50A:
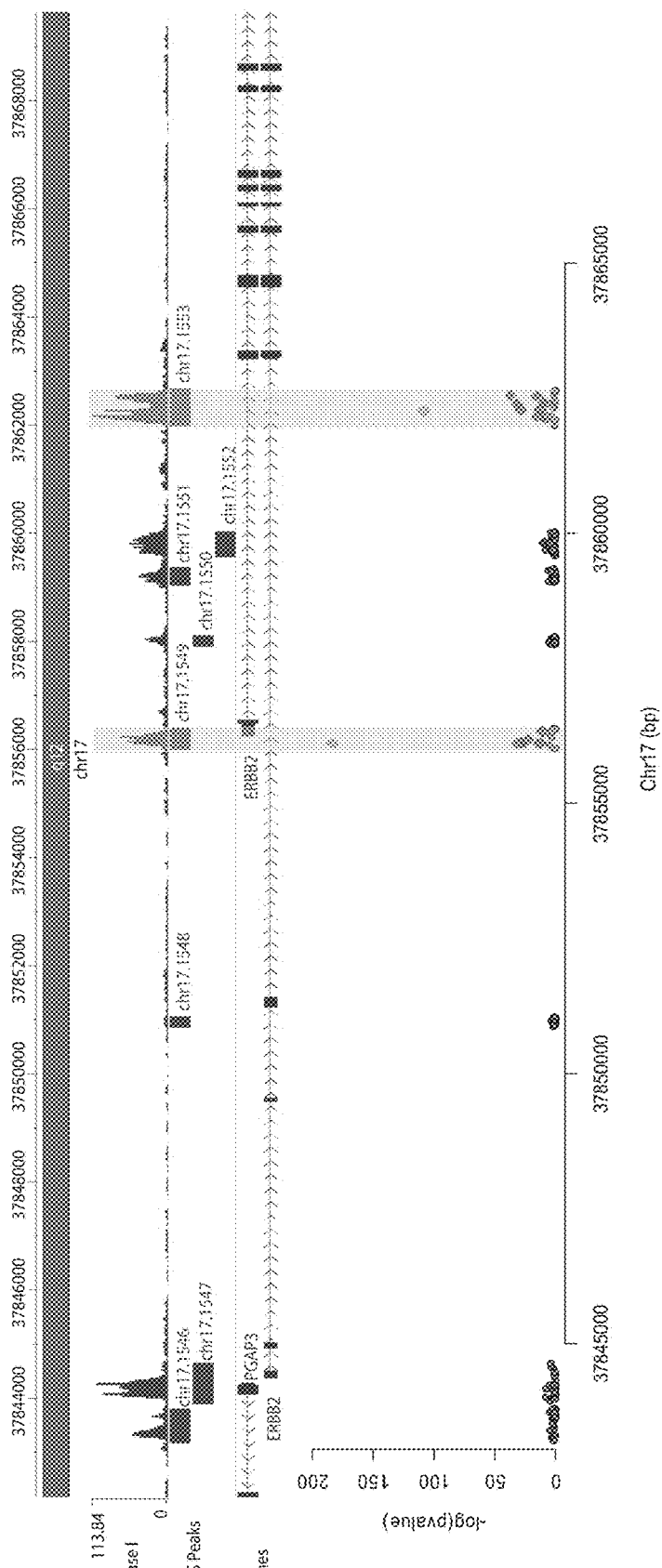
FIGS. 50A-50B show enrichment of combinations of 1549.1 and 1553.1 gRNAs identified in HER2 screen.
Figure 50B:
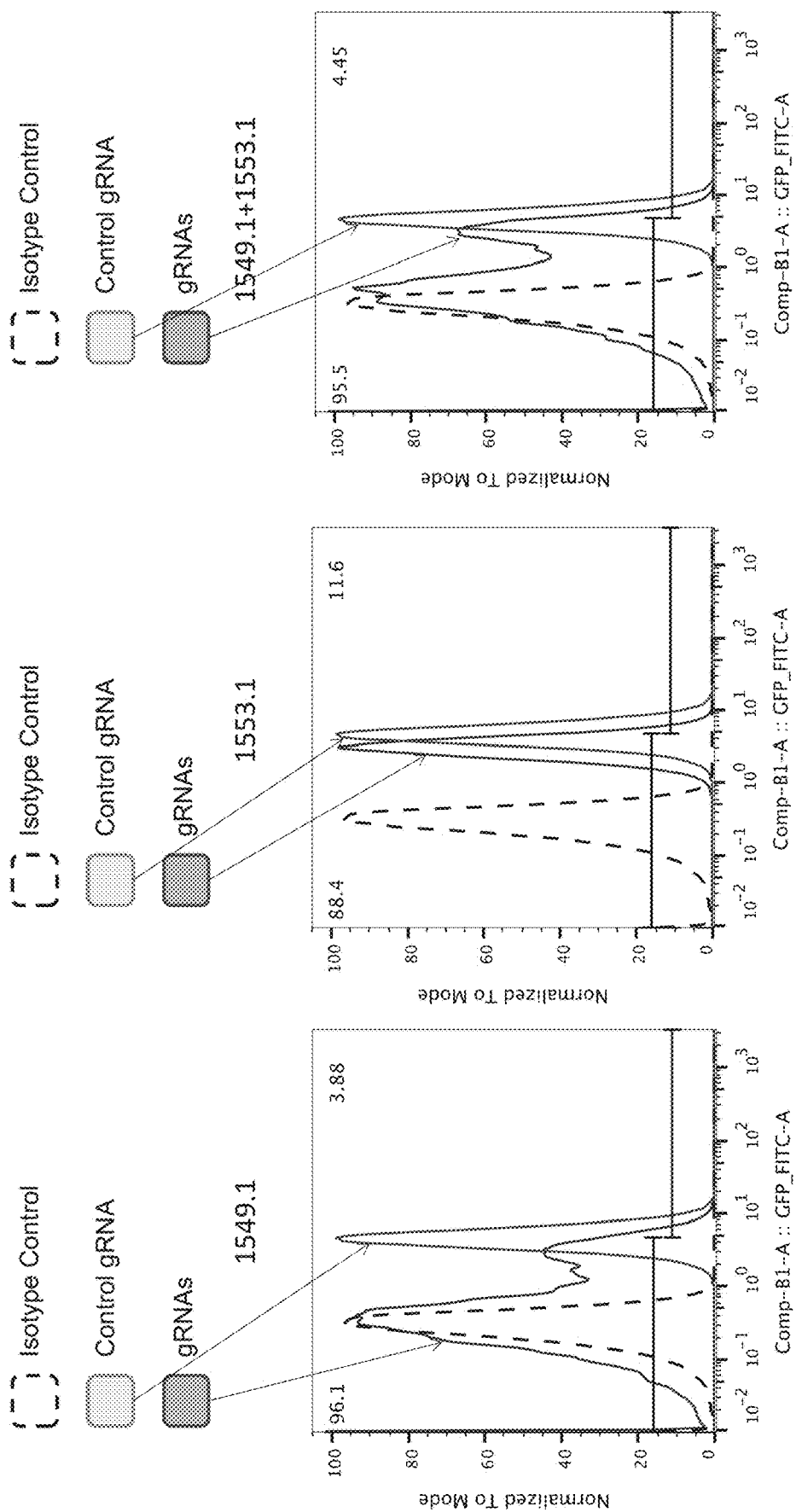
Figure 51A:
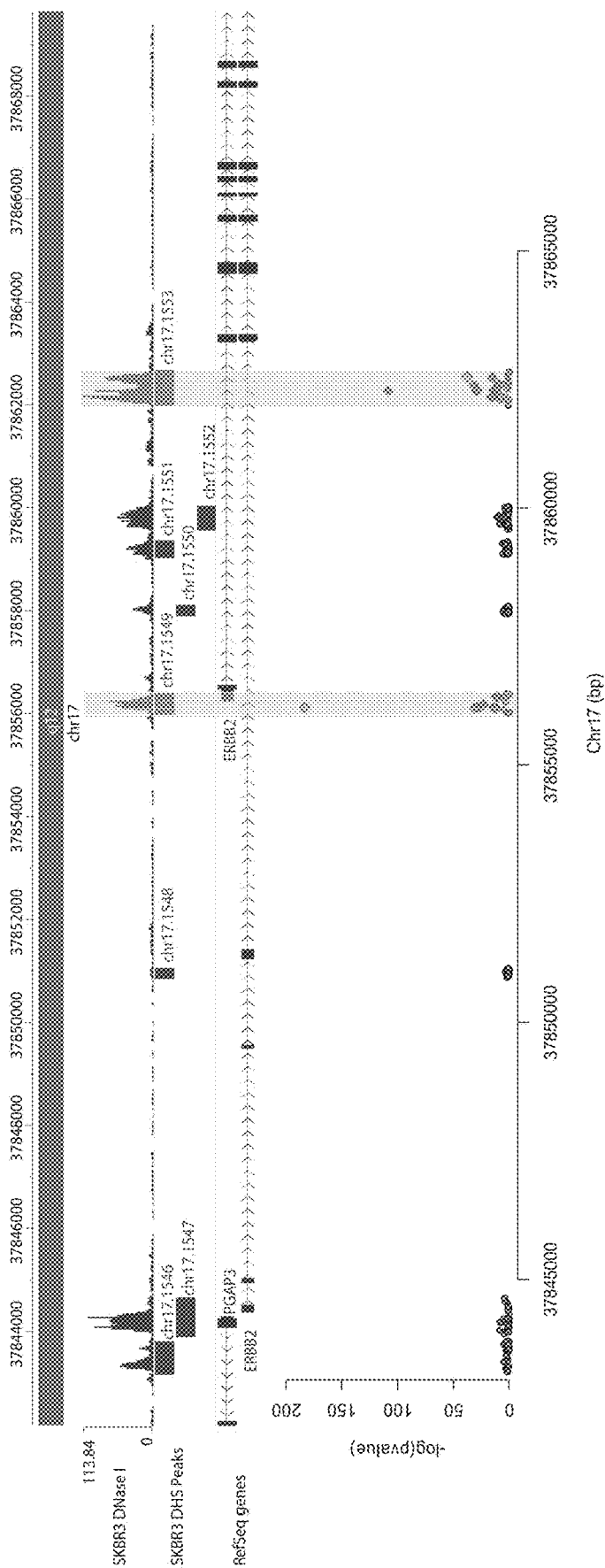
FIGS. 51A-51B show enrichment of combinations of 1549.1 and 1553.2 gRNAs identified in HER2 screen.
Figure 51B:
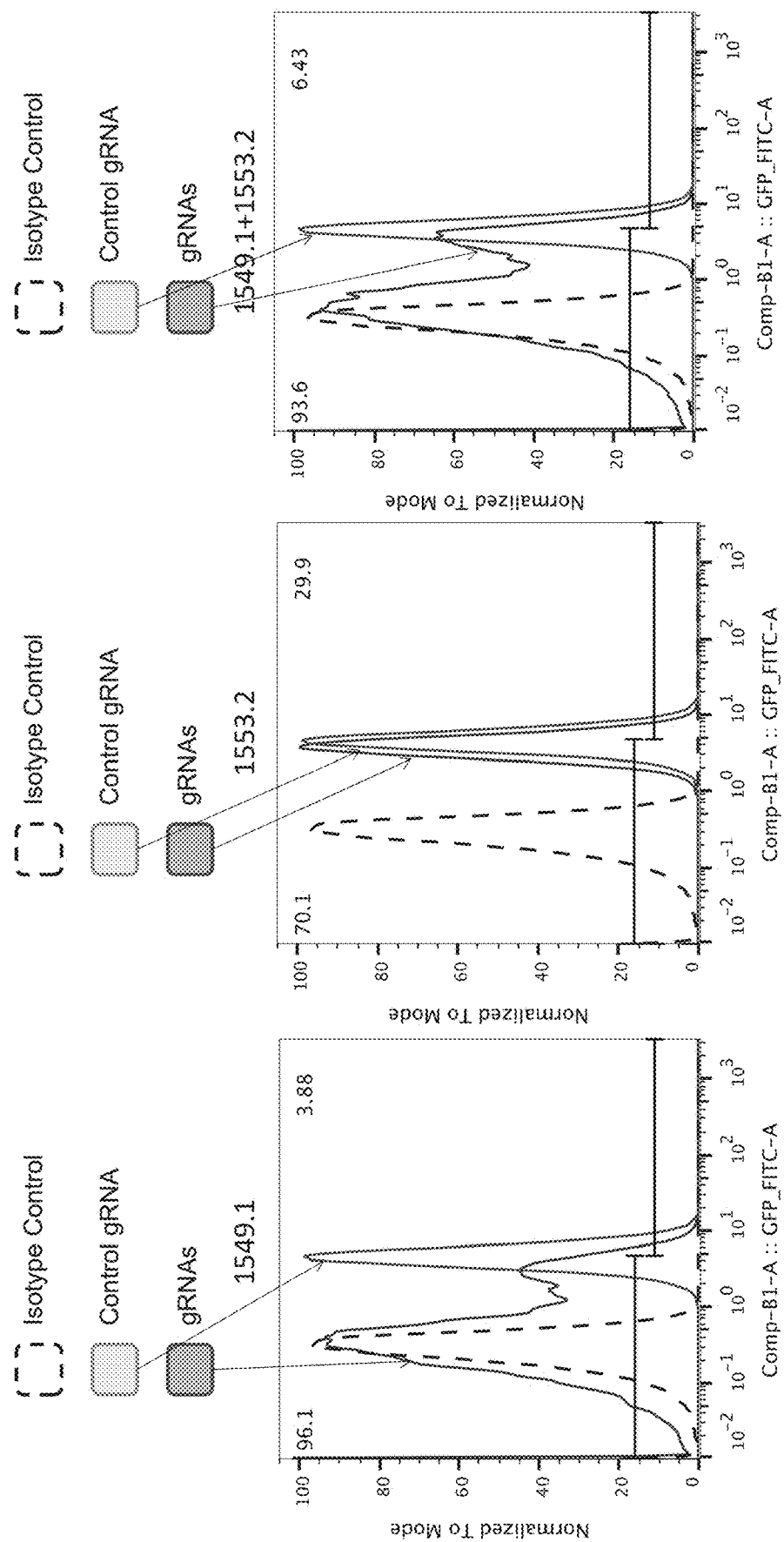
Figure 52A:
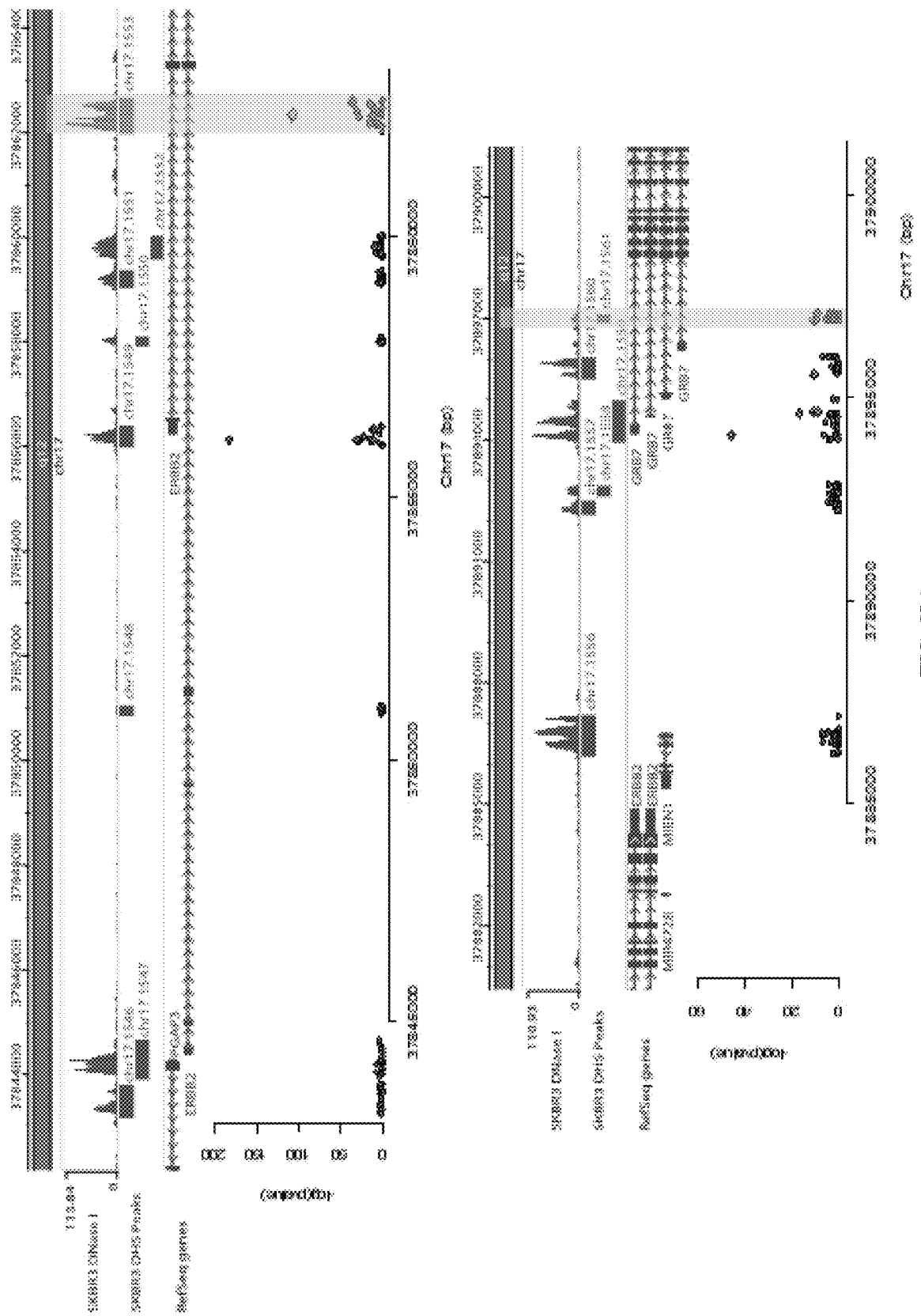
FIGS. 52A-52B show enrichment of combinations of 1553.1 and 1561.1 gRNAs identified in HER2 screen.
Figure 52B:
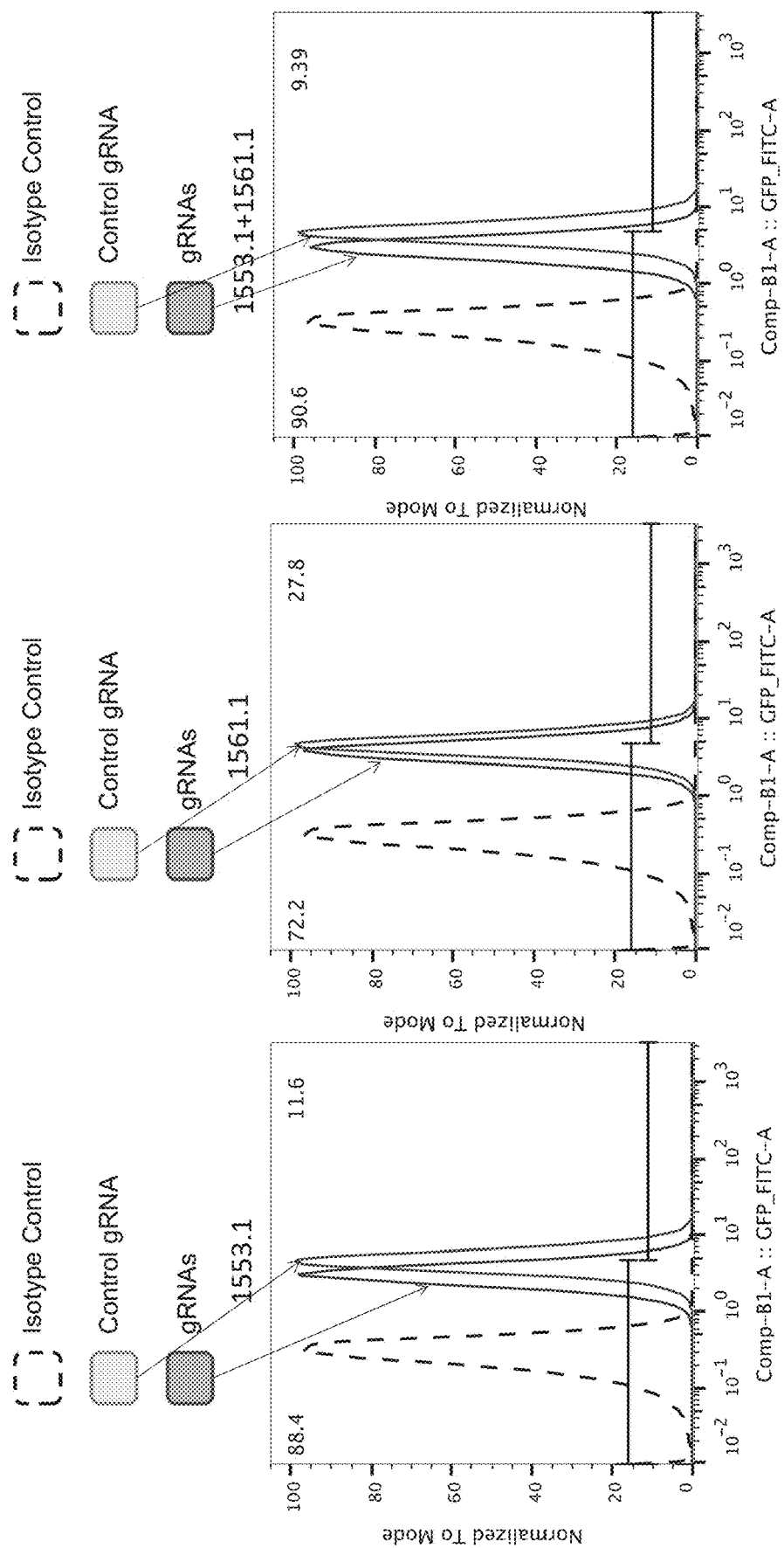
Figure 53A:
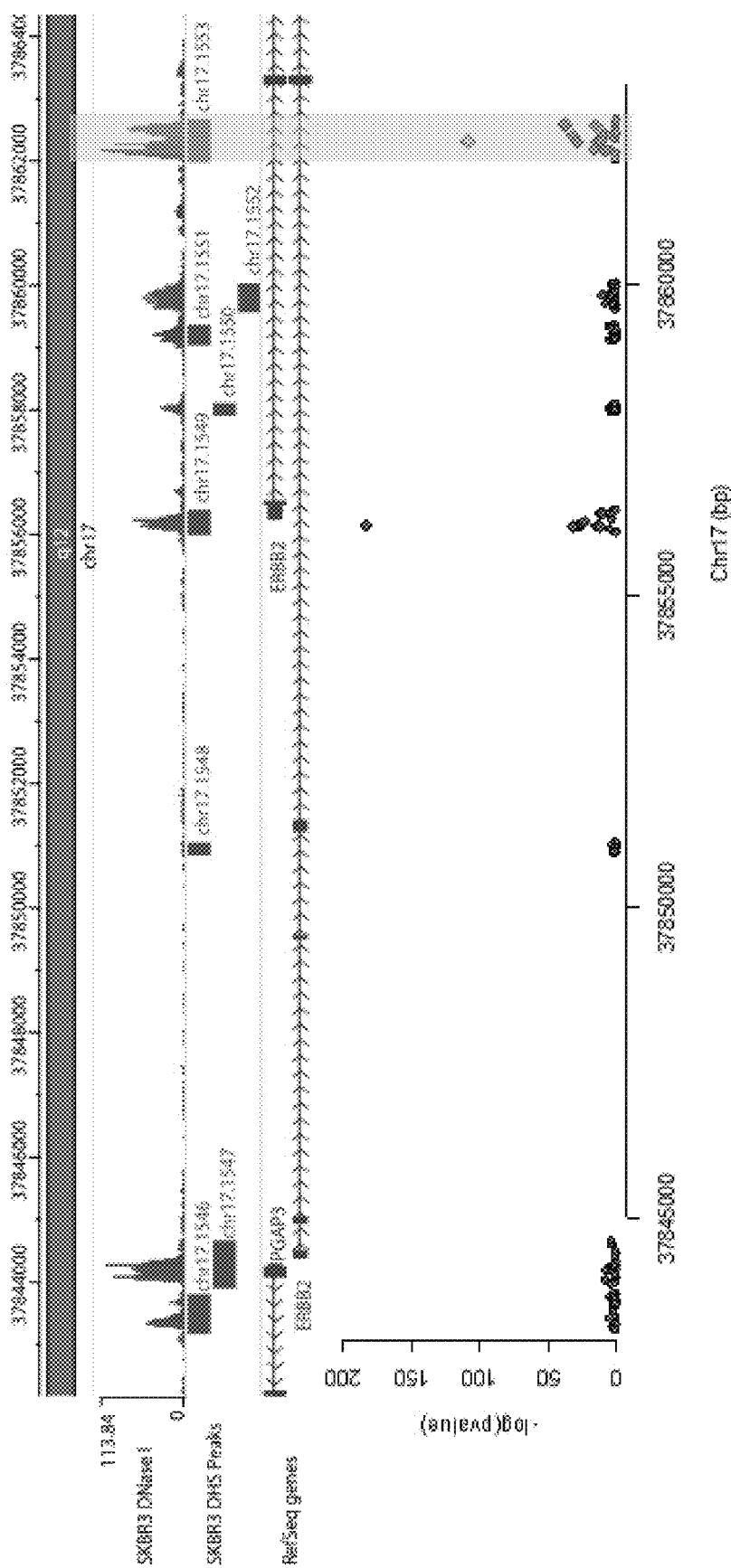
FIGS. 53A-53C show enrichment of combinations of 1553.2 and 1562.1 gRNAs identified in HER2 screen.
Figure 53B:
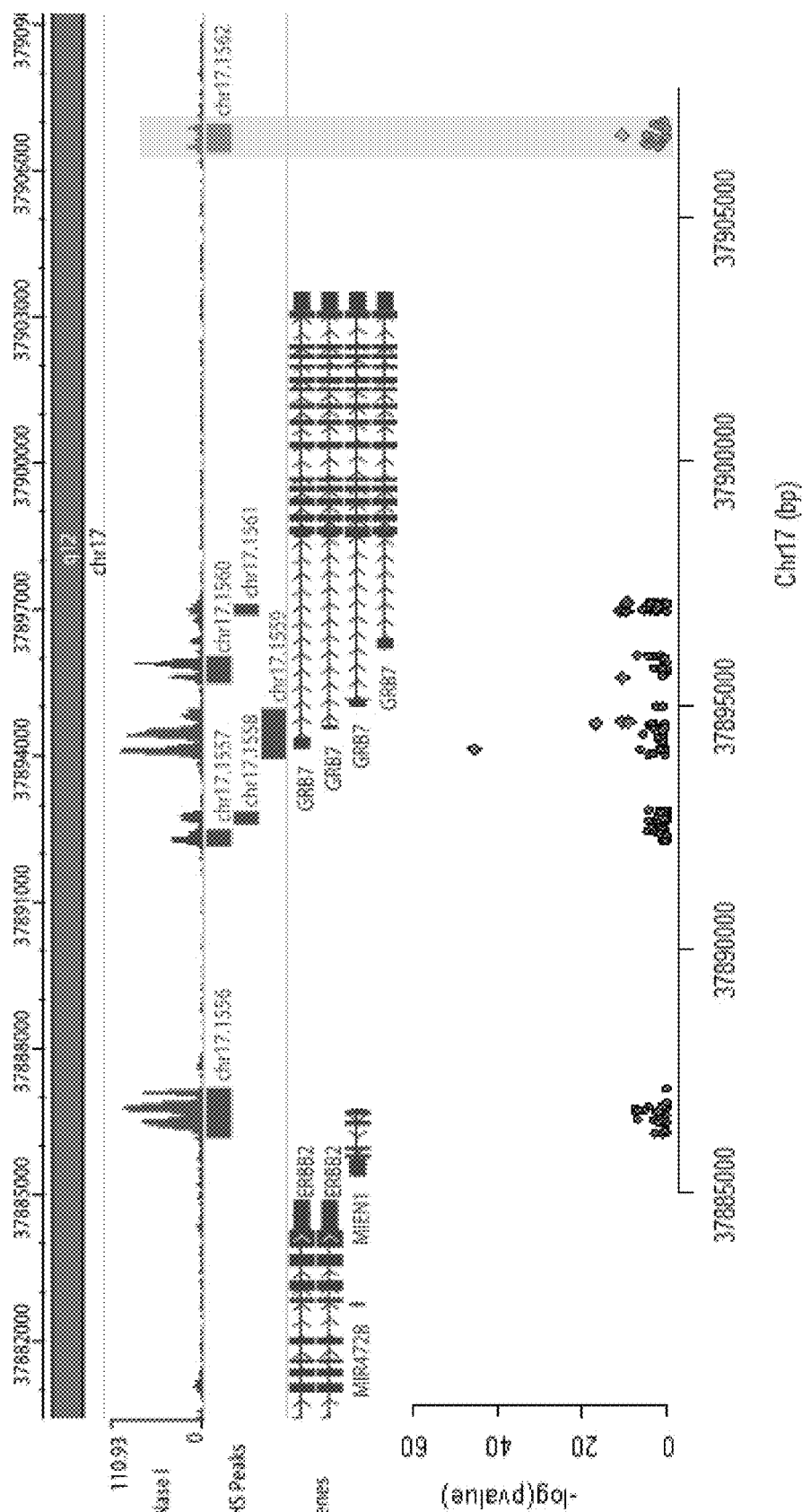
Figure 53C:
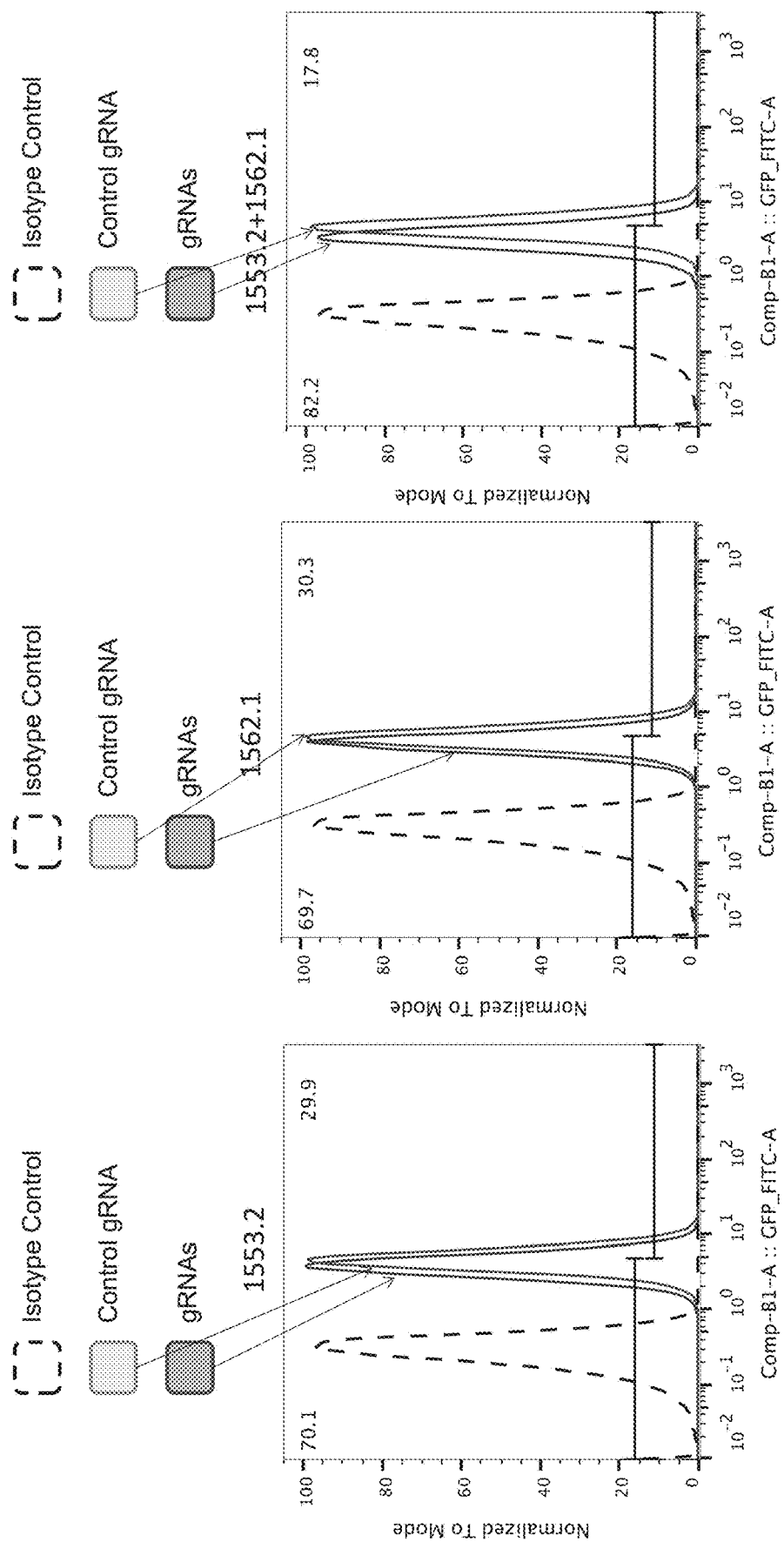
Figure 54A:
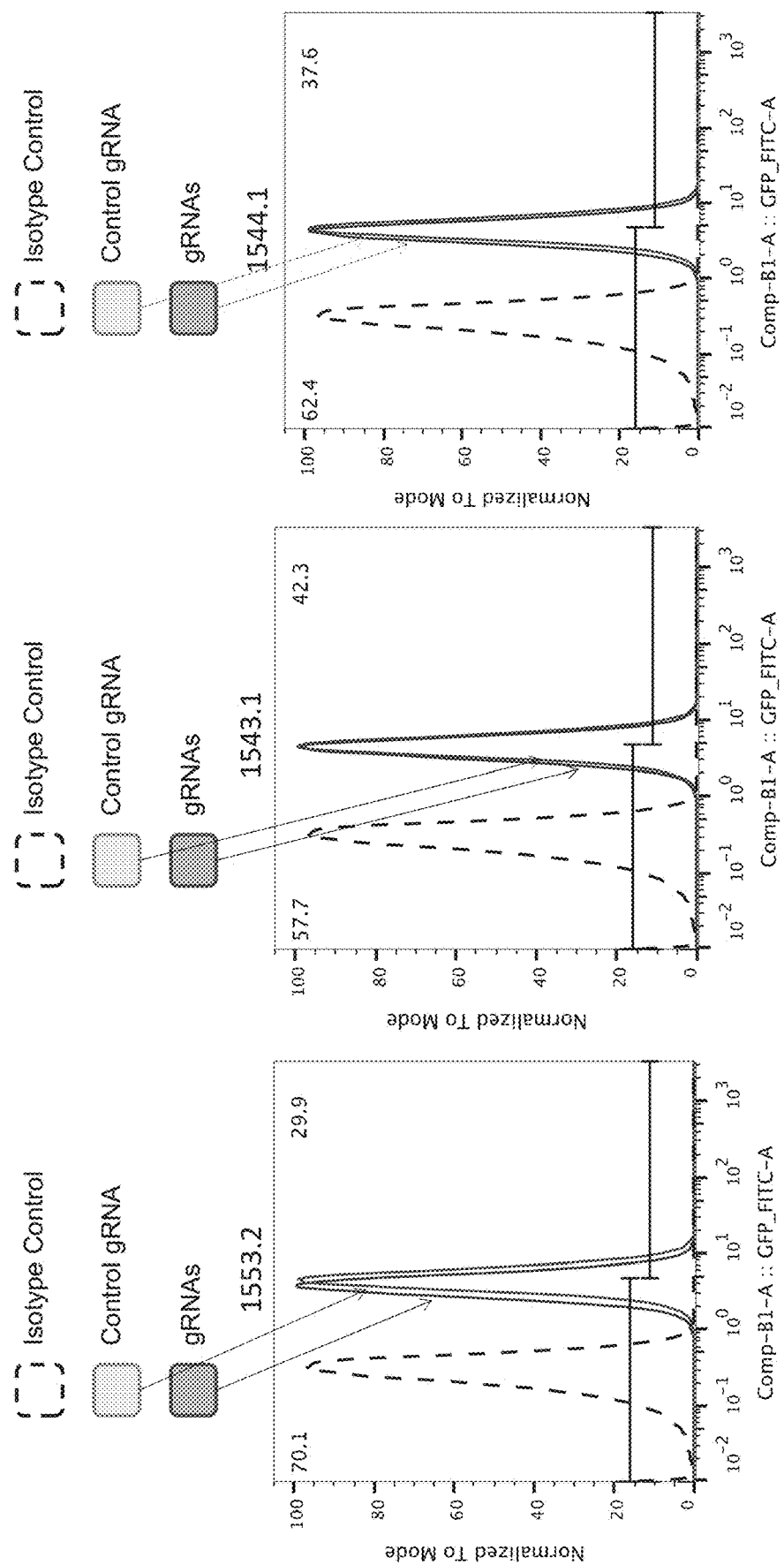
FIGS. 54A-54B show enrichment of combinations of gRNAs identified in HER2 screen.
Figure 54B:
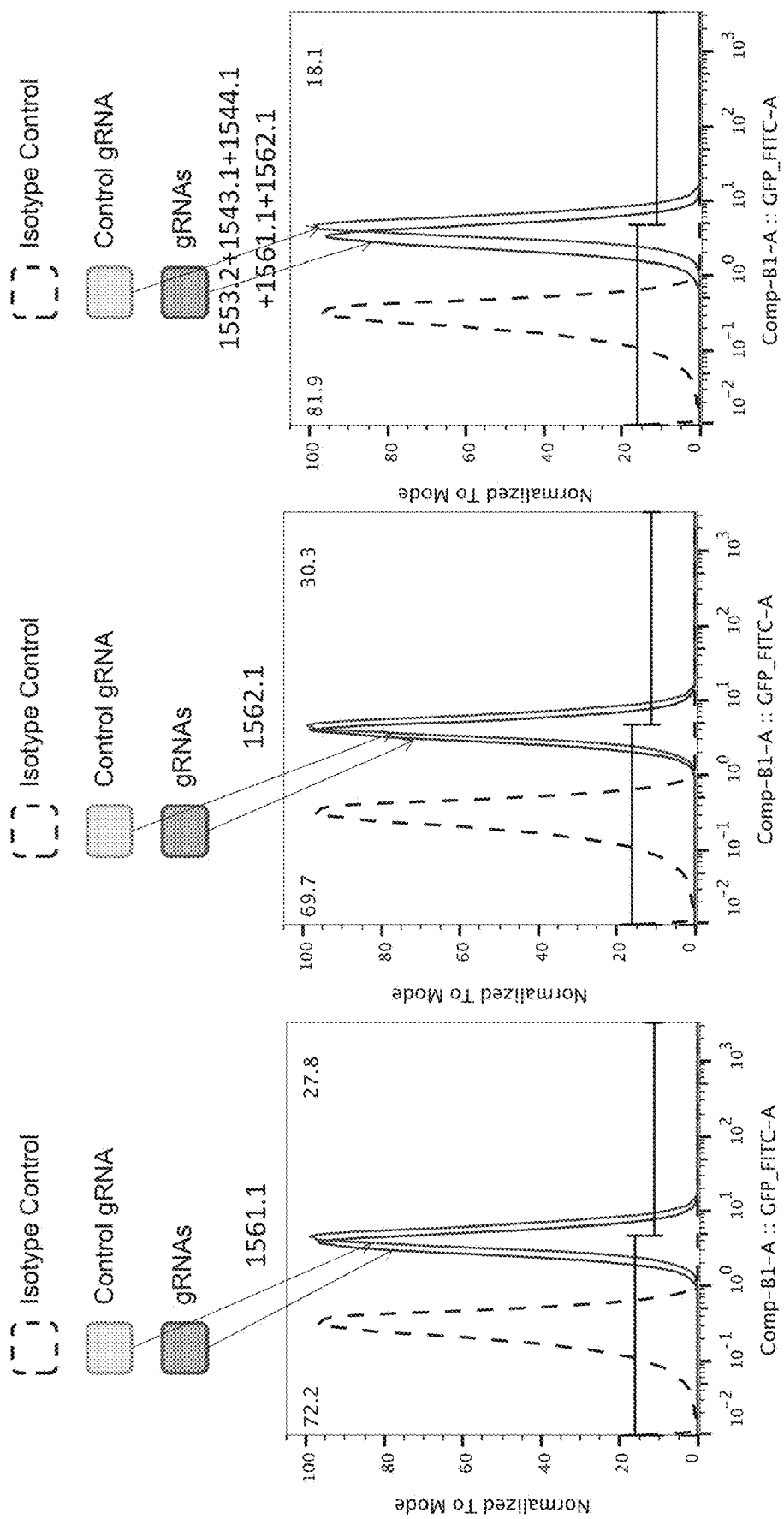
Figure 55A:
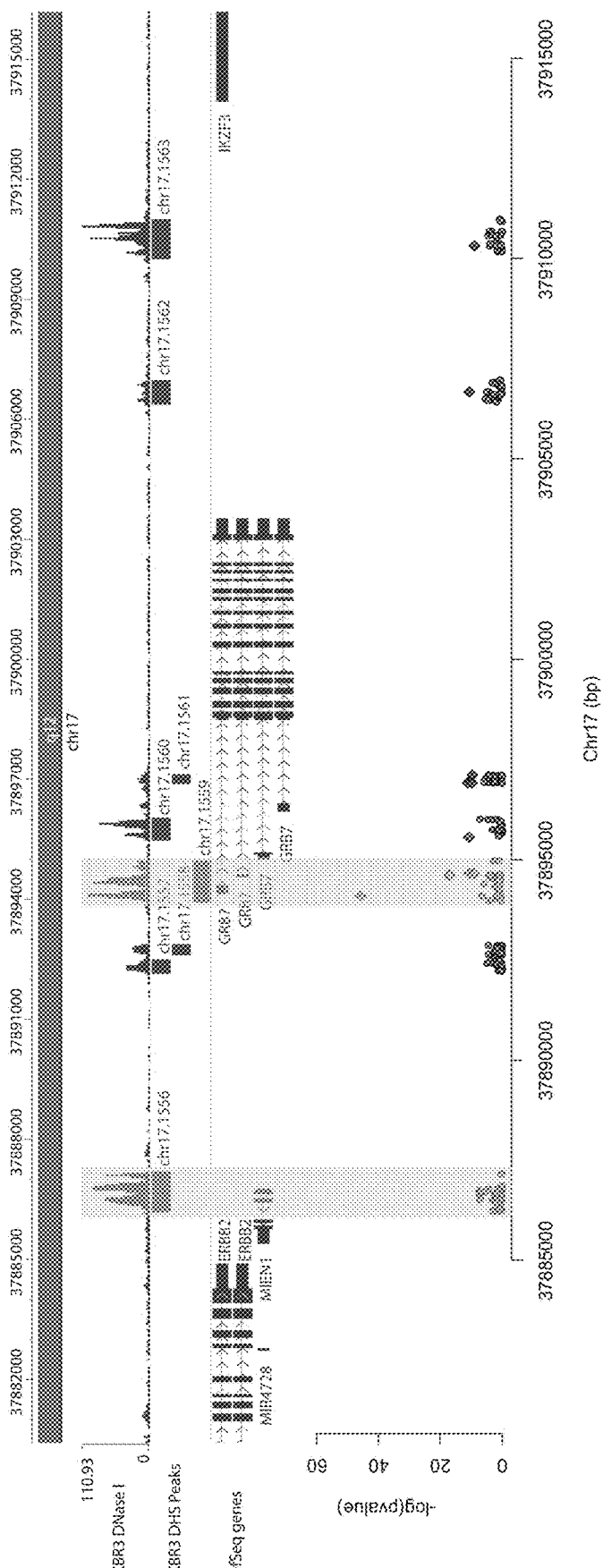
FIGS. 55A-55B show enrichment of combinations of 1556.1 and 1559.2 gRNAs identified in HER2 screen.
Figure 55B:
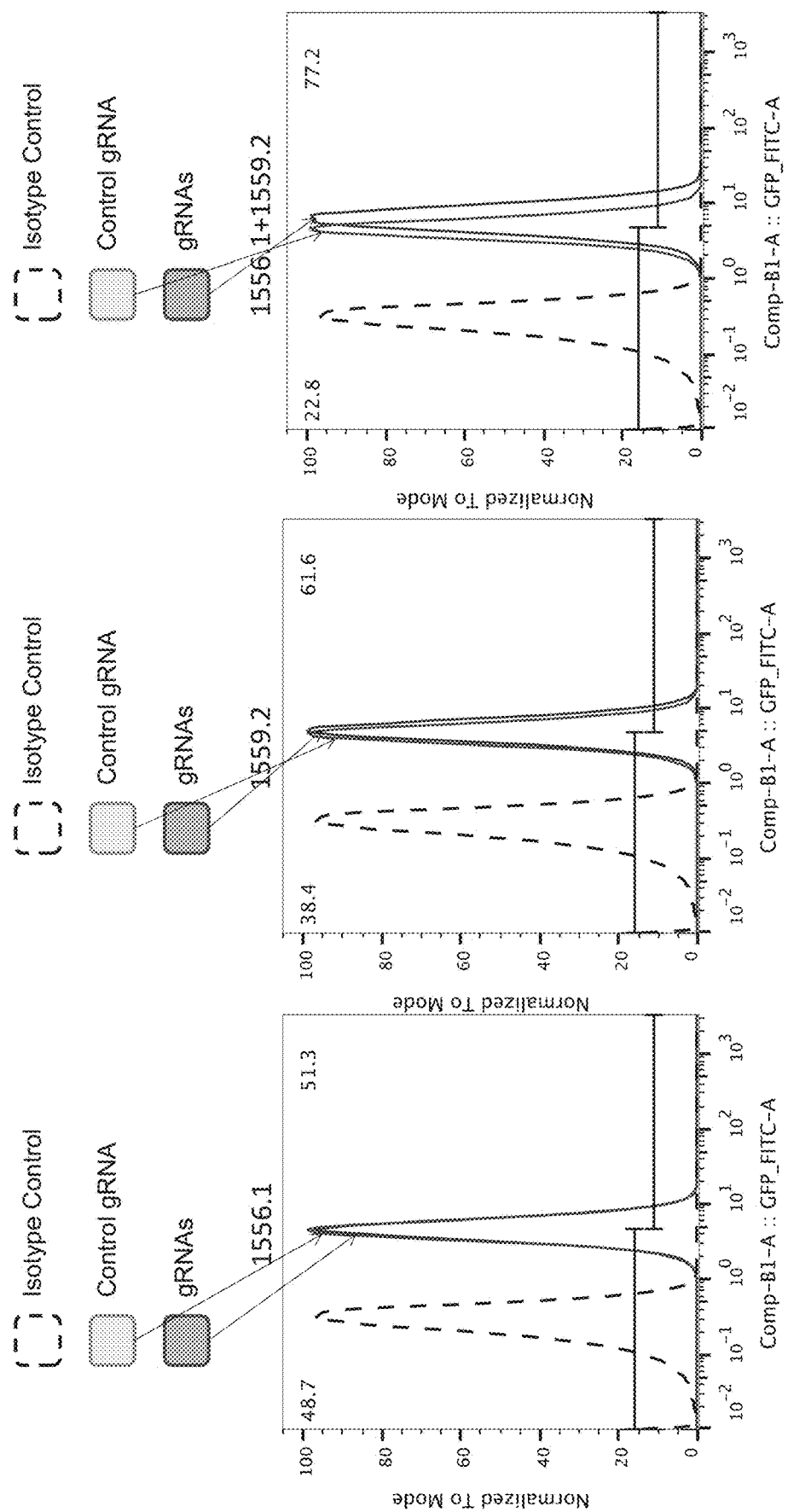
Figure 56A:
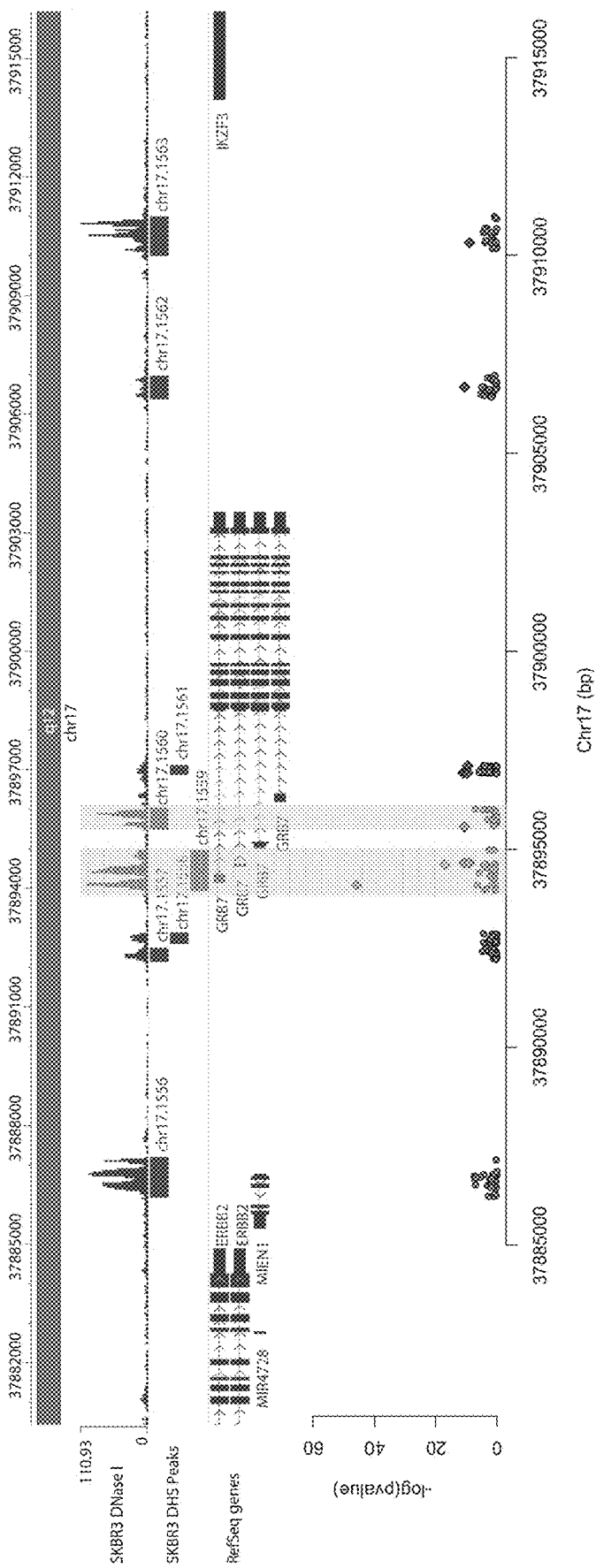
FIGS. 56A-56B show enrichment of combinations of 1559.2 and 1560.1 gRNAs identified in HER2 screen.
Figure 56B:
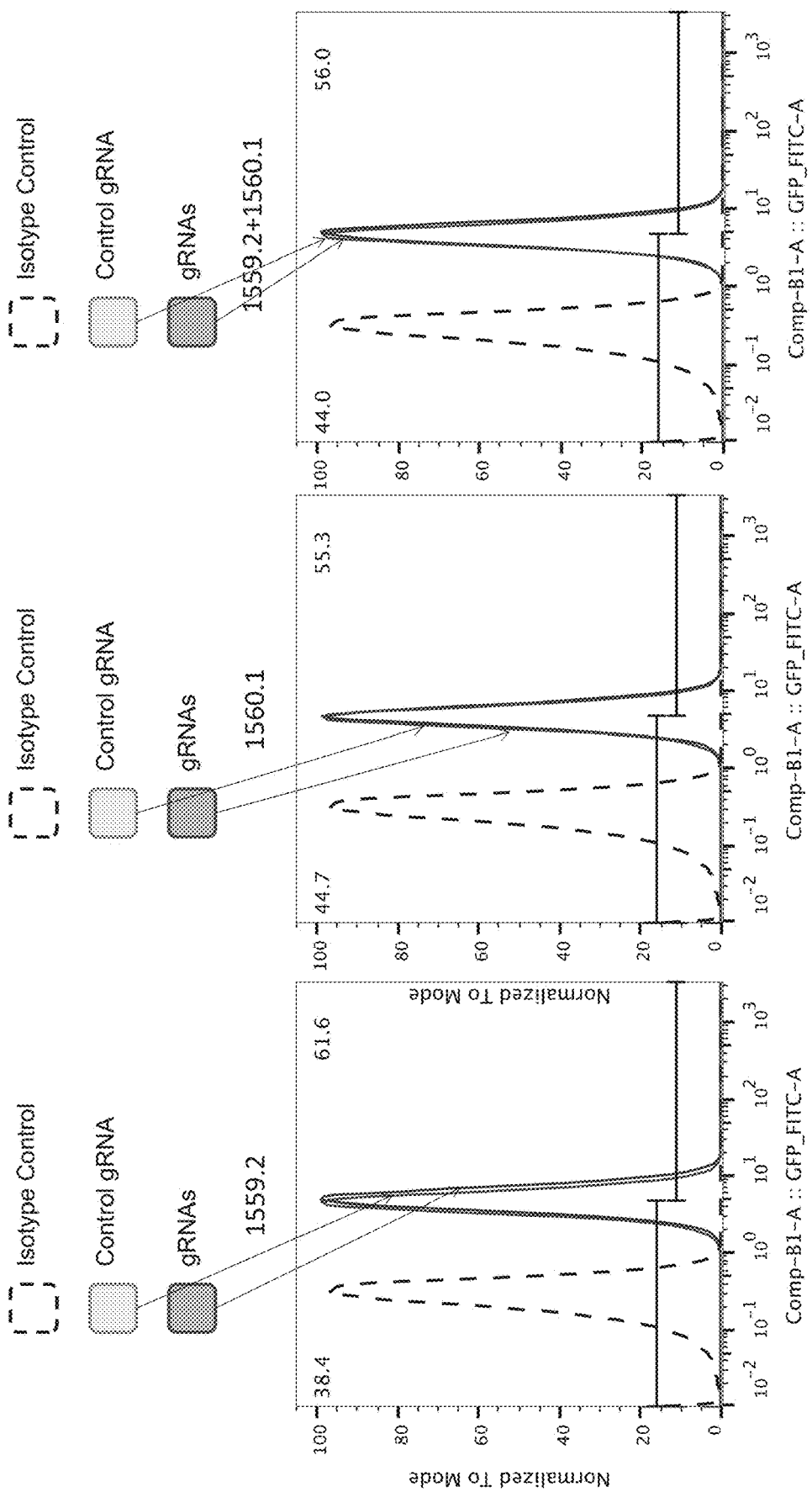
Figure 57A:
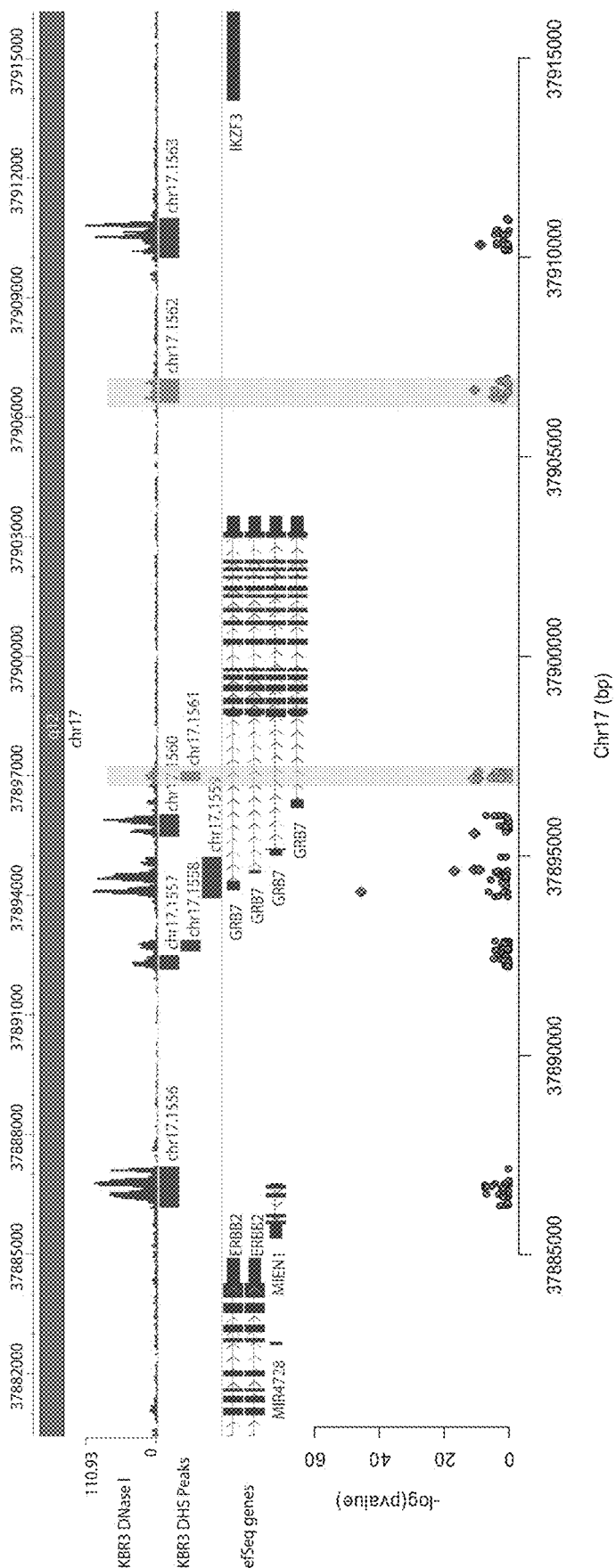
FIGS. 57A-57B show enrichment of combinations of 1561.1 and 1562.1 gRNAs identified in HER2 screen.
Figure 57B:
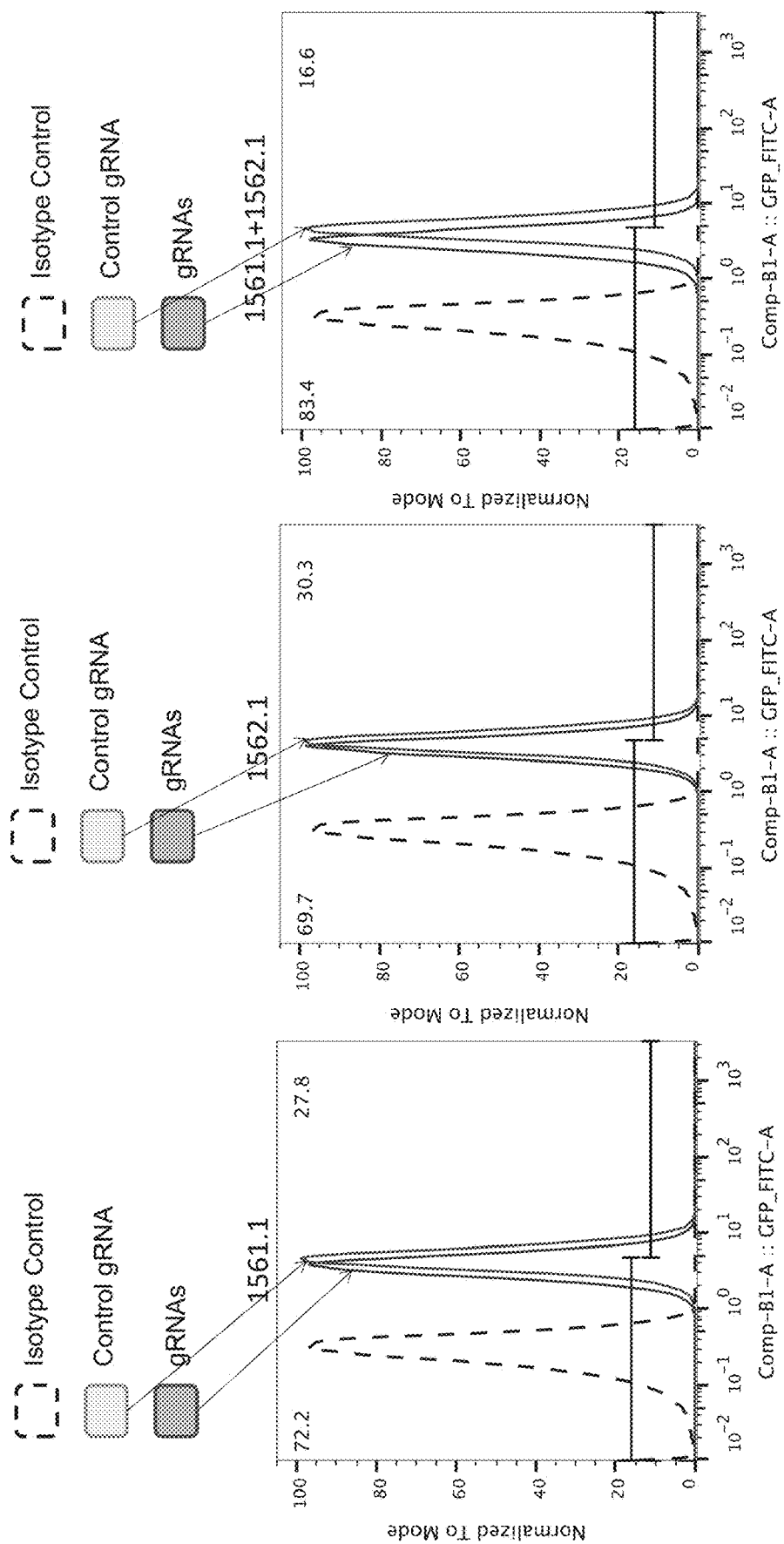
Figure 58A:
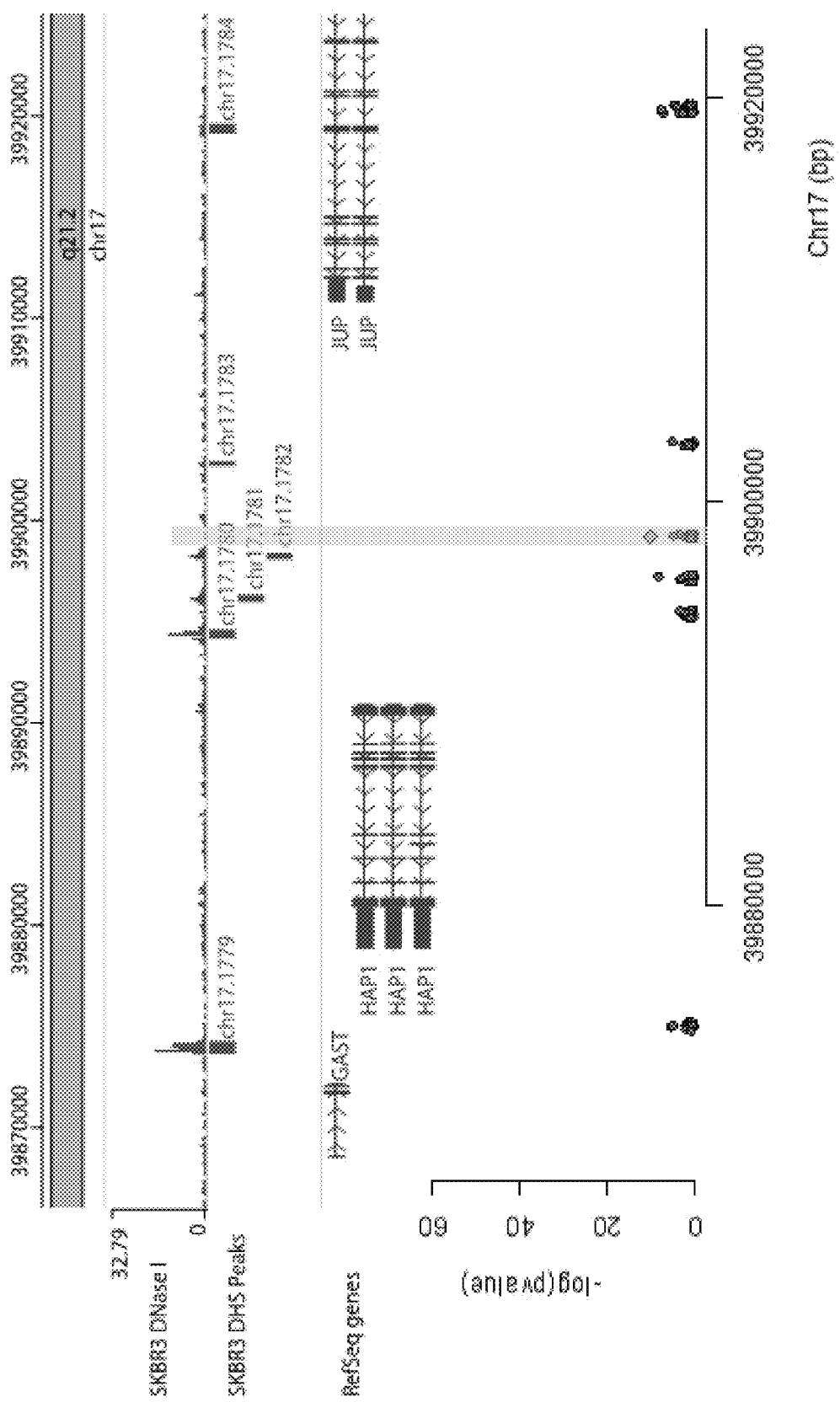
FIGS. 58A-58C show enrichment of combinations of 1782.1 and 1671.1 gRNAs identified in HER2 screen.
Figure 58B:
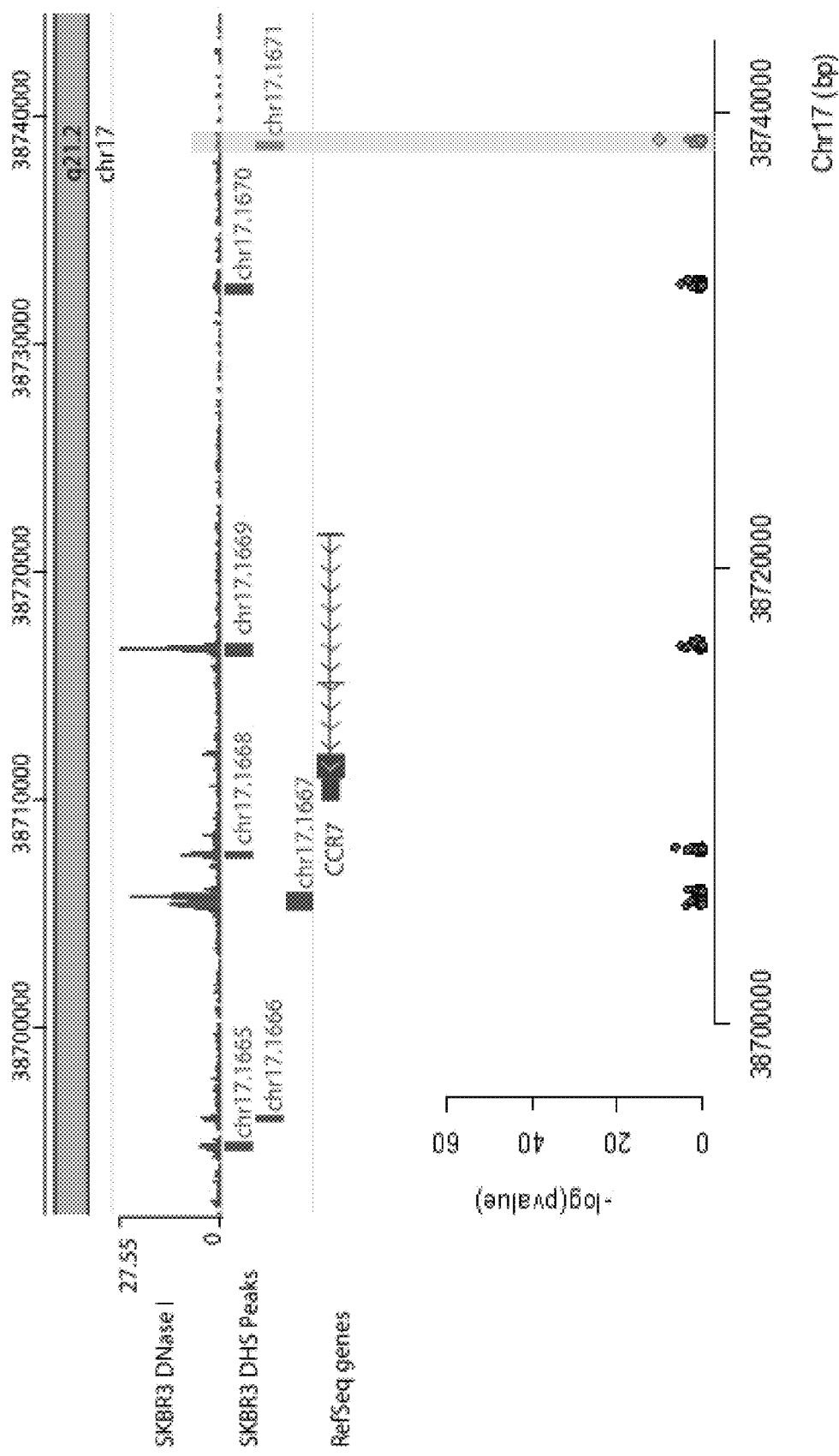
Figure 58C:
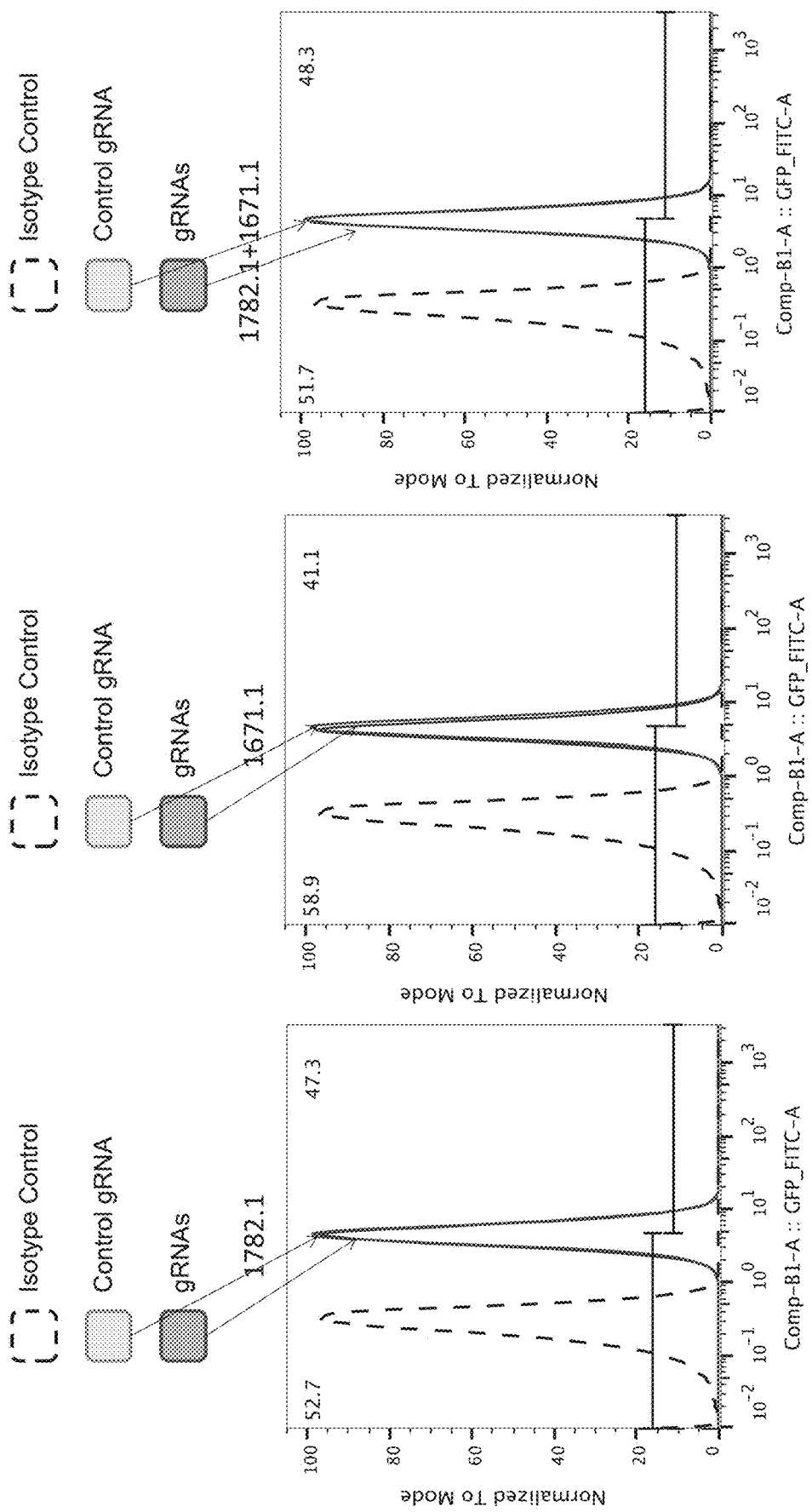

The enrichment of gRNA 1549 is shown in FIGS. 30A-30C. The enrichment of gRNA 1550 is shown in FIGS. 31A-31C. The enrichment of gRNA 1551 is shown in FIGS. 32A-32C. The enrichment of gRNA 1552 is shown in FIGS. 33A-33C. The enrichment of gRNA 1548 is shown in FIGS. 34A-34C. The enrichment of gRNA 1544 is shown in FIGS. 35A-35C. The enrichment of gRNA 1542 is shown in FIGS. 36A-36C. The enrichment of gRNA 1530 is shown in FIGS. 37A-37C. The enrichment of gRNA 1531 is shown in FIGS. 38A-38C. The enrichment of gRNA 1561 is shown in FIGS. 39A-39C. The enrichment of gRNA 1563 is shown in FIGS. 40A-40C.

Example 7

HER2 Screen Validations

Figure 10B:
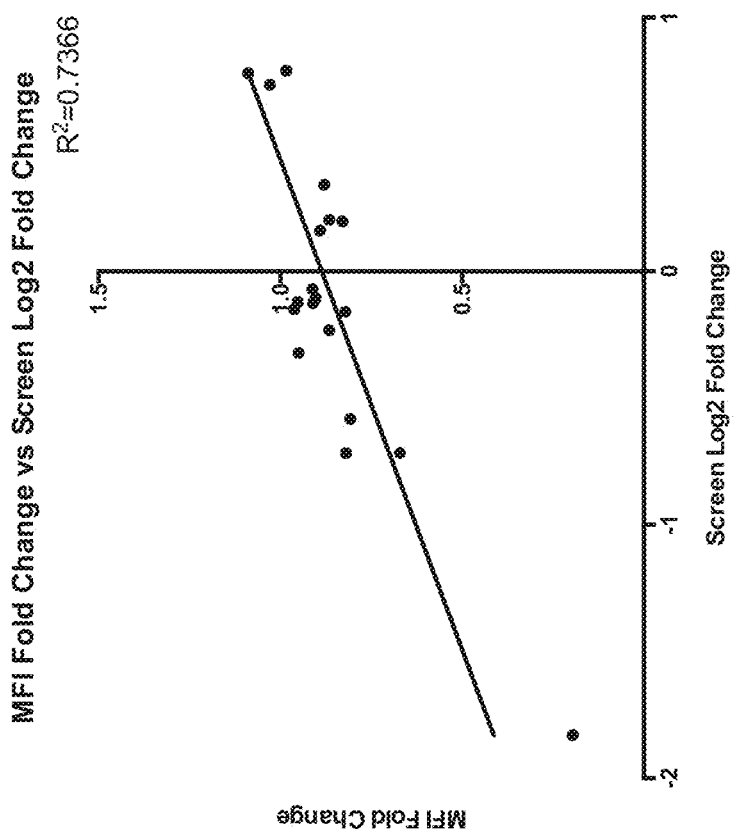
FIGS. 10A-10B show HER2 screen validation results.
Figure 10A:
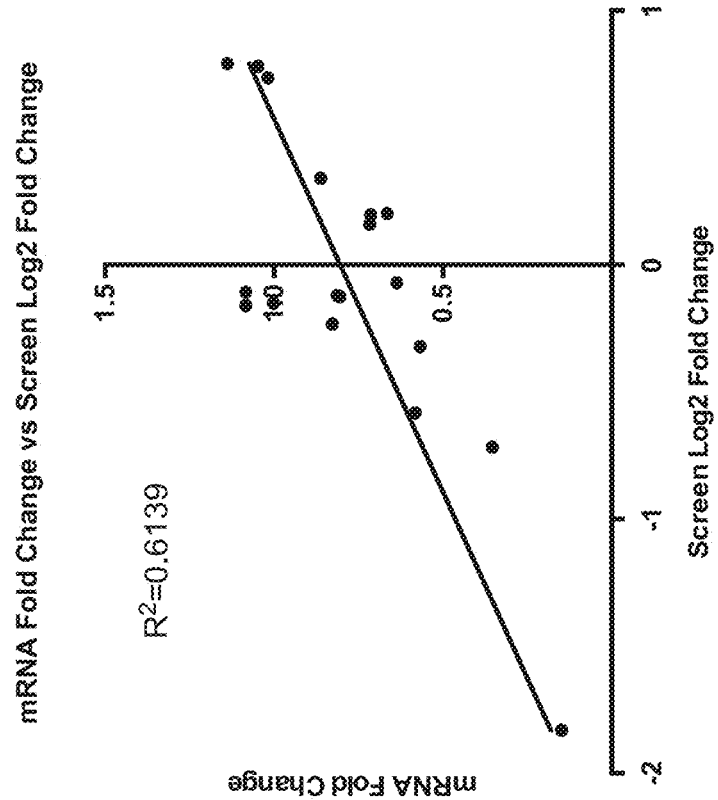
Figure 10D:
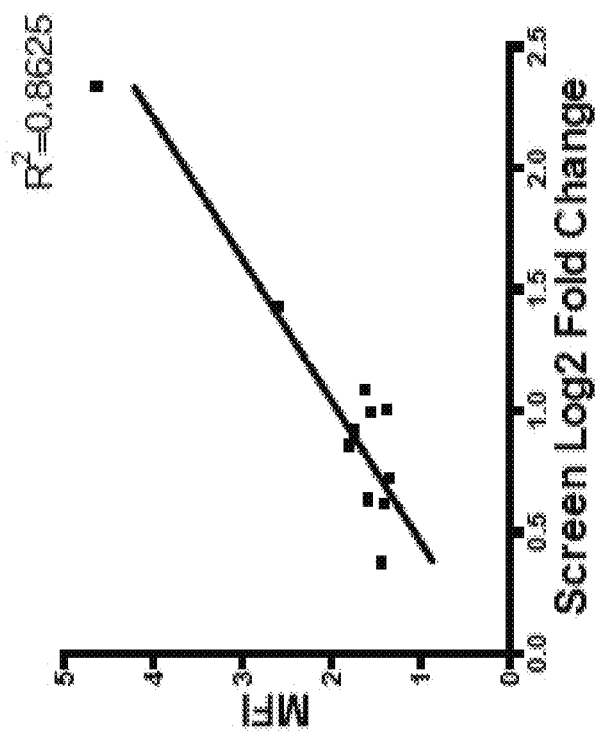
FIG. 10D shows HER2 mean fluorescent intensity measured via antibody staining us log 2 fold change in the screen for dCas9$^{p300}$ hits.
Figure 10C:
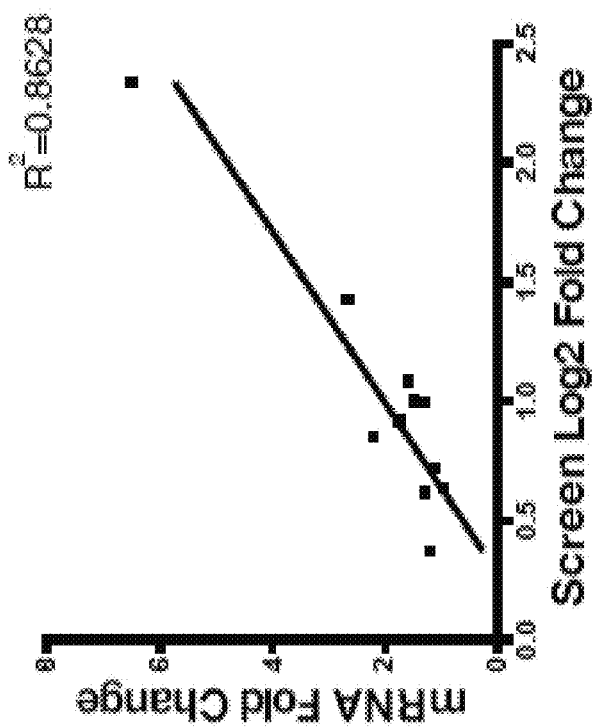
FIG. 10C shows HER2 mRNA fold change versus log 2 fold change in the screen for dCas9$^{p300}$ hits.

To validate enriched hits from both the dCas9$^{KRAB}$ and dCas9$^{p300}$ screens, several of the most enriched gRNAs were individually delivered via lentivirus to A431 or 293T cells expressing dCas9$^{KRAB}$ or dCas9$^{p300}$, respectfully, and HER2 mRNA and protein expression were measured. FIG. 10A shows dCas9$^{KRAB}$ hits: a HER2 mRNA fold change versus log 2 fold change in the screen. FIG. 10B shows dCas9$^{KRAB}$ hits: HER2 mean fluorescent intensity measured via antibody staining versus log 2 fold change in the screen. FIG. 10C shows dCas9$^{p300}$ hits: a HER2 mRNA fold change versus log 2 fold change in the screen. FIG. 10D shows dCas9$^{p300}$ hits: HER2 mean fluorescent intensity measured via antibody staining versus log 2 fold change in the screen.

Example 8

Genome-Wide Screen Experimental Design

All identified DNase I Hypersensitivity sites (DHSs) from K562 cells from the ENCODE consortium data are used as genomic coordinates for designing a gRNA library. Each DHS is limited to 10 gRNAs for a total of 112,025 gRNAs targeting 1,120,250 DHSs. The library will be synthesized by electrochemical means on arrays and assembled into a lentiviral expression plasmid and packaged into lentivirus in HEK293T cells. To achieve 1,000-fold coverage of the library at an MOI of 0.2, ~5.6 billion K562 cells expressing dCas9$^{KRAB}$ or dCas9$^{p300}$ will be transduced in a 6-liter spinner flask. After day 2, cells will be selected with antibiotic for at least 7 days to isolate transduced cells expressing gRNAs. To detect regulatory elements essential for survival in normal conditions, cells will be grown for at least 4 weeks. For identifying regulatory elements involved in drug resistance, cells will be grown until a non-transduced control is completely killed in the presence of the drug. Cells will be harvested for genomic DNA using Phenol-Chloroform extraction and the library will be recovered using PCR Enrichment or depletion of each gRNA will be determined through next generation sequencing of the library and compared to cells transduced with the same gRNA library not expressing dCas9$^{KRAB}$ or dCas9$^{p300}$ or to cells expressing dCas9$^{KRAB}$ or dCas9$^{p300}$ at earlier time points.

It is understood that the foregoing detailed description and accompanying examples are merely illustrative and are not to be taken as limitations upon the scope of the invention, which is defined solely by the appended claims and their equivalents.

Various changes and modifications to the disclosed embodiments will be apparent to those skilled in the art. Such changes and modifications, including without limitation those relating to the chemical structures, substituents, derivatives, intermediates, syntheses, compositions, formulations, or methods of use of the invention, may be made without departing from the spirit and scope thereof.

For reasons of completeness, various aspects of the invention are set out in the following numbered clauses:

Clause 1. A method of high-throughput screening for one or more putative gene regulatory elements in a genome that modulate a phenotype, the method comprising: a) contacting a plurality of modified target cells with a library of single guide RNAs (sgRNAs) that target a plurality of gene regulatory elements within the genome, thereby generating a plurality of test cells, b) selecting a population of test cells or an organism having a modulated phenotype; c) quantitating the frequency of the sgRNAs within the population of selected cells or the organism, wherein the sgRNAs that target gene regulatory elements that modulate the phenotype are overrepresented or underrepresented in the selected cells; and d) identifying and characterizing the sgRNAs within the population of selected test cells or the organism thereby identifying the gene regulatory elements that modulate the phenotype, wherein the modified target cell or organism comprises a fusion protein, the fusion protein comprising a first polypeptide domain comprising a nuclease-deficient Cas9 and a second polypeptide domain having an activity selected from the group consisting of transcription activation activity, transcription repression activity, nuclease activity, transcription release factor activity, histone modification activity, nucleic acid association activity, DNA methylase activity, and direct or indirect DNA demethylase activity.

Clause 2. The method of clause 1, wherein the modulated phenotype is a change in gene expression of at least one target gene or a change in cell or organismal phenotype and the gene regulatory element modulates the gene expression or the cell or organismal phenotype.

Clause 3. The method of clause 2, wherein the cell phenotype is at least one of cell response to stimuli, cell death, cell growth, drug resistance, or drug sensitivity.

Clause 4. The method of clause 3, wherein the stimuli comprises at least one of a physical signal, an environmental signal, a hormone, a growth factor, an inflammatory cytokine, an anti-inflammatory cytokine, a small molecule drug, or a transcription factor.

Clause 5. The method of clause 2, wherein the cell phenotype is T-cell phenotype, cell differentiation, oncogenesis, immunomodulation, cell response to stimuli, cell death, cell growth, cell motility, cell metabolism, cell immunogenicity, drug resistance, or drug sensitivity.

Clause 6. The method of any one of clauses 1-5, wherein the library of sgRNAs targets a plurality of target sites in the genome.

Clause 7. The method of clause 6, wherein the comprising promoters, DNAse I hypersensitivity sites, Transposase-Accessible Chromatin sites, DNA methylation, and/or epigenetic marks.

Clause 8. The method of clause 7, wherein the target sites are determined by DNase-sequencing (DNase-seq), Assay for Transposase-Accessible Chromatin with high throughput sequencing (ATAC-seq), ChIP-sequencing, self-transcribing active regulatory region sequencing, single molecule real time sequencing (SMRT), or Formaldehyde-Assisted Isolation of Regulatory Elements sequencing (FAIRE-seq), or micrococcal nuclease sequencing (MNase-seq).

Clause 9. The method of any one of clauses 1-8, wherein the library of sgRNAs targets one or more gene regulatory elements in a genomic region of a target gene.

Clause 10. The method of clause 9, wherein the target gene comprises an endogenous target gene.

Clause 11. The method of any one of clauses 1-10, wherein between 5 and 50 gRNAs are generated per gene regulatory element.

Clause 12. The method of any one of clauses 1-11, wherein the modified target cell comprises an intracellular or cell-surface marker.

Clause 13. The method of clause 12, wherein the intracellular or cell-surface marker is labelled by immunofluorescence staining.

Clause 14. The method of any one of clauses 1-13, wherein the modified target cell comprises at least one target gene comprising a reporter gene inserted within the coding region of the target gene.

Clause 15. The method of clause 14, wherein the reporter gene encodes a fluorescent protein.

Clause 16. The method of clause 13, wherein the cell-surface marker is labelled by a fluorescently-labelled specific binding protein for the cell-surface marker.

Clause 17. The method of any one of clauses 1-16, further comprising enriching cells expressing differential levels of the reporter gene by fluorescence-activated cell sorting or magnetic-activated cell sorting.

Clause 18. The method of any one of clauses 1-17, wherein the modulated phenotype is a change in gene expression of at least one target gene.

Clause 19. The method of any one of clauses 1-18, further comprising comparing the gene expression of at least one target gene in the test cells with the gene expression of the target gene in a plurality of control cells.

Clause 20. The method of any one of clauses 1-19, wherein the change in gene expression of the target gene is an increase or decrease in gene expression compared to a control plurality of cells.

Clause 21. The method of any one of clauses 1-20, wherein the change in gene expression is determined by a change in protein expression, RNA expression, or protein activity.

Clause 22. The method of any one of clauses 1-21, wherein identifying and characterizing the sgRNAs within the population of selected test cells comprises high-throughput sequencing, qRT-PCR, or RNA-seq.

Clause 23. The method of any one of clauses 1-22, wherein the library of sgRNAs targets one or more gene regulatory elements in the entire genome Clause 24. The method of clause 9, wherein the genomic region is between about 0 bp to about 150 Mb upstream and/or downstream of the transcription start site of at least one target gene.

Clause 25. The method of clause 24, wherein the genomic region is the β-globin locus.

Clause 26. The method of clause 25, wherein the modified target cell comprises an endogenous gene encoding hemoglobin subunit epsilon (HBE1) chain tagged with a reporter gene.

Clause 27. The method of clause 26, wherein the reporter gene is red fluorescent protein.

Clause 28. The method of clause 23, wherein the at least one target gene is HER2 gene.

Clause 29. The method of any one of clauses 1-28, wherein the fusion protein comprises a dCas9 domain and a transcriptional activator.

Clause 30. The method of clause 29, wherein the fusion protein comprises the amino acid sequence of SEQ ID NO: 2.

Clause 31. The method of any one of clauses 1-30, wherein the fusion protein comprises a dCas9 domain and a transcriptional repressor.

Clause 32. The method of clause 31, wherein the fusion protein comprises the amino acid sequence of SEQ ID NO:3.

Clause 33. The method of any one of clauses 1-32, wherein the fusion protein comprises a dCas9 domain and a site-specific nuclease.

Clause 34. The method of any one of clauses 1-33, wherein the library of sgRNAs comprises between at least about 1,000 to about 100,000,000 structurally distinct sgRNAs.

Clause 35. The method of any one of clauses 1-34, wherein the sgRNAs are selected to inhibit transcription of the target gene.

Clause 36. The method of any one of clauses 1-35, wherein the sgRNAs are selected to activate transcription of the target gene.

Clause 37. The method of any one of clauses 1-36, wherein the sgRNAs are selected to knockout at least one target gene.

Clause 38. The method of any one of clauses 1-37, wherein identifying and characterizing the sgRNAs within the population of selected test cells comprises deep sequencing of the genomic DNA of the test cell.

Clause 39. The method of any one of clauses 1-38, wherein selecting the test cells for a change in gene expression of the target gene further comprises culturing the cells and selecting the cells on the basis of cellular proliferation or survival.

Clause 40. The method of clause 39, wherein the culturing the cells is performed in the presence of a selection agent.

Clause 41. The method of clause 40, wherein the selection agent a chemotherapeutic, a DNA damaging agent, a cytotoxic agent, a growth factor, a transcription factor, a kinase, a drug, an exogenous gene under the control of a heterologous promoter, or a hormone.

Clause 42. The method of clause 40, wherein the plurality of control cells is cultured in the same conditions as the plurality of test cell but without the presence of the selection agent.

Clause 43. The method of any one of clauses 1-42, wherein the sgRNA is encoded by a polynucleotide sequence and packaged into a lentiviral vector, thereby generating a gRNA library lentiviral pool.

Clause 44. The method of clause 43, wherein the lentiviral vector comprises an expression cassette comprising a promoter operably linked to the polynucleotide sequence encoding the sgRNA.

Clause 45. The method of clause 44, wherein the promoter operably linked to the polynucleotide encoding the sgRNA is inducible.

Clause 46. The method of clause 43, wherein the target cells are transduced with the gRNA library lentiviral pool at a low multiplicity of infection such that >90% of the target cells express a single gRNA.

Clause 47. The method of clause 43, wherein the target cells are transduced with the gRNA library lentiviral pool at a high multiplicity of infection such that >90% of the target cells expression more than one gRNAs.

Clause 48. The method of any one of clauses 1-47, wherein the at least one target gene is a disease-relevant gene.

Clause 49. The method of any one of clauses 1-48, wherein the unmodified target cell is a eukaryotic cell.

Clause 50. The method of any one of clauses 1-49, wherein the unmodified target cell is a mammalian cell.

Clause 51. The method of any one of clauses 1-50, wherein the unmodified target cell is a A431, 293T, SKBR3, or K562 cell.

Clause 52. The method of any one of clauses 1-51, wherein the genome comprises a human genome.

Appendix-Sequences

*Streptococcus pyogenes* Cas 9 (with D10A, H849A) (SEQ ID NO: 1)
MDKKYSIGLAIGTNSVGWAVITDEYKVPSKKFKVLGNTDRHSIKKNLIGALLFDSGETAEATRLKRTARRRYTRRKNRICYLQEI
FSNEMAKVDDSFFHRLEESFLVEEDKKHERHPIFGNIVDEVAYHEKYPTIYHLRKKLVDSTDKADLRLIYLALAHMIKFRGHFLI
EGDLNPDNSDVDKLFIQLVQTYNQLFEENPINASGVDAKAILSARLSKSRRLENLIAQLPGEKKNGLFGNLIALSLGLTPNFKSN
FDLAEDAKLQLSKDTYDDDLDNLLAQIGDQYADLFLAAKNLSDAILLSDILRVNTEITKAPLSASMIKRYDEHHQDLTLLKALVR
QQLPEKYKEIFFDQSKNGYAGYIDGGASQEEFYKFIKPILEKMDGTEELLVKLNREDLLRKQRTFDNGSIPHQIHLGELHAILRR
QEDFYPFLKDNREKIEKILTFRIPYYVGPLARGNSRFAWMTRKSEETITPWNFEEVVDKGASAQSFIERMTNFDKNLPNEKVLPK
HSLLYEYFTVYNELTKVKYVTEGMRKPAFLSGEQKKAIVDLLFKTNRKVTVKQLKEDYFKKIECFDSVEISGVEDRFNASLGTYH
DLLKIIKDKDFLDNEENEDILEDIVLTLTLFEDREMIEERLKTYAHLFDDKVMKQLKRRRYTGWGRLSRKLINGIRDKQSGKTIL
DFLKSDGFANRNFMQLIHDDSLTFKEDIQKAQVSGQGDSLHEHIANLAGSPAIKKGILQTVKVVDELVKVMGRHKPENIVIEMAR
ENQTTQKGQKNSRERMKRIEEGIKELGSQILKEHPVENTQLQNEKLYLYYLQNGRDMYVDQELDINRLSDYDVDAIVPQSFLKDD
SIDNKVLTRSDKNRGKSDNVPSEEVVKKMKNYWRQLLNAKLITQRKFDNLTKAERGGLSELDKAGFIKRQLVETRQITKHVAQIL
DSRMNTKYDENDKLIREVKVITLKSKLVSDERKDFQFYKVREINNYHHAHDAYLNAVVGTALIKKYPKLESEFVYGDYKVYDVRK
MIAKSEQEIGKATAKYFFYSNIMNFEKTEITLANGEIRKRPLIETNGEIVWDKGRDFATVRKVLSMPQVNIVKKTEVQTGGF
SKESILPKRNSDKLIARKKDWDPKKYGGFDSPTVAYSVLVVAKVEKGKSKKLKSVKELLGITIMERSSFEKNPIDFLEAKGYKEV
KKDLIIKLPKYSLFELENGRKRMLASAGELQKGNELALPSKYVNFLYLASHYEKLKGSPEDNEQKQLFVEQHKHYLDEIIEQISE
FSKRVILADANLDKVLSAYNKHRDKPIREQAENIIHLFTLTNLGAPAAFKYFDTTIDRKRYTSTKEVLDATLIHQSITGLYETRI
DLSQLGGD dCas9^p300Core: (Addgene Plasmid 61357) amino acid sequence; 3X "Flag" Epitope, Nuclear
Localization Sequence, *Streptococcus pyogenes* Cas9 (D10A, H840A), p300 Core Effector,
"HA" Epitope (SEQ ID NO: 2)
MDYKDHDGDYKDHDIDYKDDDDKMAPKKKRKVGRGMDKKYSIGLAIGTNSVGWAVITDEYKVPSKKFKVLGNTDRHSIKKNLIGA
LLFDSGETAEATRLKRTARRRYTRRKNRICYLEQIEFSNEMAKVDDSFFHRLEESFLVEEDKKHERHPIFGNIVDEAVAYHEKYP
TIYHLRKKLVDSTDKADLRLIYLALAHMIKFRGHFLIEGDLNPDNSDVDKLFIQLVQTYNQLFEENPINASGVDAKAILSARLSK
SRRLENLIAQLPGEKKNGLFGNLIALSLGLTPNFKSNFDLAEDAKLQLSKDTYDDDLDNLLAQIGDQYADLFLAAKNLSDAILLS
DILRVNTEITKAPLSASMIKRYDEHHQDLTLLKALVRQQLPEKYKEIFFDQSKNGYAGYIDGGASQEEFYKFIKPILEKMDGTEE
LLVKLNREDLLRKQRTFDNGSIPHQIHLGELHAILRRQEDFYPFLKDNREKIEKILTFRIPYYVGPLARGNSRFAWMTRKSEETI
YVTEGMRKPAFLSGEQKKAIVDLLFKTNRKVTVKQLKEDYFKKIECFDSVEISGVEDRFNASLGTYHDLLKIIKDKDFLDNEENE
DILEDIVLTLTLFEDREMIEERLKTYAHLFDDKVMKQLKRRRYTGWGRLSRKLINGIRDKQSGKTILDFLKSDGFANRNFMQLIH
DDSLTFKEDIQKAQVSGQGDSLHEHIANLAGSPAIKKGILQTVKVVDELVKVMGRHKPENIVIEMARENQTTQKGQKNSRERMKR
IEEGIKELGSQILKEHPVENTQLQNEKLYLYYLQNGRDMYVDQELDINRLSDYDVDAIVPQSFLKKDDSIDNKVLTRSDKNRGKS
DNVPSEEVVKKMKNYWRQLLNAKLITQRKFDNLTKAERGGLSELDKAGFIKRQLVETRQITKHVAQILDSRMNTKYDENDKLIRE
VKVITLKSKLVSDFRKDFQFYKVREINNYHHAHDAYLNAVVGTALIKKYPKLESEFVYGDYKVYDVRKMIAKSEQEIGKATAKYF
FYSNIMNFFKTEITLANGEIRKRPLIETNGETGEIVWDKGRDFATVRKVLSMPQVNIVKKTEVQTGGFSKESILPKRNSDKLIAR
KKDWDPKKYGGFDSPTVAYSVLVVAKVEKGKSKKLKSVKELLGITIMERSSFEKNPIDFLEAKGYKEVKKDLIIKLPKYSLFELE
NGRKRMLASAGELQKGNELALPSKYVNFLYLASHYELKLGSPEDNEQKQLFVEQHKHYLDEIIEQISEFSKRVILADANLDKVLS
AYNKHRDKPIREQAENIIHLFTLTNLGAPAAFKYFDTTIDRKRYTSTKEVLDATLIHQSITGLYETRIDLSQLGGDPIAGSKASP
KKKRKVGRAIFKPEELRQALMPTLEALYRQDPESLPFRQPVDPQLLGIPDYFDIVKSPMDLSTIKRKLDTGQYQEPWQYVDDIWL
MFNNAWLYNRKTSRVYKYCSKLSEVFEQEIDPVMQSLGYCCGRKLEFSPQTLCCYGKQLCTIPRDATYYSYQNRYHFCEKCFNEI
QGESVSLGDDPSQPQTTINKEQFSKRKNDTLDPELFVECTECGRKMHQICVLHHEIIWPAGFVCDGCLKKSARTRKENKFSAKRL
PSTRLGTFLENRVNDFLRRQNHPESGEVTVRVVHASDKTVEVKPGMKARFVDSGEMAESFPYRTKALFAFEEIDGVDLCFFGMHV
QEYGSDCPPPNQRRVYISYLDSVHFFRPKCLRTAVYHEILIGYLEYVKKLGYTTGHIWACPPSEGDDYIFHCHPPDQKIPKPKRL
QEWYKKMLDKAVSERIVHDYKDIFKQATEDRLTSAKELPYFEGDFWPNVLEESIKELEQEEEERKREENTSNESTDVTKGDSKNA
KKKNNKKTSKNKSSLSRGNKKKPGMPNVSNDLSQKLYATMEKHKEVFFVIRLIAGPAANSLPPIVDPDPLIPCDLMGRDAFLTLA
RDKHLEFSSLRRAQWSTMCMLVELHTQSQDYPYDVPDYAS dCas9KRAB (SEQ ID NO: 3)
MDYKDHDGDYKDHDIDYKDDDDKMAPKKKRKVGRGMDKKYSIGLAIGTNSVGWAVITDEYKVPSKKFKVLGNTDRHSIKKNLIGA
LLFDSGETAEATRLKRTARRRYTRRKNRICYLQEIFSNEMAKVDDSFFHRLEESFLVEEDKKHERHPIFGNIVDEVAYHEKYPTI
YHLRKKLVDSTDKADLRLIYLALAHMIKFRGHFLIEGDLNPDNSDVDKLFIQLVQTYNQLFEENPINASGVDAKAILSARLSKSR
RLENLIAQLPGEKKNGLFGNLIALSLGLTPNFKSNFDLAEDAKLQLSKDTYDDDLDNLLAQIGDQYADLFLAAKNLSDAILLSDI
LRVNTEITKAPLSASMIKRYDEHHQDLTLLKALVRQQLPEKYKEIFFDQSKNGYAGYIDGGASQEEFYKFIKPILEKMDGTEELL
VKLNREDLLRKQRTFDNGSIPHQIHLGELHAILRRQEDFYPFLKDNREKIEKILTFRIPYYVGPLARGNSRFAWMTRKSEETITP
WNFEEVVDKGASAQSFIERMTNFDKNLPNEKVLPKHSLLYEYFTVYNELTKVKYVTEGMRKPAFLSGEQKKAIVDLLFKTNRKVT
VKQLKEDYFKKIECFDSVEISGVEDRFNASLGTYHDLLKIIKDKDFLDNEENEDILEDIVLTLTLFEDREMIEERLKTYAHLFDD
KVMKQLKRRRYTGWGRLSRKLINGIRDKQSGKTILDFLKSDGFANRNFMQLIHDDSLTFKEDIQKAQVSGQGDSLHEHIANLAGS
PAIKKGILQTVKVVDELVKVMGRHKPENIVIEMARENQTTQKGQKNSRERMKRIEEGIKELGSQILKEHPVENTQLQNEKLYLYY
LQNGRDMYVDQELDINRLSDYDVDAIVPQSFLKDDSIDNKVLTRSDKNRGKSDNVPSEEVVKKMKNYWRQLLNAKLITQRKFDNL
TKAERGGLSELDKAGFIKRQLVETRQITKHVAQILDSRMNTKYDENDKLIREVKVITLKSKLVSDFRKDFQFYKVREINNYHHAH
DAYLNAVVGTALIKKYPKLESEFVYGDYKVYDVRKMIAKSEQEIGKATAKYFFYSNIMNFFKTEITLANGEIRKRPLIETNGETG
EIVWDKGRDFATVRKVLSMPQVNIVKKTEVQTGGFSKESILPKRNSDKLIARKKDWDPKKYGGFDSPTVAYSVLVVAKVEKGKSK
KLKSVKELLGITIMERSSFEKNPIDFLEAKGYKEVKKDLIIKLPKYSLFELENGRKRMLASAGELQKGNELALPSKYVNFLYLAS
HYEKLKGSPEDNEQKQLFVEQHKHYLDEIIEQISEFSKRVILADANLDKVLSAYNKHRDKPIREQAENIIHLFTLTNLGAPAAFK
YFDTTIDRKRYTSTKEVLDATLIHQSITGLYETRIDLSQLGGDSRADPKKKRKVASDAKSLTAWSRTLVTFKDVFVDFTREEWKL
LDTAQQILYRNVMLENYKNLVSLGYQLTKPDVILRLEKGEEPWLVEREIHQETHPDSETAFEIKSSVPKKKRKVAS

| Appendix-Sequences |
|---|
| Nm-dCas9<sup>p300Core</sup>: (Addgene Plasmid 61365) amino acid sequence; *Neisseria meningitidis* Cas9 (D16A, D587A, H588A, N611A), Nuclear Localization Sequence, p300 Core Effector, "HA" Epitope (SEQ ID NO: 5)<br>MAAFKPNPINYILGLAIGIASVGWAMVEIDEDINPICLIDLGVRVFERAEVPKTGDSLAMARRLARSVRRLTRRRAHRLLRARRL<br>RARRLLKREKREVGLQAADFDENGLIKSLPNTPWQLRAAALDRKLTPLEWSAVLLHLIKHRGYLSQRKNEGETADKELGALLKGV<br>ADNAHALQTGDFRTPAELALNKFEKESGHIRNQRGDYSHTFSRKDLQAELILLFEKQKEFGNPHVSGGLKEGIETLLMTQRPALS<br>GDAVQKMLGHCTFEPAEPKAAKNTYTAERFIWLTKLNNLRILEQGSERPLTDTERATLMDEPYRKSKLTYAQARKLLGLEDTAFF<br>KGLRYGKDNAEASTLMEMKAYHAISRALEKEGLKDKKSPLNLSPELQDEIGTAFSLFKTDEDITGRLKDRIQPEILEALLKHISF<br>DKFVQISLKALRRIVPLMEQGKRYDEACAEIYGDHYGKKNTEEKIYLPPIPADEIRNPVVLRALSQARKVINGVVRRYGSPARIH<br>IETAREVGKSFKDRKEIEKRQEENRKDREKAAAKFREYFPNFVGEPKSKDILKLRLYEQQHGKCLYSGKEINLGRLNEKGYVEIA<br>ALPFSRTWDDSFNNKVLVLGSEAQNKGNQTPYEYFNGKDNSREWQEFKARVETSRFPRSKKQRILLQKFDEDGFKERNLNDTRYV<br>NRFLCQFVADRMRLTGKGKKRVFASNGQITNLLRGFWGLRKRAENDRHHALDAVVVACSTVAMQQKITRFVRYKEMNAFDGKTID<br>KETGEVLHQKTHFPQPWEFFAQEVMIRVFGKPDGKPEFEEADTPEKLRTLLAEKLSSRPEAVHEYVTPLFVSRAPNRKMSGQGHM<br>ETVKSAKRLDEGVSVLRVPLTQLKLKDLEKMVNREREPKLYEALKARLEAHKDDPAKAFAEPFYKYDKAGNRTQQVKAVRVEQVQ<br>KTGVWVRNHNGIADNATMVRVDVFEKGDKYYLVPIYSWQVAKGILPDRAVVQGKDEEDWQLIDDSFNFKFSLHPNDLVEVITKKA<br>RMFGYFASCHRGTGNINIRIHDLDHKIGKNGILEGIGVKTALSFQKYQIDELGKEIRPCRLKKRPPVRSRADPKKKRKVEASGRA<br>IFKPEELRQALMPTLEALYRQDPESLPFRQPVDPQLLGIPDYFDIVKSPMDLSTIKRKLDTGQYQEPWQYVDDIWLMFNNAWLYN<br>RKTSRVYKYCSKLSEVFEQEIDPVMQSLGYCCGRKLEFSPQTLCCYGKQLCTIPRDATYYSYQNRYHFCEKCFNEIQGESVSLGD<br>DPSQPQTTINKEQFSKRKNDTLDPELFCECTECGRKMHQICVLHHEIIWPAGFVCDGCLKKSARTRKENKFSAKRLPSTRLGTFL<br>ENRVNDFLRRQNHPESGEVTVRVVHASDKTVEVKPGMKARFVDSGEMAESFPYARTKALFAFEEIDGVDLCFFGMHVQEYGSDCP<br>PPNQRRVYISYLDSVHFFRPKCLRTAVYHEILIGYLEYVKKLGYTTGHIWACPPSEGDDYIFHCHPPDQKIPKPKRLQEWYKKML<br>DKAVSERIVHDYKDIFKQATEDRLTSAKELPYFEGDFWPNVLEESIKELEQEEEERKREENTSNESTDVTKGDSKNAKKKNNKKT<br>SKNKSSLSRGNKKKPGMPNVSNDLSQKLYATMEKHKEVFFVIRLIAGPAANSLPPIVDPDPLIPCDLMDGRDAFLTLARDKHLEF<br>SSLRRAQWSTMCMLVELHTQSQDYPYDVPDYAS |

What is claimed:

1. A method of high-throughput screening for one or more putative gene regulatory elements in a genome that modulate a phenotype, the method comprising:
   a) contacting a plurality of modified target cells with a library of single guide RNAs (sgRNAs) that target a plurality of gene regulatory elements within the genome, thereby generating a plurality of test cells,
   b) selecting a population of test cells or an organism having a modulated phenotype;
   c) quantitating the frequency of the sgRNAs within the population of selected cells or the organism, wherein the sgRNAs that target gene regulatory elements that modulate the phenotype are overrepresented or underrepresented in the selected cells; and
   d) identifying and characterizing the sgRNAs within the population of selected test cells or the organism thereby identifying the gene regulatory elements that modulate the phenotype,
   wherein the modified target cell or organism comprises a fusion protein, the fusion protein comprising a first polypeptide domain comprising a nuclease-deficient Cas9 and a second polypeptide domain having an activity selected from the group consisting of transcription activation activity, transcription repression activity, nuclease activity, transcription release factor activity, histone modification activity, nucleic acid association activity, DNA methylase activity, and direct or indirect DNA demethylase activity.

2. The method of claim 1, wherein the modulated phenotype is a change in gene expression of at least one target gene or a change in cell or organismal phenotype and the gene regulatory element modulates the gene expression or the cell or organismal phenotype.

3. The method of claim 2, wherein the cell phenotype is T-cell phenotype, cell differentiation, oncogenesis, immunomodulation, cell response to stimuli, cell death, cell growth, cell motility, cell metabolism, cell immunogenicity, drug resistance, or drug sensitivity.

4. The method of claim 1, wherein the library of sgRNAs targets a plurality of target sites in the genome, one or more gene regulatory elements in a genomic region of a target gene, or one or more gene regulatory elements in the entire genome.

5. The method of claim 1, wherein between 5 and 50 gRNAs are generated per gene regulatory element.

6. The method of claim 1, wherein the modified target cell comprises an intracellular or cell-surface marker or the modified target cell comprises at least one target gene comprising a reporter gene inserted within the coding region of the target gene.

7. The method of claim 1, further comprising enriching cells expressing differential levels of the reporter gene by fluorescence-activated cell sorting or magnetic-activated cell sorting.

8. The method of claim 1, further comprising comparing the gene expression of at least one target gene in the test cells with the gene expression of the target gene in a plurality of control cells.

9. The method of claim 1, wherein the modulated phenotype is a change in gene expression of at least one target gene.

10. The method of claim 1, wherein the change in gene expression is determined by a change in protein expression, RNA expression, or protein activity.

11. The method of claim 1, wherein identifying and characterizing the sgRNAs within the population of selected test cells comprises high-throughput sequencing, qRT-PCR, or RNA-seq.

12. The method of claim 4, wherein the genomic region is between about 0 bp to about 150 Mb upstream and/or downstream of the transcription start site of at least one target gene.

13. The method of claim 1, wherein the fusion protein comprises a dCas9 domain and a transcriptional activator, a dCas9 domain and a transcriptional repressor, or a dCas9 domain and a site-specific nuclease.

14. The method of claim 13, wherein the fusion protein comprises the amino acid sequence of SEQ ID NO: 2 or SEQ ID NO:3.

15. The method of claim 1, wherein the sgRNAs are selected to inhibit transcription of the target gene, activate transcription of the target gene, or knockout at least one target gene.

16. The method of claim 1, wherein identifying and characterizing the sgRNAs within the population of selected test cells comprises deep sequencing of the genomic DNA of the test cell, and/or wherein selecting the test cells for a change in gene expression of the target gene further comprises culturing the cells and selecting the cells on the basis of cellular proliferation or survival.

17. The method of claim 1, wherein the sgRNA is encoded by a polynucleotide sequence and packaged into a lentiviral vector, thereby generating a gRNA library lentiviral pool, and optionally, wherein the target cells are transduced with the gRNA library lentiviral pool at a low multiplicity of infection such that >90% of the target cells express a single gRNA or the target cells are transduced with the gRNA library lentiviral pool at a high multiplicity of infection such that >90% of the target cells expression more than one gRNAs.

* * * * *

SEQUENCE LISTING

<160> NUMBER OF SEQ ID NOS: 51

<210> SEQ ID NO 1
<211> LENGTH: 1368
<212> TYPE: PRT
<213> ORGANISM: Artificial sequence
<220> FEATURE:
<223> OTHER INFORMATION: Synthetic

<400> SEQUENCE: 1

```
Met Asp Lys Lys Tyr Ser Ile Gly Leu Ala Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190
```

```
Asn Gln Leu Phe Glu Glu Asn Pro Ile Asn Ala Ser Gly Val Asp Ala
            195                 200                 205

Lys Ala Ile Leu Ser Ala Arg Leu Ser Lys Ser Arg Arg Leu Glu Asn
210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
                260                 265                 270

Asp Asp Leu Asp Asn Leu Leu Ala Gln Ile Gly Asp Gln Tyr Ala Asp
            275                 280                 285

Leu Phe Leu Ala Ala Lys Asn Leu Ser Asp Ala Ile Leu Leu Ser Asp
290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
                340                 345                 350

Asp Gln Ser Lys Asn Gly Tyr Ala Gly Tyr Ile Asp Gly Gly Ala Ser
            355                 360                 365

Gln Glu Glu Phe Tyr Lys Phe Ile Lys Pro Ile Leu Glu Lys Met Asp
370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
            420                 425                 430

Leu Lys Asp Asn Arg Glu Lys Ile Glu Lys Ile Leu Thr Phe Arg Ile
            435                 440                 445

Pro Tyr Tyr Val Gly Pro Leu Ala Arg Gly Asn Ser Arg Phe Ala Trp
            450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
                500                 505                 510

Leu Leu Tyr Glu Tyr Phe Thr Val Tyr Asn Glu Leu Thr Lys Val Lys
            515                 520                 525

Tyr Val Thr Glu Gly Met Arg Lys Pro Ala Phe Leu Ser Gly Glu Gln
            530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
            580                 585                 590

Thr Tyr His Asp Leu Leu Lys Ile Ile Lys Asp Lys Asp Phe Leu Asp
            595                 600                 605
```

```
Asn Glu Glu Asn Glu Asp Ile Leu Glu Asp Ile Val Leu Thr Leu Thr
    610             615                 620

Leu Phe Glu Asp Arg Glu Met Ile Glu Arg Leu Lys Thr Tyr Ala
625             630                 635                 640

His Leu Phe Asp Asp Lys Val Met Lys Gln Leu Lys Arg Arg Tyr
                645                 650                 655

Thr Gly Trp Gly Arg Leu Ser Arg Lys Leu Ile Asn Gly Ile Arg Asp
            660                 665                 670

Lys Gln Ser Gly Lys Thr Ile Leu Asp Phe Leu Lys Ser Asp Gly Phe
        675                 680                 685

Ala Asn Arg Asn Phe Met Gln Leu Ile His Asp Ser Leu Thr Phe
690                 695                 700

Lys Glu Asp Ile Gln Lys Ala Gln Val Ser Gly Gln Gly Asp Ser Leu
705             710                 715                 720

His Glu His Ile Ala Asn Leu Ala Gly Ser Pro Ala Ile Lys Lys Gly
                725                 730                 735

Ile Leu Gln Thr Val Lys Val Val Asp Glu Leu Val Lys Val Met Gly
            740                 745                 750

Arg His Lys Pro Glu Asn Ile Val Ile Glu Met Ala Arg Glu Asn Gln
        755                 760                 765

Thr Thr Gln Lys Gly Gln Lys Asn Ser Arg Glu Arg Met Lys Arg Ile
770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
                805                 810                 815

Gln Asn Gly Arg Asp Met Tyr Val Asp Gln Glu Leu Asp Ile Asn Arg
            820                 825                 830

Leu Ser Asp Tyr Asp Val Asp Ala Ile Val Pro Gln Ser Phe Leu Lys
        835                 840                 845

Asp Asp Ser Ile Asp Asn Lys Val Leu Thr Arg Ser Asp Lys Asn Arg
850                 855                 860

Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
                885                 890                 895

Phe Asp Asn Leu Thr Lys Ala Glu Arg Gly Gly Leu Ser Glu Leu Asp
            900                 905                 910

Lys Ala Gly Phe Ile Lys Arg Gln Leu Val Glu Thr Arg Gln Ile Thr
        915                 920                 925

Lys His Val Ala Gln Ile Leu Asp Ser Arg Met Asn Thr Lys Tyr Asp
930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
                965                 970                 975

Glu Ile Asn Asn Tyr His His Ala His Asp Ala Tyr Leu Asn Ala Val
            980                 985                 990

Val Gly Thr Ala Leu Ile Lys Lys Tyr Pro Lys Leu Glu Ser Glu Phe
        995                 1000                1005

Val Tyr Gly Asp Tyr Lys Val Tyr Asp Val Arg Lys Met Ile Ala
    1010                1015                1020

Lys Ser Glu Gln Glu Ile Gly Lys Ala Thr Ala Lys Tyr Phe Phe
```

```
            1025                1030                1035

Tyr Ser Asn Ile Met Asn Phe Phe Lys Thr Glu Ile Thr Leu Ala
        1040                1045                1050

Asn Gly Glu Ile Arg Lys Arg Pro Leu Ile Glu Thr Asn Gly Glu
        1055                1060                1065

Thr Gly Glu Ile Val Trp Asp Lys Gly Arg Asp Phe Ala Thr Val
        1070                1075                1080

Arg Lys Val Leu Ser Met Pro Gln Val Asn Ile Val Lys Lys Thr
        1085                1090                1095

Glu Val Gln Thr Gly Gly Phe Ser Lys Glu Ser Ile Leu Pro Lys
        1100                1105                1110

Arg Asn Ser Asp Lys Leu Ile Ala Arg Lys Lys Asp Trp Asp Pro
        1115                1120                1125

Lys Lys Tyr Gly Gly Phe Asp Ser Pro Thr Val Ala Tyr Ser Val
        1130                1135                1140

Leu Val Val Ala Lys Val Glu Lys Gly Lys Ser Lys Lys Leu Lys
        1145                1150                1155

Ser Val Lys Glu Leu Leu Gly Ile Thr Ile Met Glu Arg Ser Ser
        1160                1165                1170

Phe Glu Lys Asn Pro Ile Asp Phe Leu Glu Ala Lys Gly Tyr Lys
        1175                1180                1185

Glu Val Lys Lys Asp Leu Ile Ile Lys Leu Pro Lys Tyr Ser Leu
        1190                1195                1200

Phe Glu Leu Glu Asn Gly Arg Lys Arg Met Leu Ala Ser Ala Gly
        1205                1210                1215

Glu Leu Gln Lys Gly Asn Glu Leu Ala Leu Pro Ser Lys Tyr Val
        1220                1225                1230

Asn Phe Leu Tyr Leu Ala Ser His Tyr Glu Lys Leu Lys Gly Ser
        1235                1240                1245

Pro Glu Asp Asn Glu Gln Lys Gln Leu Phe Val Glu Gln His Lys
        1250                1255                1260

His Tyr Leu Asp Glu Ile Ile Glu Gln Ile Ser Glu Phe Ser Lys
        1265                1270                1275

Arg Val Ile Leu Ala Asp Ala Asn Leu Asp Lys Val Leu Ser Ala
        1280                1285                1290

Tyr Asn Lys His Arg Asp Lys Pro Ile Arg Glu Gln Ala Glu Asn
        1295                1300                1305

Ile Ile His Leu Phe Thr Leu Thr Asn Leu Gly Ala Pro Ala Ala
        1310                1315                1320

Phe Lys Tyr Phe Asp Thr Thr Ile Asp Arg Lys Arg Tyr Thr Ser
        1325                1330                1335

Thr Lys Glu Val Leu Asp Ala Thr Leu Ile His Gln Ser Ile Thr
        1340                1345                1350

Gly Leu Tyr Glu Thr Arg Ile Asp Leu Ser Gln Leu Gly Gly Asp
        1355                1360                1365

<210> SEQ ID NO 2
<211> LENGTH: 2048
<212> TYPE: PRT
<213> ORGANISM: Artificial sequence
<220> FEATURE:
<223> OTHER INFORMATION: Synthetic

<400> SEQUENCE: 2

Met Asp Tyr Lys Asp His Asp Gly Asp Tyr Lys Asp His Asp Ile Asp
```

-continued

```
1               5                   10                  15
Tyr Lys Asp Asp Asp Lys Met Ala Pro Lys Lys Arg Lys Val
                20                  25                  30
Gly Arg Gly Met Asp Lys Lys Tyr Ser Ile Gly Leu Ala Ile Gly Thr
                35                  40                  45
Asn Ser Val Gly Trp Ala Val Ile Thr Asp Glu Tyr Lys Val Pro Ser
                50                  55                  60
Lys Lys Phe Lys Val Leu Gly Asn Thr Asp Arg His Ser Ile Lys Lys
65                  70                  75                  80
Asn Leu Ile Gly Ala Leu Leu Phe Asp Ser Gly Glu Thr Ala Glu Ala
                    85                  90                  95
Thr Arg Leu Lys Arg Thr Ala Arg Arg Arg Tyr Thr Arg Arg Lys Asn
                100                 105                 110
Arg Ile Cys Tyr Leu Gln Glu Ile Phe Ser Asn Glu Met Ala Lys Val
                115                 120                 125
Asp Asp Ser Phe Phe His Arg Leu Glu Glu Ser Phe Leu Val Glu Glu
130                 135                 140
Asp Lys Lys His Glu Arg His Pro Ile Phe Gly Asn Ile Val Asp Glu
145                 150                 155                 160
Val Ala Tyr His Glu Lys Tyr Pro Thr Ile Tyr His Leu Arg Lys Lys
                165                 170                 175
Leu Val Asp Ser Thr Asp Lys Ala Asp Leu Arg Leu Ile Tyr Leu Ala
                180                 185                 190
Leu Ala His Met Ile Lys Phe Arg Gly His Phe Leu Ile Glu Gly Asp
                195                 200                 205
Leu Asn Pro Asp Asn Ser Asp Val Asp Lys Leu Phe Ile Gln Leu Val
                210                 215                 220
Gln Thr Tyr Asn Gln Leu Phe Glu Glu Asn Pro Ile Asn Ala Ser Gly
225                 230                 235                 240
Val Asp Ala Lys Ala Ile Leu Ser Ala Arg Leu Ser Lys Ser Arg Arg
                245                 250                 255
Leu Glu Asn Leu Ile Ala Gln Leu Pro Gly Glu Lys Lys Asn Gly Leu
                260                 265                 270
Phe Gly Asn Leu Ile Ala Leu Ser Leu Gly Leu Thr Pro Asn Phe Lys
                275                 280                 285
Ser Asn Phe Asp Leu Ala Glu Asp Ala Lys Leu Gln Leu Ser Lys Asp
                290                 295                 300
Thr Tyr Asp Asp Asp Leu Asp Asn Leu Leu Ala Gln Ile Gly Asp Gln
305                 310                 315                 320
Tyr Ala Asp Leu Phe Leu Ala Ala Lys Asn Leu Ser Asp Ala Ile Leu
                325                 330                 335
Leu Ser Asp Ile Leu Arg Val Asn Thr Glu Ile Thr Lys Ala Pro Leu
                340                 345                 350
Ser Ala Ser Met Ile Lys Arg Tyr Asp Glu His His Gln Asp Leu Thr
                355                 360                 365
Leu Leu Lys Ala Leu Val Arg Gln Gln Leu Pro Glu Lys Tyr Lys Glu
                370                 375                 380
Ile Phe Phe Asp Gln Ser Lys Asn Gly Tyr Ala Gly Tyr Ile Asp Gly
385                 390                 395                 400
Gly Ala Ser Gln Glu Glu Phe Tyr Lys Phe Ile Lys Pro Ile Leu Glu
                405                 410                 415
Lys Met Asp Gly Thr Glu Glu Leu Leu Val Lys Leu Asn Arg Glu Asp
                420                 425                 430
```

```
Leu Leu Arg Lys Gln Arg Thr Phe Asp Asn Gly Ser Ile Pro His Gln
        435                 440                 445

Ile His Leu Gly Glu Leu His Ala Ile Leu Arg Arg Gln Glu Asp Phe
450                 455                 460

Tyr Pro Phe Leu Lys Asp Asn Arg Glu Lys Ile Glu Lys Ile Leu Thr
465                 470                 475                 480

Phe Arg Ile Pro Tyr Tyr Val Gly Pro Leu Ala Arg Gly Asn Ser Arg
                485                 490                 495

Phe Ala Trp Met Thr Arg Lys Ser Glu Glu Thr Ile Thr Pro Trp Asn
                500                 505                 510

Phe Glu Glu Val Val Asp Lys Gly Ala Ser Ala Gln Ser Phe Ile Glu
                515                 520                 525

Arg Met Thr Asn Phe Asp Lys Asn Leu Pro Asn Glu Lys Val Leu Pro
        530                 535                 540

Lys His Ser Leu Leu Tyr Glu Tyr Phe Thr Val Tyr Asn Glu Leu Thr
545                 550                 555                 560

Lys Val Lys Tyr Val Thr Glu Gly Met Arg Lys Pro Ala Phe Leu Ser
                565                 570                 575

Gly Glu Gln Lys Lys Ala Ile Val Asp Leu Leu Phe Lys Thr Asn Arg
                580                 585                 590

Lys Val Thr Val Lys Gln Leu Lys Glu Asp Tyr Phe Lys Lys Ile Glu
                595                 600                 605

Cys Phe Asp Ser Val Glu Ile Ser Gly Val Glu Asp Arg Phe Asn Ala
        610                 615                 620

Ser Leu Gly Thr Tyr His Asp Leu Leu Lys Ile Ile Lys Asp Lys Asp
625                 630                 635                 640

Phe Leu Asp Asn Glu Glu Asn Glu Asp Ile Leu Glu Asp Ile Val Leu
                645                 650                 655

Thr Leu Thr Leu Phe Glu Asp Arg Glu Met Ile Glu Glu Arg Leu Lys
                660                 665                 670

Thr Tyr Ala His Leu Phe Asp Asp Lys Val Met Lys Gln Leu Lys Arg
        675                 680                 685

Arg Arg Tyr Thr Gly Trp Gly Arg Leu Ser Arg Lys Leu Ile Asn Gly
        690                 695                 700

Ile Arg Asp Lys Gln Ser Gly Lys Thr Ile Leu Asp Phe Leu Lys Ser
705                 710                 715                 720

Asp Gly Phe Ala Asn Arg Asn Phe Met Gln Leu Ile His Asp Asp Ser
                725                 730                 735

Leu Thr Phe Lys Glu Asp Ile Gln Lys Ala Gln Val Ser Gly Gln Gly
                740                 745                 750

Asp Ser Leu His Glu His Ile Ala Asn Leu Ala Gly Ser Pro Ala Ile
                755                 760                 765

Lys Lys Gly Ile Leu Gln Thr Val Lys Val Val Asp Glu Leu Val Lys
        770                 775                 780

Val Met Gly Arg His Lys Pro Glu Asn Ile Val Ile Glu Met Ala Arg
785                 790                 795                 800

Glu Asn Gln Thr Thr Gln Lys Gly Gln Lys Asn Ser Arg Glu Arg Met
                805                 810                 815

Lys Arg Ile Glu Glu Gly Ile Lys Glu Leu Gly Ser Gln Ile Leu Lys
                820                 825                 830

Glu His Pro Val Glu Asn Thr Gln Leu Gln Asn Glu Lys Leu Tyr Leu
                835                 840                 845
```

```
Tyr Tyr Leu Gln Asn Gly Arg Asp Met Tyr Val Asp Gln Glu Leu Asp
    850                 855                 860

Ile Asn Arg Leu Ser Asp Tyr Asp Val Asp Ala Ile Val Pro Gln Ser
865                 870                 875                 880

Phe Leu Lys Asp Asp Ser Ile Asp Asn Lys Val Leu Thr Arg Ser Asp
                885                 890                 895

Lys Asn Arg Gly Lys Ser Asp Asn Val Pro Ser Glu Glu Val Val Lys
                900                 905                 910

Lys Met Lys Asn Tyr Trp Arg Gln Leu Leu Asn Ala Lys Leu Ile Thr
                915                 920                 925

Gln Arg Lys Phe Asp Asn Leu Thr Lys Ala Glu Arg Gly Gly Leu Ser
    930                 935                 940

Glu Leu Asp Lys Ala Gly Phe Ile Lys Arg Gln Leu Val Glu Thr Arg
945                 950                 955                 960

Gln Ile Thr Lys His Val Ala Gln Ile Leu Asp Ser Arg Met Asn Thr
                965                 970                 975

Lys Tyr Asp Glu Asn Asp Lys Leu Ile Arg Glu Val Lys Val Ile Thr
                980                 985                 990

Leu Lys Ser Lys Leu Val Ser Asp Phe Arg Lys Asp Phe Gln Phe Tyr
                995                 1000                1005

Lys Val Arg Glu Ile Asn Asn Tyr His His Ala His Asp Ala Tyr
    1010                1015                1020

Leu Asn Ala Val Val Gly Thr Ala Leu Ile Lys Lys Tyr Pro Lys
    1025                1030                1035

Leu Glu Ser Glu Phe Val Tyr Gly Asp Tyr Lys Val Tyr Asp Val
    1040                1045                1050

Arg Lys Met Ile Ala Lys Ser Glu Gln Glu Ile Gly Lys Ala Thr
    1055                1060                1065

Ala Lys Tyr Phe Phe Tyr Ser Asn Ile Met Asn Phe Phe Lys Thr
    1070                1075                1080

Glu Ile Thr Leu Ala Asn Gly Glu Ile Arg Lys Arg Pro Leu Ile
    1085                1090                1095

Glu Thr Asn Gly Glu Thr Gly Glu Ile Val Trp Asp Lys Gly Arg
    1100                1105                1110

Asp Phe Ala Thr Val Arg Lys Val Leu Ser Met Pro Gln Val Asn
    1115                1120                1125

Ile Val Lys Lys Thr Glu Val Gln Thr Gly Gly Phe Ser Lys Glu
    1130                1135                1140

Ser Ile Leu Pro Lys Arg Asn Ser Asp Lys Leu Ile Ala Arg Lys
    1145                1150                1155

Lys Asp Trp Asp Pro Lys Lys Tyr Gly Gly Phe Asp Ser Pro Thr
    1160                1165                1170

Val Ala Tyr Ser Val Leu Val Val Ala Lys Val Glu Lys Gly Lys
    1175                1180                1185

Ser Lys Lys Leu Lys Ser Val Lys Glu Leu Leu Gly Ile Thr Ile
    1190                1195                1200

Met Glu Arg Ser Ser Phe Glu Lys Asn Pro Ile Asp Phe Leu Glu
    1205                1210                1215

Ala Lys Gly Tyr Lys Glu Val Lys Lys Asp Leu Ile Ile Lys Leu
    1220                1225                1230

Pro Lys Tyr Ser Leu Phe Glu Leu Glu Asn Gly Arg Lys Arg Met
    1235                1240                1245

Leu Ala Ser Ala Gly Glu Leu Gln Lys Gly Asn Glu Leu Ala Leu
```

```
                    1250                1255                1260
Pro Ser Lys Tyr Val Asn Phe Leu Tyr Leu Ala Ser His Tyr Glu
    1265                1270                1275
Lys Leu Lys Gly Ser Pro Glu Asp Asn Glu Gln Lys Gln Leu Phe
    1280                1285                1290
Val Glu Gln His Lys His Tyr Leu Asp Glu Ile Ile Glu Gln Ile
    1295                1300                1305
Ser Glu Phe Ser Lys Arg Val Ile Leu Ala Asp Ala Asn Leu Asp
    1310                1315                1320
Lys Val Leu Ser Ala Tyr Asn Lys His Arg Asp Lys Pro Ile Arg
    1325                1330                1335
Glu Gln Ala Glu Asn Ile Ile His Leu Phe Thr Leu Thr Asn Leu
    1340                1345                1350
Gly Ala Pro Ala Ala Phe Lys Tyr Phe Asp Thr Thr Ile Asp Arg
    1355                1360                1365
Lys Arg Tyr Thr Ser Thr Lys Glu Val Leu Asp Ala Thr Leu Ile
    1370                1375                1380
His Gln Ser Ile Thr Gly Leu Tyr Glu Thr Arg Ile Asp Leu Ser
    1385                1390                1395
Gln Leu Gly Gly Asp Pro Ile Ala Gly Ser Lys Ala Ser Pro Lys
    1400                1405                1410
Lys Lys Arg Lys Val Gly Arg Ala Ile Phe Lys Pro Glu Glu Leu
    1415                1420                1425
Arg Gln Ala Leu Met Pro Thr Leu Glu Ala Leu Tyr Arg Gln Asp
    1430                1435                1440
Pro Glu Ser Leu Pro Phe Arg Gln Pro Val Asp Pro Gln Leu Leu
    1445                1450                1455
Gly Ile Pro Asp Tyr Phe Asp Ile Val Lys Ser Pro Met Asp Leu
    1460                1465                1470
Ser Thr Ile Lys Arg Lys Leu Asp Thr Gly Gln Tyr Gln Glu Pro
    1475                1480                1485
Trp Gln Tyr Val Asp Asp Ile Trp Leu Met Phe Asn Asn Ala Trp
    1490                1495                1500
Leu Tyr Asn Arg Lys Thr Ser Arg Val Tyr Lys Tyr Cys Ser Lys
    1505                1510                1515
Leu Ser Glu Val Phe Glu Gln Glu Ile Asp Pro Val Met Gln Ser
    1520                1525                1530
Leu Gly Tyr Cys Cys Gly Arg Lys Leu Glu Phe Ser Pro Gln Thr
    1535                1540                1545
Leu Cys Cys Tyr Gly Lys Gln Leu Cys Thr Ile Pro Arg Asp Ala
    1550                1555                1560
Thr Tyr Tyr Ser Tyr Gln Asn Arg Tyr His Phe Cys Glu Lys Cys
    1565                1570                1575
Phe Asn Glu Ile Gln Gly Glu Ser Val Ser Leu Gly Asp Asp Pro
    1580                1585                1590
Ser Gln Pro Gln Thr Thr Ile Asn Lys Glu Gln Phe Ser Lys Arg
    1595                1600                1605
Lys Asn Asp Thr Leu Asp Pro Glu Leu Phe Val Glu Cys Thr Glu
    1610                1615                1620
Cys Gly Arg Lys Met His Gln Ile Cys Val Leu His His Glu Ile
    1625                1630                1635
Ile Trp Pro Ala Gly Phe Val Cys Asp Gly Cys Leu Lys Lys Ser
    1640                1645                1650
```

Ala Arg Thr Arg Lys Glu Asn Lys Phe Ser Ala Lys Arg Leu Pro
1655            1660            1665

Ser Thr Arg Leu Gly Thr Phe Leu Glu Asn Arg Val Asn Asp Phe
1670            1675            1680

Leu Arg Arg Gln Asn His Pro Glu Ser Gly Glu Val Thr Val Arg
1685            1690            1695

Val Val His Ala Ser Asp Lys Thr Val Glu Val Lys Pro Gly Met
1700            1705            1710

Lys Ala Arg Phe Val Asp Ser Gly Glu Met Ala Glu Ser Phe Pro
1715            1720            1725

Tyr Arg Thr Lys Ala Leu Phe Ala Phe Glu Glu Ile Asp Gly Val
1730            1735            1740

Asp Leu Cys Phe Phe Gly Met His Val Gln Glu Tyr Gly Ser Asp
1745            1750            1755

Cys Pro Pro Pro Asn Gln Arg Arg Val Tyr Ile Ser Tyr Leu Asp
1760            1765            1770

Ser Val His Phe Phe Arg Pro Lys Cys Leu Arg Thr Ala Val Tyr
1775            1780            1785

His Glu Ile Leu Ile Gly Tyr Leu Glu Tyr Val Lys Lys Leu Gly
1790            1795            1800

Tyr Thr Thr Gly His Ile Trp Ala Cys Pro Pro Ser Glu Gly Asp
1805            1810            1815

Asp Tyr Ile Phe His Cys His Pro Pro Asp Gln Lys Ile Pro Lys
1820            1825            1830

Pro Lys Arg Leu Gln Glu Trp Tyr Lys Lys Met Leu Asp Lys Ala
1835            1840            1845

Val Ser Glu Arg Ile Val His Asp Tyr Lys Asp Ile Phe Lys Gln
1850            1855            1860

Ala Thr Glu Asp Arg Leu Thr Ser Ala Lys Glu Leu Pro Tyr Phe
1865            1870            1875

Glu Gly Asp Phe Trp Pro Asn Val Leu Glu Glu Ser Ile Lys Glu
1880            1885            1890

Leu Glu Gln Glu Glu Glu Glu Arg Lys Arg Glu Glu Asn Thr Ser
1895            1900            1905

Asn Glu Ser Thr Asp Val Thr Lys Gly Asp Ser Lys Asn Ala Lys
1910            1915            1920

Lys Lys Asn Asn Lys Lys Thr Ser Lys Asn Lys Ser Ser Leu Ser
1925            1930            1935

Arg Gly Asn Lys Lys Lys Pro Gly Met Pro Asn Val Ser Asn Asp
1940            1945            1950

Leu Ser Gln Lys Leu Tyr Ala Thr Met Glu Lys His Lys Glu Val
1955            1960            1965

Phe Phe Val Ile Arg Leu Ile Ala Gly Pro Ala Ala Asn Ser Leu
1970            1975            1980

Pro Pro Ile Val Asp Pro Asp Pro Leu Ile Pro Cys Asp Leu Met
1985            1990            1995

Asp Gly Arg Asp Ala Phe Leu Thr Leu Ala Arg Asp Lys His Leu
2000            2005            2010

Glu Phe Ser Ser Leu Arg Arg Ala Gln Trp Ser Thr Met Cys Met
2015            2020            2025

Leu Val Glu Leu His Thr Gln Ser Gln Asp Tyr Pro Tyr Asp Val
2030            2035            2040

```
Pro Asp Tyr Ala Ser
    2045

<210> SEQ ID NO 3
<211> LENGTH: 1521
<212> TYPE: PRT
<213> ORGANISM: Artificial sequence
<220> FEATURE:
<223> OTHER INFORMATION: Synthetic

<400> SEQUENCE: 3

Met Asp Tyr Lys Asp His Asp Gly Asp Tyr Lys Asp His Asp Ile Asp
1               5                   10                  15

Tyr Lys Asp Asp Asp Lys Met Ala Pro Lys Lys Arg Lys Val
            20                  25                  30

Gly Arg Gly Met Asp Lys Lys Tyr Ser Ile Gly Leu Ala Ile Gly Thr
        35                  40                  45

Asn Ser Val Gly Trp Ala Val Ile Thr Asp Glu Tyr Lys Val Pro Ser
    50                  55                  60

Lys Lys Phe Lys Val Leu Gly Asn Thr Asp Arg His Ser Ile Lys Lys
65                  70                  75                  80

Asn Leu Ile Gly Ala Leu Leu Phe Asp Ser Gly Glu Thr Ala Glu Ala
                85                  90                  95

Thr Arg Leu Lys Arg Thr Ala Arg Arg Arg Tyr Thr Arg Arg Lys Asn
            100                 105                 110

Arg Ile Cys Tyr Leu Gln Glu Ile Phe Ser Asn Glu Met Ala Lys Val
        115                 120                 125

Asp Asp Ser Phe Phe His Arg Leu Glu Glu Ser Phe Leu Val Glu Glu
    130                 135                 140

Asp Lys Lys His Glu Arg His Pro Ile Phe Gly Asn Ile Val Asp Glu
145                 150                 155                 160

Val Ala Tyr His Glu Lys Tyr Pro Thr Ile Tyr His Leu Arg Lys Lys
                165                 170                 175

Leu Val Asp Ser Thr Asp Lys Ala Asp Leu Arg Leu Ile Tyr Leu Ala
            180                 185                 190

Leu Ala His Met Ile Lys Phe Arg Gly His Phe Leu Ile Glu Gly Asp
        195                 200                 205

Leu Asn Pro Asp Asn Ser Asp Val Asp Lys Leu Phe Ile Gln Leu Val
    210                 215                 220

Gln Thr Tyr Asn Gln Leu Phe Glu Glu Asn Pro Ile Asn Ala Ser Gly
225                 230                 235                 240

Val Asp Ala Lys Ala Ile Leu Ser Ala Arg Leu Ser Lys Ser Arg Arg
                245                 250                 255

Leu Glu Asn Leu Ile Ala Gln Leu Pro Gly Glu Lys Lys Asn Gly Leu
            260                 265                 270

Phe Gly Asn Leu Ile Ala Leu Ser Leu Gly Leu Thr Pro Asn Phe Lys
        275                 280                 285

Ser Asn Phe Asp Leu Ala Glu Asp Ala Lys Leu Gln Leu Ser Lys Asp
    290                 295                 300

Thr Tyr Asp Asp Asp Leu Asp Asn Leu Leu Ala Gln Ile Gly Asp Gln
305                 310                 315                 320

Tyr Ala Asp Leu Phe Leu Ala Ala Lys Asn Leu Ser Asp Ala Ile Leu
                325                 330                 335

Leu Ser Asp Ile Leu Arg Val Asn Thr Glu Ile Thr Lys Ala Pro Leu
            340                 345                 350
```

```
Ser Ala Ser Met Ile Lys Arg Tyr Asp Glu His His Gln Asp Leu Thr
            355                 360                 365
Leu Leu Lys Ala Leu Val Arg Gln Gln Leu Pro Glu Lys Tyr Lys Glu
    370                 375                 380
Ile Phe Phe Asp Gln Ser Lys Asn Gly Tyr Ala Gly Tyr Ile Asp Gly
385                 390                 395                 400
Gly Ala Ser Gln Glu Glu Phe Tyr Lys Phe Ile Lys Pro Ile Leu Glu
                405                 410                 415
Lys Met Asp Gly Thr Glu Glu Leu Leu Val Lys Leu Asn Arg Glu Asp
                420                 425                 430
Leu Leu Arg Lys Gln Arg Thr Phe Asp Asn Gly Ser Ile Pro His Gln
            435                 440                 445
Ile His Leu Gly Glu Leu His Ala Ile Leu Arg Arg Gln Glu Asp Phe
        450                 455                 460
Tyr Pro Phe Leu Lys Asp Asn Arg Glu Lys Ile Glu Lys Ile Leu Thr
465                 470                 475                 480
Phe Arg Ile Pro Tyr Tyr Val Gly Pro Leu Ala Arg Gly Asn Ser Arg
                485                 490                 495
Phe Ala Trp Met Thr Arg Lys Ser Glu Glu Thr Ile Thr Pro Trp Asn
            500                 505                 510
Phe Glu Glu Val Val Asp Lys Gly Ala Ser Ala Gln Ser Phe Ile Glu
        515                 520                 525
Arg Met Thr Asn Phe Asp Lys Asn Leu Pro Asn Glu Lys Val Leu Pro
    530                 535                 540
Lys His Ser Leu Leu Tyr Glu Tyr Phe Thr Val Tyr Asn Glu Leu Thr
545                 550                 555                 560
Lys Val Lys Tyr Val Thr Glu Gly Met Arg Lys Pro Ala Phe Leu Ser
                565                 570                 575
Gly Glu Gln Lys Lys Ala Ile Val Asp Leu Leu Phe Lys Thr Asn Arg
            580                 585                 590
Lys Val Thr Val Lys Gln Leu Lys Glu Asp Tyr Phe Lys Lys Ile Glu
        595                 600                 605
Cys Phe Asp Ser Val Glu Ile Ser Gly Val Glu Asp Arg Phe Asn Ala
610                 615                 620
Ser Leu Gly Thr Tyr His Asp Leu Leu Lys Ile Ile Lys Asp Lys Asp
625                 630                 635                 640
Phe Leu Asp Asn Glu Glu Asn Glu Asp Ile Leu Glu Asp Ile Val Leu
                645                 650                 655
Thr Leu Thr Leu Phe Glu Asp Arg Glu Met Ile Glu Glu Arg Leu Lys
            660                 665                 670
Thr Tyr Ala His Leu Phe Asp Asp Lys Val Met Lys Gln Leu Lys Arg
        675                 680                 685
Arg Arg Tyr Thr Gly Trp Gly Arg Leu Ser Arg Lys Leu Ile Asn Gly
    690                 695                 700
Ile Arg Asp Lys Gln Ser Gly Lys Thr Ile Leu Asp Phe Leu Lys Ser
705                 710                 715                 720
Asp Gly Phe Ala Asn Arg Asn Phe Met Gln Leu Ile His Asp Asp Ser
                725                 730                 735
Leu Thr Phe Lys Glu Asp Ile Gln Lys Ala Gln Val Ser Gly Gln Gly
            740                 745                 750
Asp Ser Leu His Glu His Ile Ala Asn Leu Ala Gly Ser Pro Ala Ile
        755                 760                 765
Lys Lys Gly Ile Leu Gln Thr Val Lys Val Val Asp Glu Leu Val Lys
```

```
                770             775             780
    Val Met Gly Arg His Lys Pro Glu Asn Ile Val Ile Glu Met Ala Arg
    785                 790             795             800

Glu Asn Gln Thr Thr Gln Lys Gly Gln Lys Asn Ser Arg Glu Arg Met
                    805             810             815

Lys Arg Ile Glu Gly Ile Lys Glu Leu Gly Ser Gln Ile Leu Lys
                820             825             830

Glu His Pro Val Glu Asn Thr Gln Leu Gln Asn Glu Lys Leu Tyr Leu
                835             840             845

Tyr Tyr Leu Gln Asn Gly Arg Asp Met Tyr Val Asp Gln Glu Leu Asp
    850                 855             860

Ile Asn Arg Leu Ser Asp Tyr Asp Val Asp Ala Ile Val Pro Gln Ser
    865                 870             875             880

Phe Leu Lys Asp Asp Ser Ile Asp Asn Lys Val Leu Thr Arg Ser Asp
                    885             890             895

Lys Asn Arg Gly Lys Ser Asp Asn Val Pro Ser Glu Glu Val Val Lys
                    900             905             910

Lys Met Lys Asn Tyr Trp Arg Gln Leu Leu Asn Ala Lys Leu Ile Thr
                915             920             925

Gln Arg Lys Phe Asp Asn Leu Thr Lys Ala Glu Arg Gly Gly Leu Ser
                930             935             940

Glu Leu Asp Lys Ala Gly Phe Ile Lys Arg Gln Leu Val Glu Thr Arg
    945                 950             955             960

Gln Ile Thr Lys His Val Ala Gln Ile Leu Asp Ser Arg Met Asn Thr
                    965             970             975

Lys Tyr Asp Glu Asn Asp Lys Leu Ile Arg Glu Val Lys Val Ile Thr
                980             985             990

Leu Lys Ser Lys Leu Val Ser Asp Phe Arg Lys Asp Phe Gln Phe Tyr
                995             1000            1005

Lys Val Arg Glu Ile Asn Asn Tyr His His Ala His Asp Ala Tyr
                1010            1015            1020

Leu Asn Ala Val Val Gly Thr Ala Leu Ile Lys Lys Tyr Pro Lys
                1025            1030            1035

Leu Glu Ser Glu Phe Val Tyr Gly Asp Tyr Lys Val Tyr Asp Val
                1040            1045            1050

Arg Lys Met Ile Ala Lys Ser Glu Gln Glu Ile Gly Lys Ala Thr
                1055            1060            1065

Ala Lys Tyr Phe Phe Tyr Ser Asn Ile Met Asn Phe Phe Lys Thr
                1070            1075            1080

Glu Ile Thr Leu Ala Asn Gly Glu Ile Arg Lys Arg Pro Leu Ile
                1085            1090            1095

Glu Thr Asn Gly Glu Thr Gly Glu Ile Val Trp Asp Lys Gly Arg
                1100            1105            1110

Asp Phe Ala Thr Val Arg Lys Val Leu Ser Met Pro Gln Val Asn
                1115            1120            1125

Ile Val Lys Lys Thr Glu Val Gln Thr Gly Gly Phe Ser Lys Glu
                1130            1135            1140

Ser Ile Leu Pro Lys Arg Asn Ser Asp Lys Leu Ile Ala Arg Lys
                1145            1150            1155

Lys Asp Trp Asp Pro Lys Lys Tyr Gly Gly Phe Asp Ser Pro Thr
                1160            1165            1170

Val Ala Tyr Ser Val Leu Val Val Ala Lys Val Glu Lys Gly Lys
                1175            1180            1185
```

Ser Lys Lys Leu Lys Ser Val Lys Glu Leu Leu Gly Ile Thr Ile
1190                1195                1200

Met Glu Arg Ser Ser Phe Glu Lys Asn Pro Ile Asp Phe Leu Glu
1205                1210                1215

Ala Lys Gly Tyr Lys Glu Val Lys Lys Asp Leu Ile Ile Lys Leu
1220                1225                1230

Pro Lys Tyr Ser Leu Phe Glu Leu Glu Asn Gly Arg Lys Arg Met
1235                1240                1245

Leu Ala Ser Ala Gly Glu Leu Gln Lys Gly Asn Glu Leu Ala Leu
1250                1255                1260

Pro Ser Lys Tyr Val Asn Phe Leu Tyr Leu Ala Ser His Tyr Glu
1265                1270                1275

Lys Leu Lys Gly Ser Pro Glu Asp Asn Glu Gln Lys Gln Leu Phe
1280                1285                1290

Val Glu Gln His Lys His Tyr Leu Asp Glu Ile Ile Glu Gln Ile
1295                1300                1305

Ser Glu Phe Ser Lys Arg Val Ile Leu Ala Asp Ala Asn Leu Asp
1310                1315                1320

Lys Val Leu Ser Ala Tyr Asn Lys His Arg Asp Lys Pro Ile Arg
1325                1330                1335

Glu Gln Ala Glu Asn Ile Ile His Leu Phe Thr Leu Thr Asn Leu
1340                1345                1350

Gly Ala Pro Ala Ala Phe Lys Tyr Phe Asp Thr Thr Ile Asp Arg
1355                1360                1365

Lys Arg Tyr Thr Ser Thr Lys Glu Val Leu Asp Ala Thr Leu Ile
1370                1375                1380

His Gln Ser Ile Thr Gly Leu Tyr Glu Thr Arg Ile Asp Leu Ser
1385                1390                1395

Gln Leu Gly Gly Asp Ser Arg Ala Asp Pro Lys Lys Lys Arg Lys
1400                1405                1410

Val Ala Ser Asp Ala Lys Ser Leu Thr Ala Trp Ser Arg Thr Leu
1415                1420                1425

Val Thr Phe Lys Asp Val Phe Val Asp Phe Thr Arg Glu Glu Trp
1430                1435                1440

Lys Leu Leu Asp Thr Ala Gln Gln Ile Leu Tyr Arg Asn Val Met
1445                1450                1455

Leu Glu Asn Tyr Lys Asn Leu Val Ser Leu Gly Tyr Gln Leu Thr
1460                1465                1470

Lys Pro Asp Val Ile Leu Arg Leu Glu Lys Gly Glu Glu Pro Trp
1475                1480                1485

Leu Val Glu Arg Glu Ile His Gln Glu Thr His Pro Asp Ser Glu
1490                1495                1500

Thr Ala Phe Glu Ile Lys Ser Ser Val Pro Lys Lys Lys Arg Lys
1505                1510                1515

Val Ala Ser
1520

<210> SEQ ID NO 4
<211> LENGTH: 617
<212> TYPE: PRT
<213> ORGANISM: Artificial sequence
<220> FEATURE:
<223> OTHER INFORMATION: Synthetic

<400> SEQUENCE: 4

```
Tyr Lys Val Tyr Asp Val Arg Lys Met Ile Ala Lys Ser Glu Gln Glu
1               5                   10                  15

Ile Gly Lys Ala Thr Ala Lys Tyr Phe Phe Tyr Ser Asn Ile Met Asn
            20                  25                  30

Phe Phe Lys Thr Glu Ile Thr Leu Ala Asn Gly Glu Ile Arg Lys Arg
            35                  40                  45

Pro Leu Ile Glu Thr Asn Gly Glu Thr Gly Glu Ile Val Trp Asp Lys
50                  55                  60

Gly Arg Asp Phe Ala Thr Val Arg Lys Val Leu Ser Met Pro Gln Val
65                  70                  75                  80

Asn Ile Val Lys Lys Thr Glu Val Gln Thr Gly Gly Phe Ser Lys Glu
                85                  90                  95

Ser Ile Leu Pro Lys Arg Asn Ser Asp Lys Leu Ile Ala Arg Lys Lys
                100                 105                 110

Asp Trp Asp Pro Lys Lys Tyr Gly Gly Phe Asp Ser Pro Thr Val Ala
            115                 120                 125

Tyr Ser Val Leu Val Val Ala Lys Val Glu Lys Gly Lys Ser Lys Lys
    130                 135                 140

Leu Lys Ser Val Lys Glu Leu Leu Gly Ile Thr Ile Met Glu Arg Ser
145                 150                 155                 160

Ser Phe Glu Lys Asn Pro Ile Asp Phe Leu Glu Ala Lys Gly Tyr Lys
                165                 170                 175

Glu Val Lys Lys Asp Leu Ile Ile Lys Leu Pro Lys Tyr Ser Leu Phe
                180                 185                 190

Glu Leu Glu Asn Gly Arg Lys Arg Met Leu Ala Ser Ala Gly Glu Leu
            195                 200                 205

Gln Lys Gly Asn Glu Leu Ala Leu Pro Ser Lys Tyr Val Asn Phe Leu
    210                 215                 220

Tyr Leu Ala Ser His Tyr Glu Lys Leu Lys Gly Ser Pro Glu Asp Asn
225                 230                 235                 240

Glu Gln Lys Gln Leu Phe Val Glu Gln His Lys His Tyr Leu Asp Glu
                245                 250                 255

Ile Ile Glu Gln Ile Ser Glu Phe Ser Lys Arg Val Ile Leu Ala Asp
                260                 265                 270

Ala Asn Leu Asp Lys Val Leu Ser Ala Tyr Asn Lys His Arg Asp Lys
            275                 280                 285

Pro Ile Arg Glu Gln Ala Glu Asn Ile Ile His Leu Phe Thr Leu Thr
    290                 295                 300

Asn Leu Gly Ala Pro Ala Ala Phe Lys Tyr Phe Asp Thr Thr Ile Asp
305                 310                 315                 320

Arg Lys Arg Tyr Thr Ser Thr Lys Glu Val Leu Asp Ala Thr Leu Ile
                325                 330                 335

His Gln Ser Ile Thr Gly Leu Tyr Glu Thr Arg Ile Asp Leu Ser Gln
            340                 345                 350

Leu Gly Gly Asp Pro Ile Ala Gly Ser Lys Ala Ser Pro Lys Lys Lys
    355                 360                 365

Arg Lys Val Gly Arg Ala Ile Phe Lys Pro Glu Glu Leu Arg Gln Ala
370                 375                 380

Leu Met Pro Thr Leu Glu Ala Leu Tyr Arg Gln Asp Pro Glu Ser Leu
385                 390                 395                 400

Pro Phe Arg Gln Pro Val Asp Pro Gln Leu Leu Gly Ile Pro Asp Tyr
                405                 410                 415
```

-continued

Phe Asp Ile Val Lys Ser Pro Met Asp Leu Ser Thr Ile Lys Arg Lys
                420                 425                 430

Leu Asp Thr Gly Gln Tyr Gln Glu Pro Trp Gln Tyr Val Asp Asp Ile
            435                 440                 445

Trp Leu Met Phe Asn Asn Ala Trp Leu Tyr Asn Arg Lys Thr Ser Arg
        450                 455                 460

Val Tyr Lys Tyr Cys Ser Lys Leu Ser Glu Val Phe Glu Gln Glu Ile
465                 470                 475                 480

Asp Pro Val Met Gln Ser Leu Gly Tyr Cys Cys Gly Arg Lys Leu Glu
                485                 490                 495

Phe Ser Pro Gln Thr Leu Cys Cys Tyr Gly Lys Gln Leu Cys Thr Ile
            500                 505                 510

Pro Arg Asp Ala Thr Tyr Tyr Ser Tyr Gln Asn Arg Tyr His Phe Cys
        515                 520                 525

Glu Lys Cys Phe Asn Glu Ile Gln Gly Glu Ser Val Ser Leu Gly Asp
530                 535                 540

Asp Pro Ser Gln Pro Gln Thr Thr Ile Asn Lys Glu Gln Phe Ser Lys
545                 550                 555                 560

Arg Lys Asn Asp Thr Leu Asp Pro Glu Leu Phe Val Glu Cys Thr Glu
                565                 570                 575

Cys Gly Arg Lys Met His Gln Ile Cys Val Leu His His Glu Ile Ile
            580                 585                 590

Trp Pro Ala Gly Phe Val Cys Asp Gly Cys Leu Lys Lys Ser Ala Arg
        595                 600                 605

Thr Arg Lys Glu Asn Lys Phe Ser Ala
610                 615

<210> SEQ ID NO 5
<211> LENGTH: 1726
<212> TYPE: PRT
<213> ORGANISM: Artificial sequence
<220> FEATURE:
<223> OTHER INFORMATION: Synthetic

<400> SEQUENCE: 5

Met Ala Ala Phe Lys Pro Asn Pro Ile Asn Tyr Ile Leu Gly Leu Ala
1               5                   10                  15

Ile Gly Ile Ala Ser Val Gly Trp Ala Met Val Glu Ile Asp Glu Asp
            20                  25                  30

Glu Asn Pro Ile Cys Leu Ile Asp Leu Gly Val Arg Val Phe Glu Arg
        35                  40                  45

Ala Glu Val Pro Lys Thr Gly Asp Ser Leu Ala Met Ala Arg Arg Leu
    50                  55                  60

Ala Arg Ser Val Arg Arg Leu Thr Arg Arg Arg Ala His Arg Leu Leu
65                  70                  75                  80

Arg Ala Arg Arg Leu Leu Lys Arg Glu Gly Val Leu Gln Ala Ala Asp
                85                  90                  95

Phe Asp Glu Asn Gly Leu Ile Lys Ser Leu Pro Asn Thr Pro Trp Gln
            100                 105                 110

Leu Arg Ala Ala Ala Leu Asp Arg Lys Leu Thr Pro Leu Glu Trp Ser
        115                 120                 125

Ala Val Leu Leu His Leu Ile Lys His Arg Gly Tyr Leu Ser Gln Arg
    130                 135                 140

Lys Asn Glu Gly Glu Thr Ala Asp Lys Glu Leu Gly Ala Leu Leu Lys
145                 150                 155                 160

-continued

Gly Val Ala Asp Asn Ala His Ala Leu Gln Thr Gly Asp Phe Arg Thr
                165                 170                 175

Pro Ala Glu Leu Ala Leu Asn Lys Phe Glu Lys Glu Ser Gly His Ile
            180                 185                 190

Arg Asn Gln Arg Gly Asp Tyr Ser His Thr Phe Ser Arg Lys Asp Leu
        195                 200                 205

Gln Ala Glu Leu Ile Leu Leu Phe Glu Lys Gln Lys Glu Phe Gly Asn
    210                 215                 220

Pro His Val Ser Gly Leu Lys Glu Gly Ile Glu Thr Leu Leu Met
225                 230                 235                 240

Thr Gln Arg Pro Ala Leu Ser Gly Asp Ala Val Gln Lys Met Leu Gly
                245                 250                 255

His Cys Thr Phe Glu Pro Ala Glu Pro Lys Ala Ala Lys Asn Thr Tyr
            260                 265                 270

Thr Ala Glu Arg Phe Ile Trp Leu Thr Lys Leu Asn Asn Leu Arg Ile
        275                 280                 285

Leu Glu Gln Gly Ser Glu Arg Pro Leu Thr Asp Thr Glu Arg Ala Thr
    290                 295                 300

Leu Met Asp Glu Pro Tyr Arg Lys Ser Lys Leu Thr Tyr Ala Gln Ala
305                 310                 315                 320

Arg Lys Leu Leu Gly Leu Glu Asp Thr Ala Phe Phe Lys Gly Leu Arg
                325                 330                 335

Tyr Gly Lys Asp Asn Ala Glu Ala Ser Thr Leu Met Glu Met Lys Ala
            340                 345                 350

Tyr His Ala Ile Ser Arg Ala Leu Glu Lys Glu Gly Leu Lys Asp Lys
        355                 360                 365

Lys Ser Pro Leu Asn Leu Ser Pro Glu Leu Gln Asp Glu Ile Gly Thr
    370                 375                 380

Ala Phe Ser Leu Phe Lys Thr Asp Glu Asp Ile Thr Gly Arg Leu Lys
385                 390                 395                 400

Asp Arg Ile Gln Pro Glu Ile Leu Glu Ala Leu Leu Lys His Ile Ser
                405                 410                 415

Phe Asp Lys Phe Val Gln Ile Ser Leu Lys Ala Leu Arg Arg Ile Val
            420                 425                 430

Pro Leu Met Glu Gln Gly Lys Arg Tyr Asp Glu Ala Cys Ala Glu Ile
        435                 440                 445

Tyr Gly Asp His Tyr Gly Lys Lys Asn Thr Glu Glu Lys Ile Tyr Leu
    450                 455                 460

Pro Pro Ile Pro Ala Asp Glu Ile Arg Asn Pro Val Val Leu Arg Ala
465                 470                 475                 480

Leu Ser Gln Ala Arg Lys Val Ile Asn Gly Val Val Arg Arg Tyr Gly
                485                 490                 495

Ser Pro Ala Arg Ile His Ile Glu Thr Ala Arg Glu Val Gly Lys Ser
            500                 505                 510

Phe Lys Asp Arg Lys Glu Ile Glu Lys Arg Gln Glu Glu Asn Arg Lys
        515                 520                 525

Asp Arg Glu Lys Ala Ala Ala Lys Phe Arg Glu Tyr Phe Pro Asn Phe
    530                 535                 540

Val Gly Glu Pro Lys Ser Lys Asp Ile Leu Lys Leu Arg Leu Tyr Glu
545                 550                 555                 560

Gln Gln His Gly Lys Cys Leu Tyr Ser Gly Lys Glu Ile Asn Leu Gly
                565                 570                 575

Arg Leu Asn Glu Lys Gly Tyr Val Glu Ile Ala Ala Ala Leu Pro Phe

-continued

```
                580             585             590
Ser Arg Thr Trp Asp Asp Ser Phe Asn Asn Lys Val Leu Val Leu Gly
            595             600             605

Ser Glu Ala Gln Asn Lys Gly Asn Gln Thr Pro Tyr Glu Tyr Phe Asn
            610             615             620

Gly Lys Asp Asn Ser Arg Glu Trp Gln Glu Phe Lys Ala Arg Val Glu
625             630             635             640

Thr Ser Arg Phe Pro Arg Ser Lys Lys Gln Arg Ile Leu Leu Gln Lys
            645             650             655

Phe Asp Glu Asp Gly Phe Lys Glu Arg Asn Leu Asn Asp Thr Arg Tyr
            660             665             670

Val Asn Arg Phe Leu Cys Gln Phe Val Ala Asp Arg Met Arg Leu Thr
            675             680             685

Gly Lys Gly Lys Lys Arg Val Phe Ala Ser Asn Gly Gln Ile Thr Asn
            690             695             700

Leu Leu Arg Gly Phe Trp Gly Leu Arg Lys Val Arg Ala Glu Asn Asp
705             710             715             720

Arg His His Ala Leu Asp Ala Val Val Ala Cys Ser Thr Val Ala
            725             730             735

Met Gln Gln Lys Ile Thr Arg Phe Val Arg Tyr Lys Glu Met Asn Ala
            740             745             750

Phe Asp Gly Lys Thr Ile Asp Lys Glu Thr Gly Glu Val Leu His Gln
            755             760             765

Lys Thr His Phe Pro Gln Pro Trp Glu Phe Phe Ala Gln Glu Val Met
770             775             780

Ile Arg Val Phe Gly Lys Pro Asp Gly Lys Pro Glu Phe Glu Glu Ala
785             790             795             800

Asp Thr Pro Glu Lys Leu Arg Thr Leu Leu Ala Glu Lys Leu Ser Ser
            805             810             815

Arg Pro Glu Ala Val His Glu Tyr Val Thr Pro Leu Phe Val Ser Arg
            820             825             830

Ala Pro Asn Arg Lys Met Ser Gly Gln Gly His Met Glu Thr Val Lys
            835             840             845

Ser Ala Lys Arg Leu Asp Glu Gly Val Ser Val Leu Arg Val Pro Leu
            850             855             860

Thr Gln Leu Lys Leu Lys Asp Leu Glu Lys Met Val Asn Arg Glu Arg
865             870             875             880

Glu Pro Lys Leu Tyr Glu Ala Leu Lys Ala Arg Leu Glu Ala His Lys
            885             890             895

Asp Asp Pro Ala Lys Ala Phe Ala Glu Pro Phe Tyr Lys Tyr Asp Lys
            900             905             910

Ala Gly Asn Arg Thr Gln Gln Val Lys Ala Val Arg Val Glu Gln Val
            915             920             925

Gln Lys Thr Gly Val Trp Val Arg Asn His Asn Gly Ile Ala Asp Asn
            930             935             940

Ala Thr Met Val Arg Val Asp Val Phe Glu Lys Gly Asp Lys Tyr Tyr
945             950             955             960

Leu Val Pro Ile Tyr Ser Trp Gln Val Ala Lys Gly Ile Leu Pro Asp
            965             970             975

Arg Ala Val Val Gln Gly Lys Asp Glu Glu Asp Trp Gln Leu Ile Asp
            980             985             990

Asp Ser Phe Asn Phe Lys Phe Ser  Leu His Pro Asn Asp  Leu Val Glu
            995            1000            1005
```

```
Val Ile Thr Lys Lys Ala Arg Met Phe Gly Tyr Phe Ala Ser Cys
    1010            1015                1020

His Arg Gly Thr Gly Asn Ile Asn Ile Arg Ile His Asp Leu Asp
    1025            1030                1035

His Lys Ile Gly Lys Asn Gly Ile Leu Glu Gly Ile Gly Val Lys
    1040            1045                1050

Thr Ala Leu Ser Phe Gln Lys Tyr Gln Ile Asp Glu Leu Gly Lys
    1055            1060                1065

Glu Ile Arg Pro Cys Arg Leu Lys Lys Arg Pro Val Arg Ser
    1070            1075                1080

Arg Ala Asp Pro Lys Lys Arg Lys Val Glu Ala Ser Gly Arg
    1085            1090                1095

Ala Ile Phe Lys Pro Glu Glu Leu Arg Gln Ala Leu Met Pro Thr
    1100            1105                1110

Leu Glu Ala Leu Tyr Arg Gln Asp Pro Glu Ser Leu Pro Phe Arg
    1115            1120                1125

Gln Pro Val Asp Pro Gln Leu Leu Gly Ile Pro Asp Tyr Phe Asp
    1130            1135                1140

Ile Val Lys Ser Pro Met Asp Leu Ser Thr Ile Lys Arg Lys Leu
    1145            1150                1155

Asp Thr Gly Gln Tyr Gln Glu Pro Trp Gln Tyr Val Asp Asp Ile
    1160            1165                1170

Trp Leu Met Phe Asn Asn Ala Trp Leu Tyr Asn Arg Lys Thr Ser
    1175            1180                1185

Arg Val Tyr Lys Tyr Cys Ser Lys Leu Ser Glu Val Phe Glu Gln
    1190            1195                1200

Glu Ile Asp Pro Val Met Gln Ser Leu Gly Tyr Cys Cys Gly Arg
    1205            1210                1215

Lys Leu Glu Phe Ser Pro Gln Thr Leu Cys Cys Tyr Gly Lys Gln
    1220            1225                1230

Leu Cys Thr Ile Pro Arg Asp Ala Thr Tyr Tyr Ser Tyr Gln Asn
    1235            1240                1245

Arg Tyr His Phe Cys Glu Lys Cys Phe Asn Glu Ile Gln Gly Glu
    1250            1255                1260

Ser Val Ser Leu Gly Asp Asp Pro Ser Gln Pro Gln Thr Thr Ile
    1265            1270                1275

Asn Lys Glu Gln Phe Ser Lys Arg Lys Asn Asp Thr Leu Asp Pro
    1280            1285                1290

Glu Leu Phe Val Glu Cys Thr Glu Cys Gly Arg Lys Met His Gln
    1295            1300                1305

Ile Cys Val Leu His His Glu Ile Ile Trp Pro Ala Gly Phe Val
    1310            1315                1320

Cys Asp Gly Cys Leu Lys Lys Ser Ala Arg Thr Arg Lys Glu Asn
    1325            1330                1335

Lys Phe Ser Ala Lys Arg Leu Pro Ser Thr Arg Leu Gly Thr Phe
    1340            1345                1350

Leu Glu Asn Arg Val Asn Asp Phe Leu Arg Arg Gln Asn His Pro
    1355            1360                1365

Glu Ser Gly Glu Val Thr Val Arg Val Val His Ala Ser Asp Lys
    1370            1375                1380

Thr Val Glu Val Lys Pro Gly Met Lys Ala Arg Phe Val Asp Ser
    1385            1390                1395
```

```
Gly Glu Met Ala Glu Ser Phe Pro Tyr Arg Thr Lys Ala Leu Phe
    1400                1405                1410

Ala Phe Glu Glu Ile Asp Gly Val Asp Leu Cys Phe Phe Gly Met
    1415                1420                1425

His Val Gln Glu Tyr Gly Ser Asp Cys Pro Pro Asn Gln Arg
    1430                1435                1440

Arg Val Tyr Ile Ser Tyr Leu Asp Ser Val His Phe Phe Arg Pro
    1445                1450                1455

Lys Cys Leu Arg Thr Ala Val Tyr His Glu Ile Leu Ile Gly Tyr
    1460                1465                1470

Leu Glu Tyr Val Lys Lys Leu Gly Tyr Thr Thr Gly His Ile Trp
    1475                1480                1485

Ala Cys Pro Pro Ser Glu Gly Asp Asp Tyr Ile Phe His Cys His
    1490                1495                1500

Pro Pro Asp Gln Lys Ile Pro Lys Pro Lys Arg Leu Gln Glu Trp
    1505                1510                1515

Tyr Lys Lys Met Leu Asp Lys Ala Val Ser Glu Arg Ile Val His
    1520                1525                1530

Asp Tyr Lys Asp Ile Phe Lys Gln Ala Thr Glu Asp Arg Leu Thr
    1535                1540                1545

Ser Ala Lys Glu Leu Pro Tyr Phe Glu Gly Asp Phe Trp Pro Asn
    1550                1555                1560

Val Leu Glu Glu Ser Ile Lys Glu Leu Glu Gln Glu Glu Glu Glu
    1565                1570                1575

Arg Lys Arg Glu Glu Asn Thr Ser Asn Glu Ser Thr Asp Val Thr
    1580                1585                1590

Lys Gly Asp Ser Lys Asn Ala Lys Lys Lys Asn Lys Lys Thr
    1595                1600                1605

Ser Lys Asn Lys Ser Ser Leu Ser Arg Gly Asn Lys Lys Pro
    1610                1615                1620

Gly Met Pro Asn Val Ser Asn Asp Leu Ser Gln Lys Leu Tyr Ala
    1625                1630                1635

Thr Met Glu Lys His Lys Glu Val Phe Phe Val Ile Arg Leu Ile
    1640                1645                1650

Ala Gly Pro Ala Ala Asn Ser Leu Pro Pro Ile Val Asp Pro Asp
    1655                1660                1665

Pro Leu Ile Pro Cys Asp Leu Met Asp Gly Arg Asp Ala Phe Leu
    1670                1675                1680

Thr Leu Ala Arg Asp Lys His Leu Glu Phe Ser Ser Leu Arg Arg
    1685                1690                1695

Ala Gln Trp Ser Thr Met Cys Met Leu Val Glu Leu His Thr Gln
    1700                1705                1710

Ser Gln Asp Tyr Pro Tyr Asp Val Pro Asp Tyr Ala Ser
    1715                1720                1725

<210> SEQ ID NO 6
<211> LENGTH: 20
<212> TYPE: DNA
<213> ORGANISM: Artificial sequence
<220> FEATURE:
<223> OTHER INFORMATION: Synthetic

<400> SEQUENCE: 6
caatgacccc ttcattgacc                                            20
```

<210> SEQ ID NO 7
<211> LENGTH: 20
<212> TYPE: DNA
<213> ORGANISM: Artificial sequence
<220> FEATURE:
<223> OTHER INFORMATION: Synthetic

<400> SEQUENCE: 7
ttgattttgg agggatctcg					20

<210> SEQ ID NO 8
<211> LENGTH: 20
<212> TYPE: DNA
<213> ORGANISM: Artificial sequence
<220> FEATURE:
<223> OTHER INFORMATION: Synthetic

<400> SEQUENCE: 8
agaccatgtc cgggaaaacc					20

<210> SEQ ID NO 9
<211> LENGTH: 20
<212> TYPE: DNA
<213> ORGANISM: Artificial sequence
<220> FEATURE:
<223> OTHER INFORMATION: Synthetic

<400> SEQUENCE: 9
gccagcccga agtctgtaat					20

<210> SEQ ID NO 10
<211> LENGTH: 21
<212> TYPE: DNA
<213> ORGANISM: Artificial sequence
<220> FEATURE:
<223> OTHER INFORMATION: Synthetic

<400> SEQUENCE: 10
gctgagtgaa ctgcactgtg a					21

<210> SEQ ID NO 11
<211> LENGTH: 20
<212> TYPE: DNA
<213> ORGANISM: Artificial sequence
<220> FEATURE:
<223> OTHER INFORMATION: Synthetic

<400> SEQUENCE: 11
gaattctttg ccgaaatgga					20

<210> SEQ ID NO 12
<211> LENGTH: 20
<212> TYPE: DNA
<213> ORGANISM: Artificial sequence
<220> FEATURE:
<223> OTHER INFORMATION: Synthetic

<400> SEQUENCE: 12
tcactagcaa gctctcaggc					20

<210> SEQ ID NO 13
<211> LENGTH: 19
<212> TYPE: DNA
<213> ORGANISM: Artificial sequence
<220> FEATURE:
<223> OTHER INFORMATION: Synthetic

```
<400> SEQUENCE: 13
aacaacgagg agtctgccc                                              19

<210> SEQ ID NO 14
<211> LENGTH: 96
<212> TYPE: DNA
<213> ORGANISM: Artificial sequence
<220> FEATURE:
<223> OTHER INFORMATION: Synthetic

<400> SEQUENCE: 14
ggcaaggctg gccaacccat gttttagagc tagaaatagc aagttaaaat aaggctagtc    60
cgttatcaac ttgaaaaagt ggcaccgagt cggtgc                              96

<210> SEQ ID NO 15
<211> LENGTH: 96
<212> TYPE: DNA
<213> ORGANISM: Artificial sequence
<220> FEATURE:
<223> OTHER INFORMATION: Synthetic

<400> SEQUENCE: 15
cggacctgac tccacccctg gttttagagc tagaaatagc aagttaaaat aaggctagtc    60
cgttatcaac ttgaaaaagt ggcaccgagt cggtgc                              96

<210> SEQ ID NO 16
<211> LENGTH: 96
<212> TYPE: DNA
<213> ORGANISM: Artificial sequence
<220> FEATURE:
<223> OTHER INFORMATION: Synthetic

<400> SEQUENCE: 16
actatgctga gctgtgatga gttttagagc tagaaatagc aagttaaaat aaggctagtc    60
cgttatcaac ttgaaaaagt ggcaccgagt cggtgc                              96

<210> SEQ ID NO 17
<211> LENGTH: 96
<212> TYPE: DNA
<213> ORGANISM: Artificial sequence
<220> FEATURE:
<223> OTHER INFORMATION: Synthetic

<400> SEQUENCE: 17
tgccctgtaa gcatcctgct gttttagagc tagaaatagc aagttaaaat aaggctagtc    60
cgttatcaac ttgaaaaagt ggcaccgagt cggtgc                              96

<210> SEQ ID NO 18
<211> LENGTH: 96
<212> TYPE: DNA
<213> ORGANISM: Artificial sequence
<220> FEATURE:
<223> OTHER INFORMATION: Synthetic

<400> SEQUENCE: 18
ccatgagtag agggcagaca gttttagagc tagaaatagc aagttaaaat aaggctagtc    60
cgttatcaac ttgaaaaagt ggcaccgagt cggtgc                              96

<210> SEQ ID NO 19
<211> LENGTH: 96
<212> TYPE: DNA
<213> ORGANISM: Artificial sequence
```

```
<220> FEATURE:
<223> OTHER INFORMATION: Synthetic

<400> SEQUENCE: 19
tactaggctg actcactcca gttttagagc tagaaatagc aagttaaaat aaggctagtc      60
cgttatcaac ttgaaaaagt ggcaccgagt cggtgc                                96

<210> SEQ ID NO 20
<211> LENGTH: 96
<212> TYPE: DNA
<213> ORGANISM: Artificial sequence
<220> FEATURE:
<223> OTHER INFORMATION: Synthetic

<400> SEQUENCE: 20
ggtgcgtccc tcctagcgcc gttttagagc tagaaatagc aagttaaaat aaggctagtc      60
cgttatcaac ttgaaaaagt ggcaccgagt cggtgc                                96

<210> SEQ ID NO 21
<211> LENGTH: 96
<212> TYPE: DNA
<213> ORGANISM: Artificial sequence
<220> FEATURE:
<223> OTHER INFORMATION: Synthetic

<400> SEQUENCE: 21
taccccggcg cccctcacca gttttagagc tagaaatagc aagttaaaat aaggctagtc      60
cgttatcaac ttgaaaaagt ggcaccgagt cggtgc                                96

<210> SEQ ID NO 22
<211> LENGTH: 96
<212> TYPE: DNA
<213> ORGANISM: Artificial sequence
<220> FEATURE:
<223> OTHER INFORMATION: Synthetic

<400> SEQUENCE: 22
ctttggcgca tgcttcaccc gttttagagc tagaaatagc aagttaaaat aaggctagtc      60
cgttatcaac ttgaaaaagt ggcaccgagt cggtgc                                96

<210> SEQ ID NO 23
<211> LENGTH: 96
<212> TYPE: DNA
<213> ORGANISM: Artificial sequence
<220> FEATURE:
<223> OTHER INFORMATION: Synthetic

<400> SEQUENCE: 23
aaggcctcaa acattcccct gttttagagc tagaaatagc aagttaaaat aaggctagtc      60
cgttatcaac ttgaaaaagt ggcaccgagt cggtgc                                96

<210> SEQ ID NO 24
<211> LENGTH: 96
<212> TYPE: DNA
<213> ORGANISM: Artificial sequence
<220> FEATURE:
<223> OTHER INFORMATION: Synthetic

<400> SEQUENCE: 24
gcgttaggtg gtgtggtcta gttttagagc tagaaatagc aagttaaaat aaggctagtc      60
cgttatcaac ttgaaaaagt ggcaccgagt cggtgc                                96
```

<210> SEQ ID NO 25
<211> LENGTH: 96
<212> TYPE: DNA
<213> ORGANISM: Artificial sequence
<220> FEATURE:
<223> OTHER INFORMATION: Synthetic

<400> SEQUENCE: 25
gtgcctcccc cattccgctc gttttagagc tagaaatagc aagttaaaat aaggctagtc    60
cgttatcaac ttgaaaaagt ggcaccgagt cggtgc    96

<210> SEQ ID NO 26
<211> LENGTH: 96
<212> TYPE: DNA
<213> ORGANISM: Artificial sequence
<220> FEATURE:
<223> OTHER INFORMATION: Synthetic

<400> SEQUENCE: 26
ttcccacacc ccgttcctgg gttttagagc tagaaatagc aagttaaaat aaggctagtc    60
cgttatcaac ttgaaaaagt ggcaccgagt cggtgc    96

<210> SEQ ID NO 27
<211> LENGTH: 96
<212> TYPE: DNA
<213> ORGANISM: Artificial sequence
<220> FEATURE:
<223> OTHER INFORMATION: Synthetic

<400> SEQUENCE: 27
aaccaggtgc ccacccgggc gttttagagc tagaaatagc aagttaaaat aaggctagtc    60
cgttatcaac ttgaaaaagt ggcaccgagt cggtgc    96

<210> SEQ ID NO 28
<211> LENGTH: 96
<212> TYPE: DNA
<213> ORGANISM: Artificial sequence
<220> FEATURE:
<223> OTHER INFORMATION: Synthetic

<400> SEQUENCE: 28
tcgcctgcag ccttacgggc gttttagagc tagaaatagc aagttaaaat aaggctagtc    60
cgttatcaac ttgaaaaagt ggcaccgagt cggtgc    96

<210> SEQ ID NO 29
<211> LENGTH: 96
<212> TYPE: DNA
<213> ORGANISM: Artificial sequence
<220> FEATURE:
<223> OTHER INFORMATION: Synthetic

<400> SEQUENCE: 29
tccttggcta actccaggct gttttagagc tagaaatagc aagttaaaat aaggctagtc    60
cgttatcaac ttgaaaaagt ggcaccgagt cggtgc    96

<210> SEQ ID NO 30
<211> LENGTH: 96
<212> TYPE: DNA
<213> ORGANISM: Artificial sequence
<220> FEATURE:
<223> OTHER INFORMATION: Synthetic

<400> SEQUENCE: 30

```
cgcggcgccg ctctccgctg gttttagagc tagaaatagc aagttaaaat aaggctagtc    60
cgttatcaac ttgaaaaagt ggcaccgagt cggtgc                              96

<210> SEQ ID NO 31
<211> LENGTH: 96
<212> TYPE: DNA
<213> ORGANISM: Artificial sequence
<220> FEATURE:
<223> OTHER INFORMATION: Synthetic

<400> SEQUENCE: 31
agccgggtgt cctgacgctc gttttagagc tagaaatagc aagttaaaat aaggctagtc    60
cgttatcaac ttgaaaaagt ggcaccgagt cggtgc                              96

<210> SEQ ID NO 32
<211> LENGTH: 96
<212> TYPE: DNA
<213> ORGANISM: Artificial sequence
<220> FEATURE:
<223> OTHER INFORMATION: Synthetic

<400> SEQUENCE: 32
gtttaattcg ggaagaatgc gttttagagc tagaaatagc aagttaaaat aaggctagtc    60
cgttatcaac ttgaaaaagt ggcaccgagt cggtgc                              96

<210> SEQ ID NO 33
<211> LENGTH: 96
<212> TYPE: DNA
<213> ORGANISM: Artificial sequence
<220> FEATURE:
<223> OTHER INFORMATION: Synthetic

<400> SEQUENCE: 33
agcgctcgat aaatacttac gttttagagc tagaaatagc aagttaaaat aaggctagtc    60
cgttatcaac ttgaaaaagt ggcaccgagt cggtgc                              96

<210> SEQ ID NO 34
<211> LENGTH: 96
<212> TYPE: DNA
<213> ORGANISM: Artificial sequence
<220> FEATURE:
<223> OTHER INFORMATION: Synthetic

<400> SEQUENCE: 34
tgttgggcat taagagggag gttttagagc tagaaatagc aagttaaaat aaggctagtc    60
cgttatcaac ttgaaaaagt ggcaccgagt cggtgc                              96

<210> SEQ ID NO 35
<211> LENGTH: 96
<212> TYPE: DNA
<213> ORGANISM: Artificial sequence
<220> FEATURE:
<223> OTHER INFORMATION: Synthetic

<400> SEQUENCE: 35
catcgcggcc ggctccgctc gttttagagc tagaaatagc aagttaaaat aaggctagtc    60
cgttatcaac ttgaaaaagt ggcaccgagt cggtgc                              96

<210> SEQ ID NO 36
<211> LENGTH: 96
<212> TYPE: DNA
```

<213> ORGANISM: Artificial sequence
<220> FEATURE:
<223> OTHER INFORMATION: Synthetic

<400> SEQUENCE: 36

```
tgacagcaat agtggcctac gttttagagc tagaaatagc aagttaaaat aaggctagtc    60
cgttatcaac ttgaaaaagt ggcaccgagt cggtgc                              96
```

<210> SEQ ID NO 37
<211> LENGTH: 96
<212> TYPE: DNA
<213> ORGANISM: Artificial sequence
<220> FEATURE:
<223> OTHER INFORMATION: Synthetic

<400> SEQUENCE: 37

```
caggttagac ttacaaggtg gttttagagc tagaaatagc aagttaaaat aaggctagtc    60
cgttatcaac ttgaaaaagt ggcaccgagt cggtgc                              96
```

<210> SEQ ID NO 38
<211> LENGTH: 96
<212> TYPE: DNA
<213> ORGANISM: Artificial sequence
<220> FEATURE:
<223> OTHER INFORMATION: Synthetic

<400> SEQUENCE: 38

```
ctactccttc ctcttgagac gttttagagc tagaaatagc aagttaaaat aaggctagtc    60
cgttatcaac ttgaaaaagt ggcaccgagt cggtgc                              96
```

<210> SEQ ID NO 39
<211> LENGTH: 96
<212> TYPE: DNA
<213> ORGANISM: Artificial sequence
<220> FEATURE:
<223> OTHER INFORMATION: Synthetic

<400> SEQUENCE: 39

```
gggtgcgtcc ctcctagcgc gttttagagc tagaaatagc aagttaaaat aaggctagtc    60
cgttatcaac ttgaaaaagt ggcaccgagt cggtgc                              96
```

<210> SEQ ID NO 40
<211> LENGTH: 96
<212> TYPE: DNA
<213> ORGANISM: Artificial sequence
<220> FEATURE:
<223> OTHER INFORMATION: Synthetic

<400> SEQUENCE: 40

```
ggatgtactc cctggaagag gttttagagc tagaaatagc aagttaaaat aaggctagtc    60
cgttatcaac ttgaaaaagt ggcaccgagt cggtgc                              96
```

<210> SEQ ID NO 41
<211> LENGTH: 96
<212> TYPE: DNA
<213> ORGANISM: Artificial sequence
<220> FEATURE:
<223> OTHER INFORMATION: Synthetic

<400> SEQUENCE: 41

```
gtagaaagtg gagctgagct gttttagagc tagaaatagc aagttaaaat aaggctagtc    60
cgttatcaac ttgaaaaagt ggcaccgagt cggtgc                              96
```

<210> SEQ ID NO 42
<211> LENGTH: 96
<212> TYPE: DNA
<213> ORGANISM: Artificial sequence
<220> FEATURE:
<223> OTHER INFORMATION: Synthetic

<400> SEQUENCE: 42
tcaggcctga catcagacca gttttagagc tagaaatagc aagttaaaat aaggctagtc    60
cgttatcaac ttgaaaaagt ggcaccgagt cggtgc    96

<210> SEQ ID NO 43
<211> LENGTH: 96
<212> TYPE: DNA
<213> ORGANISM: Artificial sequence
<220> FEATURE:
<223> OTHER INFORMATION: Synthetic

<400> SEQUENCE: 43
gctggaggta tagaccactg gttttagagc tagaaatagc aagttaaaat aaggctagtc    60
cgttatcaac ttgaaaaagt ggcaccgagt cggtgc    96

<210> SEQ ID NO 44
<211> LENGTH: 96
<212> TYPE: DNA
<213> ORGANISM: Artificial sequence
<220> FEATURE:
<223> OTHER INFORMATION: Synthetic

<400> SEQUENCE: 44
gactgcagga ctgagctaag gttttagagc tagaaatagc aagttaaaat aaggctagtc    60
cgttatcaac ttgaaaaagt ggcaccgagt cggtgc    96

<210> SEQ ID NO 45
<211> LENGTH: 96
<212> TYPE: DNA
<213> ORGANISM: Artificial sequence
<220> FEATURE:
<223> OTHER INFORMATION: Synthetic

<400> SEQUENCE: 45
agggaccaag ctgctgggat gttttagagc tagaaatagc aagttaaaat aaggctagtc    60
cgttatcaac ttgaaaaagt ggcaccgagt cggtgc    96

<210> SEQ ID NO 46
<211> LENGTH: 96
<212> TYPE: DNA
<213> ORGANISM: Artificial sequence
<220> FEATURE:
<223> OTHER INFORMATION: Synthetic

<400> SEQUENCE: 46
gactgaggct acccctgctg gttttagagc tagaaatagc aagttaaaat aaggctagtc    60
cgttatcaac ttgaaaaagt ggcaccgagt cggtgc    96

<210> SEQ ID NO 47
<211> LENGTH: 96
<212> TYPE: DNA
<213> ORGANISM: Artificial sequence
<220> FEATURE:
<223> OTHER INFORMATION: Synthetic

```
<400> SEQUENCE: 47
ttcctgatag cccttgaccg gttttagagc tagaaatagc aagttaaaat aaggctagtc    60
cgttatcaac ttgaaaaagt ggcaccgagt cggtgc                              96

<210> SEQ ID NO 48
<211> LENGTH: 96
<212> TYPE: DNA
<213> ORGANISM: Artificial sequence
<220> FEATURE:
<223> OTHER INFORMATION: Synthetic

<400> SEQUENCE: 48
tgctagccag agcggaatgg gttttagagc tagaaatagc aagttaaaat aaggctagtc    60
cgttatcaac ttgaaaaagt ggcaccgagt cggtgc                              96

<210> SEQ ID NO 49
<211> LENGTH: 96
<212> TYPE: DNA
<213> ORGANISM: Artificial sequence
<220> FEATURE:
<223> OTHER INFORMATION: Synthetic

<400> SEQUENCE: 49
cgatggcgcg tcccctcgtg gttttagagc tagaaatagc aagttaaaat aaggctagtc    60
cgttatcaac ttgaaaaagt ggcaccgagt cggtgc                              96

<210> SEQ ID NO 50
<211> LENGTH: 120
<212> TYPE: DNA
<213> ORGANISM: Homo sapiens

<400> SEQUENCE: 50
gtgattattc tggctactca ctttggcaag gagttcaccc ctgaagtgca ggctgcctgg    60
cagaagctgg tgtctgctgt cgccattgcc ctggcccata agtaccactg agttctcttc   120

<210> SEQ ID NO 51
<211> LENGTH: 36
<212> TYPE: PRT
<213> ORGANISM: Homo sapiens

<400> SEQUENCE: 51

Val Ile Ile Leu Ala Thr His Phe Gly Lys Glu Phe Thr Pro Glu Val
1               5                   10                  15

Gln Ala Ala Trp Gln Lys Leu Val Ser Ala Val Ala Ile Ala Leu Ala
            20                  25                  30

His Lys Tyr His
            35
```